US012661336B2

(12) United States Patent
Boesen et al.

(10) Patent No.: US 12,661,336 B2
(45) Date of Patent: Jun. 23, 2026

(54) POLYMORPHS OF PHENYL PYRROLE AMINOGUANDIUM SALTS

(71) Applicant: SYNACT PHARMA APS, Holte (DK)

(72) Inventors: Thomas Boesen, Copenhagen (DK); Thomas Engelbrecht Nordkild Jonassen, Holte (DK); Hayley Ann Reece, Dalkeith (GB); Natalie Louise Kelk, Edinburgh (GB); Alice Jane Turner, Edinburgh (GB); Ross McLellan, Glasgow (GB)

(73) Assignee: SYNACT PHARMA APS, Holte (DK)

( * ) Notice: Subject to any disclaimer, the term of this patent is extended or adjusted under 35 U.S.C. 154(b) by 742 days.

(21) Appl. No.: 17/821,500

(22) Filed: Aug. 23, 2022

(65) Prior Publication Data

US 2023/0002319 A1 Jan. 5, 2023
US 2023/0271922 A9 Aug. 31, 2023

Related U.S. Application Data

(63) Continuation of application No. PCT/EP2022/066884, filed on Jun. 21, 2022.

(30) Foreign Application Priority Data

Jun. 21, 2021 (EP) ..................................... 21180702
Jun. 21, 2021 (EP) ..................................... 21180708
Nov. 23, 2021 (EP) ..................................... 21209855

(51) Int. Cl.
*A61K 31/402* (2006.01)
*A61K 9/20* (2006.01)
(Continued)

(52) U.S. Cl.
CPC .............. *A61K 31/402* (2013.01); *A61K 9/20* (2013.01); *A61K 9/2009* (2013.01);
(Continued)

(58) Field of Classification Search
CPC ...... A61K 31/402; A61K 9/20; A61K 9/2009; A61K 9/2013; A61K 9/2027;
(Continued)

(56) References Cited

U.S. PATENT DOCUMENTS 6,632,815 B2 10/2003 Zhu et al.
6,686,368 B1 2/2004 Zhu et al.
(Continued)

FOREIGN PATENT DOCUMENTS

GB 2398299 A 8/2004
KR 10-2004-0019302 A 3/2004
(Continued)

OTHER PUBLICATIONS

Schafer et al. Drug Discovery Today 2008, 13 (21/22), 913-916 (Year: 2008).*
(Continued)

*Primary Examiner* — Clinton A Brooks
*Assistant Examiner* — Jerica Katlynn Wilson
(74) *Attorney, Agent, or Firm* — BakerHostetler

(57) ABSTRACT

The present disclosure relates to crystalline forms of N-{3-[1-(2-nitrophenyl)-1H-pyrrol-2-yl]-allylidene}-aminoguanidinium salts having high solubility. The disclosure also relates to use of said crystalline forms in medicine.

8 Claims, 46 Drawing Sheets

(51) Int. Cl.
*A61K 9/28* (2006.01)
*A61K 31/519* (2006.01)
*C07D 207/335* (2006.01)

(52) U.S. Cl.
CPC .......... *A61K 9/2013* (2013.01); *A61K 9/2027* (2013.01); *A61K 9/2054* (2013.01); *A61K 9/2846* (2013.01); *A61K 31/519* (2013.01); *C07D 207/335* (2013.01); *C07B 2200/13* (2013.01)

(58) Field of Classification Search
CPC .. A61K 9/2054; A61K 9/2846; A61K 31/519; C07D 207/335; C07B 2200/13
See application file for complete search history.

(56) References Cited

U.S. PATENT DOCUMENTS

| | | | |
|---|---|---|---|
| 6,720,317 | B1 | 4/2004 | Zhu et al. |
| 6,844,367 | B1 | 1/2005 | Zhu et al. |
| 7,153,881 | B2 | 12/2006 | Lundstedt et al. |
| 7,186,748 | B2 | 3/2007 | Lundstedt et al. |
| 7,285,565 | B2 | 10/2007 | Zhu et al. |
| 7,442,807 | B2 | 10/2008 | Lundstedt et al. |
| 8,372,878 | B2 | 2/2013 | Lundstedt et al. |
| 9,662,807 | B2 | 5/2017 | Feeney et al. |
| 9,794,214 | B2 | 10/2017 | Banatwala et al. |
| 10,387,927 | B2 | 8/2019 | O'Connor et al. |
| 2003/0211150 | A1 | 11/2003 | Al-Ghazawi et al. |
| 2004/0254093 | A1 | 12/2004 | Lundstedt et al. |
| 2009/0018183 | A1 | 1/2009 | Lundstedt et al. |
| 2011/0218203 | A1 | 9/2011 | Kaye et al. |
| 2021/0121418 | A1 | 4/2021 | Jonassen |
| 2022/0211666 | A1 | 7/2022 | Jonassen |
| 2023/0211150 | A1 | 7/2023 | He |

FOREIGN PATENT DOCUMENTS

| | | | | |
|---|---|---|---|---|
| KR | 10-2013-0014523 | A | 2/2013 | |
| WO | 98/23267 | A1 | 6/1998 | |
| WO | 99/21571 | A1 | 5/1999 | |
| WO | 99/55679 | A1 | 11/1999 | |
| WO | 99/64002 | A1 | 12/1999 | |
| WO | 00/58361 | A1 | 10/2000 | |
| WO | 00/74679 | A1 | 12/2000 | |
| WO | 01/05401 | A1 | 1/2001 | |
| WO | 2001/019788 | A2 | 3/2001 | |
| WO | 2001/019798 | A2 | 3/2001 | |
| WO | 01/55106 | A2 | 8/2001 | |
| WO | 01/55107 | A2 | 8/2001 | |
| WO | 01/55109 | A1 | 8/2001 | |
| WO | 01/74679 | A1 | 10/2001 | |
| WO | 02/11715 | A2 | 2/2002 | |
| WO | 02/12166 | A2 | 2/2002 | |
| WO | 02/12178 | A1 | 2/2002 | |
| WO | 02/18327 | A2 | 3/2002 | |
| WO | 2002/069905 | A2 | 9/2002 | |
| WO | 03/13509 | A1 | 2/2003 | |
| WO | 2007/059188 | A1 | 5/2007 | |
| WO | WO-2007141343 | A1 * | 12/2007 | .............. A61P 43/00 |
| WO | 2008/071980 | A1 | 6/2008 | |
| WO | 2009/039859 | A1 | 4/2009 | |
| WO | 2009/071101 | A1 | 6/2009 | |
| WO | 2009/074157 | A1 | 6/2009 | |
| WO | 2011/111143 | A1 | 9/2011 | |
| WO | 2014/060606 | A1 | 4/2014 | |
| WO | 2015/162483 | A1 | 10/2015 | |
| WO | 2015/162486 | A1 | 10/2015 | |
| WO | 2017/141343 | A1 | 8/2017 | |
| WO | 2019/243625 | A1 | 12/2019 | |
| WO | 2020/107221 | A1 | 6/2020 | |
| WO | 2020/229297 | A1 | 11/2020 | |

OTHER PUBLICATIONS

Horig et al. Journal of Translational Medicine 2004, 2(44) (Year: 2004).*
Nair et al., "A simple practice guide for dose conversion between animals and human", J Basic Clin Pharma, Mar. 2016-May 2016, vol. 7, No. 2, pp. 27-31.
Stoycheff et al., Nephrotic Syndrome in Diabetic Kidney Disease: An Evaluation and Update of the Definition, American Journal of Kidney Diseases, vol. 54, No. 5, Jun. 26, 2009.
Waldman et al., Treatment of Idiopathic Membranous Nephropathy, Journal of American Society of Nephrology, No. 23, 1617-1630, 2012.
Appendix A—Translation—UK version of Swedish press release published 08.00 am today—SynAct Pharma investigates the possibility of AP1189 as additional therapy in hospitalized patents with COVID-19, 1Page.
Appendix B2—SynAct Pharma will test the main candidate as an additional treatment for corona patients, Mar. 31, 2020, 8 Pages.
Appendix C2—SynAct Pharma sees potential in several viral diseases—BioStock Sep. 22, 2020_2131808, 9 Pages.
Appendix D—SynAct has initiated dosing in part 2 of the clinical Phase II study with AP1189 in Covid-19 infected patients, Mar. 18, 2021, 2 Pages.
Buckley et al., "Isolation of a-Melanotropin and N, O-Diacetylserine'-a-Melanotropin From Porcine Pituitary Extracts", Int. Journal Peptide Protein Research, 1981, vol. 17, pp. 508-513.
Japan College of Rheumatology MTX, Treatment Guidelines Formulating Committee, Methotrexate (MTX) Treatment Guidelines in Rheumatoid Arthritis Treatment, 2016, revised "Summary Edition", 2016, pp. 1 to 12.
Nordheim et al., "Cardiovascular responses to melanocortin 4-receptor stimulation in conscious unrestrained normotensive rats", Peptides, vol. 27, 2006, pp. 438-443.
Rinne et al., "Melanocortin 1 Receptor Deficiency Promotes Atherosclerosis in Apolipoprotein E-/-Mice", Arterioscler Thromb Vasc Biol., Feb. 2018, vol. 38, pp. 313-323.
Tallarida, "Quantitative Methods for Assessing Drug Synergism", Genes & Cancer, 2011, vol. 2, No. 11, pp. 1003-1008.
U.S. Provisional Application filed on Sep. 17, 1999, by Zhu et al., U.S. Appl. No. 60/154,332.
Vengerovsky, "Pharmacological incompatibility", Bulletin of Siberian Medicine, No. 3, 2003, pp. 49-56.
White et al., "Usefulness of ambulatory blood pressure monitoring to assess the melanocortin receptor agonist bremelanotide", Journal of Hypertension, Apr. 2017, vol. 35, No. 4, pp. 761-768.
Galvan et al., "Review of Non-bacterial Infections in Respiratory Medicine: Viral Pneumonia," Arch Bronconeumol., 2015, vol. 51, Issue 11, pp. 590-597.
Zaki et al., "Viral Infections of the Lung," Dail and Hammar's Pulmonary Pathology, 2008, pp. 426-475.
Rath et al., "Drug combinations with methotrexate to treat rheumatoid arthritis", Clin. Exp. Rheumatol, 2010, vol. 28, Suppl. 61, pp. S52-S57.
Abdel-Malek et al., "Mitogenic and Melanogenic Stimulation of Normal Human Melanocytes by Melanotropic Peptides", Proc. Natl. Acad. Sci. USA, Feb. 1995, vol. 92, pp. 1789-1793.
Abdel-Malek, "Melanocortin receptors: their functions and regulation by physiological agonists and antagonists", Cellular and Molecular Life Science, Nov. 2001, vol. 58, pp. 434-441.
Alvaro et al., "Morphine Down-regulates Melanocortin-4 Receptor Expression in Brain Regions that Mediate Opiate Addiction", Molecular Pharmacology, Jan. 1996, vol. 50, pp. 583-591.
Berge et al., "Pharmaceutical Salts", J. Pharm. Sci., Jan. 1977, vol. 66, No. 1, pp. 1-19.
Bjerke, Synact Pharma "AP1189—A new medicine to treat inflammatory diseases", 2018, pp. 15.
Blumberg et al., "Rheumatoid Arthritis: Guidelines for Emerging Therapies", Am. J. Manag. Care, Jun. 2001, vol. 7(6), pp. 617-626.
Boston, "The Role of Melanocortins in Adipocyte Function", Annals New York Academy of Sciences, 1999, pp. 75-84.
Bresnihan et al., "Synovial tissue analysis in rheumatoid arthritis", Ballieres Clin. Rheumatol. 1999, vol. 13, pp. 645-659.

(56) References Cited

OTHER PUBLICATIONS

Brzoska et al., "a-Melanocyte-Stimulating Hormone and Related Tripeptides: Biochemistry, Anti-inflammatory and Protective Effects in Vitro and in Vivo, and Future Perspectives for the Treatment of Immune-Mediated Inflammatory Diseases", Endocr. Rev., Aug. 2008, vol. 29, pp. 581-602.
Catania et al., "a-Melanocyte Stimulating Hormone in the Modulation of Host Reactions", Endocr. Rev., Oct. 1993, vol. 14(5), pp. 564-576.
Catania et al., "Targeting Melanocortin Receptors as a Novel Strategy to Control Inflammation", Pharmacological Reviews, 2004, vol. 56, No. 1, pp. 1-29.
Chen et al., "Exocrine Gland Dysfunction in MC5-R-Deficient Mice: Evidence for Coordinated Regulation of Exocrine Gland Function by Melanocortin Peptides", Cell, Dec. 1997, vol. 91, pp. 789-798.
Chen et al., "Inactivation of the mouse melanocortin-3 receptor results in increased fat mass and reduced lean body mass", Nature Genetics, Sep. 2000, vol. 26, pp. 97-102.
Chhajlani et al., "Identification of Ligand Binding Residues in Extracellular Loops of the Melanocortin 1 Receptor", Biochem and Biophysical Research Communications, 1996, vol. 219, pp. 521-525.
De Wildt et al., "Effect of y2-Melanocyte-Stimulating Hormone on Cerebral Blood Flow in Rats", J. Cardiovascular Pharmacology, 1995, vol. 25, pp. 989-905.
Ditzel, "Trends The K/BxN mouse: A model of human inflammatory arthritis", Mol Med, 2004, vol. 10, pp. 40-45.
Dolhain et al., Methotrexate Reduces Inflammatory Cell Number, Expression of Monokines and of Adhesion Molecules in Synovial Tissue of patients with Rheumatoid Arthritis, Br. J. Rheumatol., 1998, vol. 37, pp. 502-508.
Donovan, "The behavioural actions of the hypothalamic peptides: a review", Physchol. Med, 1978, vol. 8, pp. 305-316.
Elvin et al., "Melanocortin 1 Receptor Agonist Protects Podocytes Through Catalase and RhoA Activation", Am. J. Physiol., 2016, vol. 310, No. 9, pp. F848-856.
Firestein et al., "Gene Expression (Collagenase, Tissue Inhibitor of Metalloproteinases, Complement, and HLA-DR) in Rheumatoid Arthritis and Osteoarthritis Synovium", Rheum., 1991, vol. 34, pp. 1094-1105.
Firestein et al., Mechanisms of Methotrexate Action in Rheumatoid Arthritis, Arthritis Rheum., 1994, vol. 37, No. 2, pp. 193-200.
Gantz et al., "Molecular Cloning of a Novel Melanocortin Receptor", J. Biological Chemistry, Apr. 1993, vol. 268, No. 11, pp. 8246-8250.
Garcia-Borron et al., "Melanocortin-1 receptor structure and functional regulation Pigment", Cell Res., 2005, vol. 18, pp. 393-410.
Getting et al., "MC3-R as a Novel Target for Antiinflammatory Therapy", Drug News Perspect, Feb. 2000, vol. 13(1), pp. 19-27.
Getting, "Melanocortin peptides and their receptors: new targets for anti-inflammatory therapy", Trends in Pharmacological Sciences, Oct. 2002, vol. 23, No. 10, pp. 447-449.
Gibofsky, "Overview of Epidemiology, Pathophysiology, and Diagnosis of Rheumatoid Arthritis", Am. J. Manag. Care, 2012, vol. 18, pp. S295-S302.
Gong, "Leveraging Melanocortin Pathway to Treat Glomerular Diseases", Adv. Chronic Kidney Dis., 2014, vol. 21, No. 2, pp. 134-151.
Gruber et al., "ACTH-(4-10) through r-MSH: evidence for a new class of central autonomic nervous system-regulating peptides", Am. J. Physiol., 1989, vol. 257, pp. R681-694.
Guarini et al., "MC3 receptors are involved in the protective effect of melanocortins in myocardial ischemia/reperfusion-induced arrhythmias", Naunyn-Schmiedeberg's Arch Pharmacol., May 2002, vol. 366, pp. 177-182.
Hirano et al., "Excessive production of interleukin 6/B cell stimulatory factor-2 in rheumatoid arthritis", Eur. J. Immunol., 1988, vol. 18, pp. 1797-1801.
Hirano, The biology of interleukin-6. Chem immunol., 1992, vol. 51, pp. 153-180.
Houssiau et al., "Interleukin-6 in synovial fluid and serum of patients with rheumatoid arthritis and other inflammatory arthritides", Arthritis Rheum., Jun. 1988, vol. 31, pp. 784-788.
Hunt et al., "Cultured Human Melanocytes Respond to MSH Peptides and ACTH", Pigment Cell Research, 1994, vol. 7, pp. 217-221.
International Conference on Harmonisation of Technical Requirements for Registration of Pharmaceuticals for Human Use, ICH Harmonised Tripartite Guideline, Maintenance of the ICH Guideline on Non-clinical Safety Studies for the conduct of human clinical trials for Pharmaceuticals M3(R1), Current Step 4 version, dated Nov. 9, 2000.
Jonsson et al., "Effects of Melanocortin 1 Receptor Agonists in Experimental Nephropathies", PLOS One, 2014, vol. 9, No. 1, pp. e87816.
Keller et al., "Molecular and Cellular Biology of Interleukin-6 and its Receptor Frontiers", Biosci., 1996, vol. 1, pp. 340-357.
Li et al., "Melanocortin Antagonists Define Two Distinct Pathways of Cardiovascular Control by a- and g-Melanocyte-Stimulating Hormones", J. Neuroscience, Aug. 1996, vol. 16(6), pp. 5182-5188.
Lin et al., "A y-Melanocyte Stimulating Hormone-like Peptide Causes Reflex Natriuresis After Acute Unilateral Nephrectomy", Hypertension, Dec. 1987, vol. 10, No. 6, pp. 619-627.
Lindskog et al., "Melanocortin 1 Receptor Agonists Reduce Proteinuria", J. Am. Soc., Nephrol., 2010, vol. 21, pp. 1290-1298.
Madhok et al., "Serum interleukin 6 levels in rheumatoid arthritis: correlations with clinical and laboratory indices of disease activity Arthritis", Rheum., 1993, vol. 52, pp. 232-234.
Manna et al., "a-Melanocyte-Stimulating Hormone Inhibits the Nuclear Transcription Factor NF-kB Activation Induced by Various Inflammatory Agents", J. Immunology, 1998, vol. 161, pp. 2873-2880.
Marsh et al., "Response of melanocortin-4 receptor-deficient mice to anorectic and orexigenic peptides", Nature Genetics, Jan. 1999, vol. 21, pp. 119-122.
Metzger et al., "Reduced body fat and increased hepatic lipid synthesis in mice bearing interleukin-6-secreting tumor", Am. J. Physoil. Endocrinol. Metab., Oct. 2001, vol. 281, pp. E597-E965.
Montero-Melendez et al., "Association between Periodontal Disease and Inflammatory Arthritis Reveals Modulatory Functions by Melanocortin Receptor Type 3", Am. J. Pathology, 2014, vol. 184(8), pp. 2333-2341.
Montero-Melendez et al., "Biased Agonism as a Novel Strategy to Harness the Proresolving Properties of Melanocortin Receptors Without Eliciting Melanogenic Effects", J. Immunol., 2015, vol. 194, pp. 3381-3388.
Montero-Melendez et al., "The Melanocortin Agonist AP214 Exerts Anti-Inflammatory and Proresolving Properties", Am. J. Pathol., 2011, vol. 179, pp. 259-269.
Mountjoy et al., "Localization of the Melanocortin-4 Receptor (MC4-R) in Neuroendocrine and Autonomic Control Circuits in the Brain", Mol. Endo., 1994, vol. 8, No. 10, pp. 1298-1308.
Mountjoy et al., "The Cloning of a Family of Genes That Encode the Melanocortin Receptors", Science, Aug. 1992, vol. 257, pp. 1248-1251.
O'Dell et al., The New England Journal of Medicine, "Treatment of Rheumatoid Arthritis with Methotrexate Alone, Sulfasalazine and Hydroxychloroquine, or a Combination of all Three Medications", 1996, vol. 334, No. 20, pp. 1287-1291.
Perretti et al., "Resolution Pharmacology: Opportunities for Therapeutic Innovation in Inflammation", Trends Pharmacol. Sci., 2015, vol. 36, pp. 737-755.
Poggioli et al., "ACTH-(1-24) and c-MSH Antagonize Feeding Behavior Stimulated by Kappa Opiate Agonists", Peptides, 1986, vol. 7, pp. 843-848.
Qiao et al., "MC1R is Dispensable for the Proteinuria Reducing and Glomerular Protective Effect of Melanocortin Therapy", Nature Scientific Reports, 2016, vol. 6, 27589, pp. 15.
Rooney et al., "Changes in Synovial in Lymphocyte Infiltration of the Membrane and the Clinical Course of Rheumatoid Arthritis", Arthritis Rheum., 1989, vol. 32, pp. 361-369.

(56) References Cited

OTHER PUBLICATIONS

Roselli-Rehfuss et al., "Identification of a receptor for y melanotropin and other proopiomelanocortin peptides in the hypothalamus and limbic system", Proc. Natl. Acad. Sci., USA, Oct. 1993, vol. 90, pp. 8856-8860.
Salaffi et al., Disease Activity assessment of rheumatoid arthritis in daily practice: Validity, Internal Consistency, Reliability and Congruency of the Disease Activity Score Including 28 Joints (DAS28) Compared with the Clinical Disease Activity Index (CDAI), Jul.-Aug. 2009, vol. 27(4), pp. 552-559.
Schioth et al., "Characterization of the binding of MSH.B, HP.228, GHRP.6 and 153N-6 to the human melanocortin receptor subtypes", Neuropeptides, 1997, vol. 31, pp. 565-571.
Schwartz, "Orexins and appetite: The big picture of energy homeostasis gets a little bigger", Nature Medicine, 1998, vol. 4, pp. 385-386.
Sergeant et al., "Prediction of primary non-response to methotrexate therapy using demographic, clinical and psychosocial variables: results from the UK Rheumatoid Arthritis Medication Study (RAMS)", Arthritis Research & Therapy, 2018, vol. 20, No. 147, pp. 11.
Siegrist et al., "Radioreceptor Assay for a-MSH Using Mouse 816 Melanoma Cells+", J. Recept. Res., 1988, vol. 8(1-4), pp. 323-343.
Silman et al., "Supplement Review: Epidemiology and genetics of rheumatoid arthritis", Arthritis Res., 2002, 3 Supple. 3, pp. S265-S272.
Slominski et al., "Corticotropin Releasing Hormone and Proopiomelanocortin Involvement in the Cutaneous Response to Stress Physcol.", Review, Jul. 2000, vol. 80, No. 3, pp. 979-1020.
Tamura et al., "Soluble interleukin-6 receptor triggers osteoclast formation by interleukin 6", Proc. Natl. Acad. Sci. USA, 1993, vol. 90, pp. 11924-11928.
Taub, "Hepatoprotection via the IL-6/Stat3 Pathway", J. Clin. Invest., 2003, vol. 112, pp. 978-980.
Taylor et al., "In vitro induction of CD25+ CD4+ regulatory T cells by the neuropeptide alpha-melanocyte stimulating hormone (a-MSH)", Immunology and Cell Biology, 2001, vol. 79, pp. 358-367.
The Science and Practice of Pharmacy, 19 Edition, Gennaro, Ed., Mack Publishing Co., Easton, PA., 1995.
Thody et al., "Short Communications: The Pituitary and Sebaceous Gland Activity", J. Endocr., 1970, vol. 48, pp. 139-140.
Tugwell et al., The New England Journal of Medicine, "Combination Therapy with Cyclosporine and Methotrexate in Severe Rheumatoid Arthritis", vol. 333, No. 3, Jul. 20, 1995, pp. 137-141.
U.S. Appl. No. 60/154,332, entitled Inhibitors of Factor XA, filed on Sep. 17, 1999.
Van Der Kraan et al., "Expression of Melanocortin-5 Receptor in Secretory Epithelia Supports a Functional Role in Exocrine and Endocrine Glands", Endocrinol., 1998, vol. 139, pp. 2348-2355.
Van Der Ploeg et al., "A role for the melanocortin 4 receptor in sexual function", Proc., Natl., Acad. Sci. USA, Aug. 2002, vol. 99, No. 17, pp. 11381-11386.
Vandenberk et al.,"Which QT Correction Formulae to Use for QT Monitoring?", Journal of the American Heart Association, 2016, vol. 5, pp. e003264.
Vergoni et al., "Corticotropin Inhibits Food Intake IN Rats", Neuropeptides, 1986, vol. 7, pp. 153-158.
Vergoni et al., "Differential Influence of a Selective Melanocortin MC Receptor 4 Antagonist (HS014) on Melanocortin-induced Behavioral Effects in Rats", Eur. J. Pharmacol., 1998, vol. 362, pp. 95-101.
Walters et al., "An investigation of the action of disease modifying antirheumatic drugs on the rheumatoid synovial membrane: Reduction in T lymphocyte subpopulations and HLA-DP and DQ antigen expression after gold or penicillamine therapy", Ann Rheum Dis, 1987, vol. 46, pp. 7-16.
Weinblatt, "Methotrexate in Rheumatoid Arthritis: A Quarter Century of Development", Trans. Am. Clin. Climatol. Assoc., 2013, pp. 16-25.
Williams et al., A Controlled Clinical Trial, "Comparison of Auranofin, Methotrexate, and the Combination of Both in the Treatment of Rheumatoid Arthritis", 1992, pp. 259-269.
Xia et al., "Localization of ACTH receptor mRNA by in situ hybridization in mouse adrenal gland", Cell & Tissue Research, 1996, vol. 286, pp. 63-68.
Yanni et al., "Intramuscular gold decreases cytokine expression and macrophage numbers in the rheumatoid synovial membrane", Ann Rheum Dis, 1994, vol. 53, pp. 315-322.
Youssef et al., "Effects of Pulse Methylprednisolone on Inflammatory Mediators in Peripheral Blood, Synovial Fluid, and Synovial Membrane in Rheumatoid Arthritis", Arthritis Rheum, Aug. 1997, vol. 40, No. 8, pp. 1400-1408.
Youssef et al., "Neutrophil Trafficking into Inflamed Joints in Patients with Rheumatoid Arthritis, and the Effects of Methylprednisolone", Arthritis Rheum, Feb. 1996, vol. 39, No. 2, pp. 216-225.
Rui et al., "Pathogenesis and clinical research progress of novel coronavirus pneumonia", 2020, vol. 30, No. 8, pp. 1171-1176.
Wang et al., "Melanocortin Regulation of Inflammation", Front Endocrinol (Lausanne), Oct. 9, 2019, vol. 10, Article 683, pp. 1-15.
Bastin et al., "Salt selection and optimisation procedures for pharmaceutical new chemical entities", Organic Process Research & Development, 2000, vol. 4, No. 5, pp. 427-435.

* cited by examiner

POLYMORPHS OF PHENYL PYRROLE AMINOGUANDIUM SALTS

CROSS-REFERENCE TO RELATED APPLICATIONS

This application is a continuation of International Patent Application No. PCT/EP2022/066884, filed Jun. 21, 2022, which claims priority to European Patent Application No. 21180708.6, filed Jun. 21, 2021, the disclosures of which are incorporated by reference herein.

TECHNICAL FIELD

The present invention relates to salts of N-{3-[1-(2-nitrophenyl)-1H-pyrrol-2-yl]-allylidene}-aminoguanidine having a high solubility at low pH.

BACKGROUND

The melanocortin system is a set of neuropeptidergic and immuneendocrine signalling pathways that play an integral role in the homeostatic control of a diverse array of physiological functions, including melanogenesis, stress response, inflammation, immunomodulation and adrenocortical steroidogenesis. It consists of multiple components, including the five G protein-couple melanocortin receptors: melanocortin receptor 1 (MC1R) to MC5R; peptide ligands; α, β, γ-melanocyte stimulating hormone (α, β, γ-MSH); adrenocorticotropic hormone (ACTH) secreted by the anterior pituitary; and endogenous antagonists. The biological functions of the melanocortin system are mediated by the five melanocortin receptors (MCRs), which have distinct tissue distribution, convey different signalling and exert varying biological activities in different organ systems.

Phenyl pyrrole aminoguanidine derivatives with activity on the melanocortin receptors have previously been disclosed. One example of such compound is the anti-inflammatory AP1189 (N-{3-[1-(2-nitrophenyl)-1H-pyrrol-2-yl]-allylidene}-aminoguanidine) which was first shown to bind the MC1R and later was identified as a biased dual agonist at receptors MC1R and MC3R that does not provoke canonical cAMP generation (and hence no MC1R-induced melanogenesis) but instead appear to induce alternative pathways including ERK1/2-phosphorylation and $Ca^{2+}$ mobilisation.

SUMMARY

The present inventors have discovered salts of AP1189 with particularly favourable solubility profiles for gastric delivery. The inventors found that certain polymorphs of AP1189 salts have very high solubilities, especially at low pH.

Thus, one aspect of the present disclosure provides for a crystalline Form A of N-{3-[1-(2-nitrophenyl)-1H-pyrrol-2-yl]-allylidene}-aminoguanidinium acetate exhibiting at least X-ray lines (2-theta values) in a powder diffraction pattern when measured using Cu $K_\alpha$ radiation at 11.5±0.2, 23.5±0.2, and 27.0±0.2.

Another aspect of the present disclosure provides for a crystalline Form B of N-{3-[1-(2-nitrophenyl)-1H-pyrrol-2-yl]-allylidene}-aminoguanidinium succinate exhibiting at least X-ray lines (2-theta values) in a powder diffraction pattern when measured using Cu $K_\alpha$ radiation at 9.7±0.2, 22.8±0.2, and 26.7±0.2.

The present disclosure also provides methods of producing such crystalline forms.

One aspect of the present disclosure provides a method for producing the N-{3-[1-(2-nitrophenyl)-1H-pyrrol-2-yl]-allylidene}-aminoguanidinium acetate of crystalline Form A as disclosed herein, said method comprising:

i. mixing N-{3-[1-(2-nitrophenyl)-1H-pyrrol-2-yl]-allylidene}-aminoguanidine and acetic acid in a solvent to form a mixture; and
ii. isolating the N-{3-[1-(2-nitrophenyl)-1H-pyrrol-2-yl]-allylidene}-aminoguanidinium acetate of crystalline Form A from said mixture.

One aspect of the present disclosure provides a method for producing the N-{3-[1-(2-nitrophenyl)-1H-pyrrol-2-yl]-allylidene}-aminoguanidinium acetate of crystalline Form A as disclosed herein, said method comprising:

i. mixing a N-{3-[1-(2-nitrophenyl)-1H-pyrrol-2-yl]-allylidene}-aminoguanidinium salt and acetic acid in a solvent to form a mixture; and
ii. isolating the N-{3-[1-(2-nitrophenyl)-1H-pyrrol-2-yl]-allylidene}-aminoguanidinium acetate of crystalline Form A from the mixture.

One aspect of the present disclosure provides a method for producing the N-{3-[1-(2-nitrophenyl)-1H-pyrrol-2-yl]-allylidene}-aminoguanidinium acetate of crystalline Form A as disclosed herein, said method comprising:

i. mixing N-{3-[1-(2-nitrophenyl)-1H-pyrrol-2-yl]-allylidene}-aminoguanidinium acetate in a solvent to form a composition; and
ii. isolating the N-{3-[1-(2-nitrophenyl)-1H-pyrrol-2-yl]-allylidene}-aminoguanidinium acetate of crystalline Form A from said composition.

One aspect of the present disclosure provides a method for producing N-{3-[1-(2-nitrophenyl)-1H-pyrrol-2-yl]-allylidene}-aminoguanidinium succinate of crystalline Form B as disclosed herein, said method comprising:

i. mixing N-{3-[1-(2-nitrophenyl)-1H-pyrrol-2-yl]-allylidene}-aminoguanidine and succinic acid in a solvent to form a mixture; and
ii. isolating the N-{3-[1-(2-nitrophenyl)-1H-pyrrol-2-yl]-allylidene}-aminoguanidinium succinate of crystalline Form B from the mixture.

One aspect of the present disclosure provides a method for producing N-{3-[1-(2-nitrophenyl)-1H-pyrrol-2-yl]-allylidene}-aminoguanidinium succinate of crystalline Form B as disclosed herein, said method comprising:

i. mixing a N-{3-[1-(2-nitrophenyl)-1H-pyrrol-2-yl]-allylidene}-aminoguanidinium salt and succinic acid in a solvent to form a mixture, and
ii. isolating the N-{3-[1-(2-nitrophenyl)-1H-pyrrol-2-yl]-allylidene}-aminoguanidinium succinate of crystalline Form B from the mixture.

One aspect of the present disclosure provides a crystalline Form A of N-{3-[1-(2-nitrophenyl)-1H-pyrrol-2-yl]-allylidene}-aminoguanidinium acetate produced by a method as disclosed herein.

One aspect of the present disclosure provides a crystalline Form B of N-{3-[1-(2-nitrophenyl)-1H-pyrrol-2-yl]-allylidene}-aminoguanidinium succinate produced by a method as disclosed herein.

One aspect of the present disclosure provides a pharmaceutical composition comprising the crystalline Form A of N-{3-[1-(2-nitrophenyl)-1H-pyrrol-2-yl]-allylidene}-aminoguanidinium acetate as disclosed herein and a pharmaceutically acceptable excipient.

One aspect of the present disclosure provides a pharmaceutical composition comprising the crystalline Form B of N-{3-[1-(2-nitrophenyl)-1H-pyrrol-2-yl]-allylidene}-aminoguanidinium succinate as disclosed herein and a pharmaceutically acceptable excipient.

One aspect of the present disclosure provides a method of preparing a pharmaceutical composition comprising mixing the crystalline Form A of N-{3-[1-(2-nitrophenyl)-1H-pyrrol-2-yl]-allylidene}-aminoguanidinium acetate as disclosed herein and a pharmaceutically acceptable excipient.

One aspect of the present disclosure provides a method of preparing a pharmaceutical composition, said method comprising mixing the crystalline Form B of N-{3-[1-(2-nitrophenyl)-1H-pyrrol-2-yl]-allylidene}-aminoguanidinium succinate as disclosed herein with a pharmaceutically acceptable excipient.

One aspect of the present disclosure provides a method of treating a disease or disorder in a subject in need thereof, said method comprising administering crystalline Form A of N-{3-[1-(2-nitrophenyl)-1H-pyrrol-2-yl]-allylidene}-aminoguanidinium acetate as disclosed herein, the crystalline Form B of N-{3-[1-(2-nitrophenyl)-1H-pyrrol-2-yl]-allylidene}-aminoguanidinium succinate as disclosed herein, or the pharmaceutical composition as disclosed herein to a subject in need thereof.

One aspect of the disclosure provides for a use of the crystalline Form A of N-{3-[1-(2-nitrophenyl)-1H-pyrrol-2-yl]-allylidene}-aminoguanidinium acetate as disclosed herein or the crystalline Form B of N-{3-[1-(2-nitrophenyl)-1H-pyrrol-2-yl]-allylidene}-aminoguanidinium succinate as disclosed herein, or the pharmaceutical composition as disclosed herein, for the manufacture of a medicament for treatment of a disease or disorder.

One aspect of the present disclosure is to provide for crystalline forms of N-{3-[1-(2-nitrophenyl)-1H-pyrrol-2-yl]-allylidene}-aminoguanidinium salts having high solubility at low pH, e.g. at pH 1.2. Thus, one aspect provides for a crystalline Form of an N-{3-[1-(2-nitrophenyl)-1H-pyrrol-2-yl]-allylidene}-aminoguanidinium salt selected from the group consisting of:

i. a crystalline Form XIV of AP1189 besylate exhibiting at least X-ray lines (2-theta values) in a powder diffraction pattern when measured using Cu $K_\alpha$ radiation at 13.0±0.2, 15.1±0.2, and 19.9±0.2, ii. a crystalline Form XIX of AP1189 oxoglutarate exhibiting at least X-ray lines (2-theta values) in a powder diffraction pattern when measured using Cu $K_\alpha$ radiation at 16.8±0.2, 23.4±0.2, and 23.6±0.2, iii. a crystalline Form XX of AP1189 DL-mandelic acid exhibiting at least X-ray lines (2-theta values) in a powder diffraction pattern when measured using Cu $K_\alpha$ radiation at 14.8±0.2, 24.2±0.2, and 25.5±0.2, iv. a crystalline Form XXII of AP1189 hippuric exhibiting at least X-ray lines (2-theta values) in a powder diffraction pattern when measured using Cu $K_\alpha$ radiation at 20.1±0.2, 24.1±0.2, and 24.5±0.2, v. a crystalline Form XXIII of AP1189 formate exhibiting at least X-ray lines (2-theta values) in a powder diffraction pattern when measured using Cu $K_\alpha$ radiation at 13.3±0.2, 15.1±0.2, and 25.6±0.2, vi. a crystalline Form XXIV of AP1189 DL-lactic acid exhibiting at least X-ray lines (2-theta values) in a powder diffraction pattern when measured using Cu $K_\alpha$ radiation at 3.8±0.2, 9.9±0.2, and 11.9±0.2, vii. a crystalline Form XXV of AP1189 DL-lactic acid exhibiting at least X-ray lines (2-theta values) in a powder diffraction pattern when measured using Cu $K_\alpha$ radiation at 9.8±0.2, 11.9±0.2, and 27.6±0.2, viii. a crystalline Form XXVI of AP1189 glutaric acid exhibiting at least X-ray lines (2-theta values) in a powder diffraction pattern when measured using Cu $K_\alpha$ radiation at 8.3±0.2, 15.9±0.2, and 21.9±0.2, and ix. a crystalline Form XXIX of AP1189 adipic acid exhibiting at least X-ray lines (2-theta values) in a powder diffraction pattern when measured using Cu $K_\alpha$ radiation at 13.4±0.2, 14.5±0.2, and 25.5±0.2.

One aspect of the present disclosure is to provide crystalline forms of N-{3-[1-(2-nitrophenyl)-1H-pyrrol-2-yl]-allylidene}-aminoguanidinium salts that can be converted into useful crystalline forms of N-{3-[1-(2-nitrophenyl)-1H-pyrrol-2-yl]-allylidene}-aminoguanidinium salts. Thus, one aspect of the present disclosure provides for a crystalline Form of an N-{3-[1-(2-nitrophenyl)-1H-pyrrol-2-yl]-allylidene}-aminoguanidinium salt selected from the group consisting of:

i. a crystalline Form III of AP1189 napadisylate exhibiting at least X-ray lines (2-theta values) in a powder diffraction pattern when measured using Cu $K_\alpha$ radiation at 13.4±0.2, 22.2±0.2, and 26.8±0.2, ii. a crystalline Form IV of AP1189 napadisylate exhibiting at least X-ray lines (2-theta values) in a powder diffraction pattern when measured using Cu $K_\alpha$ radiation at 5.4±0.2, 15.6±0.2, and 23.4±0.2, iii. a crystalline Form V of AP1189 esylate exhibiting at least X-ray lines (2-theta values) in a powder diffraction pattern when measured using Cu $K_\alpha$ radiation at 14.5±0.2, 16.5±0.2, and 18.6±0.2, iv. a crystalline Form VI of AP1189 edisylate exhibiting at least X-ray lines (2-theta values) in a powder diffraction pattern when measured using Cu $K_\alpha$ radiation at 4.8±0.2, 12.8±0.2, and 16.5±0.2, v. a crystalline Form VII of AP1189 edisylate exhibiting at least X-ray lines (2-theta values) in a powder diffraction pattern when measured using Cu $K_\alpha$ radiation at 6.1±0.2, 15.7±0.2, and 23.6±0.2, vi. a crystalline Form VIII of AP1189 edisylate exhibiting at least X-ray lines (2-theta values) in a powder diffraction pattern when measured using Cu $K_\alpha$ radiation at 15.5±0.2, 20.7±0.2, and 21.7±0.2, vii. a crystalline Form IX of AP1189 edisylate exhibiting at least X-ray lines (2-theta values) in a powder diffraction pattern when measured using Cu $K_\alpha$ radiation at 4.5±0.2, 16.7±0.2, and 24.7±0.2, viii. a crystalline Form X of AP1189 nitrate exhibiting at least X-ray lines (2-theta values) in a powder diffraction pattern when measured using Cu $K_\alpha$ radiation at 15.3±0.2, 21.4±0.2, and 25.1±0.2, ix. a crystalline Form XI of AP1189 cyclamate exhibiting at least X-ray lines (2-theta values) in a powder diffraction pattern when measured using Cu $K_\alpha$ radiation at 7.0±0.2, 13.8±0.2, and 15.7±0.2, x. a crystalline Form XII of AP1189 cyclamate exhibiting at least X-ray lines (2-theta values) in a powder diffraction pattern when measured using Cu $K_\alpha$ radiation at 7.3±0.2, 15.3±0.2, and 17.9±0.2, xi. a crystalline Form XIII of AP1189 cyclamate exhibiting at least X-ray lines (2-theta values) in a powder diffraction pattern when measured using Cu $K_\alpha$ radiation at 15.3±0.2, 18.5±0.2, and 18.7±0.2, xii. a crystalline Form XV of AP1189 oxalate exhibiting at least X-ray lines (2-theta values) in a powder diffraction pattern when measured using Cu $K_\alpha$ radiation at 19.5±0.2, 23.3±0.2, and 25.8±0.2, xiii. a crystalline Form XVI of AP1189 oxalate exhibiting at least X-ray lines (2-theta values) in a powder diffraction pattern when measured using Cu $K_{\alpha}$ radiation at 17.1±0.2, 17.9±0.2, and 19.6±0.2, xiv. a crystalline Form XVII of AP1189 oxalate exhibiting at least X-ray lines (2-theta values) in a powder diffraction pattern when measured using Cu $K_{\alpha}$ radiation at 6.3±0.2, 10.6±0.2, and 19.8±0.2, xv. a crystalline Form XVIII of AP1189 (+)-camphor-10-sulfonic acid exhibiting at least X-ray lines (2-theta values) in a powder diffraction pattern when measured using Cu $K_{\alpha}$ radiation at 6.5±0.2, 11.5±0.2, and 14.8±0.2, xvi. a crystalline Form XXI of AP1189 DL-mandelic acid exhibiting at least X-ray lines (2-theta values) in a powder diffraction pattern when measured using Cu $K_{\alpha}$ radiation at 5.4±0.2, 10.0±0.2, and 24.6±0.2, xvii. a crystalline Form XXVII of AP1189 glutaric acid further exhibiting one or more X-ray lines (2-theta values) in a powder diffraction pattern when measured using Cu $K_{\alpha}$ radiation selected from the group consisting of 16.9±0.2, 25.6±0.2, 27.1±0.2, 28.2±0.2, and 28.7±0.2, and xviii. a crystalline Form XXVIII of AP1189 glutaric acid exhibiting at least X-ray lines (2-theta values) in a powder diffraction pattern when measured using Cu $K_{\alpha}$ radiation at 14.2±0.2, 16.9±0.2, and 24.5±0.2.

One aspect of the present disclosure is to provide for N-{3-[1-(2-nitrophenyl)-1H-pyrrol-2-yl]-allylidene}-aminoguanidinium salts that can be converted into useful crystalline Forms of N-{3-[1-(2-nitrophenyl)-1H-pyrrol-2-yl]-allylidene}-aminoguanidinium salts. Thus, one aspect of the disclosure provides for a compound selected from the group consisting of:

i. N-{3-[1-(2-nitrophenyl)-1H-pyrrol-2-yl]-allylidene}-aminoguanidinium succinate, ii. N-{3-[1-(2-nitrophenyl)-1H-pyrrol-2-yl]-allylidene}-aminoguanidinium tosylate, iii. N-{3-[1-(2-nitrophenyl)-1H-pyrrol-2-yl]-allylidene}-aminoguanidinium fumarate, iv. N-{3-[1-(2-nitrophenyl)-1H-pyrrol-2-yl]-allylidene}-aminoguanidinium napadisylate, v. N-{3-[1-(2-nitrophenyl)-1H-pyrrol-2-yl]-allylidene}-aminoguanidinium esylate, vi. N-{3-[1-(2-nitrophenyl)-1H-pyrrol-2-yl]-allylidene}-aminoguanidinium edisylate, vii. N-{3-[1-(2-nitrophenyl)-1H-pyrrol-2-yl]-allylidene}-aminoguanidinium nitrate, viii. N-{3-[1-(2-nitrophenyl)-1H-pyrrol-2-yl]-allylidene}-aminoguanidinium cyclamate, ix. N-{3-[1-(2-nitrophenyl)-1H-pyrrol-2-yl]-allylidene}-aminoguanidinium besylate, x. N-{3-[1-(2-nitrophenyl)-1H-pyrrol-2-yl]-allylidene}-aminoguanidinium oxalate, xi. N-{3-[1-(2-nitrophenyl)-1H-pyrrol-2-yl]-allylidene}-aminoguanidine (+)-camphor-10-sulfonic acid salt, xii. N-{3-[1-(2-nitrophenyl)-1H-pyrrol-2-yl]-allylidene}-aminoguanidinium oxoglutarate, xiii. N-{3-[1-(2-nitrophenyl)-1H-pyrrol-2-yl]-allylidene}-aminoguanidine DL-mandelic acid salt, xiv. N-{3-[1-(2-nitrophenyl)-1H-pyrrol-2-yl]-allylidene}-aminoguanidine hippuric acid salt, xv. N-{3-[1-(2-nitrophenyl)-1H-pyrrol-2-yl]-allylidene}-aminoguanidinium formate, xvi. N-{3-[1-(2-nitrophenyl)-1H-pyrrol-2-yl]-allylidene}-aminoguanidine L-lactic acid salt, xvii. N-{3-[1-(2-nitrophenyl)-1H-pyrrol-2-yl]-allylidene}-aminoguanidine DL-lactic acid salt, xviii. N-{3-[1-(2-nitrophenyl)-1H-pyrrol-2-yl]-allylidene}-aminoguanidine glutaric acid salt, and xix. N-{3-[1-(2-nitrophenyl)-1H-pyrrol-2-yl]-allylidene}-aminoguanidine adipic acid salt.

One aspect of the disclosure provides for a composition, a pharmaceutical composition, a liquid composition, a unit dosage form, or an oral formulation comprising the crystalline forms of N-{3-[1-(2-nitrophenyl)-1H-pyrrol-2-yl]-allylidene}-aminoguanidinium salt disclosed herein.

One aspect of the disclosure provides for use of such crystalline form of N-{3-[1-(2-nitrophenyl)-1H-pyrrol-2-yl]-allylidene}-aminoguanidinium salt, composition, pharmaceutical composition, liquid composition, unit dosage form, or oral formulation in medicine.

One aspect of the disclosure provides for use of such crystalline form of N-{3-[1-(2-nitrophenyl)-1H-pyrrol-2-yl]-allylidene}-aminoguanidinium salt, composition, pharmaceutical composition, liquid composition, unit dosage form, or oral formulation in the treatment of a kidney disease, an arthritic disease, a cardiovascular disease, atherosclerosis, a viral disease or disorder, or a systemic inflammatory disorder.

DETAILED DESCRIPTION

Definitions

Figure 1:
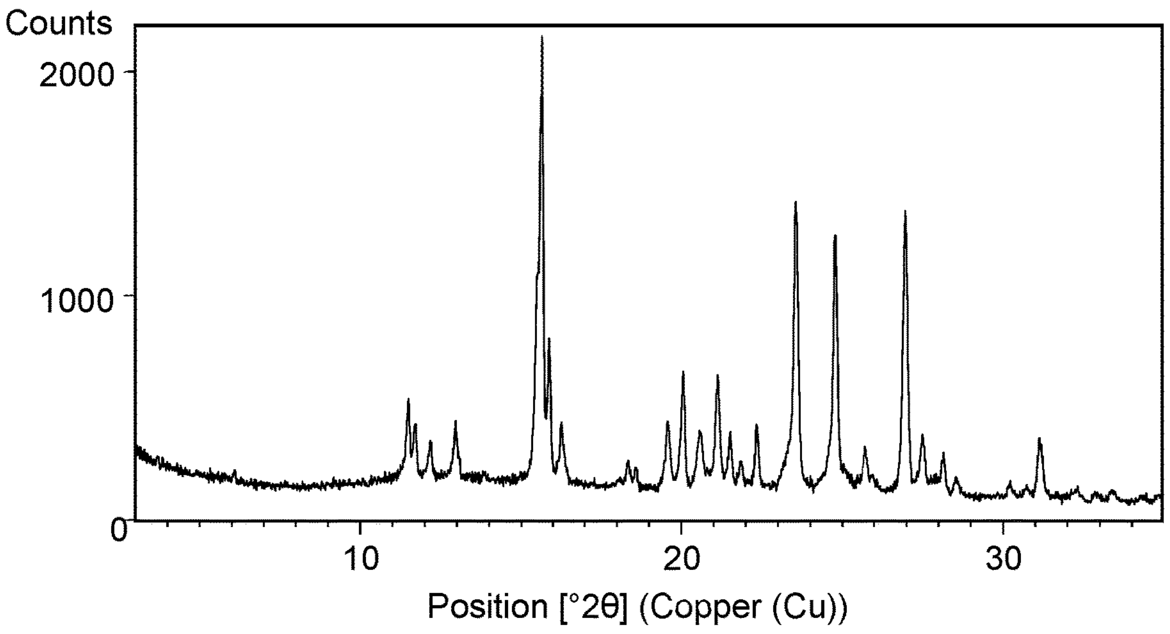
FIG. 1: XRPD diffractogram for AP1189 acetate salt Pattern 1 crystallised from acetonitrile.

By a "compound of formula I", "compound I", and "AP1189" is meant the compound N-{3-[1-(2-nitrophenyl)-1H-pyrrol-2-yl]-allylidene}-aminoguanidine, which has the chemical structure of formula I:

formula I

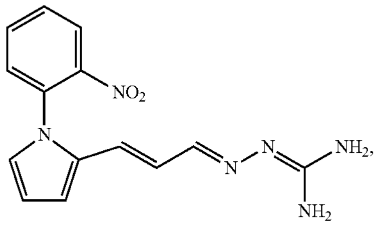

as well as tautomers and stereoisomers thereof. Another name for the compound is N"-[(E)-[(2E)-3-[1-(2-nitrophenyl)-1H-pyrrol-2-yl]prop-2-en-1-ylidene]amino]guanidine.

In some instances the term "AP1189" may refer to either the free base structure of Formula I or it may refer to the acetate salt of AP1189. Preferable, the term "AP1189 free base" refers to the structure of Formula I. Preferably, the term "AP1189 acetate" refers to the acetate salt of the structure of Formula I.

As used herein, the term "SP1189" refers to the succinate salt of the structure of Formula I. The terms "SP1189" and "AP1189 succinate" are synonymous as used herein.

Regarding the naming of salts, it is to be construed that terms such as "N-{3-[1-(2-nitrophenyl)-1H-pyrrol-2-yl]-allylidene}-aminoguanidine acetate" and N-{3-[1-(2-nitrophenyl)-1H-pyrrol-2-yl]-allylidene}-aminoguanidinium acetate" are synonymous, i.e. when an anion is written immediately after "N-{3-[1-(2-nitrophenyl)-1H-pyrrol-2-yl]-allylidene}-aminoguanidine", then the protonated form of "N-{3-[1-(2-nitrophenyl)-1H-pyrrol-2-yl]-allylidene}-aminoguanidine" is meant, i.e. "N-{3-[1-(2-nitrophenyl)-1H-pyrrol-2-yl]-allylidene}-aminoguanidinium". Similarly, when an acid is written as part of the name of a protonated compound, e.g. "N-{3-[1-(2-nitrophenyl)-1H-pyrrol-2-yl]-allylidene}-aminoguanidinium acetic acid", then the non-protonated form is meant of that compound, e.g. "N-{3-[1-(2-nitrophenyl)-1H-pyrrol-2-yl]-allylidene}-aminoguanidine acetic acid" is meant. These considerations also apply to other salts of the disclosed compound.

In one embodiment, the compound of the disclosure N-{3-[1-(2-nitrophenyl)-1H-pyrrol-2-yl]-allylidene}-aminoguanidine, including tautomers and stereoisomers thereof. In one embodiment, the compound of the disclosure is N-{(1E)-3-[1-(2-nitrophenyl)-1H-pyrrol-2-yl]-allylidene}-aminoguanidine, including tautomers and stereoisomers thereof. In one embodiment, the compound of the disclosure is N"-[(E)-[3-[1-(2-nitrophenyl)-1H-pyrrol-2-yl]prop-2-en-1-ylidene]amino]guanidine, including tautomers and stereoisomers thereof.

In one embodiment, the compound of the disclosure is N-{(2E)-3-[1-(2-nitrophenyl)-1H-pyrrol-2-yl]-allylidene}-aminoguanidine, including tautomers and stereoisomers thereof. In one embodiment, the compound of the disclosure is N"-[[(2E)-3-[1-(2-nitrophenyl)-1H-pyrrol-2-yl]prop-2-en-1-ylidene]amino]guanidine, including tautomers and stereoisomers thereof.

In one embodiment, the compound of the disclosure is N-{(1E,2E)-3-[1-(2-nitrophenyl)-1H-pyrrol-2-yl]-allylidene}-aminoguanidine (also termed (E)-N-trans-{3-[1-(2-nitrophenyl)-1H-pyrrol-2-yl]-allylidene}-aminoguanidine herein)), including tautomers thereof. In one embodiment, the compound of the disclosure is N"-[(E)-[(2E)-3-[1-(2-nitrophenyl)-1H-pyrrol-2-yl]prop-2-en-1-ylidene]amino]guanidine, including tautomers thereof. These compounds may also appear as the salts and corresponding crystalline forms disclosed herein. In one embodiment, the compound of the disclosure is selected from the group consisting of N-{(1Z)-3-[1-(2-nitrophenyl)-1H-pyrrol-2-yl]-allylidene}-aminoguanidine, N-{(2Z)-3-[1-(2-nitrophenyl)-1H-pyrrol-2-yl]-allylidene}-aminoguanidine, N-{(1Z,2Z)-3-[1-(2-nitrophenyl)-1H-pyrrol-2-yl]-allylidene}-aminoguanidine, N-{(1Z,2E)-3-[1-(2-nitrophenyl)-1H-pyrrol-2-yl]-allylidene}-aminoguanidine, and N-{(1E,2Z)-3-[1-(2-nitrophenyl)-1H-pyrrol-2-yl]-allylidene}-aminoguanidine.

In one embodiment, the compound of the disclosure is selected from the group consisting of N"-[(Z)-[3-[1-(2-nitrophenyl)-1H-pyrrol-2-yl]prop-2-en-1-ylidene]amino]guanidine, N"-[[(2Z)-3-[1-(2-nitrophenyl)-1H-pyrrol-2-yl]prop-2-en-1-ylidene]amino]guanidine, N"-[(Z)-[(2Z)-3-[1-(2-nitrophenyl)-1H-pyrrol-2-yl]prop-2-en-1-ylidene]amino]guanidine, N"-[(Z)-[(2E)-3-[1-(2-nitrophenyl)-1H-pyrrol-2-yl]prop-2-en-1-ylidene]amino]guanidine, and N"-[(E)-[(2Z)-3-[1-(2-nitrophenyl)-1H-pyrrol-2-yl]prop-2-en-1-ylidene]amino]guanidine.

In a preferred embodiment, the alkene moiety of the compound is in the E configuration, and the imine moiety is in the Z or the E configuration. In one embodiment, the compound is a mixture of N"-[(E)-[(2E)-3-[1-(2-nitrophenyl)-1H-pyrrol-2-yl]prop-2-en-1-ylidene]amino]guanidine and N"-[(Z)-[(2E)-3-[1-(2-nitrophenyl)-1H-pyrrol-2-yl]prop-2-en-1-ylidene]amino]guanidine.

The compound of the disclosure may additionally be any tautomer of the above structures. As used herein, "tautomer" means other structural isomers that exist in equilibrium resulting from the migration of a hydrogen atom.

In reporting results of a measurement, such as the measurement of a 2-theta value, e.g. the reading of a 2-theta value from an XRPD diffractogram, the skilled person will understand that the method of measuring the value inherently comprises some degree of uncertainty. For example, measurements of 2-theta values may have an uncertainty of 0.2°.

By a crystalline "Form A" of AP1189 acetate is meant the crystalline form of AP1189 acetate that exhibits the X-ray lines (2-theta values) in a powder diffraction pattern when measured using Cu $K_\alpha$ radiation corresponding to AP1189 acetate Pattern 1 as disclosed herein.

By a crystalline "Form B" of AP1189 succinate is meant the crystalline form of AP1189 succinate that exhibits the X-ray lines (2-theta values) in a powder diffraction pattern when measured using Cu $K_\alpha$ radiation corresponding to AP1189 succinate Pattern 1 as disclosed herein.

Unless otherwise specified, the unit of 2-theta values is degrees (°).

By "onset temperature" is meant the designed intersection point of the extrapolated baseline and the inflectional tangent at the beginning of the melting.

As used herein, "seeding" refers to the technique of adding a "seed" crystal to the crystallization solution to promote the formation of crystals. Preferably, the composition of the seed crystal is the same as the composition of the crystals being formed.

Compounds

In one embodiment, the present disclosure provides the compound AP1189, specifically a salt thereof. One embodiment provides for the compound AP1189, including tautomeric forms thereof and/or isomeric forms thereof, such as enantiomeric forms and/or diastereomeric forms thereof. In one embodiment, the diastereomeric forms comprise cis and trans forms of the compound, specifically with respect to the alkene moiety. The compound may also exist as either the E or Z form with respect to the C═N double bond of the structure of Formula I. The person of skill in the art understands that in certain instances, E configuration is synonymous to trans configuration, and that in certain instances, Z configuration is synonymous to cis configuration. For example, in the specific case where both of the atoms forming part of a double bond are each bound to exactly 1 further moiety that is not a hydrogen moiety or a lone pair. One embodiment of the present disclosure provides for the acetate salt of AP1189. Another embodiment of the present disclosure provides for the succinate salt of AP1189. In one embodiment the term "compound of the disclosure" means the crystalline Form A of AP1189 acetate. In one embodiment the term "compound of the disclosure" means the crystalline Form B of AP1189 succinate.

In some embodiments, the pharmaceutically acceptable salt of AP1189 is selected from the group consisting of:

(E)-N-[1-(2-nitrophenyl)-1-H-pyrrole-2-yl-allylideneamino]-guanidinium acetate, including tautomeric and stereoisomeric forms thereof;

(E)-N-[1-(2-nitrophenyl)-1-H-pyrrole-2-yl-allylideneamino]-guanidinium succinate, including tautomeric and stereoisomeric forms thereof;

(E)-N-[1-(2-nitrophenyl)-1-H-pyrrole-2-yl-allylideneamino]-guanidine DL-mandelic acid salt, including tautomeric and stereoisomeric forms thereof;

(E)-N-[1-(2-nitrophenyl)-1-H-pyrrole-2-yl-allylideneamino]-guanidine hippuric acid salt, including tautomeric and stereoisomeric forms thereof;

(E)-N-[1-(2-nitrophenyl)-1-H-pyrrole-2-yl-allylideneamino]-guanidine L-lactic acid salt, including tautomeric and stereoisomeric forms thereof; >50 mM (E)-N-[1-(2-nitrophenyl)-1-H-pyrrole-2-yl-allylideneamino]-guanidinium besylate, including tautomeric and stereoisomeric forms thereof;

(E)-N-[1-(2-nitrophenyl)-1-H-pyrrole-2-yl-allylideneamino]-guanidinium oxoglutarate, including tautomeric and stereoisomeric forms thereof;

(E)-N-[1-(2-nitrophenyl)-1-H-pyrrole-2-yl-allylideneamino]-guanidine formic acid salt, including tautomeric and stereoisomeric forms thereof;

(E)-N-[1-(2-nitrophenyl)-1-H-pyrrole-2-yl-allylideneamino]-guanidine DL-lactic acid salt, including tautomeric and stereoisomeric forms thereof;

(E)-N-[1-(2-nitrophenyl)-1-H-pyrrole-2-yl-allylideneamino]-guanidine glutaric acid salt, including tautomeric and stereoisomeric forms thereof;

(E)-N-[1-(2-nitrophenyl)-1-H-pyrrole-2-yl-allylideneamino]-guanidine adipic acid salt, including tautomeric and stereoisomeric forms thereof; and (E)-N-[1-(2-nitrophenyl)-1-H-pyrrole-2-yl-allylideneamino]-guanidinium nitrate salt, including tautomeric and stereoisomeric forms thereof.

In one embodiment, a pharmaceutically acceptable salt of AP1189 is selected from the group consisting of the acetate salt of AP1189, the succinate salt of AP1189, the DL-mandelic acid salt of AP1189, the hippuric acid salt of AP1189, the L-lactic acid salt of AP1189, the besylate salt of AP1189, the oxoglutarate salt of AP1189, the formic acid salt of AP1189, the DL-lactic acid salt of AP1189, the glutaric acid salt of AP1189, the adipic acid salt of AP1189 and the nitrate salt of AP1189.

One embodiment provides for a salt of AP1189 selected from the group consisting of:

(E)-N-[1-(2-nitrophenyl)-1-H-pyrrole-2-yl-allylideneamino]-guanidinium napadisylate, including tautomeric and stereoisomeric forms thereof;

(E)-N-[1-(2-nitrophenyl)-1-H-pyrrole-2-yl-allylideneamino]-guanidinium esylate, including tautomeric and stereoisomeric forms thereof;

(E)-N-[1-(2-nitrophenyl)-1-H-pyrrole-2-yl-allylideneamino]-guanidinium edisylate, including tautomeric and stereoisomeric forms thereof;

(E)-N-[1-(2-nitrophenyl)-1-H-pyrrole-2-yl-allylideneamino]-guanidinium cyclamate, including tautomeric and stereoisomeric forms thereof;

(E)-N-[1-(2-nitrophenyl)-1-H-pyrrole-2-yl-allylideneamino]-guanidinium oxalate, including tautomeric and stereoisomeric forms thereof; and (E)-N-[1-(2-nitrophenyl)-1-H-pyrrole-2-yl-allylideneamino]-guanidine (+)-Camphor-10-sulfonic acid salt, including tautomeric and stereoisomeric forms thereof.

The terms "treatment" and "treating" as used herein refer to the management and care of a subject for the purpose of combating a condition, disease or disorder. The term is intended to include the full spectrum of treatments for a given condition from which the subject is suffering. The subject to be treated is preferably a mammal, in particular a human being. Treatment of animals, such as mice, rats, dogs, cats, horses, cows, sheep and pigs, is, however, also within the scope of the present context. The subjects to be treated can be of various ages.

It is an aspect of the present disclosure to provide an oral formulation as disclosed herein comprising a crystalline form of an AP1189 salt disclosed herein, for use in the treatment of a disease or disorder in a subject, wherein the subject to be treated is a mammal. In some embodiment the mammal is a human being. In some embodiments the mammal is a domestic animal. In some embodiments the mammal is selected from the group consisting of mice, rats, dogs, cats, horses, cows, sheep and pigs.

Crystalline Forms

The present disclosure relates to crystalline forms of N-{3-[1-(2-nitrophenyl)-1H-pyrrol-2-yl]-allylidene}-aminoguanidinium salts. It is an object of the disclosure to provide crystalline forms of N-{3-[1-(2-nitrophenyl)-1H-pyrrol-2-yl]-allylidene}-aminoguanidinium salts having high solubility in aqueous medium, particularly at low pH. It is likewise an object of the disclosure to provide crystalline forms of N-{3-[1-(2-nitrophenyl)-1H-pyrrol-2-yl]-allylidene}-aminoguanidinium salts having high dissolution rate in aqueous medium, particularly at low pH.

Crystalline forms of AP1189 and salts thereof may be characterised by X-Ray Powder Diffraction (XRPD) analysis. Such analysis may be carried out using a suitable X-ray powder diffractometer such as a PANalytical X'pert pro with PIXcel detector (128 channels). Scanning of samples may be performed between 3 and 35° 2θ. Samples may be gently ground prior to measurement to release any agglomerates. Samples may be loaded onto a multi-well plate with Kapton or Mylar polymer film to support the sample. Measurements may be carried out by placing the multi-well plate in the diffractometer followed by analysis using Cu K radiation ($\alpha 1\lambda$=1.54060 Å; $\alpha 2$=1.54443 Å; $\beta$=1.39225 Å; $\alpha 1:\alpha 2$ ratio=0.5) running in transmission mode (step size 0.0130° 2θ, step time 18.87 s) using 40 kV/40 mA generator settings.

Table 1 shows an overview of the polymorphs disclosed herein

TABLE 1 overview of polymorphs

| Salt and polymorph form of AP1189 | XRPD pattern | Figures XRPD | Figures TGA/DSC | Figures FT-IR | Counterion trivial and/or systematic name |
|---|---|---|---|---|---|
| Acetate Form A | 1 | 1 | 7, 8 | | Acetic acid |
| Acetate Form I | 1 + 2 | 2 | 9 | | Acetic acid |
| Succinate Form B | 1 | 6 | 13 | | Succinic acid |
| Tosylate Form C | 1 | 4 | 11 | | Toluenesulfonic acid |
| Fumarate Form D | 1 | 5 | 12 | | (2E)-But-2-enedioic acid |
| Acetate Form II | 3 | 3 | 10 | | Acetic acid |
| Napadisylate Form III | 1 | 14 | 40 | 57 | Naphthalene-1,5-disulfonic acid |
| Napadisylate Form IV | 2 | 15 | 81 | 58 | Naphthalene-1,5-disulfonic acid |
| Esylate Form V | 1 | 16 | 41 | 59 | Ethanesulfonic acid |
| Edisylate Form VI | 1 | 17 | 82 | | Ethane-1,2-disulfonic acid |
| Edisylate Form VII | 2 | 18 | 42 | 60 | Ethane-1,2-disulfonic acid |
| Edisylate Form VIII | 4 | 19 | 43 | 61 | Ethane-1,2-disulfonic acid |
| Edisylate Form IX | 5 | 20 | 44 | 62 | Ethane-1,2-disulfonic acid |
| Nitrate Form X | 1 | 21 | 45 | 63 | Nitric acid |
| Cyclamate Form XI | 2 | 22 | 46 | 64 | Cyclohexylsulfamic acid |
| Cyclamate Form XII | 4 | 23 | 47 | 65 | Cyclohexylsulfamic acid |
| Cyclamate Form XIII | 5 | 24 | 83 | 66 | Cyclohexylsulfamic acid |
| Besylate Form XIV | 1 | 25 | 48 | 67 | Benzenesulfonic acid |
| Oxalate Form XV | 1 | 26 | 49 | 68 | Oxalic acid |
| Oxalate Form XVI | 2 | 27 | 50 | 69 | Oxalic acid |

TABLE 1-continued

| overview of polymorphs | | | | | |
|---|---|---|---|---|---|
| Salt and polymorph form of AP1189 | XRPD pattern | Figures XRPD | TGA/DSC | FT-IR | Counterion trivial and/or systematic name |
| Oxalate Form XVII | 4 | 28 | 51 | 70 | Oxalic acid |
| (+)-Camphor-10-sulfonic acid Form XVIII | 1 | 29 | 52 | 71 | (+)-Camphor-10-sulfonic acid |
| Oxoglutarate Form XIX | 1 | 30 | 53 | 72 | 2-oxoglutaric acid, ketoglutaric acid, 2-oxopentanedioic acid α-ketoglutaric acid alpha-ketoglutaric acid |
| DL-Mandelic acid Form XX | 2 | 31 | 54 | 73 | Hydroxy(phenyl)acetic acid |
| DL-Mandelic acid Form XXI | 3 | 32 | 55 | 74 | Hydroxy(phenyl)acetic acid |
| Hippuric acid Form XXII | 1 | 33 | 56 | 75 | N-Benzoylglycine |
| Formic acid Form XXIII | 1 | 34 | 84 | 76 | Formic acid |
| L-Lactic acid Form XXIV | 1 | 35 | 85 | 77 | 2-Hydroxypropanoic acid |
| DL-Lactic acid Form XXV | 1 | 36 | 86 | 78 | 2-Hydroxypropanoic acid |
| Glutaric acid Form XXVI | 1 | 37 | 87 | 79 | Pentanedioic acid |
| Glutaric acid Form XXVII | 2 | 38 | 88 | 80 | Pentanedioic acid |
| Glutaric acid Form XXVIII | 4 | 91 | 89 | | Pentanedioic acid |
| Adipic acid Form XXIX | 1 | 39 | 90 | | Hexanedioic acid |

AP1189 Acetate Form A

The present disclosure provides for a crystalline Form A of AP1189 acetate. Crystalline Form A of AP1189 acetate exhibits an XRPD diffractogram as shown in FIG. 1. One embodiment of the present disclosure provides for a crystalline Form A of AP1189 acetate exhibiting at least X-ray lines (2-theta values) in a powder diffraction pattern when measured using Cu $K_\alpha$ radiation at 11.5±0.2, 23.5±0.2, and 27.0±0.2. One embodiment provides for a crystalline Form A of AP1189 acetate further exhibiting one or more X-ray lines (2-theta values) in a powder diffraction pattern when measured using Cu $K_\alpha$ radiation selected from the group consisting of 11.7±0.2, 13.0±0.2, 15.5±0.2, 15.6±0.2, 16.2±0.2, 19.6±0.2, 20.0±0.2, 21.1±0.2, and 24.8±0.2. One embodiment of the present disclosure provides for a crystalline Form A of AP1189 acetate exhibiting an X-ray pattern (2-theta values) in a powder diffraction when measured using Cu $K_\alpha$ radiation according to FIG. 1.

One embodiment of the disclosure provides for a crystalline Form A of AP1189 acetate exhibiting one or more X-ray lines (2-theta values) in a powder diffraction pattern when measured using Cu $K_\alpha$ radiation selected from the group consisting of 6.1, 11.5, 11.7, 12.2, 13.0, 15.5, 15.6, 15.9, 16.2, 18.3, 18.6, 19.6, 20.0, 20.6, 21.1, 21.5, 21.8, 22.3, 23.5, 24.8, 25.7, 27.0, 27.5, 28.2, 28.5, 30.2, 30.7, 31.2, 32.3, 32.9, 33.4, and 34.3. One embodiment of the disclosure provides for a crystalline Form A of AP1189 acetate exhibiting one or more X-ray lines (2-theta values) in a powder diffraction pattern when measured using Cu $K_\alpha$ radiation selected from the group consisting of 6.1±0.2, 11.5±0.2, 11.7±0.2, 12.2±0.2, 13.0±0.2, 15.5±0.2, 15.6±0.2, 15.9±0.2, 16.2±0.2, 18.3±0.2, 18.6±0.2, 19.6±0.2, 20.0±0.2, 20.6±0.2, 21.1±0.2, 21.5±0.2, 21.8±0.2, 22.3±0.2, 23.5±0.2, 24.8±0.2, 25.7±0.2, 27.0±0.2, 27.5±0.2, 28.2±0.2, 28.5±0.2, 30.2±0.2, 30.7±0.2, 31.2±0.2, 32.3±0.2, 32.9±0.2, 33.4±0.2, and 34.3±0.2. It may be advantageous to identify the crystalline Form A of AP1189 acetate by X-ray lines (2-theta values) having a high relative intensity, and/or by characteristic X-ray lines. Thus, one embodiment of the present disclosure provides for a crystalline Form A of AP1189 acetate exhibiting one or more X-ray lines (2-theta values) in a powder diffraction pattern when measured using Cu $K_\alpha$ radiation selected from the group consisting of 11.5, 11.7, 13.0, 15.5, 15.6, 16.2, 19.6, 20.0, 21.1, 23.5, 24.8, and 27.0. One embodiment of the present disclosure provides for a crystalline Form A of AP1189 acetate exhibiting one or more X-ray lines (2-theta values) in a powder diffraction pattern when measured using Cu $K_\alpha$ radiation selected from the group consisting of 11.5±0.2, 11.7±0.2, 13.0±0.2, 15.5±0.2, 15.6±0.2, 16.2±0.2, 19.6±0.2, 20.0±0.2, 21.1±0.2, 23.5±0.2, 24.8±0.2, and 27.0±0.2. One embodiment of the present disclosure provides for a crystalline Form A of AP1189 acetate exhibiting one or more X-ray lines (2-theta values) in a powder diffraction pattern when measured using Cu $K_\alpha$ radiation selected from the group consisting of the 2-theta values in listed in Table 2.

AP1189 Acetate Form I

Another crystalline form of AP1189 acetate has been identified herein which exhibits a mixture of a XRPD Pattern 1 and XRPD Pattern 2. In a preferred embodiment, the crystalline Form A of AP1189 acetate is substantially free of the polymorph of AP1189 acetate, which gives rise to XRPD Pattern 2. In one embodiment, "substantially free" means that the crystalline Form A of AP1189 acetate comprises less than 90% of the polymorph of AP1189 acetate which gives rise to XRPD Pattern 2, such as less than 80%, such as less than 70%, such as less than 60%, such as less than 50%, such as less than 40%, such as less than 30%, such as less than 20%, such as less than 15%, such as less than 10%, such as less than 5% of the polymorph of AP1189 acetate, which gives rise to XRPD Pattern 2. The content of the polymorph of AP1189 acetate, which gives rise to XRPD Pattern 2, may be assessed by the intensity of X-ray lines of Pattern 2 relative to the intensity of the X-ray lines of Pattern 1 of AP1189 acetate. For example, Pattern 2 exhibits X-ray lines at (2-theta values) 14.9, 18.0, and 24.2 which do not overlap with X-ray lines originating from Pattern 1 of AP1189. Thus, one embodiment of the present disclosure provides for a crystalline Form A of AP1189 acetate substantially free of a second crystalline form of AP1189 acetate, the second crystalline form of AP1189 acetate exhibits X-ray lines (2-theta values) in a powder diffraction pattern when measured using Cu $K_\alpha$ radiation at 14.9±0.2, 18.0±0.2, and/or 24.2±0.2. One embodiment of the present disclosure provides for a crystalline Form A of AP1189 acetate substantially free of a second crystalline form of AP1189 acetate, the second crystalline form of AP1189 acetate exhibits X-ray lines (2-theta values) in a powder diffraction pattern when measured using Cu $K_\alpha$ radiation at 14.9, 18.0, and/or 24.2. In one embodiment of the present disclosure, the crystalline Form A of AP1189 acetate exhibits no X-ray lines at 14.9±0.2, 18.0 0.2, and/or 24.2±0.2 in an powder diffraction pattern, or the crystalline Form A of AP1189 acetate exhibits lines at 14.9±0.2, 18.0±0.2, and/or 24.2±0.2 that have a relative intensity less than 30%, such as less than 25%, such as less than 20%, such as less than 15%, such as less than 10%, such as less than 5%.

AP1189 Succinate Form B

Figure 6:
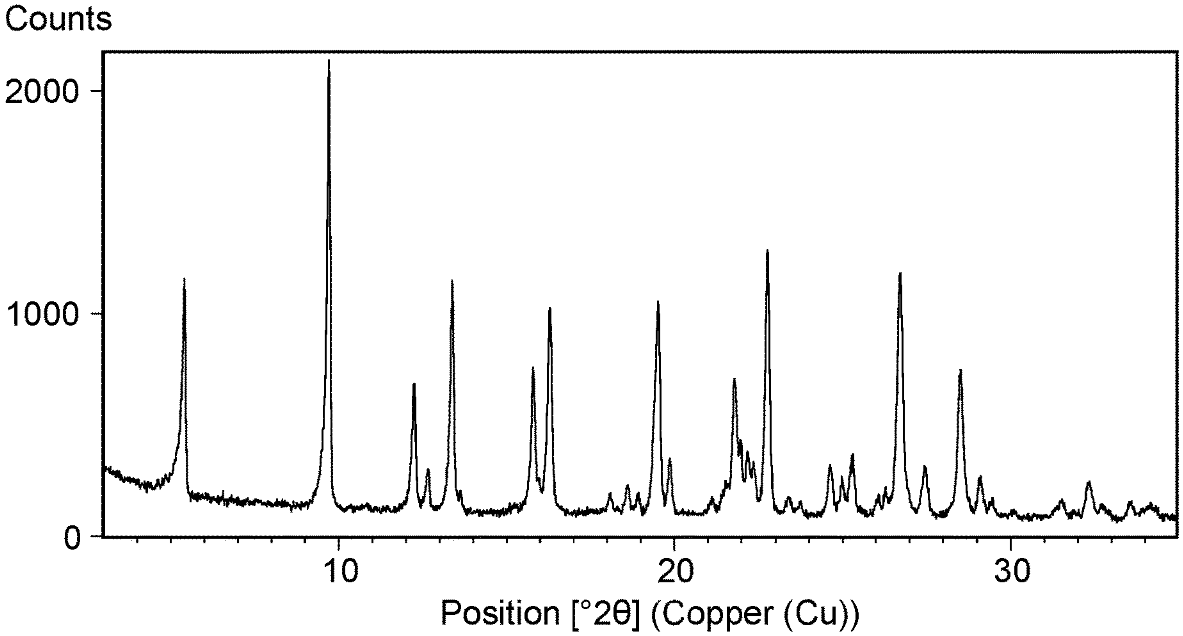
FIG. 6: XRPD diffractogram for AP1189 succinate salt Pattern 1 crystallised from isopropylalcohol:water 90:10 v/v.
Figure 7:
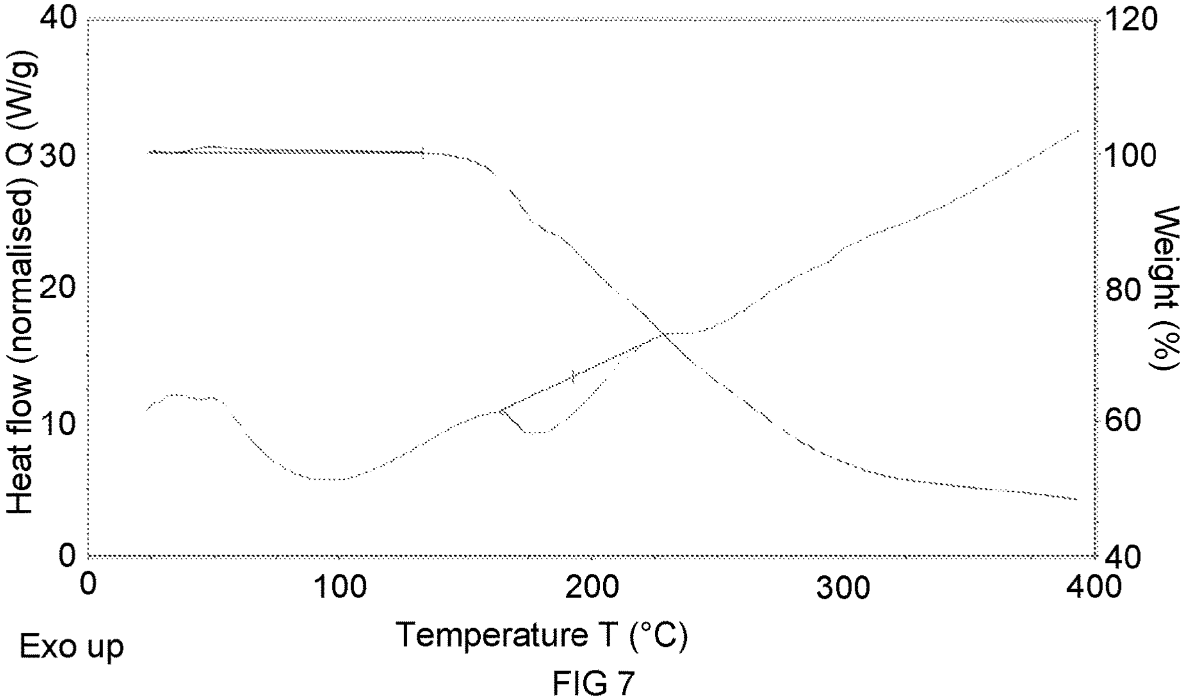
FIG. 7: TGA/DSC thermogram of AP1189 acetate Pattern 1 from 1,4-dioxane. Peak temperature: 183.75° C.; onset: 164.62° C.; enthalpy (normalised): 629.95 J/g. Weight loss: 0.001 mg; weight percent loss: 0.057%.

The present disclosure provides for a crystalline Form B of AP1189 succinate. Crystalline Form B of AP1189 succinate exhibits an XRPD diffractogram as shown in FIG. 6. One embodiment of the present disclosure provides for a crystalline Form B of AP1189 succinate exhibiting at least X-ray lines (2-theta values) in a powder diffraction pattern when measured using Cu $K_\alpha$ radiation at 9.7±0.2, 22.8±0.2, and 26.7±0.2. One embodiment provides for a crystalline Form B of AP1189 succinate further exhibiting one or more X-ray lines (2-theta values) in a powder diffraction pattern when measured using Cu $K_\alpha$ radiation selected from the group consisting of 5.4±0.2, 13.4±0.2, 16.3±0.2, and 19.5±0.2. One embodiment of the present disclosure provides for a crystalline Form B of AP1189 succinate further exhibiting one or more X-ray lines (2-theta values) in a powder diffraction pattern when measured using Cu $K_\alpha$ radiation selected from the group consisting of 12.2±0.2, 15.8±0.2, 21.8±0.2, and 28.5±0.2. One embodiment of the disclosure provides for a crystalline Form B of AP1189 succinate exhibiting an X-ray pattern (2-theta values) in a powder diffraction when measured using Cu $K_\alpha$ radiation according to FIG. 6.

One embodiment of the disclosure provides for a crystalline Form B of AP1189 succinate exhibiting one or more X-ray lines (2-theta values) in a powder diffraction pattern when measured using Cu $K_\alpha$ radiation selected from the group consisting of 5.4, 9.7, 12.2, 12.7, 13.4, 13.6, 15.8, 16.3, 18.1, 18.6, 18.9, 19.5, 19.9, 21.1, 21.8, 21.8, 22.0, 22.2, 22.4, 22.8, 23.4, 23.7, 24.6, 25.0, 25.3, 26.1, 26.3, 26.7, 27.5, 28.5, 29.1, 29.4, 30.0, 31.5, 32.3, 32.7, 33.6, and 34.1. One embodiment of the disclosure provides for a crystalline Form B of AP1189 succinate exhibiting one or more X-ray lines (2-theta values) in a powder diffraction pattern when measured using Cu $K_\alpha$ radiation selected from the group consisting of 5.4±0.2, 9.7±0.2, 12.2±0.2, 12.7±0.2, 13.4±0.2, 13.6±0.2, 15.8±0.2, 16.3±0.2, 18.1±0.2, 18.6±0.2, 18.9±0.2, 19.5±0.2, 19.9±0.2, 21.1±0.2, 21.8±0.2, 21.8±0.2, 22.0±0.2, 22.2±0.2, 22.4±0.2, 22.8±0.2, 23.4±0.2, 23.7±0.2, 24.6±0.2, 25.0±0.2, 25.3±0.2, 26.1±0.2, 26.3±0.2, 26.7±0.2, 27.5±0.2, 28.5±0.2, 29.1±0.2, 29.4±0.2, 30.0±0.2, 31.5±0.2, 32.3±0.2, 32.7±0.2, 33.6±0.2, and 34.1±0.2. It may be advantageous to identify the crystalline Form B of AP1189 succinate by X-ray lines (2-theta values) having a high relative intensity, and/or by characteristic X-ray lines. Thus, one embodiment of the present disclosure provides for a crystalline Form B of AP1189 succinate exhibiting one or more X-ray lines (2-theta values) in a powder diffraction pattern when measured using Cu $K_\alpha$ radiation selected from the group consisting of 5.4, 9.7, 12.2, 13.4, 15.8, 16.3, 19.5, 21.8, 22.8, 26.7, and 28.5. One embodiment of the present disclosure provides for a crystalline Form B of AP1189 succinate exhibiting one or more X-ray lines (2-theta values) in a powder diffraction pattern when measured using Cu $K_\alpha$ radiation selected from the group consisting of 5.4±0.2, 9.7±0.2, 12.2±0.2, 13.4±0.2, 15.8±0.2, 16.3±0.2, 19.5±0.2, 21.8±0.2, 22.8±0.2, 26.7±0.2, and 28.5±0.2. One embodiment of the present disclosure provides for a crystalline Form B of AP1189 succinate exhibiting one or more X-ray lines (2-theta values) in a powder diffraction pattern when measured using Cu $K_\alpha$ radiation selected from the group consisting of the 2-theta values in listed in Table 7.

AP1189 Acetate Form II

Figure 2:
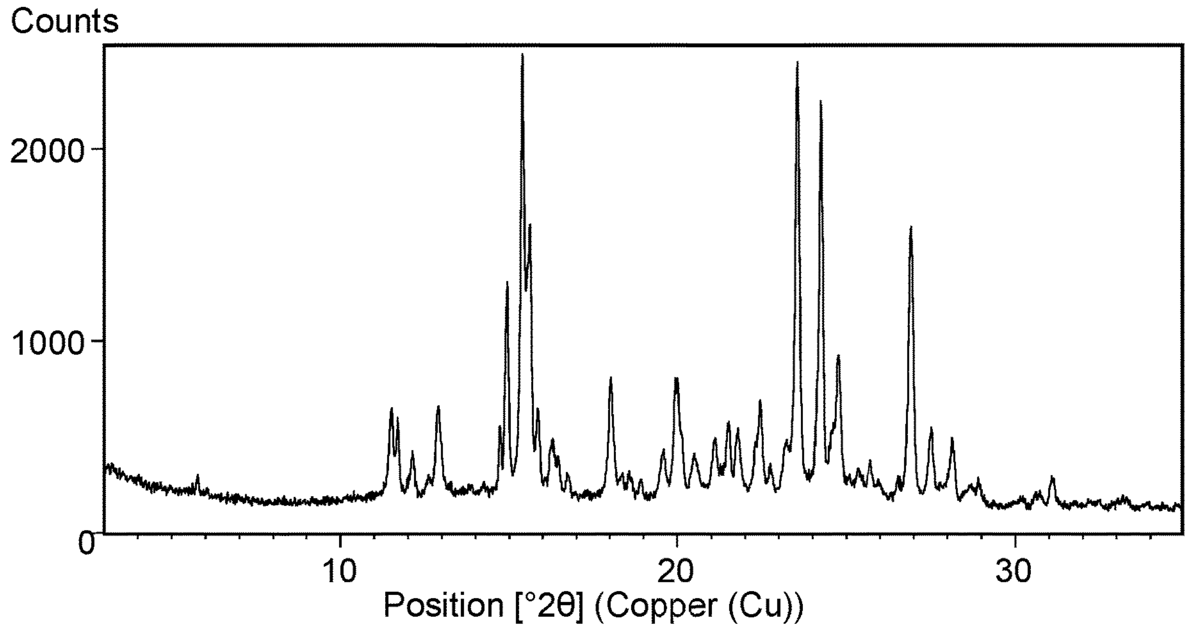
FIG. 2: XRPD diffractogram for AP1189 acetate salt Pattern 1 and 2 crystallised from ethyl acetate.
Figure 3:
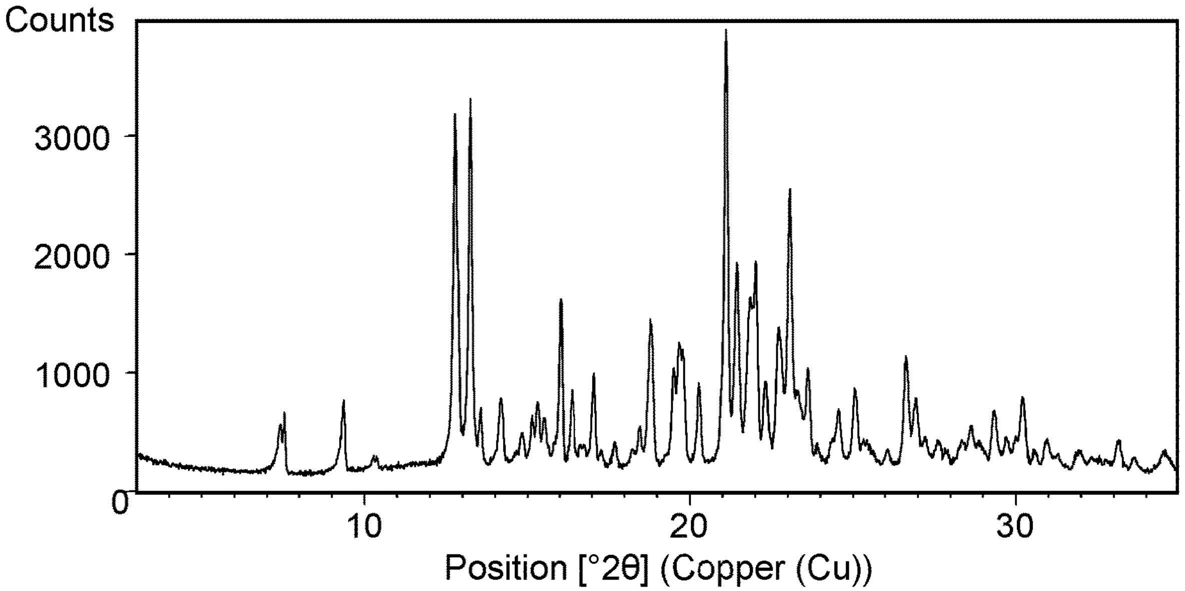
FIG. 3: XRPD diffractogram for AP1189 acetate salt Pattern 3 crystallised from THF.

One embodiment provides for crystalline forms of N-{3-[1-(2-nitrophenyl)-1H-pyrrol-2-yl]-allylidene}-aminoguanidinium acetate, which may be converted to AP1189 acetate of crystalline Form A. One embodiment provides for a crystalline Form I of AP1189 acetate corresponding to XRPD Pattern 1 and 2. A specific embodiment provides for a crystalline Form I of AP1189 acetate exhibiting X-ray lines (2-theta values) in a powder diffraction pattern when measured using Cu $K_\alpha$ radiation at one or more of 11.5±0.2, 11.7±0.2, 12.9±0.2, 14.9±0.2, 15.4±0.2, 15.6±0.2, 18.0±0.2, 19.9±0.2, 20.0±0.2, 21.1±0.2, 21.5±0.2, 21.8±0.2, 22.4±0.2, 23.5±0.2, 24.2±0.2, 24.7±0.2, and 26.9±0.2. One embodiment provides for a crystalline Form I of AP1189 acetate exhibiting X-ray lines (2-theta values) in a powder diffraction pattern when measured using Cu $K_\alpha$ radiation as shown in FIG. 2. One embodiment of the present disclosure provides for a crystalline Form II of AP1189 acetate corresponding to XRPD Pattern 3. A specific embodiment provides for a crystalline Form II of AP1189 acetate exhibiting X-ray lines (2-theta values) in a powder diffraction pattern when measured using Cu $K_\alpha$ radiation at one or more of 7.5±0.2, 9.4±0.2, 12.8±0.2, 13.3±0.2, 14.2±0.2, 15.3±0.2, 16.0±0.2, 17.0±0.2, 18.8±0.2, 19.7±0.2, 20.3±0.2, 21.1±0.2, 21.4±0.2, 21.9±0.2, 22.0±0.2, 22.7±0.2, and 23.1±0.2. One embodiment provides for a crystalline Form II of AP1189 acetate exhibiting X-ray lines (2-theta values) in a powder diffraction pattern when measured using Cu $K_\alpha$ radiation as shown in FIG. 3.

AP1189 Solid and/or Amorphous Forms

One embodiment of the present disclosure provides for a solid form of N-{3-[1-(2-nitrophenyl)-1H-pyrrol-2-yl]-allylidene}-aminoguanidinium succinate. One embodiment of the present disclosure provides for a solid, amorphous form of N-{3-[1-(2-nitrophenyl)-1H-pyrrol-2-yl]-allylidene}-aminoguanidinium succinate.

AP1189 Tosylate Form C

Figure 4:
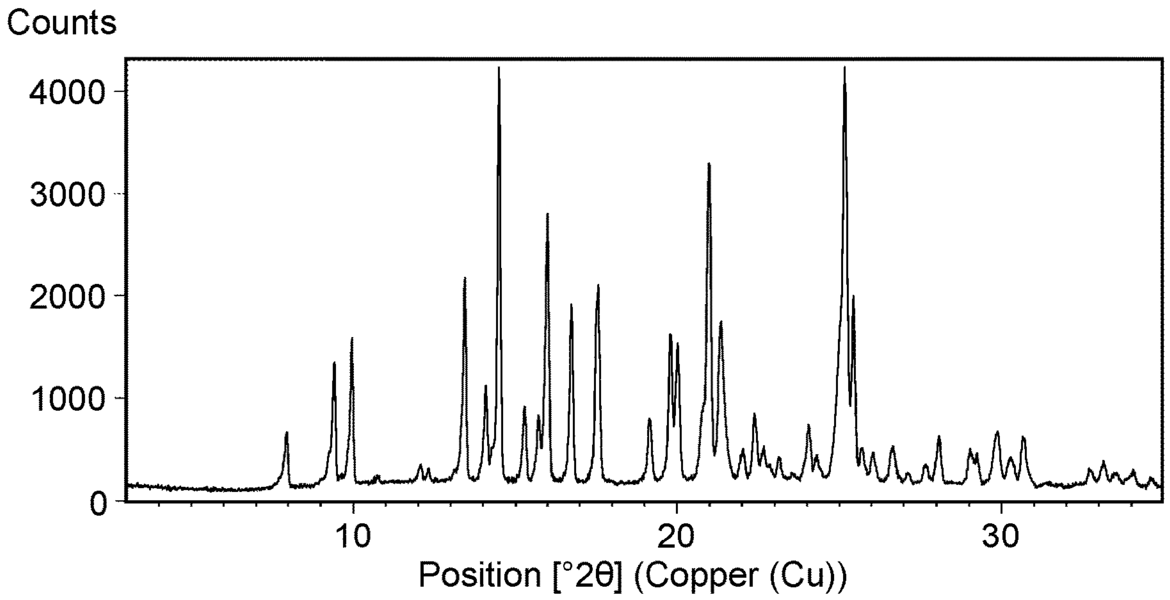
FIG. 4: XRPD diffractogram for AP1189 tosylate salt Pattern 1 crystallised from methanol.

The disclosure also provides for a crystalline Form C of AP1189 tosylate. Crystalline Form C of AP1189 tosylate exhibits an XRPD diffractogram as shown in FIG. 4. One embodiment of the present disclosure provides for a crystalline Form C of AP1189 tosylate exhibiting at least X-ray lines (2-theta values) in a powder diffraction pattern when measured using Cu $K_\alpha$ radiation at 14.5±0.2, 21.0±0.2, and 25.2±0.2. In one embodiment of the present disclosure, the crystalline Form C of AP1189 tosylate further exhibits one or more X-ray lines (2-theta values) in a powder diffraction pattern when measured using Cu $K_\alpha$ radiation selected from the group consisting of 13.4±0.2 and 16.0±0.2. In one embodiment of the present disclosure, the crystalline Form C of AP1189 tosylate further exhibits one or more X-ray lines (2-theta values) in a powder diffraction pattern when measured using Cu $K_\alpha$ radiation selected from the group consisting of 8.0±0.2, 9.4±0.2, 10.0±0.2, 15.3±0.2, 16.7±0.2, 17.6±0.2, 19.2±0.2, 19.8±0.2, 21.3±0.2, and 25.4±0.2. In one embodiment, the crystalline Form C of AP1189 tosylate exhibits an X-ray pattern (2-theta values) in a powder diffraction when measured using Cu $K_\alpha$ radiation according to FIG. 4.

One embodiment of the disclosure provides for a crystalline Form C of AP1189 tosylate exhibiting one or more X-ray lines (2-theta values) in a powder diffraction pattern when measured using Cu $K_\alpha$ radiation selected from the group consisting of 8.0, 9.4, 10.0, 10.8, 12.1, 12.3, 13.4, 14.1, 14.5, 15.3, 15.7, 16.0, 16.7, 17.6, 19.2, 19.8, 20.0, 20.7, 21.0, 21.3, 22.0, 22.4, 22.7, 22.8, 23.1, 23.6, 24.1, 24.3, 25.2, 25.4, 25.7, 26.1, 26.7, 27.1, 27.7, 28.1, 29.0, 29.2, 29.9, 30.3, 30.7, 31.4, 32.7, 33.2, 33.5, and 34.1. 34.6. One embodiment of the disclosure provides for a crystalline Form C of AP1189 tosylate exhibiting one or more X-ray lines (2-theta values) in a powder diffraction pattern when measured using Cu $K_\alpha$ radiation selected from the group consisting of 8.0±0.2, 9.4±0.2, 10.0±0.2, 10.8±0.2, 12.1±0.2, 12.3±0.2, 13.4±0.2, 14.1±0.2, 14.5±0.2, 15.3±0.2, 15.7±0.2, 16.0±0.2, 16.7±0.2, 17.6±0.2, 19.2±0.2, 19.8±0.2, 20.0±0.2, 20.7±0.2, 21.0±0.2, 21.3±0.2, 22.0±0.2, 22.4±0.2, 22.7±0.2, 22.8±0.2, 23.1±0.2, 23.6±0.2, 24.1±0.2, 24.3±0.2, 25.2±0.2, 25.4±0.2, 25.7±0.2, 26.1±0.2, 26.7±0.2, 27.1±0.2, 27.7±0.2, 28.1±0.2, 29.0±0.2, 29.2±0.2, 29.9±0.2, 30.3±0.2, 30.7±0.2, 31.4±0.2, 32.7±0.2, 33.2±0.2, 33.5±0.2, and 34.1±0.2. It may be advantageous to identify the crystalline Form C of AP1189 tosylate by X-ray lines (2-theta values) having a high relative intensity, and/or by characteristic X-ray lines. Thus, one embodiment of the present disclosure provides for a crystalline Form C of AP1189 tosylate exhibiting one or more X-ray lines (2-theta values) in a powder diffraction pattern when measured using Cu $K_\alpha$ radiation selected from the group consisting of 8.0, 9.4, 10.0, 13.4, 14.5, 15.3, 16.0, 16.7, 17.6, 19.2, 19.8, 21.0, 21.3, 25.2, and 25.4. One embodiment of the present disclosure provides for a crystalline Form C of AP1189 tosylate exhibiting one or more X-ray lines (2-theta values) in a powder diffraction pattern when measured using Cu $K_\alpha$ radiation selected from the group consisting of 8.0±0.2, 9.4±0.2, 10.0 0.2, 13.4±0.2, 14.5±0.2, 15.3±0.2, 16.0±0.2, 16.7±0.2, 17.6±0.2, 19.2±0.2, 19.8±0.2, 21.0±0.2, 21.3±0.2, 25.2±0.2, and 25.4±0.2. One embodiment of the present disclosure provides for a crystalline Form C of AP1189 tosylate exhibiting one or more X-ray lines (2-theta values) in a powder diffraction pattern when measured using Cu $K_\alpha$ radiation selected from the group consisting of the 2-theta values in listed in Table 5.

AP1189 Fumarate Form D

Figure 5:
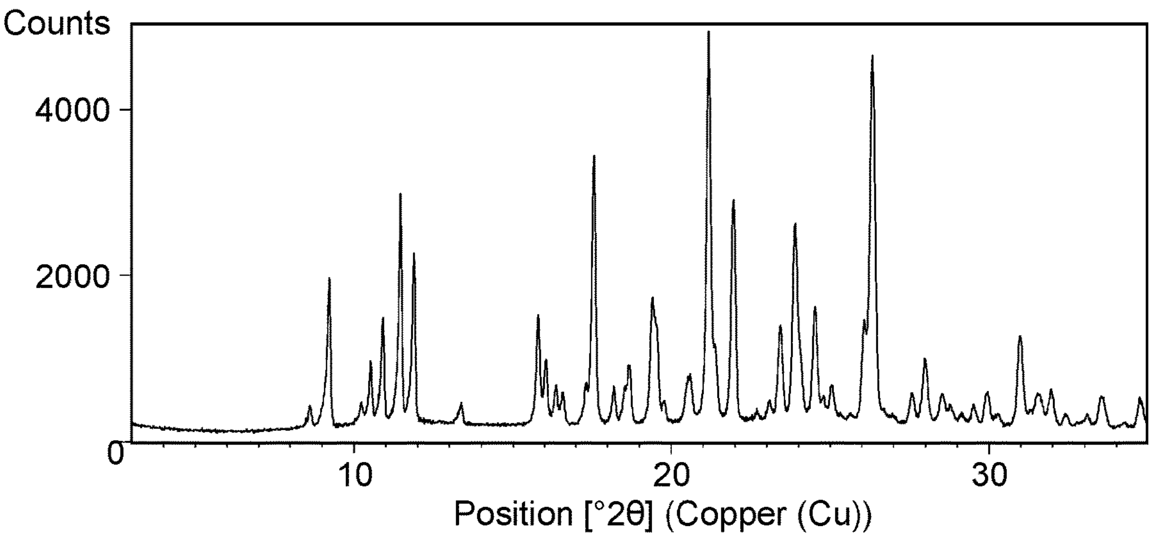
FIG. 5: XRPD diffractogram for AP1189 fumarate salt Pattern 1 crystallised from isopropylalcohol:water 90:10 v/v.

The disclosure also provides for a crystalline Form D of AP1189 fumarate. Crystalline Form D of AP1189 fumarate exhibits an XRPD diffractogram as shown in FIG. 5. One embodiment of the present disclosure provides for a crystalline Form D of AP1189 fumarate exhibiting at least X-ray lines (2-theta values) in a powder diffraction pattern when measured using Cu $K_\alpha$ radiation at 17.6±0.2, 21.2±0.2, and 26.3±0.2. In one embodiment of the present disclosure, the crystalline Form D of AP1189 fumarate further exhibits one or more X-ray lines (2-theta values) in a powder diffraction pattern when measured using Cu $K_\alpha$ radiation selected from the group consisting of 11.5±0.2, 21.9±0.2, and 23.9±0.2. In one embodiment of the present disclosure, the crystalline Form D of AP1189 fumarate further exhibits one or more X-ray lines (2-theta values) in a powder diffraction pattern when measured using Cu $K_\alpha$ radiation selected from the group consisting of 9.2±0.2, 10.5±0.2, 10.9±0.2, 11.9±0.2, 15.8±0.2, 18.7±0.2, 19.4±0.2, 23.4±0.2, and 24.5±0.2. In one embodiment, the crystalline Form D of AP1189 fumarate exhibits an X-ray pattern (2-theta values) in a powder diffraction when measured using Cu $K_\alpha$ radiation according to FIG. 5.

One embodiment of the disclosure provides for a crystalline Form D of AP1189 fumarate exhibiting one or more X-ray lines (2-theta values) in a powder diffraction pattern when measured using Cu $K_\alpha$ radiation selected from the group consisting of 8.6, 9.2, 10.2, 10.5, 10.9, 11.5, 11.9, 13.4, 15.8, 16.0, 16.4, 16.6, 17.3, 17.6, 18.2, 18.5, 18.7, 19.4, 19.6, 19.8, 20.6, 21.2, 21.4, 21.9, 22.7, 23.1, 23.4, 23.9, 24.5, 24.8, 25.0, 26.1, 26.3, 27.0, 27.6, 28.0, 28.5, 28.8, 29.1, 29.5, 29.9, 30.3, 31.0, 31.0, 31.5, 32.0, 32.4, 33.1, 33.5, 34.2, and 34.7. One embodiment of the disclosure provides for a crystalline Form D of AP1189 fumarate exhibiting one or more X-ray lines (2-theta values) in a powder diffraction pattern when measured using Cu $K_\alpha$ radiation selected from the group consisting of 8.6±0.2, 9.2±0.2, 10.2±0.2, 10.5±0.2, 10.9±0.2, 11.5±0.2, 11.9±0.2, 13.4±0.2, 15.8±0.2, 16.0±0.2, 16.4±0.2, 16.6±0.2, 17.3±0.2, 17.6±0.2, 18.2±0.2, 18.5±0.2, 18.7±0.2, 19.4±0.2, 19.6±0.2, 19.8±0.2, 20.6±0.2, 21.2±0.2, 21.4±0.2, 21.9±0.2, 22.7±0.2, 23.1±0.2, 23.4±0.2, 23.9±0.2, 24.5±0.2, 24.8±0.2, 25.0±0.2, 26.1±0.2, 26.3±0.2, 27.0±0.2, 27.6±0.2, 28.0±0.2, 28.5±0.2, 28.8±0.2, 29.1±0.2, 29.5±0.2, 29.9±0.2, 30.3±0.2, 31.0±0.2, 31.0±0.2, 31.5±0.2, 32.0±0.2, 32.4±0.2, 33.1±0.2, 33.5±0.2, 34.2±0.2, and 34.7±0.2. It may be advantageous to identify the crystalline Form D of AP1189 fumarate by X-ray lines (2-theta values) having a high relative intensity, and/or by characteristic X-ray lines. Thus, one embodiment of the present disclosure provides for a crystalline Form D of AP1189 fumarate exhibiting one or more X-ray lines (2-theta values) in a powder diffraction pattern when measured using Cu $K_\alpha$ radiation selected from the group consisting of 9.2, 10.5, 10.9, 11.5, 11.9, 15.8, 17.6, 18.7, 19.4, 21.2, 21.9, 23.4, 23.9, 24.5, 26.3. One embodiment of the present disclosure provides for a crystalline Form D of AP1189 fumarate exhibiting one or more X-ray lines (2-theta values) in a powder diffraction pattern when measured using Cu $K_\alpha$ radiation selected from the group consisting of 9.2±0.2, 10.5±0.2, 10.9±0.2, 11.5±0.2, 11.9±0.2, 15.8±0.2, 17.6±0.2, 18.7±0.2, 19.4±0.2, 21.2±0.2, 21.9±0.2, 23.4±0.2, 23.9±0.2, 24.5±0.2, 26.3±0.2. One embodiment of the present disclosure provides for a crystalline Form D of AP1189 fumarate exhibiting one or more X-ray lines (2-theta values) in a powder diffraction pattern when measured using Cu $K_\alpha$ radiation selected from the group consisting of the 2-theta values in listed in Table 6.

AP1189 Napadisylate Form III

Figure 14:
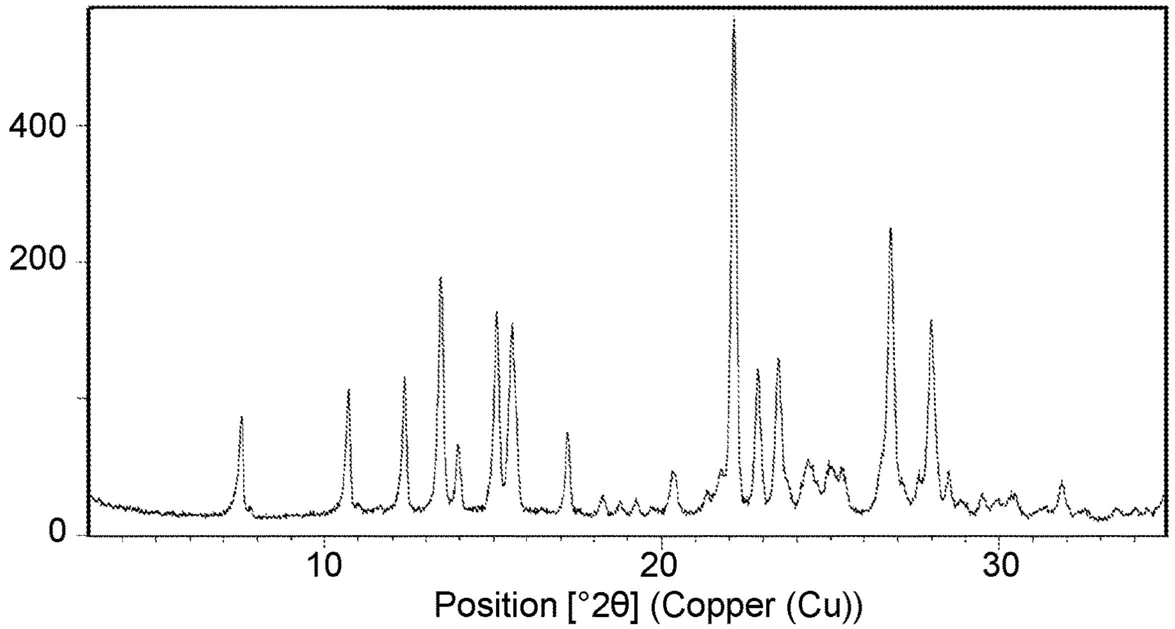
FIG. 14: XRPD Diffractogram of AP1189 Napadisylate Pattern 1.

The present disclosure provides for a crystalline Form III of AP1189 napadisylate. Crystalline Form III of AP1189 napadisylate exhibits an XRPD diffractogram as shown in FIG. 14. One embodiment of the present disclosure provides for a crystalline Form III of AP1189 napadisylate exhibiting at least X-ray lines (2-theta values) in a powder diffraction pattern when measured using Cu $K_\alpha$ radiation at 13.4±0.2, 22.2±0.2, and 26.8±0.2. One embodiment provides for a crystalline Form III of AP1189 napadisylate further exhibiting one or more X-ray lines (2-theta values) in a powder diffraction pattern when measured using Cu $K_\alpha$ radiation selected from the group consisting of 15.1±0.2, 15.5±0.2, 23.5±0.2, and 28.0±0.2. One embodiment of the present disclosure provides for a crystalline Form III of AP1189 napadisylate further exhibiting one or more X-ray lines (2-theta values) in a powder diffraction pattern when measured using Cu $K_\alpha$ radiation selected from the group consisting of 7.6±0.2, 10.7±0.2, 12.4±0.2, and 22.8±0.2. One embodiment of the disclosure provides for a crystalline Form III of AP1189 napadisylate exhibiting an X-ray pattern (2-theta values) in a powder diffraction when measured using Cu $K_\alpha$ radiation according to FIG. 14.

One embodiment of the disclosure provides for a crystalline Form III of AP1189 napadisylate exhibiting one or more X-ray lines (2-theta values) in a powder diffraction pattern when measured using Cu $K_\alpha$ radiation selected from the group consisting of 7.5, 10.7, 12.4, 13.4, 14.0, 15.1, 15.5, 17.2, 18.3, 18.8, 19.3, 20.3, 21.4, 21.8, 22.2, 22.8, 23.5, 24.3, 24.9, 25.3, 26.8, 27.1, 27.6, 28.0, 28.5, 28.9, 29.5, 29.9, 30.5, 31.4, 31.9, 32.6, and 33.5. embodiment of the disclosure provides for a crystalline Form III of AP1189 napadisylate exhibiting one or more X-ray lines (2-theta values) in a powder diffraction pattern when measured using Cu $K_{\alpha}$ radiation selected from the group consisting of 7.5±0.2, 10.7±0.2, 12.4±0.2, 13.4±0.2, 14.0±0.2, 15.1±0.2, 15.5±0.2, 17.2±0.2, 18.3±0.2, 18.8±0.2, 19.3±0.2, 20.3±0.2, 21.4±0.2, 21.8±0.2, 22.2±0.2, 22.8±0.2, 23.5±0.2, 24.3±0.2, 24.9±0.2, 25.3±0.2, 26.8±0.2, 27.1±0.2, 27.6±0.2, 28.0±0.2, 28.5±0.2, 28.9±0.2, 29.5±0.2, 29.9±0.2, 30.5±0.2, 31.4±0.2, 31.9±0.2, 32.6±0.2, and 33.5±0.2. It may be advantageous to identify the crystalline Form III of AP1189 napadisylate by X-ray lines (2-theta values) having a high relative intensity, and/or by characteristic X-ray lines. Thus, one embodiment of the present disclosure provides for a crystalline Form III of AP1189 napadisylate exhibiting one or more X-ray lines (2-theta values) in a powder diffraction pattern when measured using Cu $K_{\alpha}$ radiation selected from the group consisting of 7.6, 10.7, 12.4, 13.4, 15.1, 15.5, 22.2, 22.8, 23.5, 26.8, and 28.0. One embodiment of the present disclosure provides for a crystalline Form III of AP1189 napadisylate exhibiting one or more X-ray lines (2-theta values) in a powder diffraction pattern when measured using Cu $K_{\alpha}$ radiation selected from the group consisting of 7.6±0.2, 10.7±0.2, 12.4±0.2, 13.4±0.2, 15.1±0.2, 15.5±0.2, 22.2±0.2, 22.8±0.2, 23.5±0.2, 26.8±0.2, and 28.0±0.2. One embodiment of the present disclosure provides for a crystalline Form III of AP1189 napadisylate exhibiting one or more X-ray lines (2-theta values) in a powder diffraction pattern when measured using Cu $K_{\alpha}$ radiation selected from the group consisting of the 2-theta values in listed in Table 9.

AP1189 Napadisylate Form IV

Figure 15:
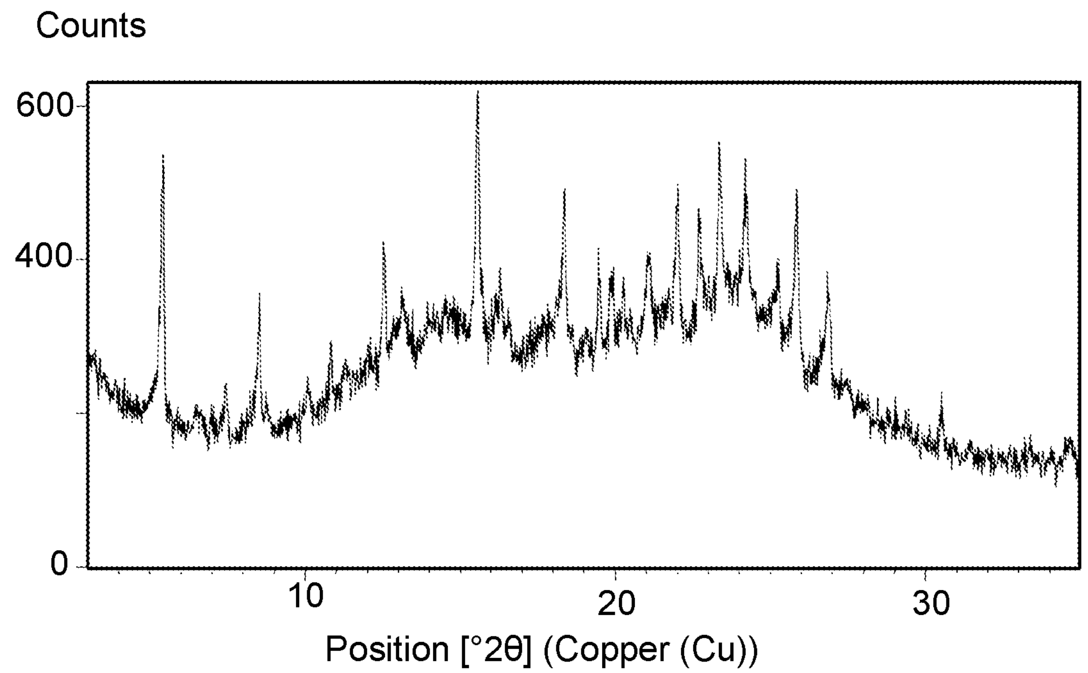
FIG. 15: XRPD Diffractogram of AP1189 Napadisylate Pattern 2.

The present disclosure provides for a crystalline Form IV of AP1189 napadisylate. Crystalline Form IV of AP1189 napadisylate exhibits an XRPD diffractogram as shown in FIG. 15. One embodiment of the present disclosure provides for a crystalline Form IV of AP1189 napadisylate exhibiting at least X-ray lines (2-theta values) in a powder diffraction pattern when measured using Cu $K_{\alpha}$ radiation at 5.4±0.2, 15.6±0.2, and 23.4±0.2. One embodiment provides for a crystalline Form IV of AP1189 napadisylate further exhibiting one or more X-ray lines (2-theta values) in a powder diffraction pattern when measured using Cu $K_{\alpha}$ radiation selected from the group consisting of 18.4±0.2, 22.0 0.2, 24.2±0.2, and 25.8±0.2. One embodiment of the present disclosure provides for a crystalline Form IV of AP1189 napadisylate further exhibiting one or more X-ray lines (2-theta values) in a powder diffraction pattern when measured using Cu $K_{\alpha}$ radiation selected from the group consisting of 8.5±0.2, 10.8±0.2, 12.6±0.2, 13.1±0.2, 19.5±0.2, 19.9±0.2, 21.1±0.2, 22.7±0.2, and 25.2±0.2. One embodiment of the disclosure provides for a crystalline Form IV of AP1189 napadisylate exhibiting an X-ray pattern (2-theta values) in a powder diffraction when measured using Cu $K_{\alpha}$ radiation according to FIG. 15.

One embodiment of the disclosure provides for a crystalline Form IV of AP1189 napadisylate exhibiting one or more X-ray lines (2-theta values) in a powder diffraction pattern when measured using Cu $K_{\alpha}$ radiation selected from the group consisting of 5.4, 6.5, 7.4, 8.5, 10.1, 10.8, 11.3, 12.1, 12.6, 13.1, 15.6, 16.3, 16.6, 18.4, 19.0, 19.5, 19.9, 20.3, 21.1, 22.0, 22.7, 23.4, 24.2, 25.2, 25.8, 26.9, and 30.5. One embodiment of the disclosure provides for a crystalline Form IV of AP1189 napadisylate exhibiting one or more X-ray lines (2-theta values) in a powder diffraction pattern when measured using Cu $K_{\alpha}$ radiation selected from the group consisting of 5.4±0.2, 6.5±0.2, 7.4±0.2, 8.5±0.2, 10.1±0.2, 10.8±0.2, 11.3±0.2, 12.1±0.2, 12.6±0.2, 13.1±0.2, 15.6±0.2, 16.3±0.2, 16.6±0.2, 18.4±0.2, 19.0±0.2, 19.5±0.2, 19.9±0.2, 20.3±0.2, 21.1±0.2, 22.0±0.2, 22.7±0.2, 23.4±0.2, 24.2±0.2, 25.2±0.2, 25.8±0.2, 26.9±0.2, and 30.5±0.2. It may be advantageous to identify the crystalline Form IV of AP1189 napadisylate by X-ray lines (2-theta values) having a high relative intensity, and/or by characteristic X-ray lines. Thus, one embodiment of the present disclosure provides for a crystalline Form IV of AP1189 napadisylate exhibiting one or more X-ray lines (2-theta values) in a powder diffraction pattern when measured using Cu $K_{\alpha}$ radiation selected from the group consisting of 5.4, 8.5, 10.8, 12.6, 13.1, 15.6, 18.4, 19.5, 19.9, 21.1, 22.0, 22.7, 23.4, 24.2, 25.2, and 25.8. One embodiment of the present disclosure provides for a crystalline Form IV of AP1189 napadisylate exhibiting one or more X-ray lines (2-theta values) in a powder diffraction pattern when measured using Cu $K_{\alpha}$ radiation selected from the group consisting of 5.4±0.2, 8.5±0.2, 10.8±0.2, 12.6±0.2, 13.1±0.2, 15.6±0.2, 18.4±0.2, 19.5±0.2, 19.9±0.2, 21.1±0.2, 22.0±0.2, 22.7±0.2, 23.4±0.2, 24.2±0.2, 25.2±0.2, and 25.8±0.2. One embodiment of the present disclosure provides for a crystalline Form IV of AP1189 napadisylate exhibiting one or more X-ray lines (2-theta values) in a powder diffraction pattern when measured using Cu $K_{\alpha}$ radiation selected from the group consisting of the 2-theta values in listed in Table 10.

AP1189 Esylate Form V

Figure 16:
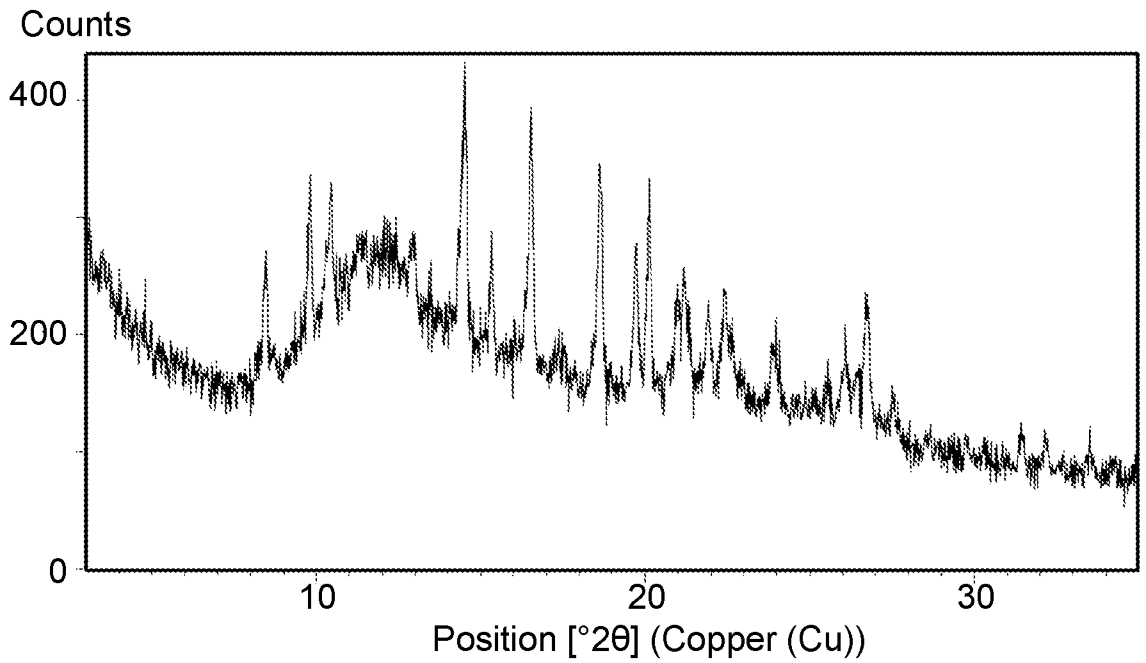
FIG. 16: XRPD Diffractogram of AP1189 Esylate Pattern 1.

The present disclosure provides for a crystalline Form V of AP1189 esylate. Crystalline Form V of AP1189 esylate exhibits an XRPD diffractogram as shown in FIG. 16. One embodiment of the present disclosure provides for a crystalline Form V of AP1189 esylate exhibiting at least X-ray lines (2-theta values) in a powder diffraction pattern when measured using Cu $K_{\alpha}$ radiation at 14.5±0.2, 16.5±0.2, and 18.6±0.2. One embodiment provides for a crystalline Form V of AP1189 esylate further exhibiting one or more X-ray lines (2-theta values) in a powder diffraction pattern when measured using Cu $K_{\alpha}$ radiation selected from the group consisting of 9.8±0.2, 19.7±0.2, 20.1±0.2, and 26.8±0.2. One embodiment of the present disclosure provides for a crystalline Form V of AP1189 esylate further exhibiting one or more X-ray lines (2-theta values) in a powder diffraction pattern when measured using Cu $K_{\alpha}$ radiation selected from the group consisting of 8.5±0.2, 10.4±0.2, 15.3±0.2, 21.9±0.2, 22.5±0.2, and 26.1±0.2. One embodiment of the disclosure provides for a crystalline Form V of AP1189 esylate exhibiting an X-ray pattern (2-theta values) in a powder diffraction when measured using Cu $K_{\alpha}$ radiation according to FIG. 16.

One embodiment of the disclosure provides for a crystalline Form V of AP1189 esylate exhibiting one or more X-ray lines (2-theta values) in a powder diffraction pattern when measured using Cu $K_{\alpha}$ radiation selected from the group consisting of 8.5, 9.8, 10.4, 11.3, 11.5, 13.0, 14.3, 14.5, 15.3, 16.5, 18.6, 19.7, 20.1, 21.0, 21.1, 21.9, 22.4, 23.9, 25.5, 26.1, 26.4, 26.8, 27.5, 29.7, 31.4, 32.2, and 33.5. One embodiment of the disclosure provides for a crystalline Form V of AP1189 esylate exhibiting one or more X-ray lines (2-theta values) in a powder diffraction pattern when measured using Cu $K_{\alpha}$ radiation selected from the group consisting of 8.5±0.2, 9.8±0.2, 10.4±0.2, 11.3±0.2, 11.5±0.2, 13.0±0.2, 14.3±0.2, 14.5±0.2, 15.3±0.2, 16.5±0.2, 18.6±0.2, 19.7±0.2, 20.1±0.2, 21.0±0.2, 21.1±0.2, 21.9±0.2, 22.4±0.2, 23.9±0.2, 25.5±0.2, 26.1±0.2, 26.4±0.2, 26.8±0.2, 27.5±0.2, 29.7±0.2, 31.4±0.2, 32.2±0.2, and 33.5±0.2. It may be advantageous to identify the crystalline Form V of AP1189 esylate by X-ray lines (2-theta values) having a high relative intensity, and/or by characteristic X-ray lines. Thus, one embodiment of the present disclosure provides for a crystalline Form V of AP1189 esylate exhibiting one or more X-ray lines (2-theta values) in a powder diffraction pattern when measured using Cu $K_\alpha$ radiation selected from the group consisting of 8.5, 9.8, 10.4, 14.5, 15.3, 16.5, 18.6, 19.7, 20.1, 21.9, 22.5, 26.1, and 26.8. One embodiment of the present disclosure provides for a crystalline Form V of AP1189 esylate exhibiting one or more X-ray lines (2-theta values) in a powder diffraction pattern when measured using Cu $K_\alpha$ radiation selected from the group consisting of 8.5±0.2, 9.8±0.2, 10.4±0.2, 14.5±0.2, 15.3±0.2, 16.5±0.2, 18.6±0.2, 19.7±0.2, 20.1±0.2, 21.9±0.2, 22.5±0.2, 26.1±0.2, and 26.8±0.2. One embodiment of the present disclosure provides for a crystalline Form V of AP1189 esylate exhibiting one or more X-ray lines (2-theta values) in a powder diffraction pattern when measured using Cu $K_\alpha$ radiation selected from the group consisting of the 2-theta values in listed in Table 11.

AP1189 Edisylate Form VI

Figure 17:
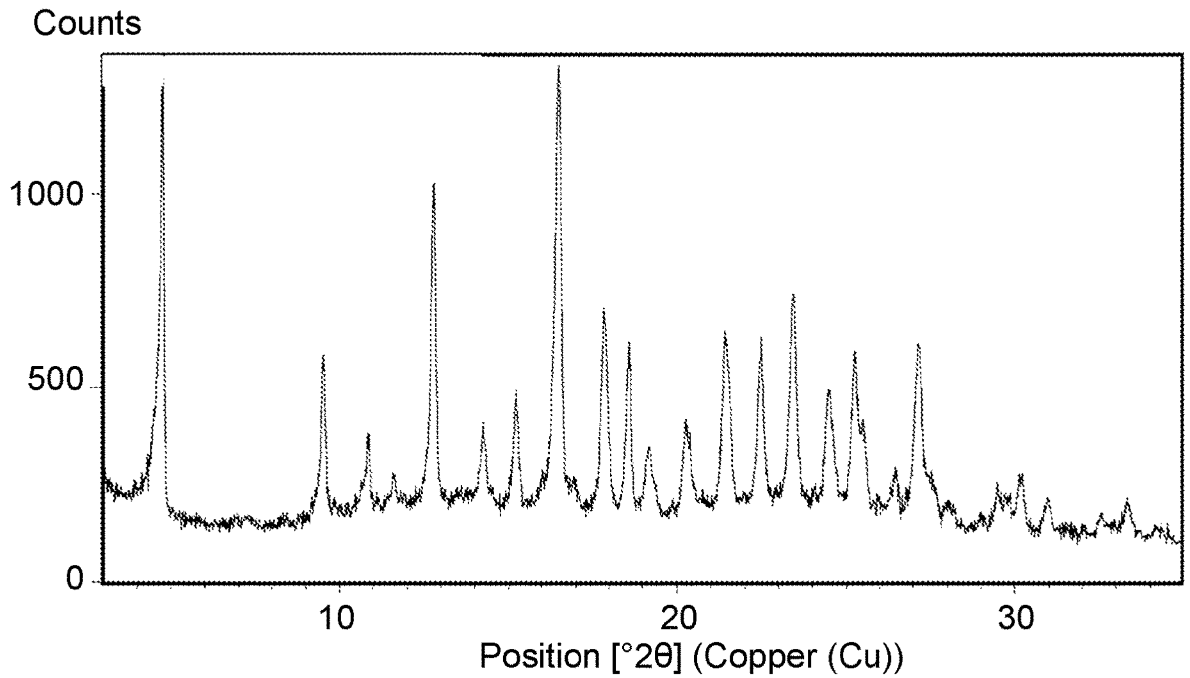
FIG. 17: XRPD Diffractogram of AP1189 Edisylate Pattern 1.

The present disclosure provides for a crystalline Form VI of AP1189 edisylate. Crystalline Form VI of AP1189 edisylate exhibits an XRPD diffractogram as shown in FIG. 17. One embodiment of the present disclosure provides for a crystalline Form VI of AP1189 edisylate exhibiting at least X-ray lines (2-theta values) in a powder diffraction pattern when measured using Cu $K_\alpha$ radiation at 4.8±0.2, 12.8±0.2, and 16.5±0.2. One embodiment provides for a crystalline Form VI of AP1189 edisylate further exhibiting one or more X-ray lines (2-theta values) in a powder diffraction pattern when measured using Cu $K_\alpha$ radiation selected from the group consisting of 17.9±0.2, 21.4±0.2, 23.4±0.2, and 27.1±0.2. One embodiment of the present disclosure provides for a crystalline Form VI of AP1189 edisylate further exhibiting one or more X-ray lines (2-theta values) in a powder diffraction pattern when measured using Cu $K_\alpha$ radiation selected from the group consisting of 9.5±0.2, 10.9±0.2, 14.3±0.2, 15.2±0.2, 18.6±0.2, and 24.5±0.2. One embodiment of the disclosure provides for a crystalline Form VI of AP1189 edisylate exhibiting an X-ray pattern (2-theta values) in a powder diffraction when measured using Cu $K_\alpha$ radiation according to FIG. 17.

One embodiment of the disclosure provides for a crystalline Form VI of AP1189 edisylate exhibiting one or more X-ray lines (2-theta values) in a powder diffraction pattern when measured using Cu $K_\alpha$ radiation selected from the group consisting of 4.8, 9.5, 10.9, 11.6, 12.8, 14.3, 15.2, 16.5, 17.0, 17.9, 18.6, 19.2, 20.3, 21.4, 22.5, 23.4, 24.5, 25.3, 25.5, 26.5, 27.2, 28.0, 29.5, 29.7, 30.2, 31.0, 32.6, 33.3, and 34.3. One embodiment of the disclosure provides for a crystalline Form VI of AP1189 edisylate exhibiting one or more X-ray lines (2-theta values) in a powder diffraction pattern when measured using Cu $K_\alpha$ radiation selected from the group consisting of 4.8±0.2, 9.5±0.2, 10.9±0.2, 11.6±0.2, 12.8±0.2, 14.3±0.2, 15.2±0.2, 16.5±0.2, 17.0±0.2, 17.9±0.2, 18.6±0.2, 19.2±0.2, 20.3±0.2, 21.4±0.2, 22.5±0.2, 23.4±0.2, 24.5±0.2, 25.3±0.2, 25.5±0.2, 26.5±0.2, 27.2±0.2, 28.0±0.2, 29.5±0.2, 29.7±0.2, 30.2±0.2, 31.0±0.2, 32.6±0.2, 33.3±0.2, and 34.3±0.2. It may be advantageous to identify the crystalline Form VI of AP1189 edisylate by X-ray lines (2-theta values) having a high relative intensity, and/or by characteristic X-ray lines. Thus, one embodiment of the present disclosure provides for a crystalline Form VI of AP1189 edisylate exhibiting one or more X-ray lines (2-theta values) in a powder diffraction pattern when measured using Cu $K_\alpha$ radiation selected from the group consisting of 4.8, 9.5, 10.9, 12.8, 14.3, 15.2, 16.5, 17.9, 18.6, 21.4, 23.4, 24.5, and 27.1. One embodiment of the present disclosure provides for a crystalline Form VI of AP1189 edisylate exhibiting one or more X-ray lines (2-theta values) in a powder diffraction pattern when measured using Cu $K_\alpha$ radiation selected from the group consisting of 4.8±0.2, 9.5±0.2, 10.9±0.2, 12.8±0.2, 14.3±0.2, 15.2±0.2, 16.5±0.2, 17.9±0.2, 18.6±0.2, 21.4±0.2, 23.4±0.2, 24.5±0.2, and 27.1±0.2. One embodiment of the present disclosure provides for a crystalline Form VI of AP1189 edisylate exhibiting one or more X-ray lines (2-theta values) in a powder diffraction pattern when measured using Cu $K_\alpha$ radiation selected from the group consisting of the 2-theta values in listed in Table 12.

AP1189 Edisylate Form VII

Figure 18:
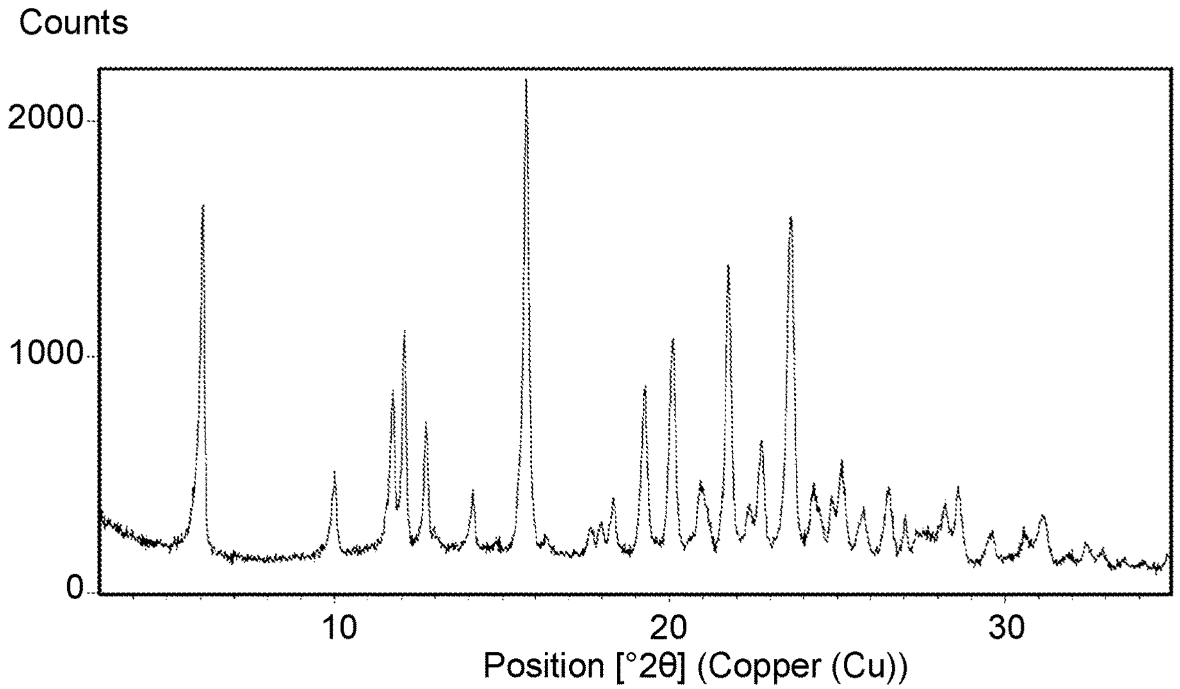
FIG. 18: XRPD Diffractogram of AP1189 Edisylate Pattern 2.

The present disclosure provides for a crystalline Form VII of AP1189 edisylate. Crystalline Form VII of AP1189 edisylate exhibits an XRPD diffractogram as shown in FIG. 18. One embodiment of the present disclosure provides for a crystalline Form VII of AP1189 edisylate exhibiting at least X-ray lines (2-theta values) in a powder diffraction pattern when measured using Cu $K_\alpha$ radiation at 6.1±0.2, 15.7±0.2, and 23.6±0.2. One embodiment provides for a crystalline Form VII of AP1189 edisylate further exhibiting one or more X-ray lines (2-theta values) in a powder diffraction pattern when measured using Cu $K_\alpha$ radiation selected from the group consisting of 12.1, 20.1±0.2, and 21.8±0.2. One embodiment of the present disclosure provides for a crystalline Form VII of AP1189 edisylate further exhibiting one or more X-ray lines (2-theta values) in a powder diffraction pattern when measured using Cu $K_\alpha$ radiation selected from the group consisting of 11.7±0.2, 12.7±0.2, and 19.3±0.2. One embodiment of the disclosure provides for a crystalline Form VII of AP1189 edisylate exhibiting an X-ray pattern (2-theta values) in a powder diffraction when measured using Cu $K_\alpha$ radiation according to FIG. 18.

One embodiment of the disclosure provides for a crystalline Form VII of AP1189 edisylate exhibiting one or more X-ray lines (2-theta values) in a powder diffraction pattern when measured using Cu $K_\alpha$ radiation selected from the group consisting of 6.1, 10.0, 11.7, 12.1, 12.7, 14.1, 15.7, 16.3, 17.6, 17.9, 18.3, 19.3, 20.1, 20.9, 21.8, 22.4, 22.7, 23.6, 24.3, 24.8, 25.1, 25.8, 26.5, 27.0, 27.5, 28.2, 28.6, 29.7, 30.6, 31.2, 31.9, 32.4, 32.9, 33.5, and 34.1. One embodiment of the disclosure provides for a crystalline Form VII of AP1189 edisylate exhibiting one or more X-ray lines (2-theta values) in a powder diffraction pattern when measured using Cu $K_\alpha$ radiation selected from the group consisting of 6.1±0.2, 10.0±0.2, 11.7±0.2, 12.1±0.2, 12.7±0.2, 14.1±0.2, 15.7±0.2, 16.3±0.2, 17.6±0.2, 17.9±0.2, 18.3±0.2, 19.3±0.2, 20.1±0.2, 20.9±0.2, 21.8±0.2, 22.4±0.2, 22.7±0.2, 23.6±0.2, 24.3±0.2, 24.8±0.2, 25.1±0.2, 25.8±0.2, 26.5±0.2, 27.0±0.2, 27.5±0.2, 28.2±0.2, 28.6±0.2, 29.7±0.2, 30.6±0.2, 31.2±0.2, 31.9±0.2, 32.4±0.2, 32.9±0.2, 33.5±0.2, and 34.1±0.2. It may be advantageous to identify the crystalline Form VII of AP1189 edisylate by X-ray lines (2-theta values) having a high relative intensity, and/or by characteristic X-ray lines. Thus, one embodiment of the present disclosure provides for a crystalline Form VII of AP1189 edisylate exhibiting one or more X-ray lines (2-theta values) in a powder diffraction pattern when measured using Cu $K_\alpha$ radiation selected from the group consisting of 6.1, 11.7, 12.1, 12.7, 15.7, 19.3, 20.1, 21.8, and 23.6. One embodiment of the present disclosure provides for a crystalline Form VII of AP1189 edisylate exhibiting one or more X-ray lines (2-theta values) in a powder diffraction pattern when measured using Cu $K_\alpha$ radiation selected from the group consisting of 6.1±0.2, 11.7±0.2, 12.1±0.2, 12.7±0.2, 15.7±0.2, 19.3±0.2, 20.1±0.2, 21.8±0.2, and 23.6±0.2. One embodiment of the present disclosure provides for a crystalline Form VII of AP1189 edisylate exhibiting one or more X-ray lines (2-theta values) in a powder diffraction pattern when measured using Cu $K_\alpha$ radiation selected from the group consisting of the 2-theta values in listed in Table 13.

AP1189 Edisylate Form VIII

Figure 19:
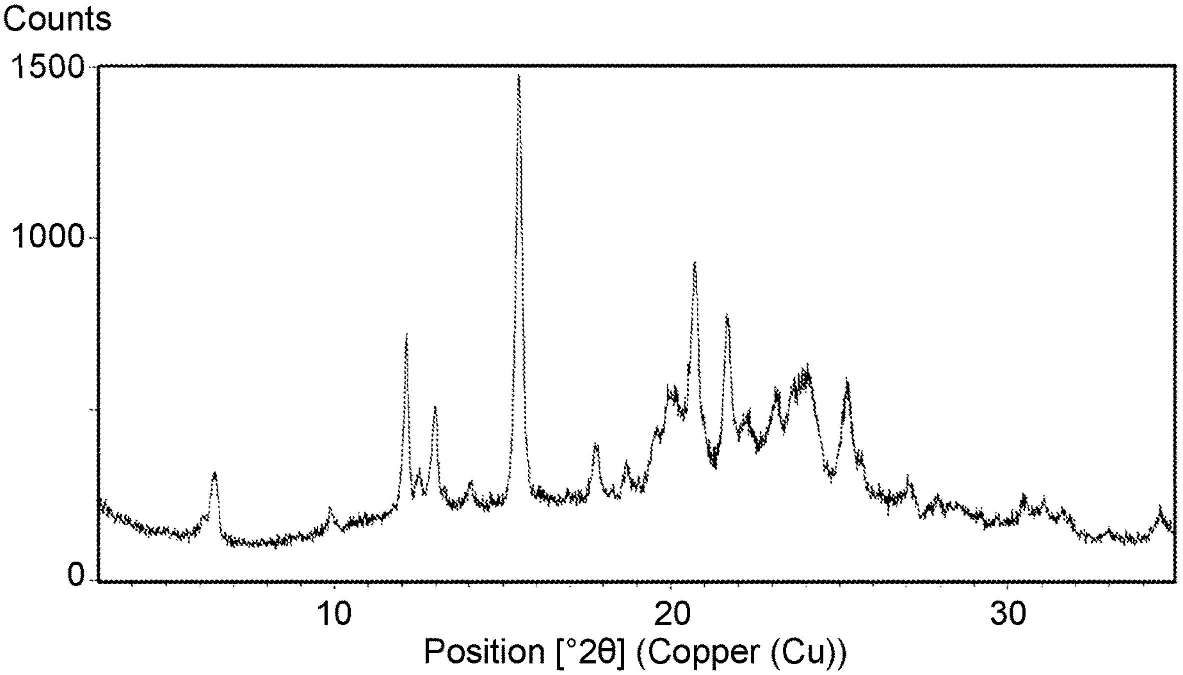
FIG. 19: XRPD Diffractogram of AP1189 Edisylate Pattern 4.

The present disclosure provides for a crystalline Form VIII of AP1189 edisylate. Crystalline Form VIII of AP1189 edisylate exhibits an XRPD diffractogram as shown in FIG. 19. One embodiment of the present disclosure provides for a crystalline Form VIII of AP1189 edisylate exhibiting at least X-ray lines (2-theta values) in a powder diffraction pattern when measured using Cu $K_\alpha$ radiation at 15.5±0.2, 20.7±0.2, and 21.7±0.2. One embodiment provides for a crystalline Form VIII of AP1189 edisylate further exhibiting one or more X-ray lines (2-theta values) in a powder diffraction pattern when measured using Cu $K_\alpha$ radiation selected from the group consisting of 12.1±0.2, 13.0±0.2, and 24.1±0.2. One embodiment of the present disclosure provides for a crystalline Form VIII of AP1189 edisylate further exhibiting one or more X-ray lines (2-theta values) in a powder diffraction pattern when measured using Cu $K_\alpha$ radiation selected from the group consisting of 6.4±0.2 and 25.2±0.2. One embodiment of the disclosure provides for a crystalline Form VIII of AP1189 edisylate exhibiting an X-ray pattern (2-theta values) in a powder diffraction when measured using Cu $K_\alpha$ radiation according to FIG. 19.

One embodiment of the disclosure provides for a crystalline Form VIII of AP1189 edisylate exhibiting one or more X-ray lines (2-theta values) in a powder diffraction pattern when measured using Cu $K_\alpha$ radiation selected from the group consisting of 6.4, 9.9, 12.1, 12.5, 13.0, 14.0, 15.5, 17.8, 18.3, 18.7, 19.5, 20.0, 20.7, 21.7, 22.2, 23.1, 24.1, 25.2, 25.7, 27.1, 27.9, 30.7, 31.1, 31.6, and 34.5. One embodiment of the disclosure provides for a crystalline Form VIII of AP1189 edisylate exhibiting one or more X-ray lines (2-theta values) in a powder diffraction pattern when measured using Cu $K_\alpha$ radiation selected from the group consisting of 6.4±0.2, 9.9±0.2, 12.1±0.2, 12.5±0.2, 13.0±0.2, 14.0±0.2, 15.5±0.2, 17.8±0.2, 18.3±0.2, 18.7±0.2, 19.5±0.2, 20.0±0.2, 20.7±0.2, 21.7±0.2, 22.2±0.2, 23.1±0.2, 24.1±0.2, 25.2±0.2, 25.7±0.2, 27.1±0.2, 27.9±0.2, 30.7±0.2, 31.1±0.2, 31.6±0.2, and 34.5±0.2. It may be advantageous to identify the crystalline Form VIII of AP1189 edisylate by X-ray lines (2-theta values) having a high relative intensity, and/or by characteristic X-ray lines. Thus, one embodiment of the present disclosure provides for a crystalline Form VIII of AP1189 edisylate exhibiting one or more X-ray lines (2-theta values) in a powder diffraction pattern when measured using Cu $K_\alpha$ radiation selected from the group consisting of 6.4, 12.1, 13.0, 15.5, 20.7, 21.7, 24.1, and 25.2. One embodiment of the present disclosure provides for a crystalline Form VIII of AP1189 edisylate exhibiting one or more X-ray lines (2-theta values) in a powder diffraction pattern when measured using Cu $K_\alpha$ radiation selected from the group consisting of 6.4±0.2, 12.1±0.2, 13.0±0.2, 15.5±0.2, 20.7±0.2, 21.7±0.2, 24.1±0.2, and 25.2±0.2. One embodiment of the present disclosure provides for a crystalline Form VIII of AP1189 edisylate exhibiting one or more X-ray lines (2-theta values) in a powder diffraction pattern when measured using Cu $K_\alpha$ radiation selected from the group consisting of the 2-theta values in listed in Table 14.

AP1189 Edisylate Form IX

Figure 20:
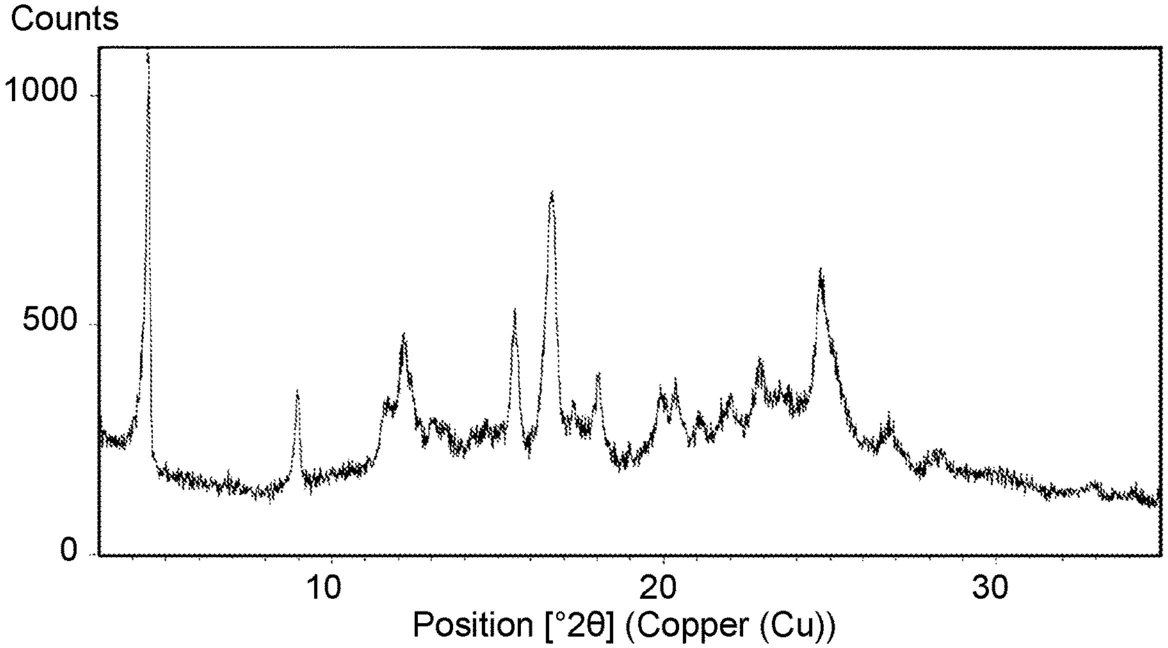
FIG. 20: XRPD Diffractogram of AP1189 Edisylate Pattern 5.

The present disclosure provides for a crystalline Form IX of AP1189 edisylate. Crystalline Form IX of AP1189 edisylate exhibits an XRPD diffractogram as shown in FIG. 20. One embodiment of the present disclosure provides for a crystalline Form IX of AP1189 edisylate exhibiting at least X-ray lines (2-theta values) in a powder diffraction pattern when measured using Cu $K_\alpha$ radiation at 4.5±0.2, 16.7±0.2, and 24.7±0.2. One embodiment provides for a crystalline Form IX of AP1189 edisylate further exhibiting one or more X-ray lines (2-theta values) in a powder diffraction pattern when measured using Cu $K_\alpha$ radiation selected from the group consisting of 12.2±0.2 and 15.5±0.2. One embodiment of the present disclosure provides for a crystalline Form IX of AP1189 edisylate further exhibiting one or more X-ray lines (2-theta values) in a powder diffraction pattern when measured using Cu $K_\alpha$ radiation selected from the group consisting of 9.0±0.2 and 18.0. One embodiment of the disclosure provides for a crystalline Form IX of AP1189 edisylate exhibiting an X-ray pattern (2-theta values) in a powder diffraction when measured using Cu $K_\alpha$ radiation according to FIG. 20.

One embodiment of the disclosure provides for a crystalline Form IX of AP1189 edisylate exhibiting one or more X-ray lines (2-theta values) in a powder diffraction pattern when measured using Cu $K_\alpha$ radiation selected from the group consisting of 4.5, 9.0, 11.7, 12.2, 12.4, 13.1, 15.5, 16.7, 17.3, 18.0, 19.9, 20.4, 21.1, 22.0, 22.9, 24.7, 26.8, and 28.3. One embodiment of the disclosure provides for a crystalline Form IX of AP1189 edisylate exhibiting one or more X-ray lines (2-theta values) in a powder diffraction pattern when measured using Cu $K_\alpha$ radiation selected from the group consisting of 4.5±0.2, 9.0±0.2, 11.7±0.2, 12.2±0.2, 12.4±0.2, 13.1±0.2, 15.5±0.2, 16.7±0.2, 17.3±0.2, 18.0±0.2, 19.9±0.2, 20.4±0.2, 21.1±0.2, 22.0±0.2, 22.9±0.2, 24.7±0.2, 26.8±0.2, and 28.3±0.2. It may be advantageous to identify the crystalline Form IX of AP1189 edisylate by X-ray lines (2-theta values) having a high relative intensity, and/or by characteristic X-ray lines. Thus, one embodiment of the present disclosure provides for a crystalline Form IX of AP1189 edisylate exhibiting one or more X-ray lines (2-theta values) in a powder diffraction pattern when measured using Cu $K_\alpha$ radiation selected from the group consisting of 4.5, 9.0, 12.2, 15.5, 16.7, 18.0, and 24.7. One embodiment of the present disclosure provides for a crystalline Form IX of AP1189 edisylate exhibiting one or more X-ray lines (2-theta values) in a powder diffraction pattern when measured using Cu $K_\alpha$ radiation selected from the group consisting of 4.5±0.2, 9.0±0.2, 12.2±0.2, 15.5±0.2, 16.7±0.2, 18.0±0.2, and 24.7±0.2. One embodiment of the present disclosure provides for a crystalline Form IX of AP1189 edisylate exhibiting one or more X-ray lines (2-theta values) in a powder diffraction pattern when measured using Cu $K_\alpha$ radiation selected from the group consisting of the 2-theta values in listed in Table 15.

AP1189 Nitrate Form X

Figure 21:
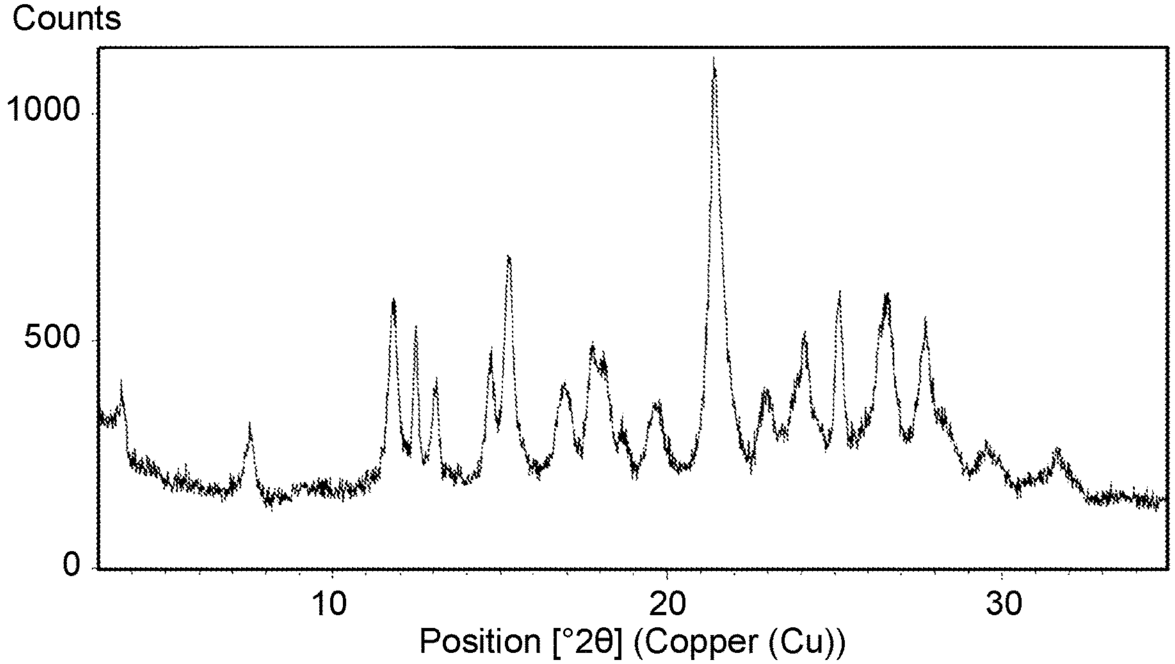
FIG. 21: XRPD Diffractogram of AP1189 Nitrate Pattern 1.

The present disclosure provides for a crystalline Form X of AP1189 nitrate. Crystalline Form X of AP1189 nitrate exhibits an XRPD diffractogram as shown in FIG. 21. One embodiment of the present disclosure provides for a crystalline Form X of AP1189 nitrate exhibiting at least X-ray lines (2-theta values) in a powder diffraction pattern when measured using Cu $K_\alpha$ radiation at 15.3±0.2, 21.4±0.2, and 25.1±0.2. One embodiment provides for a crystalline Form X of AP1189 nitrate further exhibiting one or more X-ray lines (2-theta values) in a powder diffraction pattern when measured using Cu $K_\alpha$ radiation selected from the group consisting of 11.9±0.2, 12.5±0.2, and 27.7±0.2. One embodiment of the present disclosure provides for a crystalline Form X of AP1189 nitrate further exhibiting one or more X-ray lines (2-theta values) in a powder diffraction pattern when measured using Cu $K_\alpha$ radiation selected from the group consisting of 3.7±0.2, 7.5±0.2, 14.7±0.2, 17.7±0.2, and 18.1±0.2. One embodiment of the disclosure provides for a crystalline Form X of AP1189 nitrate exhibiting an X-ray pattern (2-theta values) in a powder diffraction when measured using Cu $K_\alpha$ radiation according to FIG. 21.

One embodiment of the disclosure provides for a crystalline Form X of AP1189 nitrate exhibiting one or more X-ray lines (2-theta values) in a powder diffraction pattern when measured using Cu $K_\alpha$ radiation selected from the group consisting of 3.7, 7.5, 11.9, 12.5, 13.1, 14.7, 15.3, 16.9, 17.7, 18.1, 18.7, 19.6, 21.4, 23.0, 24.1, 25.1, 26.6, 27.7, 29.5, and 31.7. One embodiment of the disclosure provides for a crystalline Form X of AP1189 nitrate exhibiting one or more X-ray lines (2-theta values) in a powder diffraction pattern when measured using Cu $K_\alpha$ radiation selected from the group consisting of 3.7±0.2, 7.5±0.2, 11.9±0.2, 12.5±0.2, 13.1±0.2, 14.7±0.2, 15.3±0.2, 16.9±0.2, 17.7±0.2, 18.1±0.2, 18.7±0.2, 19.6±0.2, 21.4±0.2, 23.0±0.2, 24.1±0.2, 25.1±0.2, 26.6±0.2, 27.7±0.2, 29.5±0.2, and 31.7±0.2. It may be advantageous to identify the crystalline Form X of AP1189 nitrate by X-ray lines (2-theta values) having a high relative intensity, and/or by characteristic X-ray lines. Thus, one embodiment of the present disclosure provides for a crystalline Form X of AP1189 nitrate exhibiting one or more X-ray lines (2-theta values) in a powder diffraction pattern when measured using Cu $K_\alpha$ radiation selected from the group consisting of 3.7, 7.5, 11.9, 12.5, 14.7, 15.3, 17.7, 18.1, 21.4, 25.1, and 27.7. One embodiment of the present disclosure provides for a crystalline Form X of AP1189 nitrate exhibiting one or more X-ray lines (2-theta values) in a powder diffraction pattern when measured using Cu $K_\alpha$ radiation selected from the group consisting of 3.7±0.2, 7.5±0.2, 11.9±0.2, 12.5±0.2, 14.7±0.2, 15.3±0.2, 17.7±0.2, 18.1±0.2, 21.4±0.2, 25.1±0.2, and 27.7±0.2. One embodiment of the present disclosure provides for a crystalline Form X of AP1189 nitrate exhibiting one or more X-ray lines (2-theta values) in a powder diffraction pattern when measured using Cu $K_\alpha$ radiation selected from the group consisting of the 2-theta values in listed in Table 16.

AP1189 Cyclamate Form XI

Figure 22:
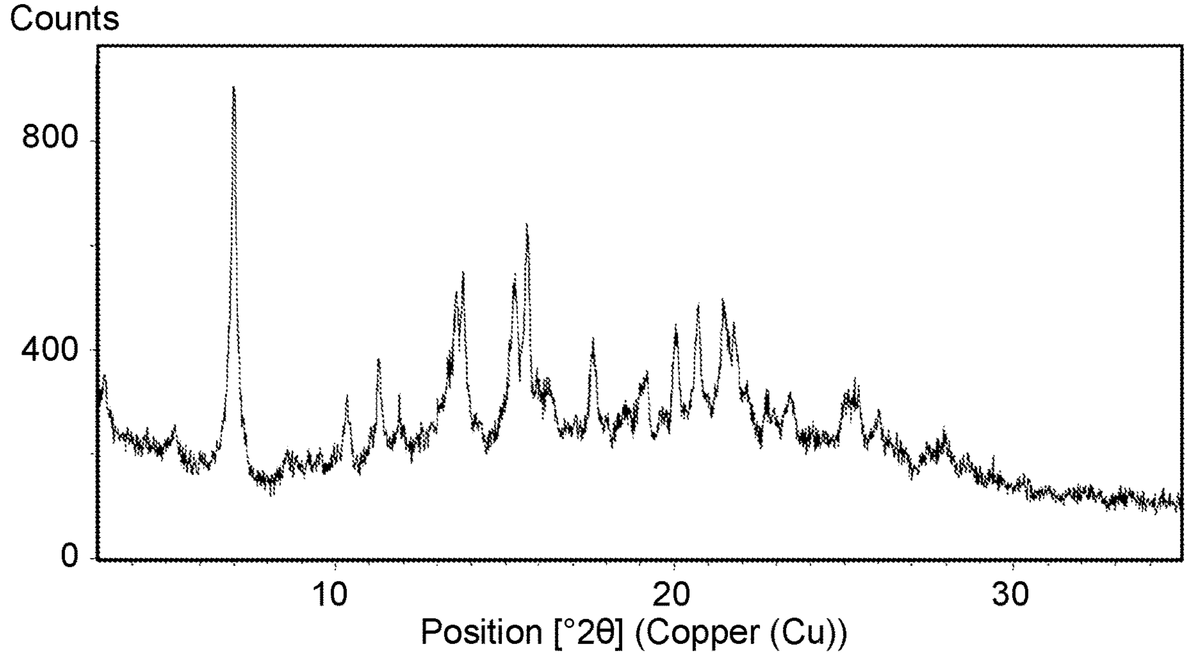
FIG. 22: XRPD Diffractogram of AP1189 Cyclamate Pattern 2.

The present disclosure provides for a crystalline Form XI of AP1189 cyclamate. Crystalline Form XI of AP1189 cyclamate exhibits an XRPD diffractogram as shown in FIG. 22. One embodiment of the present disclosure provides for a crystalline Form XI of AP1189 cyclamate exhibiting at least X-ray lines (2-theta values) in a powder diffraction pattern when measured using Cu $K_\alpha$ radiation at 7.0±0.2, 13.8±0.2, and 15.7±0.2. One embodiment provides for a crystalline Form XI of AP1189 cyclamate further exhibiting one or more X-ray lines (2-theta values) in a powder diffraction pattern when measured using Cu $K_\alpha$ radiation selected from the group consisting of 15.3±0.2, 20.7±0.2, and 21.5±0.2. One embodiment of the present disclosure provides for a crystalline Form XI of AP1189 cyclamate further exhibiting one or more X-ray lines (2-theta values) in a powder diffraction pattern when measured using Cu $K_\alpha$ radiation selected from the group consisting of 3.2±0.2, 11.3±0.2, and 21.8±0.2. One embodiment of the disclosure provides for a crystalline Form XI of AP1189 cyclamate exhibiting an X-ray pattern (2-theta values) in a powder diffraction when measured using Cu $K_\alpha$ radiation according to FIG. 22.

One embodiment of the disclosure provides for a crystalline Form XI of AP1189 cyclamate exhibiting one or more X-ray lines (2-theta values) in a powder diffraction pattern when measured using Cu $K_\alpha$ radiation selected from the group consisting of 3.2, 5.2, 7.0, 10.4, 11.3, 11.9, 13.8, 14.2, 15.3, 15.7, 16.3, 17.6, 18.5, 19.2, 20.1, 20.7, 21.5, 21.8, 22.1, 22.7, 23.4, 25.2, 26.0, and 27.8. One embodiment of the disclosure provides for a crystalline Form XI of AP1189 cyclamate exhibiting one or more X-ray lines (2-theta values) in a powder diffraction pattern when measured using Cu $K_\alpha$ radiation selected from the group consisting of 3.2±0.2, 5.2±0.2, 7.0±0.2, 10.4±0.2, 11.3±0.2, 11.9±0.2, 13.8±0.2, 14.2±0.2, 15.3±0.2, 15.7±0.2, 16.3±0.2, 17.6±0.2, 18.5±0.2, 19.2±0.2, 20.1±0.2, 20.7±0.2, 21.5±0.2, 21.8±0.2, 22.1±0.2, 22.7±0.2, 23.4±0.2, 25.2±0.2, 26.0±0.2, and 27.8±0.2. It may be advantageous to identify the crystalline Form XI of AP1189 cyclamate by X-ray lines (2-theta values) having a high relative intensity, and/or by characteristic X-ray lines. Thus, one embodiment of the present disclosure provides for a crystalline Form XI of AP1189 cyclamate exhibiting one or more X-ray lines (2-theta values) in a powder diffraction pattern when measured using Cu $K_\alpha$ radiation selected from the group consisting of 3.2, 7.0, 11.3, 13.8, 15.3, 15.7, 20.7, 21.5, and 21.8. One embodiment of the present disclosure provides for a crystalline Form XI of AP1189 cyclamate exhibiting one or more X-ray lines (2-theta values) in a powder diffraction pattern when measured using Cu $K_\alpha$ radiation selected from the group consisting of 3.2±0.2, 7.0±0.2, 11.3±0.2, 13.8±0.2, 15.3±0.2, 15.7±0.2, 20.7±0.2, 21.5±0.2, and 21.8±0.2. One embodiment of the present disclosure provides for a crystalline Form XI of AP1189 cyclamate exhibiting one or more X-ray lines (2-theta values) in a powder diffraction pattern when measured using Cu $K_\alpha$ radiation selected from the group consisting of the 2-theta values in listed in Table 17.

AP1189 Cyclamate Form XII

Figure 23:
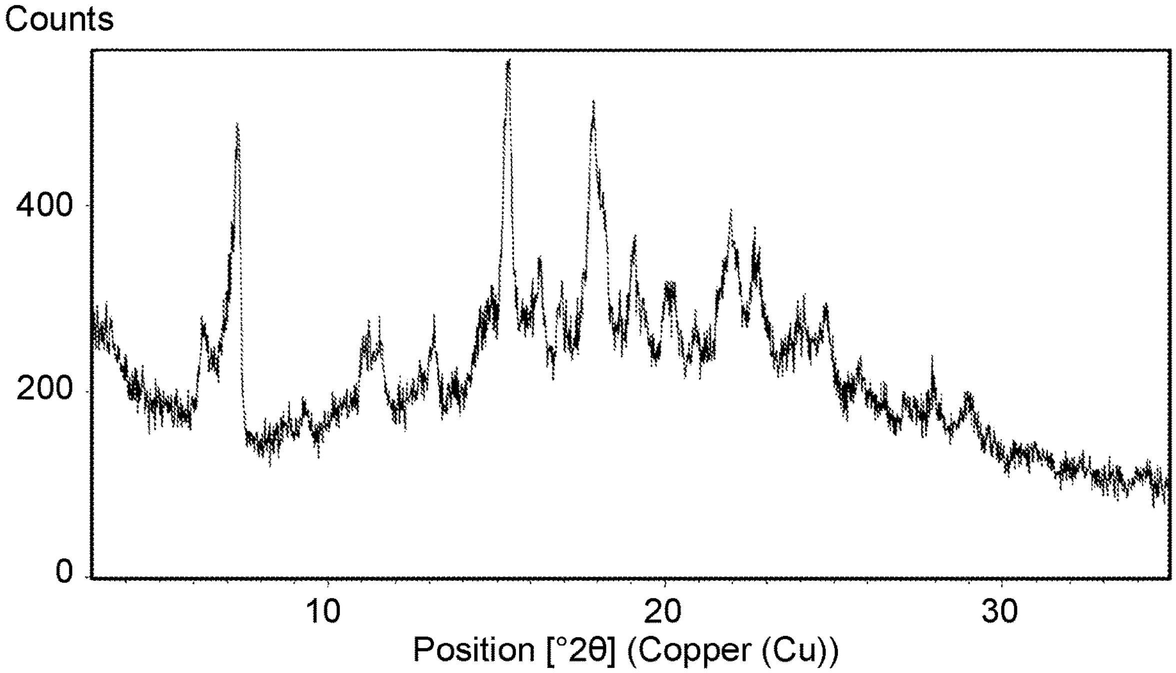
FIG. 23: XRPD Diffractogram of AP1189 Cyclamate Pattern 4.

The present disclosure provides for a crystalline Form XII of AP1189 cyclamate. Crystalline Form XII of AP1189 cyclamate exhibits an XRPD diffractogram as shown in FIG. 23. One embodiment of the present disclosure provides for a crystalline Form XII of AP1189 cyclamate exhibiting at least X-ray lines (2-theta values) in a powder diffraction pattern when measured using Cu $K_\alpha$ radiation at 7.3±0.2, 15.3±0.2, and 17.9±0.2. One embodiment provides for a crystalline Form XII of AP1189 cyclamate further exhibiting one or more X-ray lines (2-theta values) in a powder diffraction pattern when measured using Cu $K_\alpha$ radiation selected from the group consisting of 16.3±0.2, 19.1±0.2, 22.0 0.2, and 22.7±0.2. One embodiment of the present disclosure provides for a crystalline Form XII of AP1189 cyclamate further exhibiting one or more X-ray lines (2-theta values) in a powder diffraction pattern when measured using Cu $K_\alpha$ radiation selected from the group consisting of 11.3±0.2, 13.1±0.2, and 16.9±0.2. One embodiment of the disclosure provides for a crystalline Form XII of AP1189 cyclamate exhibiting an X-ray pattern (2-theta values) in a powder diffraction when measured using Cu $K_\alpha$ radiation according to FIG. 23.

One embodiment of the disclosure provides for a crystalline Form XII of AP1189 cyclamate exhibiting one or more X-ray lines (2-theta values) in a powder diffraction pattern when measured using Cu $K_\alpha$ radiation selected from the group consisting of 6.3, 7.3, 9.3, 11.3, 12.7, 13.1, 14.8, 15.3, 16.3, 16.9, 17.9, 19.1, 19.3, 20.1, 22.0, 22.7, 24.1, 24.8, 25.8, 27.1, 28.0, and 29.0. One embodiment of the disclosure provides for a crystalline Form XII of AP1189 cyclamate exhibiting one or more X-ray lines (2-theta values) in a powder diffraction pattern when measured using Cu $K_\alpha$ radiation selected from the group consisting of 6.3±0.2, 7.3±0.2, 9.3±0.2, 11.3±0.2, 12.7±0.2, 13.1±0.2, 14.8±0.2, 15.3±0.2, 16.3±0.2, 16.9±0.2, 17.9±0.2, 19.1±0.2, 19.3±0.2, 20.1±0.2, 22.0±0.2, 22.7±0.2, 24.1±0.2, 24.8±0.2, 25.8±0.2, 27.1±0.2, 28.0±0.2, and 29.0±0.2. It may be advantageous to identify the crystalline Form XII of AP1189 cyclamate by X-ray lines (2-theta values) having a high relative intensity, and/or by characteristic X-ray lines. Thus, one embodiment of the present disclosure provides for a crystalline Form XII of AP1189 cyclamate exhibiting one or more X-ray lines (2-theta values) in a powder diffraction pattern when measured using Cu $K_\alpha$ radiation selected from the group consisting of 7.3, 11.3, 13.1, 14.3, 16.3, 16.9, 17.9, 19.1, 22.0, and 22.7. One embodiment of the present disclosure provides for a crystalline Form XII of AP1189 cyclamate exhibiting one or more X-ray lines (2-theta values) in a powder diffraction pattern when measured using Cu $K_\alpha$ radiation selected from the group consisting of 7.3±0.2, 11.3±0.2, 13.1±0.2, 14.3±0.2, 16.3±0.2, 16.9±0.2, 17.9±0.2, 19.1±0.2, 22.0±0.2, and 22.7±0.2. One embodiment of the present disclosure provides for a crystalline Form XII of AP1189 cyclamate exhibiting one or more X-ray lines (2-theta values) in a powder diffraction pattern when measured using Cu $K_\alpha$ radiation selected from the group consisting of the 2-theta values in listed in Table 18.

AP1189 Cyclamate Form XIII

Figure 24:
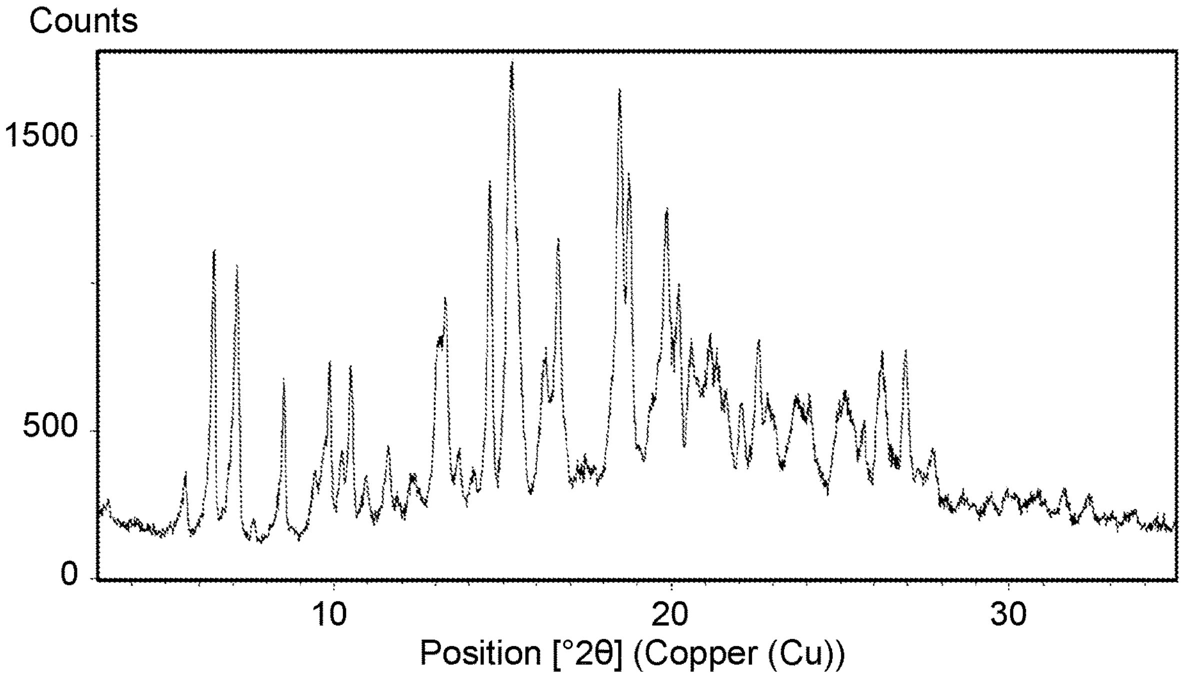
FIG. 24: XRPD Diffractogram of AP1189 Cyclamate Pattern 5.

The present disclosure provides for a crystalline Form XIII of AP1189 cyclamate. Crystalline Form XIII of AP1189 cyclamate exhibits an XRPD diffractogram as shown in FIG. 24. One embodiment of the present disclosure provides for a crystalline Form XIII of AP1189 cyclamate exhibiting at least X-ray lines (2-theta values) in a powder diffraction pattern when measured using Cu $K_\alpha$ radiation at 15.3±0.2, 18.5±0.2, and 18.7±0.2. One embodiment provides for a crystalline Form XIII of AP1189 cyclamate further exhibiting one or more X-ray lines (2-theta values) in a powder diffraction pattern when measured using Cu $K_\alpha$ radiation selected from the group consisting of 6.4±0.2, 14.6±0.2, 16.7±0.2, and 19.8±0.2. One embodiment of the present disclosure provides for a crystalline Form XIII of AP1189 cyclamate further exhibiting one or more X-ray lines (2-theta values) in a powder diffraction pattern when measured using Cu $K_\alpha$ radiation selected from the group consisting of 5.6±0.2, 7.1±0.2, 8.5±0.2, 10.5±0.2, 13.1±0.2, and 16.2±0.2. One embodiment of the disclosure provides for a crystalline Form XIII of AP1189 cyclamate exhibiting an X-ray pattern (2-theta values) in a powder diffraction when measured using Cu $K_\alpha$ radiation according to FIG. 24.

One embodiment of the disclosure provides for a crystalline Form XIII of AP1189 cyclamate exhibiting one or more X-ray lines (2-theta values) in a powder diffraction pattern when measured using Cu $K_\alpha$ radiation selected from the group consisting of 3.3, 5.6, 6.4, 7.1, 7.6, 8.5, 9.4, 9.9, 10.2, 10.5, 10.9, 11.6, 11.9, 12.3, 13.1, 13.3, 13.7, 14.1, 14.6, 15.3, 16.2, 16.7, 17.5, 18.5, 18.7, 19.8, 20.2, 20.6, 21.1, 21.1, 21.3, 21.7, 22.1, 22.6, 22.8, 23.7, 24.1, 24.9, 25.1, 25.7, 26.2, 27.0, 27.7, 28.7, 29.4, 30.0, 30.8, 31.6, 32.4, and 33.6. One embodiment of the disclosure provides for a crystalline Form XIII of AP1189 cyclamate exhibiting one or more X-ray lines (2-theta values) in a powder diffraction pattern when measured using Cu $K_\alpha$ radiation selected from the group consisting of 3.3±0.2, 5.6±0.2, 6.4±0.2, 7.1±0.2, 7.6±0.2, 8.5±0.2, 9.4±0.2, 9.9±0.2, 10.2±0.2, 10.5±0.2, 10.9±0.2, 11.6±0.2, 11.9±0.2, 12.3±0.2, 13.1±0.2, 13.3±0.2, 13.7±0.2, 14.1±0.2, 14.6±0.2, 15.3±0.2, 16.2±0.2, 16.7±0.2, 17.5±0.2, 18.5±0.2, 18.7±0.2, 19.8±0.2, 20.2±0.2, 20.6±0.2, 21.1±0.2, 21.1±0.2, 21.3±0.2, 21.7±0.2, 22.1±0.2, 22.6±0.2, 22.8±0.2, 23.7±0.2, 24.1±0.2, 24.9±0.2, 25.1±0.2, 25.7±0.2, 26.2±0.2, 27.0±0.2, 27.7±0.2, 28.7±0.2, 29.4±0.2, 30.0±0.2, 30.8±0.2, 31.6±0.2, 32.4±0.2, and 33.6±0.2. It may be advantageous to identify the crystalline Form XIII of AP1189 cyclamate by X-ray lines (2-theta values) having a high relative intensity, and/or by characteristic X-ray lines. Thus, one embodiment of the present disclosure provides for a crystalline Form XIII of AP1189 cyclamate exhibiting one or more X-ray lines (2-theta values) in a powder diffraction pattern when measured using Cu $K_\alpha$ radiation selected from the group consisting of 5.6, 6.4, 7.1, 8.5, 10.5, 13.1, 14.6, 15.3, 16.2, 16.7, 18.5, 18.7, 19.8, 26.2, and 27.0. One embodiment of the present disclosure provides for a crystalline Form XIII of AP1189 cyclamate exhibiting one or more X-ray lines (2-theta values) in a powder diffraction pattern when measured using Cu $K_\alpha$ radiation selected from the group consisting of 5.6±0.2, 6.4±0.2, 7.1±0.2, 8.5±0.2, 10.5±0.2, 13.1±0.2, 14.6±0.2, 15.3±0.2, 16.2±0.2, 16.7±0.2, 18.5±0.2, 18.7±0.2, 19.8±0.2, 26.2±0.2, and 27.0±0.2. One embodiment of the present disclosure provides for a crystalline Form XIII of AP1189 cyclamate exhibiting one or more X-ray lines (2-theta values) in a powder diffraction pattern when measured using Cu $K_\alpha$ radiation selected from the group consisting of the 2-theta values in listed in Table 19.

AP1189 Besylate Form XIV

Figure 25:
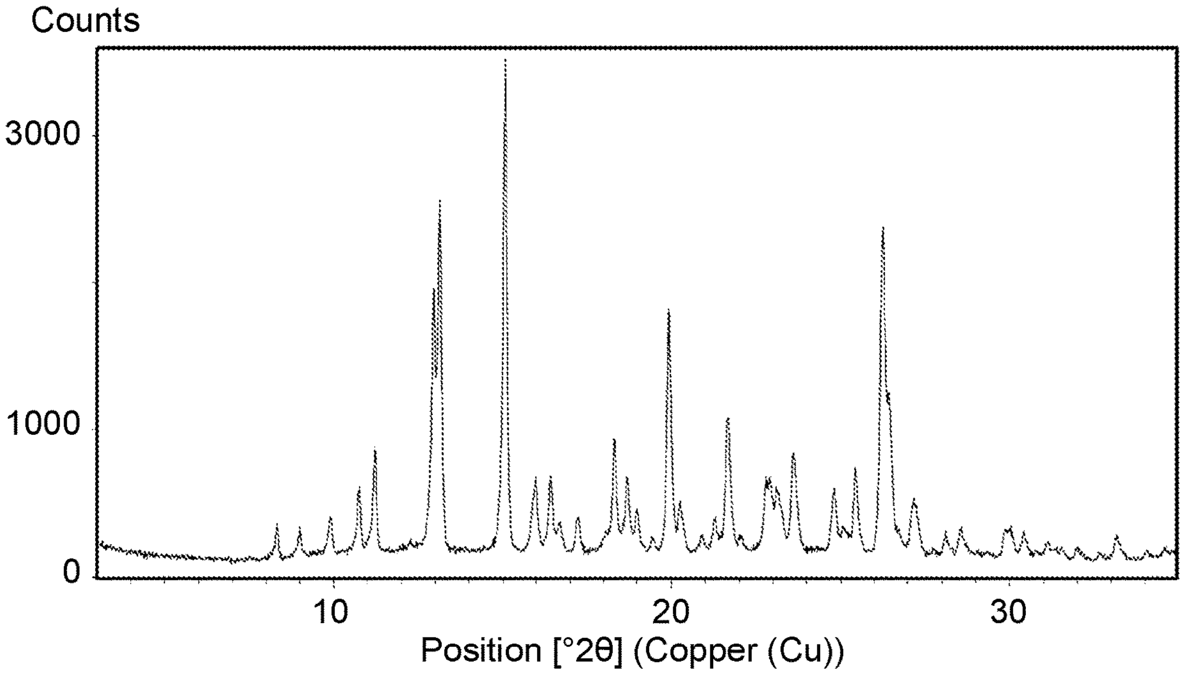
FIG. 25: XRPD Diffractogram of AP1189 Besylate Pattern 1.

The present disclosure provides for a crystalline Form XIV of AP1189 besylate. Crystalline Form XIV of AP1189 besylate exhibits an XRPD diffractogram as shown in FIG. 25. One embodiment of the present disclosure provides for a crystalline Form XIV of AP1189 besylate exhibiting at least X-ray lines (2-theta values) in a powder diffraction pattern when measured using Cu $K_\alpha$ radiation at 13.0±0.2, 15.1±0.2, and 19.9±0.2. One embodiment provides for a crystalline Form XIV of AP1189 besylate further exhibiting one or more X-ray lines (2-theta values) in a powder diffraction pattern when measured using Cu $K_\alpha$ radiation selected from the group consisting of 11.2±0.2 and 18.3±0.2. One embodiment of the present disclosure provides for a crystalline Form XIV of AP1189 besylate further exhibiting one or more X-ray lines (2-theta values) in a powder diffraction pattern when measured using Cu $K_\alpha$ radiation selected from the group consisting of 8.3±0.2, 9.0 0.2, 16.4±0.2, and 18.7±0.2. One embodiment of the disclosure provides for a crystalline Form XIV of AP1189 besylate exhibiting an X-ray pattern (2-theta values) in a powder diffraction when measured using Cu $K_\alpha$ radiation according to FIG. 25.

One embodiment of the disclosure provides for a crystalline Form XIV of AP1189 besylate exhibiting one or more X-ray lines (2-theta values) in a powder diffraction pattern when measured using Cu $K_\alpha$ radiation selected from the group consisting of 3.2, 8.3, 9.0, 9.9, 10.8, 11.2, 13.0, 13.1, 15.1, 16.0, 16.4, 16.7, 17.3, 18.1, 18.3, 18.7, 19.0, 19.4, 19.9, 20.3, 20.9, 21.3, 21.7, 22.0, 22.8, 23.1, 23.6, 24.8, 25.1, 25.4, 26.3, 26.5, 27.1, 28.1, 28.5, 29.8, 30.4, 31.1, 32.0, 33.2, and 34.1. One embodiment of the disclosure provides for a crystalline Form XIV of AP1189 besylate exhibiting one or more X-ray lines (2-theta values) in a powder diffraction pattern when measured using Cu $K_\alpha$ radiation selected from the group consisting of 3.2±0.2, 8.3±0.2, 9.0±0.2, 9.9±0.2, 10.8±0.2, 11.2±0.2, 13.0±0.2, 13.1±0.2, 15.1±0.2, 16.0±0.2, 16.4±0.2, 16.7±0.2, 17.3±0.2, 18.1±0.2, 18.3±0.2, 18.7±0.2, 19.0±0.2, 19.4±0.2, 19.9±0.2, 20.3±0.2, 20.9±0.2, 21.3±0.2, 21.7±0.2, 22.0±0.2, 22.8±0.2, 23.1±0.2, 23.6±0.2, 24.8±0.2, 25.1±0.2, 25.4±0.2, 26.3±0.2, 26.5±0.2, 27.1±0.2, 28.1±0.2, 28.5±0.2, 29.8±0.2, 30.4±0.2, 31.1±0.2, 32.0±0.2, 33.2±0.2, and 34.1±0.2. It may be advantageous to identify the crystalline Form XIV of AP1189 besylate by X-ray lines (2-theta values) having a high relative intensity, and/or by characteristic X-ray lines. Thus, one embodiment of the present disclosure provides for a crystalline Form XIV of AP1189 besylate exhibiting one or more X-ray lines (2-theta values) in a powder diffraction pattern when measured using Cu $K_\alpha$ radiation selected from the group consisting of 8.3, 9.0, 11.2, 13.0, 15.1, 16.4, 18.3, 18.7, and 19.9. One embodiment of the present disclosure provides for a crystalline Form XIV of AP1189 besylate exhibiting one or more X-ray lines (2-theta values) in a powder diffraction pattern when measured using Cu $K_\alpha$ radiation selected from the group consisting of 8.3±0.2, 9.0±0.2, 11.2±0.2, 13.0±0.2, 15.1±0.2, 16.4±0.2, 18.3±0.2, 18.7±0.2, and 19.9±0.2. One embodiment of the present disclosure provides for a crystalline Form XIV of AP1189 besylate exhibiting one or more X-ray lines (2-theta values) in a powder diffraction pattern when measured using Cu $K_\alpha$ radiation selected from the group consisting of the 2-theta values in listed in Table 20.

AP1189 Oxalate Form XV

Figure 26:
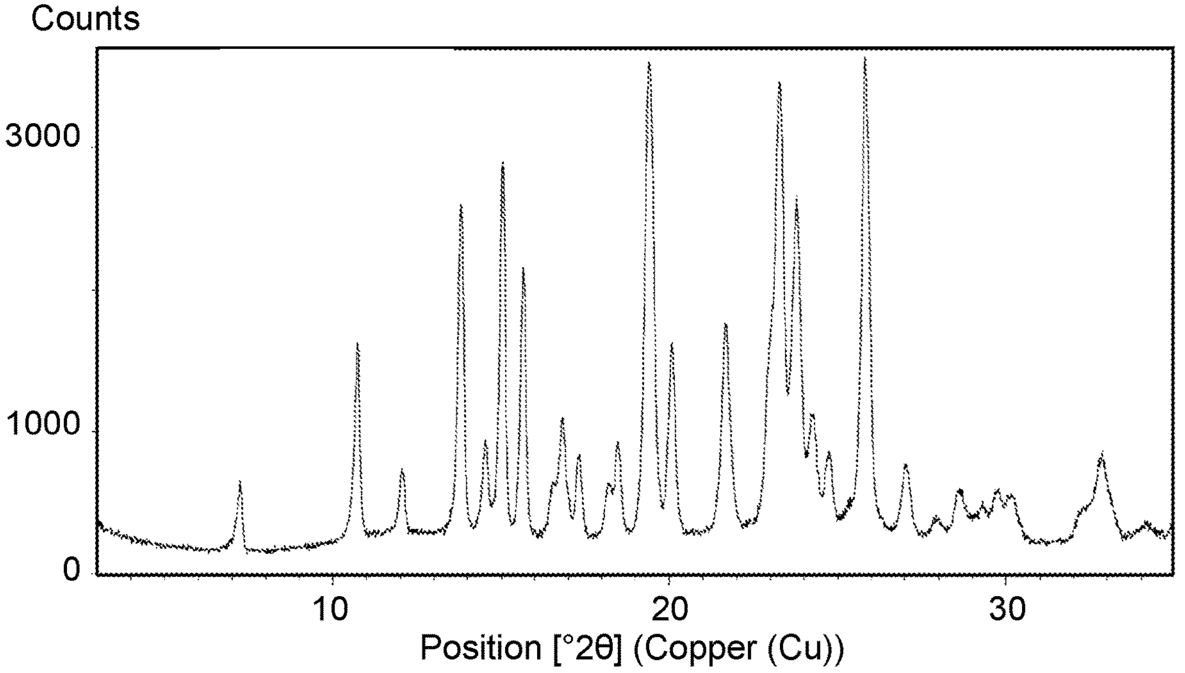
FIG. 26: XRPD Diffractogram of AP1189 Oxalate Pattern 1.

The present disclosure provides for a crystalline Form XV of AP1189 oxalate. Crystalline Form XV of AP1189 oxalate exhibits an XRPD diffractogram as shown in FIG. 26. One embodiment of the present disclosure provides for a crystalline Form XV of AP1189 oxalate exhibiting at least X-ray lines (2-theta values) in a powder diffraction pattern when measured using Cu $K_\alpha$ radiation at 19.5±0.2, 23.3±0.2, and 25.8±0.2. One embodiment provides for a crystalline Form XV of AP1189 oxalate further exhibiting one or more X-ray lines (2-theta values) in a powder diffraction pattern when measured using Cu $K_\alpha$ radiation selected from the group consisting of 13.9±0.2, 15.6±0.2, and 23.8±0.2. One embodiment of the present disclosure provides for a crystalline Form XV of AP1189 oxalate further exhibiting one or more X-ray lines (2-theta values) in a powder diffraction pattern when measured using Cu $K_\alpha$ radiation selected from the group consisting of 7.2±0.2, 10.8±0.2, and 21.7±0.2. One embodiment of the disclosure provides for a crystalline Form XV of AP1189 oxalate exhibiting an X-ray pattern (2-theta values) in a powder diffraction when measured using Cu $K_\alpha$ radiation according to FIG. 26.

One embodiment of the disclosure provides for a crystalline Form XV of AP1189 oxalate exhibiting one or more X-ray lines (2-theta values) in a powder diffraction pattern when measured using Cu $K_\alpha$ radiation selected from the group consisting of 7.2, 10.8, 12.1, 13.9, 14.5, 15.0, 15.6, 16.5, 16.8, 17.3, 18.2, 18.5, 19.5, 20.1, 21.7, 22.9, 23.3, 23.8, 24.3, 24.8, 25.8, 27.0, 27.9, 28.6, 29.3, 29.7, 30.2, 32.2, and 32.9. One embodiment of the disclosure provides for a crystalline Form XV of AP1189 oxalate exhibiting one or more X-ray lines (2-theta values) in a powder diffraction pattern when measured using Cu $K_\alpha$ radiation selected from the group consisting of 7.2±0.2, 10.8±0.2, 12.1±0.2, 13.9±0.2, 14.5±0.2, 15.0±0.2, 15.6±0.2, 16.5±0.2, 16.8±0.2, 17.3±0.2, 18.2±0.2, 18.5±0.2, 19.5±0.2, 20.1±0.2, 21.7±0.2, 22.9±0.2, 23.3±0.2, 23.8±0.2, 24.3±0.2, 24.8±0.2, 25.8±0.2, 27.0±0.2, 27.9±0.2, 28.6±0.2, 29.3±0.2, 29.7±0.2, 30.2±0.2, 32.2±0.2, and 32.9±0.2. It may be advantageous to identify the crystalline Form XV of AP1189 oxalate by X-ray lines (2-theta values) having a high relative intensity, and/or by characteristic X-ray lines. Thus, one embodiment of the present disclosure provides for a crystalline Form XV of AP1189 oxalate exhibiting one or more X-ray lines (2-theta values) in a powder diffraction pattern when measured using Cu $K_\alpha$ radiation selected from the group consisting of 7.2, 10.8, 13.9, 15.6, 19.5, 21.7, 23.3, 23.8, and 25.8. One embodiment of the present disclosure provides for a crystalline Form XV of AP1189 oxalate exhibiting one or more X-ray lines (2-theta values) in a powder diffraction pattern when measured using Cu $K_\alpha$ radiation selected from the group consisting of 7.2±0.2, 10.8±0.2, 13.9±0.2, 15.6±0.2, 19.5±0.2, 21.7±0.2, 23.3±0.2, 23.8±0.2, and 25.8±0.2. One embodiment of the present disclosure provides for a crystalline Form XV of AP1189 oxalate exhibiting one or more X-ray lines (2-theta values) in a powder diffraction pattern when measured using Cu $K_\alpha$ radiation selected from the group consisting of the 2-theta values in listed in Table 21.

AP1189 Oxalate Form XVI

Figure 27:
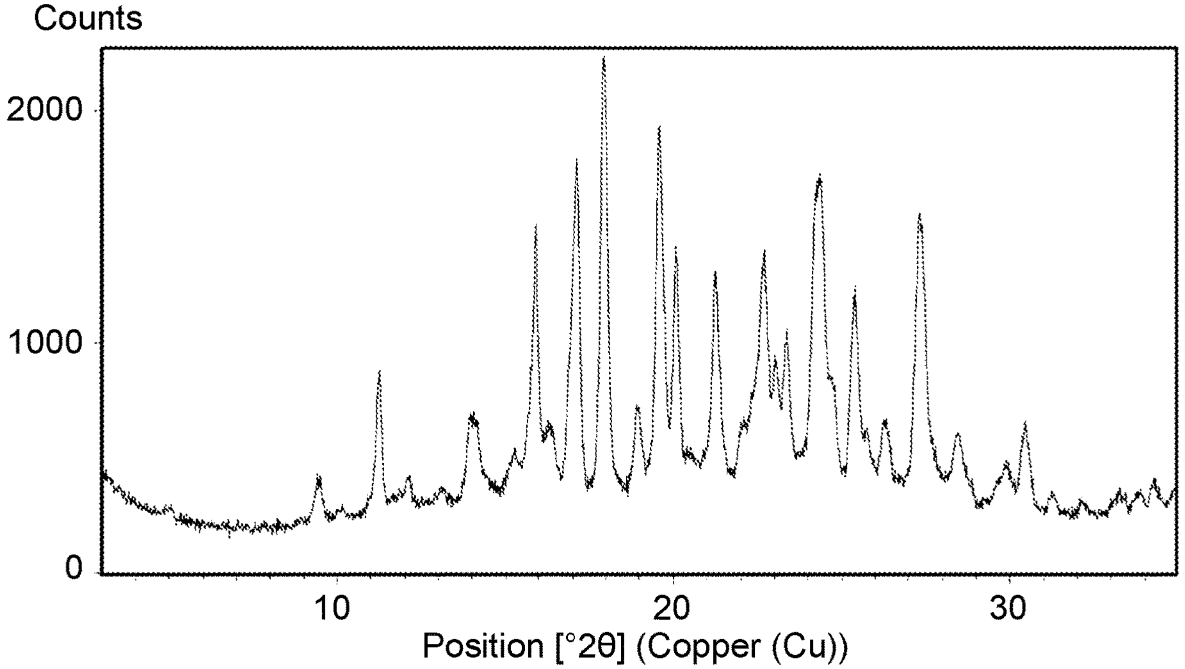
FIG. 27: XRPD Diffractogram of AP1189 Oxalate Pattern 2.

The present disclosure provides for a crystalline Form XVI of AP1189 oxalate. Crystalline Form XVI of AP1189 oxalate exhibits an XRPD diffractogram as shown in FIG. 27. One embodiment of the present disclosure provides for a crystalline Form XVI of AP1189 oxalate exhibiting at least X-ray lines (2-theta values) in a powder diffraction pattern when measured using Cu $K_\alpha$ radiation at 17.1±0.2, 17.9±0.2, and 19.6±0.2. One embodiment provides for a crystalline Form XVI of AP1189 oxalate further exhibiting one or more X-ray lines (2-theta values) in a powder diffraction pattern when measured using Cu $K_\alpha$ radiation selected from the group consisting of 15.9±0.2, 24.2±0.2, 24.4±0.2, and 27.3±0.2. One embodiment of the present disclosure provides for a crystalline Form XVI of AP1189 oxalate further exhibiting one or more X-ray lines (2-theta values) in a powder diffraction pattern when measured using Cu $K_\alpha$ radiation selected from the group consisting of 9.5±0.2, 11.3±0.2, 21.2±0.2, and 25.4±0.2. One embodiment of the disclosure provides for a crystalline Form XVI of AP1189 oxalate exhibiting an X-ray pattern (2-theta values) in a powder diffraction when measured using Cu $K_\alpha$ radiation according to FIG. 27.

One embodiment of the disclosure provides for a crystalline Form XVI of AP1189 oxalate exhibiting one or more X-ray lines (2-theta values) in a powder diffraction pattern when measured using Cu $K_\alpha$ radiation selected from the group consisting of 9.5, 11.3, 12.1, 13.1, 14.0, 15.3, 15.9, 16.4, 17.1, 17.9, 18.9, 19.6, 20.0, 21.2, 22.0, 22.7, 23.0, 23.4, 24.2, 24.4, 24.8, 25.4, 25.7, 26.3, 27.3, 28.4, 29.9, 30.4, 31.3, 32.2, 33.3, 33.9, 34.3, and 34.9. One embodiment of the disclosure provides for a crystalline Form XVI of AP1189 oxalate exhibiting one or more X-ray lines (2-theta values) in a powder diffraction pattern when measured using Cu $K_\alpha$ radiation selected from the group consisting of 9.5±0.2, 11.3±0.2, 12.1±0.2, 13.1±0.2, 14.0±0.2, 15.3±0.2, 15.9±0.2, 16.4±0.2, 17.1±0.2, 17.9±0.2, 18.9±0.2, 19.6±0.2, 20.0±0.2, 21.2±0.2, 22.0±0.2, 22.7±0.2, 23.0±0.2, 23.4±0.2, 24.2±0.2, 24.4±0.2, 24.8±0.2, 25.4±0.2, 25.7±0.2, 26.3±0.2, 27.3±0.2, 28.4±0.2, 29.9±0.2, 30.4±0.2, 31.3±0.2, 32.2±0.2, 33.3±0.2, 33.9±0.2, 34.3±0.2, and 34.9±0.2. It may be advantageous to identify the crystalline Form XVI of AP1189 oxalate by X-ray lines (2-theta values) having a high relative intensity, and/or by characteristic X-ray lines. Thus, one embodiment of the present disclosure provides for a crystalline Form XVI of AP1189 oxalate exhibiting one or more X-ray lines (2-theta values) in a powder diffraction pattern when measured using Cu $K_\alpha$ radiation selected from the group consisting of 9.5, 11.3, 15.9, 17.1, 17.9, 19.6, 21.2, 24.2, 24.4, 25.4, and 27.3. One embodiment of the present disclosure provides for a crystalline Form XVI of AP1189 oxalate exhibiting one or more X-ray lines (2-theta values) in a powder diffraction pattern when measured using Cu $K_\alpha$ radiation selected from the group consisting of 9.5±0.2, 11.3±0.2, 15.9±0.2, 17.1±0.2, 17.9±0.2, 19.6±0.2, 21.2±0.2, 24.2±0.2, 24.4±0.2, 25.4±0.2, and 27.3±0.2. One embodiment of the present disclosure provides for a crystalline Form XVI of AP1189 oxalate exhibiting one or more X-ray lines (2-theta values) in a powder diffraction pattern when measured using Cu $K_\alpha$ radiation selected from the group consisting of the 2-theta values in listed in Table 22.

AP1189 Oxalate Form XVII

Figure 28:
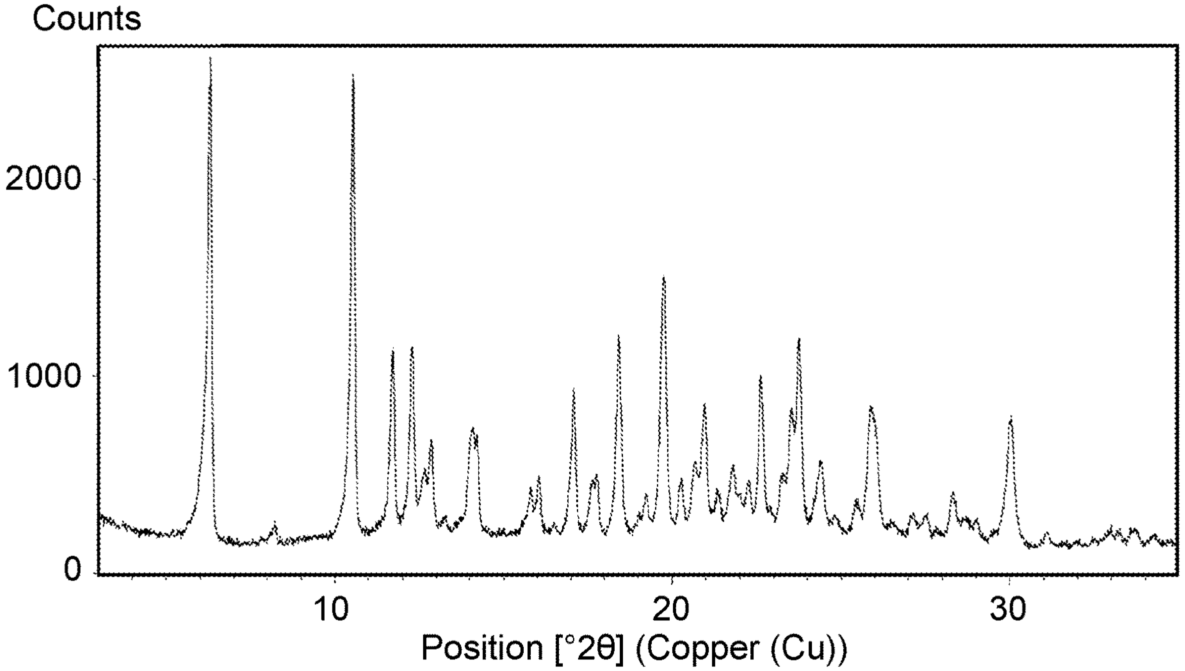
FIG. 28: XRPD Diffractogram of AP1189 Oxalate Pattern 4.

The present disclosure provides for a crystalline Form XVII of AP1189 oxalate. Crystalline Form XVII of AP1189 oxalate exhibits an XRPD diffractogram as shown in FIG. 28. One embodiment of the present disclosure provides for a crystalline Form XVII of AP1189 oxalate exhibiting at least X-ray lines (2-theta values) in a powder diffraction pattern when measured using Cu $K_\alpha$ radiation at 6.3±0.2, 10.6±0.2, and 19.8±0.2. One embodiment provides for a crystalline Form XVII of AP1189 oxalate further exhibiting one or more X-ray lines (2-theta values) in a powder diffraction pattern when measured using Cu $K_\alpha$ radiation selected from the group consisting of 11.7±0.2, 12.3±0.2, 18.4±0.2, and 23.8±0.2. One embodiment of the present disclosure provides for a crystalline Form XVII of AP1189 oxalate further exhibiting one or more X-ray lines (2-theta values) in a powder diffraction pattern when measured using Cu $K_\alpha$ radiation selected from the group consisting of 14.1±0.2, 23.5±0.2, and 30.0±0.2. One embodiment of the disclosure provides for a crystalline Form XVII of AP1189 oxalate exhibiting an X-ray pattern (2-theta values) in a powder diffraction when measured using Cu $K_\alpha$ radiation according to FIG. 28.

One embodiment of the disclosure provides for a crystalline Form XVII of AP1189 oxalate exhibiting one or more X-ray lines (2-theta values) in a powder diffraction pattern when measured using Cu $K_\alpha$ radiation selected from the group consisting of 6.3, 8.2, 10.6, 11.7, 12.3, 12.6, 12.9, 13.2, 14.1, 14.2, 15.8, 16.1, 17.1, 17.8, 18.4, 19.0, 19.2, 19.8, 20.3, 20.7, 21.0, 21.4, 21.8, 22.0, 22.3, 22.6, 23.2, 23.5, 23.8, 24.4, 24.8, 25.4, 25.9, 26.1, 26.6, 27.1, 27.5, 27.8, 28.3, 28.7, 29.0, 30.0, 31.1, 33.0, 33.7, and 34.3. One embodiment of the disclosure provides for a crystalline Form XVII of AP1189 oxalate exhibiting one or more X-ray lines (2-theta values) in a powder diffraction pattern when measured using Cu $K_\alpha$ radiation selected from the group consisting of 6.3±0.2, 8.2±0.2, 10.6±0.2, 11.7±0.2, 12.3±0.2, 12.6±0.2, 12.9±0.2, 13.2±0.2, 14.1±0.2, 14.2±0.2, 15.8±0.2, 16.1±0.2, 17.1±0.2, 17.8±0.2, 18.4±0.2, 19.0±0.2, 19.2±0.2, 19.8±0.2, 20.3±0.2, 20.7±0.2, 21.0±0.2, 21.4±0.2, 21.8±0.2, 22.0±0.2, 22.3±0.2, 22.6±0.2, 23.2±0.2, 23.5±0.2, 23.8±0.2, 24.4±0.2, 24.8±0.2, 25.4±0.2, 25.9±0.2, 26.1±0.2, 26.6±0.2, 27.1±0.2, 27.5±0.2, 27.8±0.2, 28.3±0.2, 28.7±0.2, 29.0±0.2, 30.0±0.2, 31.1±0.2, 33.0±0.2, 33.7±0.2, and 34.3±0.2. It may be advantageous to identify the crystalline Form XVII of AP1189 oxalate by X-ray lines (2-theta values) having a high relative intensity, and/or by characteristic X-ray lines. Thus, one embodiment of the present disclosure provides for a crystalline Form XVII of AP1189 oxalate exhibiting one or more X-ray lines (2-theta values) in a powder diffraction pattern when measured using Cu $K_\alpha$ radiation selected from the group consisting of 6.3, 10.6, 11.7, 12.3, 14.1, 18.4, 19.8, 23.5, 23.8, and 30.0. One embodiment of the present disclosure provides for a crystalline Form XVII of AP1189 oxalate exhibiting one or more X-ray lines (2-theta values) in a powder diffraction pattern when measured using Cu $K_\alpha$ radiation selected from the group consisting of 6.3±0.2, 10.6±0.2, 11.7±0.2, 12.3±0.2, 14.1±0.2, 18.4±0.2, 19.8±0.2, 23.5±0.2, 23.8±0.2, and 30.0±0.2. One embodiment of the present disclosure provides for a crystalline Form XVII of AP1189 oxalate exhibiting one or more X-ray lines (2-theta values) in a powder diffraction pattern when measured using Cu $K_\alpha$ radiation selected from the group consisting of the 2-theta values in listed in Table 23.

AP1189 (+)-Camphor-10-Sulfonic Acid Form XVIII

Figure 29:
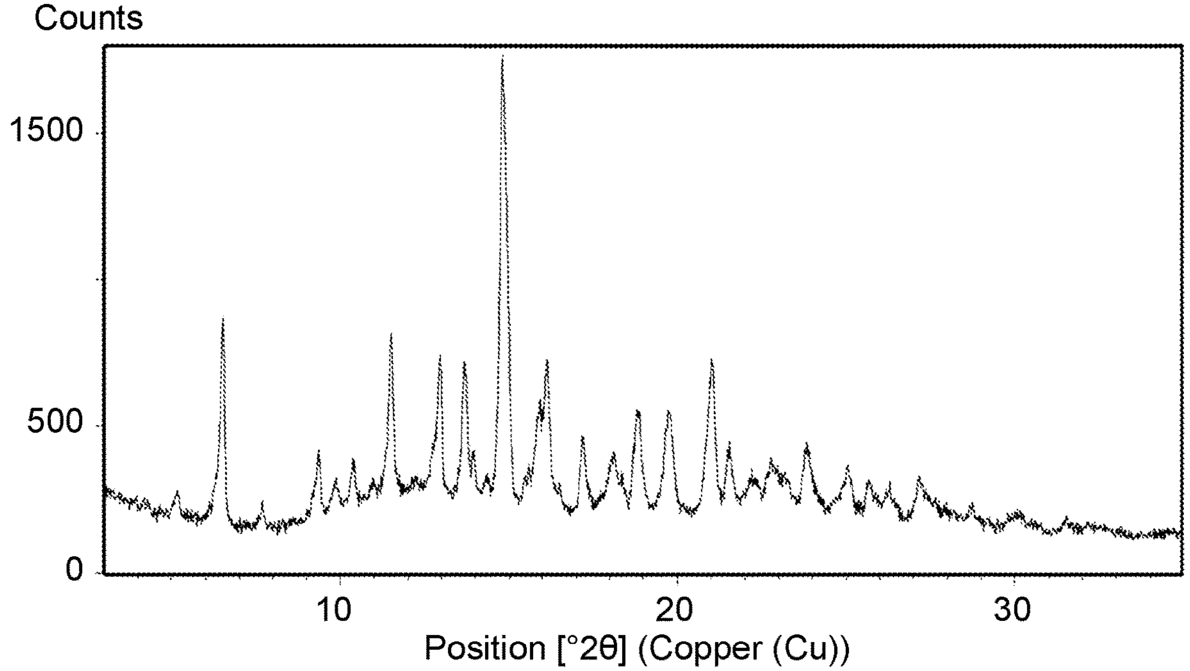
FIG. 29: XRPD Diffractogram of AP1189 (+)-Camphor-10-sulfonic acid Pattern 1.

The present disclosure provides for a crystalline Form XVIII of AP1189 (+)-camphor-10-sulfonic acid. Crystalline Form XVIII of AP1189 (+)-camphor-10-sulfonic acid exhibits an XRPD diffractogram as shown in FIG. 29. One embodiment of the present disclosure provides for a crystalline Form XVIII of AP1189 (+)-camphor-10-sulfonic acid exhibiting at least X-ray lines (2-theta values) in a powder diffraction pattern when measured using Cu $K_\alpha$ radiation at 6.5±0.2, 11.5±0.2, and 14.8±0.2. One embodiment provides for a crystalline Form XVIII of AP1189 (+)-camphor-10-sulfonic acid further exhibiting one or more X-ray lines (2-theta values) in a powder diffraction pattern when measured using Cu $K_\alpha$ radiation selected from the group consisting of 13.0±0.2, 13.7±0.2, 16.1±0.2, and 21.1±0.2. One embodiment of the present disclosure provides for a crystalline Form XVIII of AP1189 (+)-camphor-10-sulfonic acid further exhibiting one or more X-ray lines (2-theta values) in a powder diffraction pattern when measured using Cu $K_\alpha$ radiation selected from the group consisting of 15.9±0.2, 18.8±0.2, and 19.8±0.2. One embodiment of the disclosure provides for a crystalline Form XVIII of AP1189 (+)-camphor-10-sulfonic acid exhibiting an X-ray pattern (2-theta values) in a powder diffraction when measured using Cu $K_\alpha$ radiation according to FIG. 29.

One embodiment of the disclosure provides for a crystalline Form XVIII of AP1189 (+)-camphor-10-sulfonic acid exhibiting one or more X-ray lines (2-theta values) in a powder diffraction pattern when measured using Cu $K_\alpha$ radiation selected from the group consisting of 5.1, 6.5, 7.7, 9.4, 9.9, 10.4, 11.0, 11.5, 12.2, 13.0, 13.7, 14.0, 14.3, 14.8, 15.6, 15.9, 16.1, 17.2, 18.1, 18.4, 18.8, 19.8, 21.1, 21.5, 22.2, 22.7, 23.2, 23.8, 25.1, 25.7, 26.1, 27.2, 28.7, 30.1, and 31.5. One embodiment of the disclosure provides for a crystalline Form XVIII of AP1189 (+)-camphor-10-sulfonic acid exhibiting one or more X-ray lines (2-theta values) in a powder diffraction pattern when measured using Cu $K_\alpha$ radiation selected from the group consisting of 5.1±0.2, 6.5±0.2, 7.7±0.2, 9.4±0.2, 9.9±0.2, 10.4±0.2, 11.0±0.2, 11.5±0.2, 12.2±0.2, 13.0±0.2, 13.7±0.2, 14.0±0.2, 14.3±0.2, 14.8±0.2, 15.6±0.2, 15.9±0.2, 16.1±0.2, 17.2±0.2, 18.1±0.2, 18.4±0.2, 18.8±0.2, 19.8±0.2, 21.1±0.2, 21.5±0.2, 22.2±0.2, 22.7±0.2, 23.2±0.2, 23.8±0.2, 25.1±0.2, 25.7±0.2, 26.1±0.2, 27.2±0.2, 28.7±0.2, 30.1±0.2, and 31.5±0.2. It may be advantageous to identify the crystalline Form XVIII of AP1189 (+)-camphor-10-sulfonic acid by X-ray lines (2-theta values) having a high relative intensity, and/or by characteristic X-ray lines. Thus, one embodiment of the present disclosure provides for a crystalline Form XVIII of AP1189 (+)-camphor-10-sulfonic acid exhibiting one or more X-ray lines (2-theta values) in a powder diffraction pattern when measured using Cu $K_\alpha$ radiation selected from the group consisting of 6.5, 11.5, 13.0, 13.7, 14.8, 15.9, 16.1, 18.8, 19.8, and 21.1. One embodiment of the present disclosure provides for a crystalline Form XVIII of AP1189 (+)-camphor-10-sulfonic acid exhibiting one or more X-ray lines (2-theta values) in a powder diffraction pattern when measured using Cu $K_\alpha$ radiation selected from the group consisting of 6.5±0.2, 11.5±0.2, 13.0±0.2, 13.7±0.2, 14.8±0.2, 15.9±0.2, 16.1±0.2, 18.8±0.2, 19.8±0.2, and 21.1±0.2. One embodiment of the present disclosure provides for a crystalline Form XVIII of AP1189 (+)-camphor-10-sulfonic acid exhibiting one or more X-ray lines (2-theta values) in a powder diffraction pattern when measured using Cu $K_\alpha$ radiation selected from the group consisting of the 2-theta values in listed in Table 24.

AP1189 Oxoglutarate Form XIX

Figure 30:
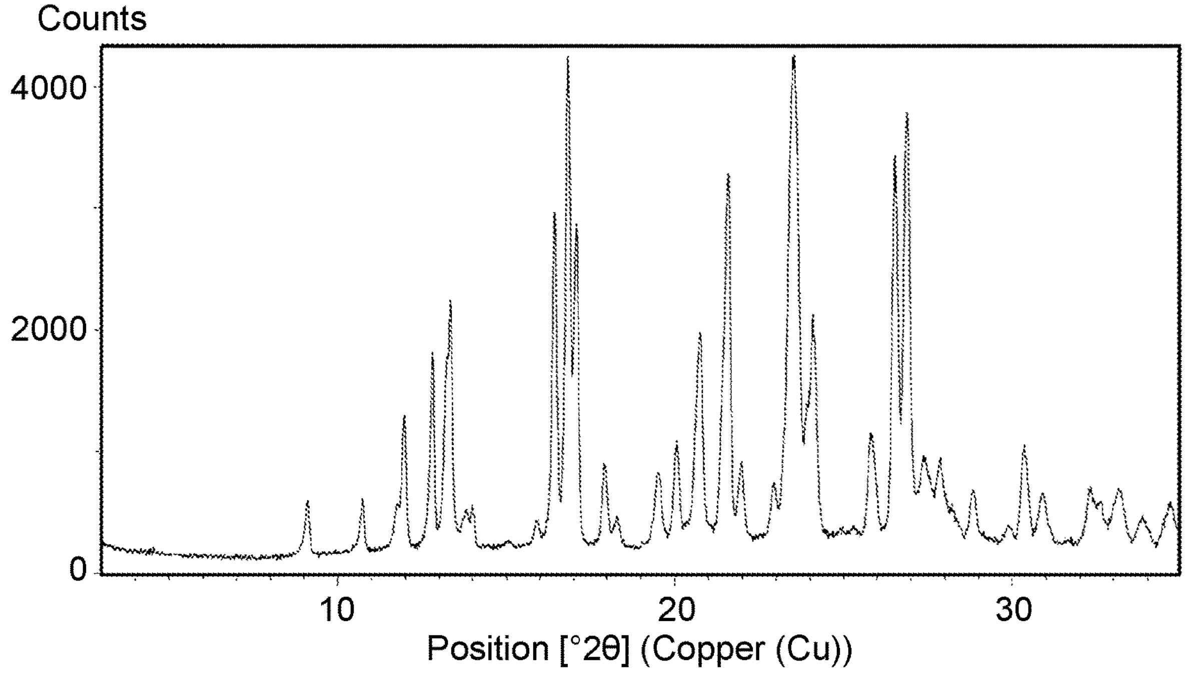
FIG. 30: XRPD Diffractogram of AP1189 Oxoglutarate Pattern 1.

The present disclosure provides for a crystalline Form XIX of AP1189 oxoglutarate. Crystalline Form XIX of AP1189 oxoglutarate exhibits an XRPD diffractogram as shown in FIG. 30. One embodiment of the present disclosure provides for a crystalline Form XIX of AP1189 oxoglutarate exhibiting at least X-ray lines (2-theta values) in a powder diffraction pattern when measured using Cu $K_\alpha$ radiation at 16.8±0.2, 23.4±0.2, and 23.6±0.2. One embodiment provides for a crystalline Form XIX of AP1189 oxoglutarate further exhibiting one or more X-ray lines (2-theta values) in a powder diffraction pattern when measured using Cu $K_\alpha$ radiation selected from the group consisting of 13.4±0.2, 16.4±0.2, 21.6±0.2, and 26.5±0.2. One embodiment of the present disclosure provides for a crystalline Form XIX of AP1189 oxoglutarate further exhibiting one or more X-ray lines (2-theta values) in a powder diffraction pattern when measured using Cu $K_\alpha$ radiation selected from the group consisting of 9.1±0.2, 10.7±0.2, 12.8±0.2, 13.2±0.2, 20.8±0.2, 24.1±0.2, and 24.2±0.2. One embodiment of the disclosure provides for a crystalline Form XIX of AP1189 oxoglutarate exhibiting an X-ray pattern (2-theta values) in a powder diffraction when measured using Cu $K_\alpha$ radiation according to FIG. 30.

One embodiment of the disclosure provides for a crystalline Form XIX of AP1189 oxoglutarate exhibiting one or more X-ray lines (2-theta values) in a powder diffraction pattern when measured using Cu $K_\alpha$ radiation selected from the group consisting of 9.1, 10.7, 11.8, 12.0, 12.8, 13.2, 13.4, 13.8, 14.0, 15.9, 16.4, 16.8, 17.1, 17.9, 18.3, 19.5, 20.1, 20.8, 21.6, 22.0, 22.9, 23.4, 23.6, 24.1, 24.2, 25.8, 26.5, 26.9, 27.4, 27.9, 28.9, 29.9, 30.3, 30.9, 32.3, 32.6, 33.1, 33.8, and 34.7. One embodiment of the disclosure provides for a crystalline Form XIX of AP1189 oxoglutarate exhibiting one or more X-ray lines (2-theta values) in a powder diffraction pattern when measured using Cu $K_\alpha$ radiation selected from the group consisting of 9.1±0.2, 10.7±0.2, 11.8±0.2, 12.0±0.2, 12.8±0.2, 13.2±0.2, 13.4±0.2, 13.8±0.2, 14.0±0.2, 15.9±0.2, 16.4±0.2, 16.8±0.2, 17.1±0.2, 17.9±0.2, 18.3±0.2, 19.5±0.2, 20.1±0.2, 20.8±0.2, 21.6±0.2, 22.0±0.2, 22.9±0.2, 23.4±0.2, 23.6±0.2, 24.1±0.2, 24.2±0.2, 25.8±0.2, 26.5±0.2, 26.9±0.2, 27.4±0.2, 27.9±0.2, 28.9±0.2, 29.9±0.2, 30.3±0.2, 30.9±0.2, 32.3±0.2, 32.6±0.2, 33.1±0.2, 33.8±0.2, and 34.7±0.2. It may be advantageous to identify the crystalline Form XIX of AP1189 oxoglutarate by X-ray lines (2-theta values) having a high relative intensity, and/or by characteristic X-ray lines. Thus, one embodiment of the present disclosure provides for a crystalline Form XIX of AP1189 oxoglutarate exhibiting one or more X-ray lines (2-theta values) in a powder diffraction pattern when measured using Cu $K_\alpha$ radiation selected from the group consisting of 9.1, 10.7, 12.8, 13.2, 13.4, 16.4, 16.8, 20.8, 21.6, 23.4, 23.6, 24.1, 24.2, 26.5, and 26.9. One embodiment of the present disclosure provides for a crystalline Form XIX of AP1189 oxoglutarate exhibiting one or more X-ray lines (2-theta values) in a powder diffraction pattern when measured using Cu $K_\alpha$ radiation selected from the group consisting of 9.1±0.2, 10.7±0.2, 12.8±0.2, 13.2±0.2, 13.4±0.2, 16.4±0.2, 16.8±0.2, 20.8±0.2, 21.6±0.2, 23.4±0.2, 23.6±0.2, 24.1±0.2, 24.2±0.2, 26.5±0.2, and 26.9±0.2. One embodiment of the present disclosure provides for a crystalline Form XIX of AP1189 oxoglutarate exhibiting one or more X-ray lines (2-theta values) in a powder diffraction pattern when measured using Cu $K_\alpha$ radiation selected from the group consisting of the 2-theta values in listed in Table 25.

AP1189 DL-Mandelic Acid Form XX

Figure 31:
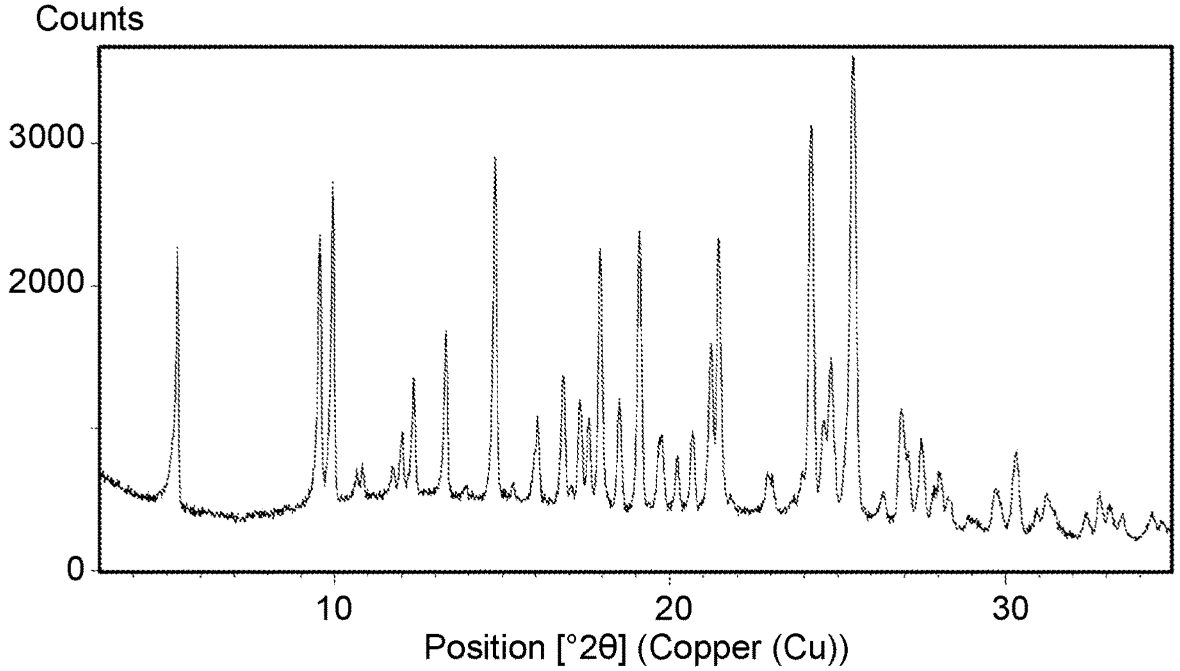
FIG. 31: XRPD Diffractogram of AP1189 DL-mandelic acid Pattern 2.

The present disclosure provides for a crystalline Form XX of AP1189 DL-mandelic acid. Crystalline Form XX of AP1189 DL-mandelic acid exhibits an XRPD diffractogram as shown in FIG. 31. One embodiment of the present disclosure provides for a crystalline Form XX of AP1189 DL-mandelic acid exhibiting at least X-ray lines (2-theta values) in a powder diffraction pattern when measured using Cu $K_\alpha$ radiation at 14.8±0.2, 24.2±0.2, and 25.5±0.2. One embodiment provides for a crystalline Form XX of AP1189 DL-mandelic acid further exhibiting one or more X-ray lines (2-theta values) in a powder diffraction pattern when measured using Cu $K_\alpha$ radiation selected from the group consisting of 9.6±0.2, 10.0±0.2, 19.1±0.2, and 21.5±0.2. One embodiment of the present disclosure provides for a crystalline Form XX of AP1189 DL-mandelic acid further exhibiting one or more X-ray lines (2-theta values) in a powder diffraction pattern when measured using Cu $K_\alpha$ radiation selected from the group consisting of 5.3±0.2, 12.4±0.2, 13.3±0.2, 16.0±0.2, 16.8±0.2, 17.9±0.2, 21.2±0.2, and 24.8±0.2. One embodiment of the disclosure provides for a crystalline Form XX of AP1189 DL-mandelic acid exhibiting an X-ray pattern (2-theta values) in a powder diffraction when measured using Cu $K_\alpha$ radiation according to FIG. 31.

One embodiment of the disclosure provides for a crystalline Form XX of AP1189 DL-mandelic acid exhibiting one or more X-ray lines (2-theta values) in a powder diffraction pattern when measured using Cu $K_\alpha$ radiation selected from the group consisting of 5.3, 9.6, 10.0, 10.7, 10.9, 11.7, 12.0, 12.4, 13.3, 13.9, 14.8, 15.3, 16.0, 16.8, 17.0, 17.3, 17.6, 17.9, 18.5, 19.1, 19.8, 20.2, 20.7, 21.2, 21.5, 21.8, 22.9, 24.2, 24.5, 24.8, 25.5, 26.4, 26.9, 27.1, 27.5, 28.1, 28.4, 29.7, 30.3, 31.2, 32.4, 32.8, 33.1, 33.5, 34.4, and 34.7. One embodiment of the disclosure provides for a crystalline Form XX of AP1189 DL-mandelic acid exhibiting one or more X-ray lines (2-theta values) in a powder diffraction pattern when measured using Cu $K_\alpha$ radiation selected from the group consisting of 5.3±0.2, 9.6±0.2, 10.0±0.2, 10.7±0.2, 10.9±0.2, 11.7±0.2, 12.0±0.2, 12.4±0.2, 13.3±0.2, 13.9±0.2, 14.8±0.2, 15.3±0.2, 16.0±0.2, 16.8±0.2, 17.0±0.2, 17.3±0.2, 17.6±0.2, 17.9±0.2, 18.5±0.2, 19.1±0.2, 19.8±0.2, 20.2±0.2, 20.7±0.2, 21.2±0.2, 21.5±0.2, 21.8±0.2, 22.9±0.2, 24.2±0.2, 24.5±0.2, 24.8±0.2, 25.5±0.2, 26.4±0.2, 26.9±0.2, 27.1±0.2, 27.5±0.2, 28.1±0.2, 28.4±0.2, 29.7±0.2, 30.3±0.2, 31.2±0.2, 32.4±0.2, 32.8±0.2, 33.1±0.2, 33.5±0.2, 34.4±0.2, and 34.7±0.2. It may be advantageous to identify the crystalline Form XX of AP1189 DL-mandelic acid by X-ray lines (2-theta values) having a high relative intensity, and/or by characteristic X-ray lines. Thus, one embodiment of the present disclosure provides for a crystalline Form XX of AP1189 DL-mandelic acid exhibiting one or more X-ray lines (2-theta values) in a powder diffraction pattern when measured using Cu $K_\alpha$ radiation selected from the group consisting of 5.3, 9.6, 10.0, 12.4, 13.3, 14.8, 16.0, 16.8, 17.9, 19.1, 21.2, 21.5, 24.2, 24.8, and 25.5. One embodiment of the present disclosure provides for a crystalline Form XX of AP1189 DL-mandelic acid exhibiting one or more X-ray lines (2-theta values) in a powder diffraction pattern when measured using Cu $K_\alpha$ radiation selected from the group consisting of 5.3±0.2, 9.6±0.2, 10.0±0.2, 12.4±0.2, 13.3±0.2, 14.8±0.2, 16.0±0.2, 16.8±0.2, 17.9±0.2, 19.1±0.2, 21.2±0.2, 21.5±0.2, 24.2±0.2, 24.8±0.2, and 25.5±0.2. One embodiment of the present disclosure provides for a crystalline Form XX of AP1189

DL-mandelic acid exhibiting one or more X-ray lines (2-theta values) in a powder diffraction pattern when measured using Cu $K_\alpha$ radiation selected from the group consisting of the 2-theta values in listed in Table 26.

AP1189 DL-Mandelic Acid Form XXI

Figure 32:
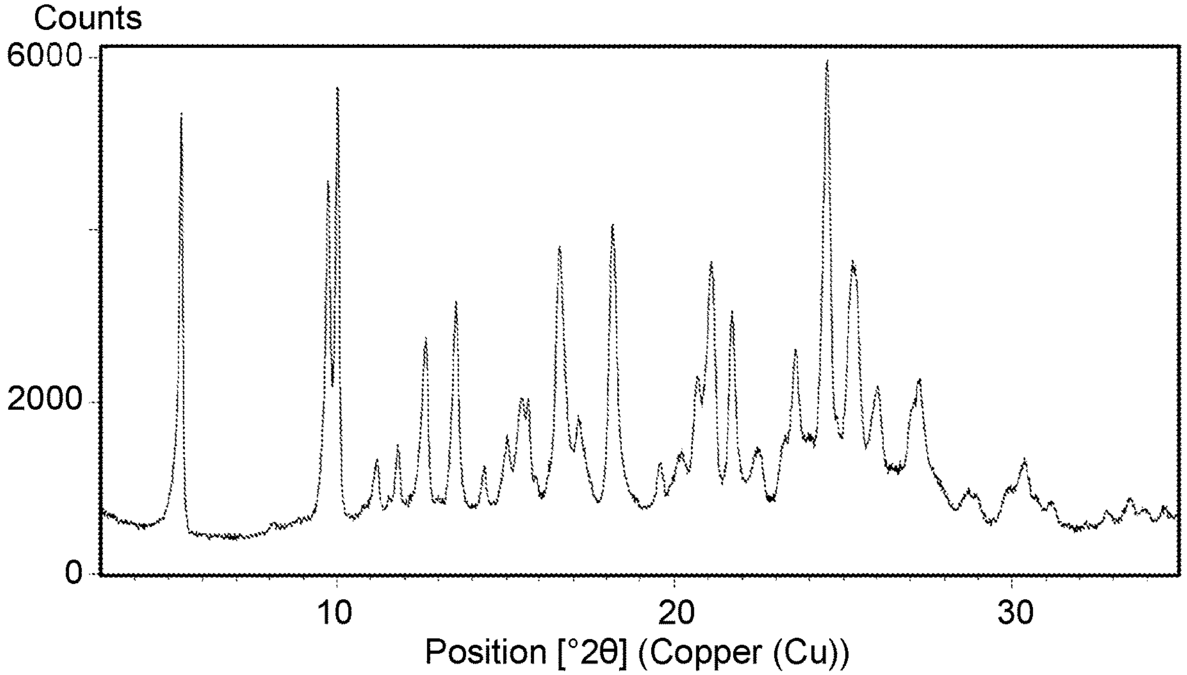
FIG. 32: XRPD Diffractogram of AP1189 DL-mandelic acid Pattern 3.

The present disclosure provides for a crystalline Form XXI of AP1189 DL-mandelic acid. Crystalline Form XXI of AP1189 DL-mandelic acid exhibits an XRPD diffractogram as shown in FIG. 32. One embodiment of the present disclosure provides for a crystalline Form XXI of AP1189 DL-mandelic acid exhibiting at least X-ray lines (2-theta values) in a powder diffraction pattern when measured using Cu $K_\alpha$ radiation at 5.4±0.2, 10.0±0.2, and 24.6±0.2. One embodiment provides for a crystalline Form XXI of AP1189 further exhibiting one or more X-ray lines (2-theta values) in a powder diffraction pattern when measured using Cu $K_\alpha$ radiation selected from the group consisting of 9.8±0.2, 16.6±0.2, 18.1±0.2, and 21.1±0.2. One embodiment of the present disclosure provides for a crystalline Form XXI of AP1189 DL-mandelic acid further exhibiting one or more X-ray lines (2-theta values) in a powder diffraction pattern when measured using Cu $K_\alpha$ radiation selected from the group consisting of 12.7±0.2, 13.5±0.2, 21.7±0.2, and 25.4±0.2. One embodiment of the disclosure provides for a crystalline Form XXI of AP1189 DL-mandelic acid exhibiting an X-ray pattern (2-theta values) in a powder diffraction when measured using Cu $K_\alpha$ radiation according to FIG. 32.

One embodiment of the disclosure provides for a crystalline Form XXI of AP1189 DL-mandelic acid exhibiting one or more X-ray lines (2-theta values) in a powder diffraction pattern when measured using Cu $K_\alpha$ radiation selected from the group consisting of 5.4, 9.8, 10.0, 11.2, 11.5, 11.8, 12.7, 13.5, 14.4, 15.0, 15.5, 15.7, 15.8, 16.6, 17.2, 18.1, 19.6, 20.2, 20.7, 21.1, 21.7, 22.6, 23.3, 23.6, 24.6, 25.4, 26.1, 27.0, 27.3, 28.7, 29.0, 29.8, 30.4, 30.7, 31.2, 32.8, 33.5, 34.0, and 34.5. One embodiment of the disclosure provides for a crystalline Form XXI of AP1189 DL-mandelic acid exhibiting one or more X-ray lines (2-theta values) in a powder diffraction pattern when measured using Cu $K_\alpha$ radiation selected from the group consisting of 5.4±0.2, 9.8±0.2, 10.0±0.2, 11.2±0.2, 11.5±0.2, 11.8±0.2, 12.7±0.2, 13.5±0.2, 14.4±0.2, 15.0±0.2, 15.5±0.2, 15.7±0.2, 15.8±0.2, 16.6±0.2, 17.2±0.2, 18.1±0.2, 19.6±0.2, 20.2±0.2, 20.7±0.2, 21.1±0.2, 21.7±0.2, 22.6±0.2, 23.3±0.2, 23.6±0.2, 24.6±0.2, 25.4±0.2, 26.1±0.2, 27.0±0.2, 27.3±0.2, 28.7±0.2, 29.0±0.2, 29.8±0.2, 30.4±0.2, 30.7±0.2, 31.2±0.2, 32.8±0.2, 33.5±0.2, 34.0±0.2, and 34.5±0.2. It may be advantageous to identify the crystalline Form XXI of AP1189 DL-mandelic acid by X-ray lines (2-theta values) having a high relative intensity, and/or by characteristic X-ray lines. Thus, one embodiment of the present disclosure provides for a crystalline Form XXI of AP1189 DL-mandelic acid exhibiting one or more X-ray lines (2-theta values) in a powder diffraction pattern when measured using Cu $K_\alpha$ radiation selected from the group consisting of 5.4, 9.8, 10.0, 12.7, 13.5, 16.6, 18.1, 21.1, 21.7, 24.6, and 25.4. One embodiment of the present disclosure provides for a crystalline Form XXI of AP1189 DL-mandelic acid exhibiting one or more X-ray lines (2-theta values) in a powder diffraction pattern when measured using Cu $K_\alpha$ radiation selected from the group consisting of 5.4±0.2, 9.8±0.2, 10.0±0.2, 12.7±0.2, 13.5±0.2, 16.6±0.2, 18.1±0.2, 21.1±0.2, 21.7±0.2, 24.6±0.2, and 25.4±0.2. One embodiment of the present disclosure provides for a crystalline Form XXI of AP1189 DL-mandelic acid exhibiting one or more X-ray lines (2-theta values) in a powder diffraction pattern when measured using Cu $K_\alpha$ radiation selected from the group consisting of the 2-theta values in listed in Table 27.

AP1189 Hippuric Acid Form XXII

Figure 33:
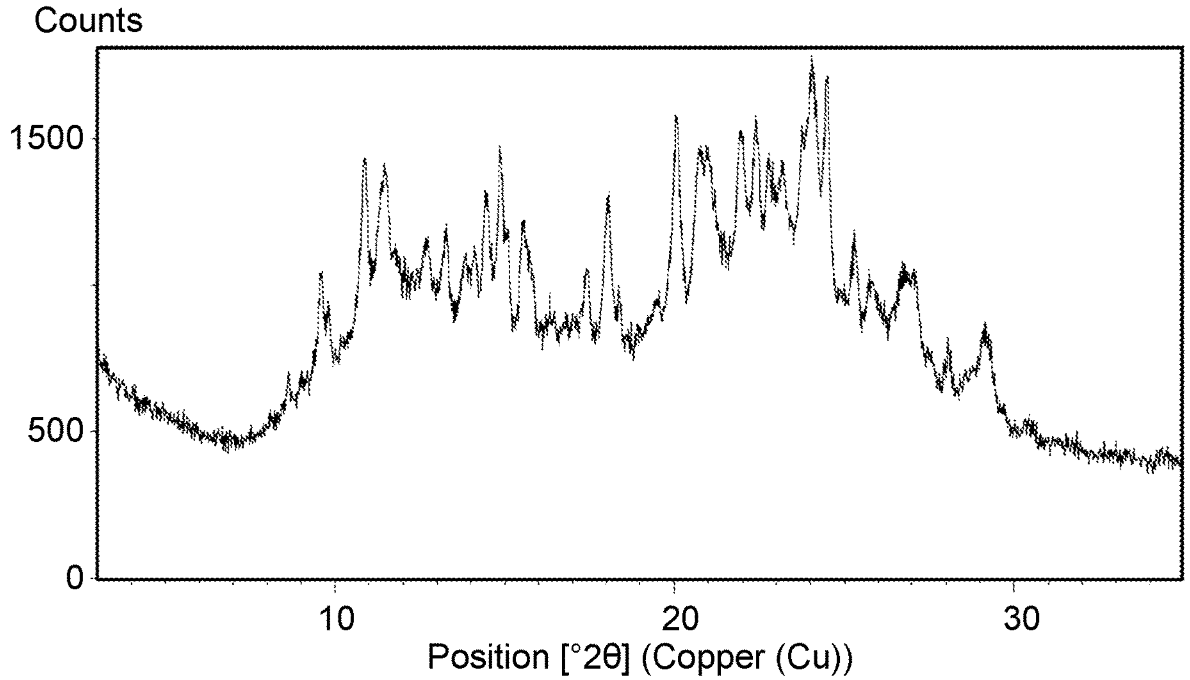
FIG. 33: XRPD Diffractogram of AP1189 Hippuric acid Pattern 1.

The present disclosure provides for a crystalline Form XXII of AP1189 hippuric acid. Crystalline Form XXII of AP1189 hippuric acid exhibits an XRPD diffractogram as shown in FIG. 33. One embodiment of the present disclosure provides for a crystalline Form XXII of AP1189 hippuric exhibiting at least X-ray lines (2-theta values) in a powder diffraction pattern when measured using Cu $K_\alpha$ radiation at 20.1±0.2, 24.1±0.2, and 24.5±0.2. One embodiment provides for a crystalline Form XXII of AP1189 hippuric acid further exhibiting one or more X-ray lines (2-theta values) in a powder diffraction pattern when measured using Cu $K_\alpha$ radiation selected from the group consisting of 10.9±0.2, 11.5±0.2, 14.4±0.2, 14.9±0.2, and 18.1±0.2. One embodiment of the present disclosure provides for a crystalline Form XXII of AP1189 hippuric acid further exhibiting one or more X-ray lines (2-theta values) in a powder diffraction pattern when measured using Cu $K_\alpha$ radiation selected from the group consisting of 9.6±0.2, 14.1±0.2, and 15.5±0.2. One embodiment of the disclosure provides for a crystalline Form XXII of AP1189 hippuric acid exhibiting an X-ray pattern (2-theta values) in a powder diffraction when measured using Cu $K_\alpha$ radiation according to FIG. 33.

One embodiment of the disclosure provides for a crystalline Form XXII of AP1189 hippuric acid exhibiting one or more X-ray lines (2-theta values) in a powder diffraction pattern when measured using Cu $K_\alpha$ radiation selected from the group consisting of 8.6, 9.6, 9.8, 10.9, 11.5, 11.8, 12.7, 13.3, 13.8, 14.1, 14.4, 14.9, 15.5, 16.4, 17.5, 18.1, 19.5, 20.1, 20.7, 21.0, 22.0, 22.4, 22.8, 23.1, 24.1, 24.5, 25.3, 25.8, 27.1, 28.1, and 29.1. One embodiment of the disclosure provides for a crystalline Form XXII of AP1189 hippuric acid exhibiting one or more X-ray lines (2-theta values) in a powder diffraction pattern when measured using Cu $K_\alpha$ radiation selected from the group consisting of 8.6±0.2, 9.6±0.2, 9.8±0.2, 10.9±0.2, 11.5±0.2, 11.8±0.2, 12.7±0.2, 13.3±0.2, 13.8±0.2, 14.1±0.2, 14.4±0.2, 14.9±0.2, 15.5±0.2, 16.4±0.2, 17.5±0.2, 18.1±0.2, 19.5±0.2, 20.1±0.2, 20.7±0.2, 21.0±0.2, 22.0±0.2, 22.4±0.2, 22.8±0.2, 23.1±0.2, 24.1±0.2, 24.5±0.2, 25.3±0.2, 25.8±0.2, 27.1±0.2, 28.1±0.2, and 29.1±0.2. It may be advantageous to identify the crystalline Form XXII of AP1189 hippuric acid by X-ray lines (2-theta values) having a high relative intensity, and/or by characteristic X-ray lines. Thus, one embodiment of the present disclosure provides for a crystalline Form XXII of AP1189 hippuric acid exhibiting one or more X-ray lines (2-theta values) in a powder diffraction pattern when measured using Cu $K_\alpha$ radiation selected from the group consisting of 9.6, 10.9, 11.5, 14.1, 14.4, 14.9, 15.5, 18.1, 20.1, 24.1, and 24.5. One embodiment of the present disclosure provides for a crystalline Form XXII of AP1189 hippuric acid exhibiting one or more X-ray lines (2-theta values) in a powder diffraction pattern when measured using Cu $K_\alpha$ radiation selected from the group consisting of 9.6±0.2, 10.9±0.2, 11.5±0.2, 14.1±0.2, 14.4±0.2, 14.9±0.2, 15.5±0.2, 18.1±0.2, 20.1±0.2, 24.1±0.2, and 24.5±0.2. One embodiment of the present disclosure provides for a crystalline Form XXII of AP1189 hippuric acid exhibiting one or more X-ray lines (2-theta values) in a powder diffraction pattern when measured using Cu $K_\alpha$ radiation selected from the group consisting of the 2-theta values in listed in Table 28.

AP1189 Formic Acid Form XXIII

Figure 34:
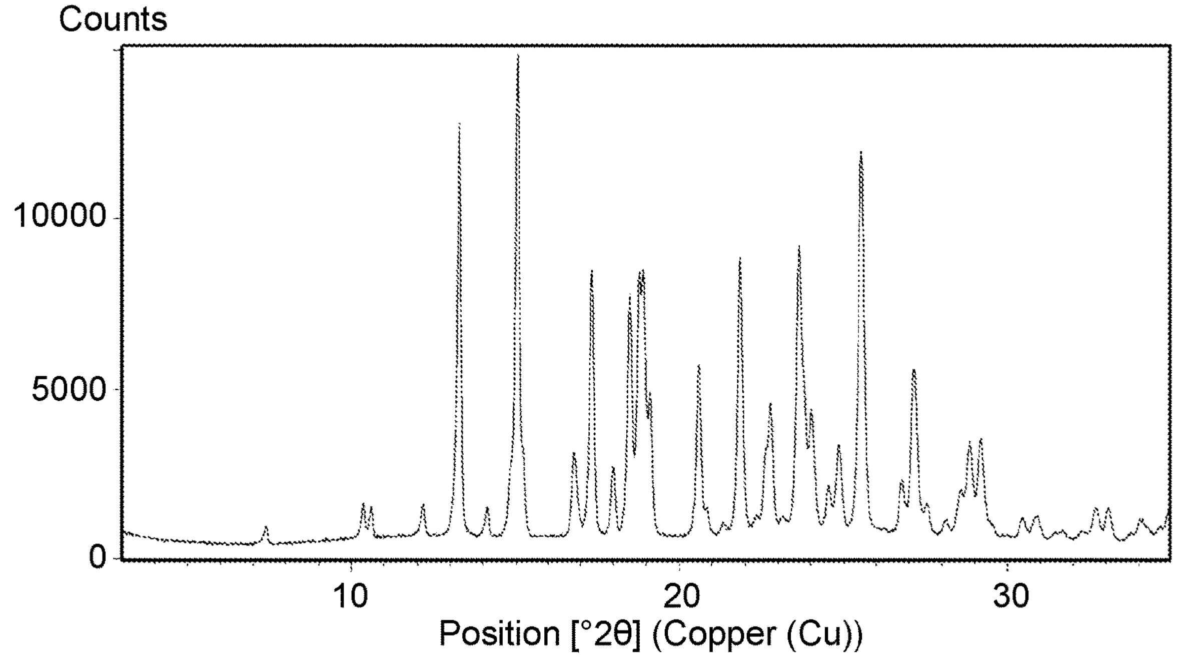
FIG. 34: XRPD Diffractogram of AP1189 Formic acid Pattern 1.

The present disclosure provides for a crystalline Form XXIII of AP1189 formate. Crystalline Form XXIII of AP1189 formate exhibits an XRPD diffractogram as shown in FIG. 34. One embodiment of the present disclosure provides for a crystalline Form XXIII of AP1189 formate exhibiting at least X-ray lines (2-theta values) in a powder diffraction pattern when measured using Cu $K_\alpha$ radiation at 13.3±0.2, 15.1±0.2, and 25.6±0.2. One embodiment provides for a crystalline Form XXIII of AP1189 formate further exhibiting one or more X-ray lines (2-theta values) in a powder diffraction pattern when measured using Cu $K_\alpha$ radiation selected from the group consisting of 17.3±0.2, 18.9±0.2, 21.8±0.2, and 23.6±0.2. One embodiment of the present disclosure provides for a crystalline Form XXIII of AP1189 formate further exhibiting one or more X-ray lines (2-theta values) in a powder diffraction pattern when measured using Cu $K_\alpha$ radiation selected from the group consisting of 12.2±0.2, 20.6±0.2, 22.8±0.2, 28.9±0.2, and 29.2±0.2. One embodiment of the disclosure provides for a crystalline Form XXIII of AP1189 formate exhibiting an X-ray pattern (2-theta values) in a powder diffraction when measured using Cu $K_\alpha$ radiation according to FIG. 34.

One embodiment of the disclosure provides for a crystalline Form XXIII of AP1189 formate exhibiting one or more X-ray lines (2-theta values) in a powder diffraction pattern when measured using Cu $K_\alpha$ radiation selected from the group consisting of 7.4, 10.4, 10.6, 12.2, 13.3, 14.1, 15.1, 15.2, 16.8, 17.3, 18.0, 18.5, 18.8, 18.9, 19.1, 20.6, 20.9, 21.4, 21.8, 22.3, 22.6, 22.8, 23.1, 23.6, 24.0, 24.5, 24.9, 25.6, 26.8, 27.1, 27.6, 28.1, 28.6, 28.9, 29.2, 30.5, 30.9, 31.7, 32.2, 32.7, 33.1, and 34.0. One embodiment of the disclosure provides for a crystalline Form XXIII of AP1189 formate exhibiting one or more X-ray lines (2-theta values) in a powder diffraction pattern when measured using Cu $K_\alpha$ radiation selected from the group consisting of 7.4±0.2, 10.4±0.2, 10.6±0.2, 12.2±0.2, 13.3±0.2, 14.1±0.2, 15.1±0.2, 15.2±0.2, 16.8±0.2, 17.3±0.2, 18.0±0.2, 18.5±0.2, 18.8±0.2, 18.9±0.2, 19.1±0.2, 20.6±0.2, 20.9±0.2, 21.4±0.2, 21.8±0.2, 22.3±0.2, 22.6±0.2, 22.8±0.2, 23.1±0.2, 23.6±0.2, 24.0±0.2, 24.5±0.2, 24.9±0.2, 25.6±0.2, 26.8±0.2, 27.1±0.2, 27.6±0.2, 28.1±0.2, 28.6±0.2, 28.9±0.2, 29.2±0.2, 30.5±0.2, 30.9±0.2, 31.7±0.2, 32.2±0.2, 32.7±0.2, 33.1±0.2, and 34.0±0.2. It may be advantageous to identify the crystalline Form XXIII of AP1189 formate by X-ray lines (2-theta values) having a high relative intensity, and/or by characteristic X-ray lines. Thus, one embodiment of the present disclosure provides for a crystalline Form XXIII of AP1189 formate exhibiting one or more X-ray lines (2-theta values) in a powder diffraction pattern when measured using Cu $K_\alpha$ radiation selected from the group consisting of 12.2, 13.3, 15.1, 17.3, 18.9, 20.6, 21.8, 22.8, 23.6, 25.6, 28.9, and 29.2. One embodiment of the present disclosure provides for a crystalline Form XXIII of AP1189 formate exhibiting one or more X-ray lines (2-theta values) in a powder diffraction pattern when measured using Cu $K_\alpha$ radiation selected from the group consisting of 12.2±0.2, 13.3±0.2, 15.1±0.2, 17.3±0.2, 18.9±0.2, 20.6±0.2, 21.8±0.2, 22.8±0.2, 23.6±0.2, 25.6±0.2, 28.9±0.2, and 29.2±0.2. One embodiment of the present disclosure provides for a crystalline Form XXIII of AP1189 formate exhibiting one or more X-ray lines (2-theta values) in a powder diffraction pattern when measured using Cu $K_\alpha$ radiation selected from the group consisting of the 2-theta values in listed in Table 29.

AP1189 DL-Lactic Acid Form XXIV

Figure 35:
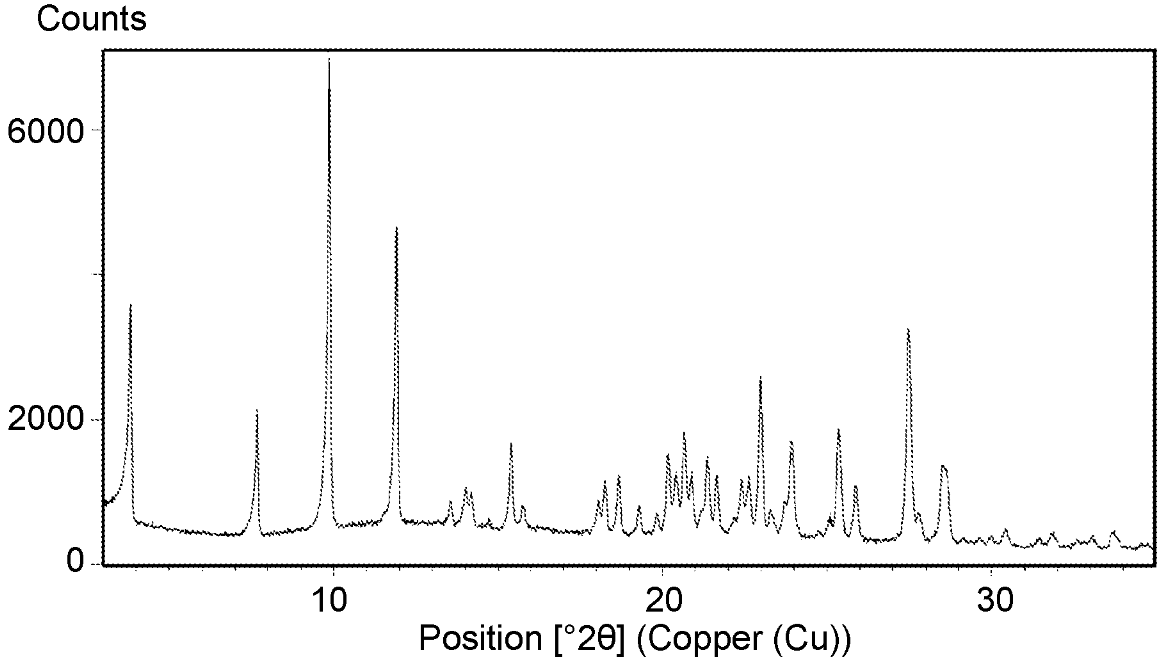
FIG. 35: XRPD Diffractogram of AP1189 DL-Lactic acid Pattern 1.

The present disclosure provides for a crystalline Form XXIV of AP1189 DL-lactic acid. Crystalline Form XXIV of AP1189 DL-lactic acid exhibits an XRPD diffractogram as shown in FIG. 35. One embodiment of the present disclosure provides for a crystalline Form XXIV of AP1189 DL-lactic acid exhibiting at least X-ray lines (2-theta values) in a powder diffraction pattern when measured using Cu $K_\alpha$ radiation at 3.8±0.2, 9.9±0.2, and 11.9±0.2. One embodiment provides for a crystalline Form XXIV of AP1189 DL-lactic acid further exhibiting one or more X-ray lines (2-theta values) in a powder diffraction pattern when measured using Cu $K_\alpha$ radiation selected from the group consisting of 7.7±0.2, 23.0±0.2, and 27.5±0.2. One embodiment of the present disclosure provides for a crystalline Form XXIV of AP1189 DL-lactic acid further exhibiting one or more X-ray lines (2-theta values) in a powder diffraction pattern when measured using Cu $K_\alpha$ radiation selected from the group consisting of 15.4±0.2, 23.9±0.2, and 25.3±0.2. One embodiment of the disclosure provides for a crystalline Form XXIV of AP1189 DL-lactic acid exhibiting an X-ray pattern (2-theta values) in a powder diffraction when measured using Cu $K_\alpha$ radiation according to FIG. 35.

One embodiment of the disclosure provides for a crystalline Form XXIV of AP1189 DL-lactic exhibiting one or more X-ray lines (2-theta values) in a powder diffraction pattern when measured using Cu $K_\alpha$ radiation selected from the group consisting of 3.8, 7.7, 9.9, 11.9, 13.6, 14.0, 14.2, 14.7, 15.4, 15.8, 18.0, 18.3, 18.7, 19.3, 19.8, 20.2, 20.4, 20.7, 20.9, 21.4, 21.6, 22.4, 22.6, 23.0, 23.3, 23.7, 23.9, 25.3, 25.9, 27.5, 27.8, 28.5, 28.7, 29.6, 30.0, 30.4, 31.4, 31.8, 33.1, and 33.6. One embodiment of the disclosure provides for a crystalline Form XXIV of AP1189 DL-lactic acid exhibiting one or more X-ray lines (2-theta values) in a powder diffraction pattern when measured using Cu $K_\alpha$ radiation selected from the group consisting of 3.8±0.2, 7.7±0.2, 9.9±0.2, 11.9±0.2, 13.6±0.2, 14.0±0.2, 14.2±0.2, 14.7±0.2, 15.4±0.2, 15.8±0.2, 18.0±0.2, 18.3±0.2, 18.7±0.2, 19.3±0.2, 19.8±0.2, 20.2±0.2, 20.4±0.2, 20.7±0.2, 20.9±0.2, 21.4±0.2, 21.6±0.2, 22.4±0.2, 22.6±0.2, 23.0±0.2, 23.3±0.2, 23.7±0.2, 23.9±0.2, 25.3±0.2, 25.9±0.2, 27.5±0.2, 27.8±0.2, 28.5±0.2, 28.7±0.2, 29.6±0.2, 30.0±0.2, 30.4±0.2, 31.4±0.2, 31.8±0.2, 33.1±0.2, and 33.6±0.2. It may be advantageous to identify the crystalline Form XXIV of AP1189 DL-lactic acid by X-ray lines (2-theta values) having a high relative intensity, and/or by characteristic X-ray lines. Thus, one embodiment of the present disclosure provides for a crystalline Form XXIV of AP1189 DL-lactic acid exhibiting one or more X-ray lines (2-theta values) in a powder diffraction pattern when measured using Cu $K_\alpha$ radiation selected from the group consisting of 3.8, 7.7, 9.9, 11.9, 15.4, 23.0, 23.9, 25.3, and 27.5. One embodiment of the present disclosure provides for a crystalline Form XXIV of AP1189 DL-lactic acid exhibiting one or more X-ray lines (2-theta values) in a powder diffraction pattern when measured using Cu $K_\alpha$ radiation selected from the group consisting of 3.8±0.2, 7.7±0.2, 9.9±0.2, 11.9±0.2, 15.4±0.2, 23.0±0.2, 23.9±0.2, 25.3±0.2, and 27.5±0.2. One embodiment of the present disclosure provides for a crystalline Form XXIV of AP1189 DL-lactic acid exhibiting one or more X-ray lines (2-theta values) in a powder diffraction pattern when measured using Cu $K_\alpha$ radiation selected from the group consisting of the 2-theta values in listed in Table 30.

AP1189 DL-Lactic Acid Form XXV

Figure 36:
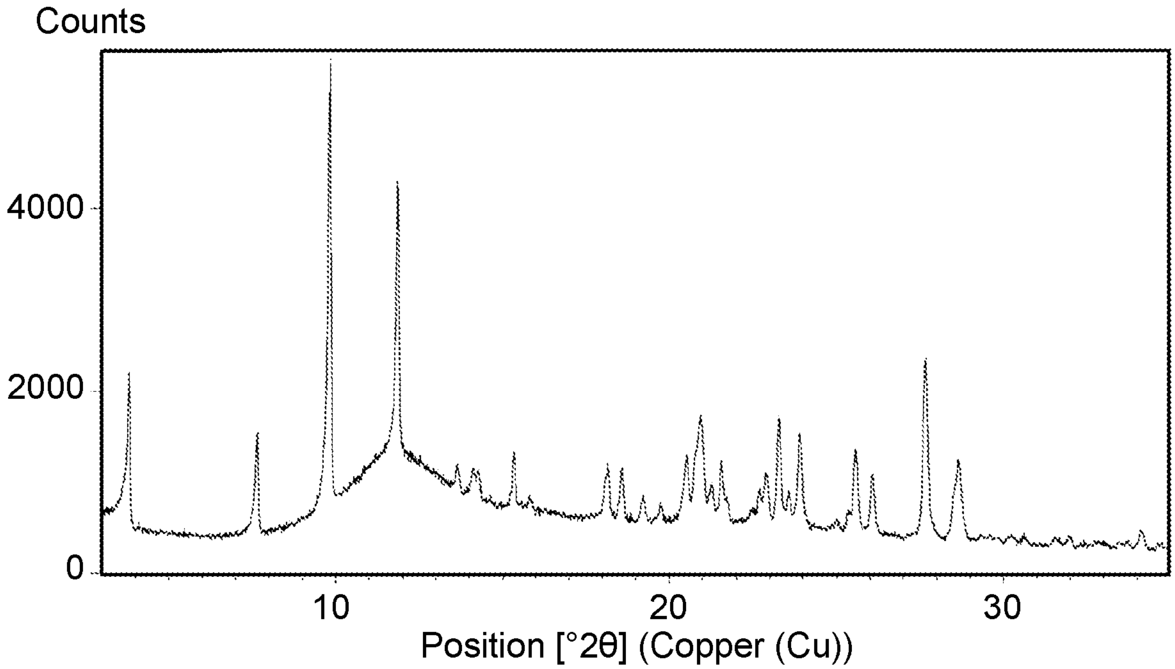
FIG. 36: XRPD Diffractogram of AP1189 DL-Lactic acid Pattern 1.

The present disclosure provides for a crystalline Form XXV of AP1189 DL-lactic acid. Crystalline Form XXV of AP1189 DL-lactic acid exhibits an XRPD diffractogram as shown in FIG. 36. One embodiment of the present disclosure provides for a crystalline Form XXV of AP1189 DL-lactic acid exhibiting at least X-ray lines (2-theta values) in a powder diffraction pattern when measured using Cu $K_\alpha$ radiation at 9.8±0.2, 11.9±0.2, and 27.6±0.2. One embodiment provides for a crystalline Form XXV of AP1189 DL-lactic acid further exhibiting one or more X-ray lines (2-theta values) in a powder diffraction pattern when measured using Cu $K_\alpha$ radiation selected from the group consisting of 3.8±0.2, 23.3±0.2, and 23.9±0.2. One embodiment of the present disclosure provides for a crystalline Form XXV of AP1189 DL-lactic acid further exhibiting one or more X-ray lines (2-theta values) in a powder diffraction pattern when measured using Cu $K_\alpha$ radiation selected from the group consisting of 7.6±0.2, 15.3±0.2, and 25.6±0.2. One embodiment of the disclosure provides for a crystalline Form XXV of AP1189 DL-lactic acid exhibiting an X-ray pattern (2-theta values) in a powder diffraction when measured using Cu $K_\alpha$ radiation according to FIG. 36.

One embodiment of the disclosure provides for a crystalline Form XXV of AP1189 DL-lactic acid exhibiting one or more X-ray lines (2-theta values) in a powder diffraction pattern when measured using Cu $K_\alpha$ radiation selected from the group consisting of 3.8, 7.6, 9.8, 11.9, 13.7, 14.1, 14.3, 15.3, 15.8, 18.2, 18.6, 19.2, 19.8, 20.5, 21.0, 21.3, 21.5, 22.5, 22.7, 22.9, 23.3, 23.6, 23.9, 25.0, 25.6, 26.1, 27.6, 28.7, 29.4, 29.6, 29.8, 30.2, 30.6, 31.6, 32.0, and 34.1. One embodiment of the disclosure provides for a crystalline Form XXV of AP1189 DL-lactic acid exhibiting one or more X-ray lines (2-theta values) in a powder diffraction pattern when measured using Cu $K_\alpha$ radiation selected from the group consisting of 3.8±0.2, 7.6±0.2, 9.8±0.2, 11.9±0.2, 13.7±0.2, 14.1±0.2, 14.3±0.2, 15.3±0.2, 15.8±0.2, 18.2±0.2, 18.6±0.2, 19.2±0.2, 19.8±0.2, 20.5±0.2, 21.0±0.2, 21.3±0.2, 21.5±0.2, 22.5±0.2, 22.7±0.2, 22.9±0.2, 23.3±0.2, 23.6±0.2, 23.9±0.2, 25.0±0.2, 25.6±0.2, 26.1±0.2, 27.6±0.2, 28.7±0.2, 29.4±0.2, 29.6±0.2, 29.8±0.2, 30.2±0.2, 30.6±0.2, 31.6±0.2, 32.0±0.2, and 34.1±0.2. It may be advantageous to identify the crystalline Form XXV of AP1189 DL-lactic acid by X-ray lines (2-theta values) having a high relative intensity, and/or by characteristic X-ray lines. Thus, one embodiment of the present disclosure provides for a crystalline Form XXV of AP1189 DL-lactic acid exhibiting one or more X-ray lines (2-theta values) in a powder diffraction pattern when measured using Cu $K_\alpha$ radiation selected from the group consisting of 3.8, 7.6, 9.8, 11.9, 15.3, 23.3, 23.9, 25.6, and 27.6. One embodiment of the present disclosure provides for a crystalline Form XXV of AP1189 DL-lactic acid exhibiting one or more X-ray lines (2-theta values) in a powder diffraction pattern when measured using Cu $K_\alpha$ radiation selected from the group consisting of 3.8±0.2, 7.6±0.2, 9.8±0.2, 11.9±0.2, 15.3±0.2, 23.3±0.2, 23.9±0.2, 25.6±0.2, and 27.6±0.2. One embodiment of the present disclosure provides for a crystalline Form XXV of AP1189 DL-lactic acid exhibiting one or more X-ray lines (2-theta values) in a powder diffraction pattern when measured using Cu $K_\alpha$ radiation selected from the group consisting of the 2-theta values in listed in Table 31.

AP1189 Glutaric Acid Form XXVI

Figure 37:
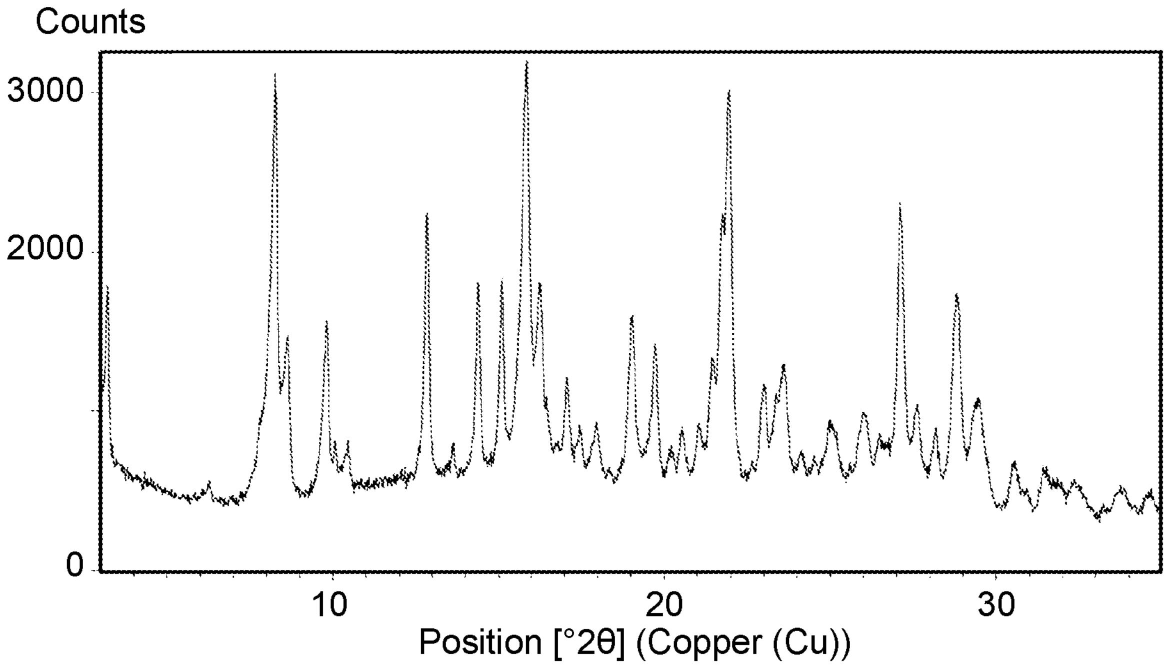
FIG. 37: XRPD Diffractogram of AP1189 Glutaric acid Pattern 1.

The present disclosure provides for a crystalline Form XXVI of AP1189 glutaric acid. Crystalline Form XXVI of AP1189 glutaric acid exhibits an XRPD diffractogram as shown in FIG. 37. One embodiment of the present disclosure provides for a crystalline Form XXVI of AP1189 glutaric acid exhibiting at least X-ray lines (2-theta values) in a powder diffraction pattern when measured using Cu $K_\alpha$ radiation at 8.3±0.2, 15.9±0.2, and 21.9±0.2. One embodiment provides for a crystalline Form XXVI of AP1189 glutaric acid further exhibiting one or more X-ray lines (2-theta values) in a powder diffraction pattern when measured using Cu $K_\alpha$ radiation selected from the group consisting of 12.8±0.2, 15.1±0.2, and 27.1±0.2. One embodiment of the present disclosure provides for a crystalline Form XXVI of AP1189 glutaric acid further exhibiting one or more X-ray lines (2-theta values) in a powder diffraction pattern when measured using Cu $K_\alpha$ radiation selected from the group consisting of 3.2±0.2, 8.7±0.2, 14.4±0.2, 16.2±0.2, 19.0±0.2, 19.8±0.2, 28.8±0.2, and 29.5±0.2. One embodiment of the disclosure provides for a crystalline Form XXVI of AP1189 glutaric acid exhibiting an X-ray pattern (2-theta values) in a powder diffraction when measured using Cu $K_\alpha$ radiation according to FIG. 37.

One embodiment of the disclosure provides for a crystalline Form XXVI of AP1189 glutaric acid exhibiting one or more X-ray lines (2-theta values) in a powder diffraction pattern when measured using Cu $K_\alpha$ radiation selected from the group consisting of 3.2, 6.3, 8.3, 8.7, 9.8, 10.1, 10.5, 12.8, 13.6, 14.4, 15.1, 15.9, 16.2, 17.1, 17.5, 18.0, 18.3, 19.0, 19.8, 20.2, 20.5, 21.0, 21.4, 21.7, 21.9, 23.0, 23.6, 24.1, 24.5, 25.0, 26.0, 26.5, 27.1, 27.6, 28.2, 28.8, 29.5, 30.6, 31.4, 32.3, and 33.8. One embodiment of the disclosure provides for a crystalline Form XXVI of AP1189 glutaric acid exhibiting one or more X-ray lines (2-theta values) in a powder diffraction pattern when measured using Cu $K_\alpha$ radiation selected from the group consisting of 3.2±0.2, 6.3±0.2, 8.3±0.2, 8.7±0.2, 9.8±0.2, 10.1±0.2, 10.5±0.2, 12.8±0.2, 13.6±0.2, 14.4±0.2, 15.1±0.2, 15.9±0.2, 16.2±0.2, 17.1±0.2, 17.5±0.2, 18.0±0.2, 18.3±0.2, 19.0±0.2, 19.8±0.2, 20.2±0.2, 20.5±0.2, 21.0±0.2, 21.4±0.2, 21.7±0.2, 21.9±0.2, 23.0±0.2, 23.6±0.2, 24.1±0.2, 24.5±0.2, 25.0±0.2, 26.0±0.2, 26.5±0.2, 27.1±0.2, 27.6±0.2, 28.2±0.2, 28.8±0.2, 29.5±0.2, 30.6±0.2, 31.4±0.2, 32.3±0.2, and 33.8±0.2. It may be advantageous to identify the crystalline Form XXVI of AP1189 glutaric acid by X-ray lines (2-theta values) having a high relative intensity, and/or by characteristic X-ray lines. Thus, one embodiment of the present disclosure provides for a crystalline Form XXVI of AP1189 glutaric acid exhibiting one or more X-ray lines (2-theta values) in a powder diffraction pattern when measured using Cu $K_\alpha$ radiation selected from the group consisting of 3.2, 8.3, 8.7, 12.8, 14.4, 15.1, 15.9, 16.2, 19.0, 19.8, 21.9, 27.1, 28.8, and 29.5. One embodiment of the present disclosure provides for a crystalline Form XXVI of AP1189 glutaric acid exhibiting one or more X-ray lines (2-theta values) in a powder diffraction pattern when measured using Cu $K_\alpha$ radiation selected from the group consisting of 3.2±0.2, 8.3±0.2, 8.7±0.2, 12.8±0.2, 14.4±0.2, 15.1±0.2, 15.9±0.2, 16.2±0.2, 19.0±0.2, 19.8±0.2, 21.9±0.2, 27.1±0.2, 28.8±0.2, and 29.5±0.2. One embodiment of the present disclosure provides for a crystalline Form XXVI of AP1189 glutaric acid exhibiting one or more X-ray lines (2-theta values) in a powder diffraction pattern when measured using Cu $K_\alpha$ radiation selected from the group consisting of the 2-theta values in listed in Table 32.

AP1189 Glutaric Acid Form XXVII

Figure 38:
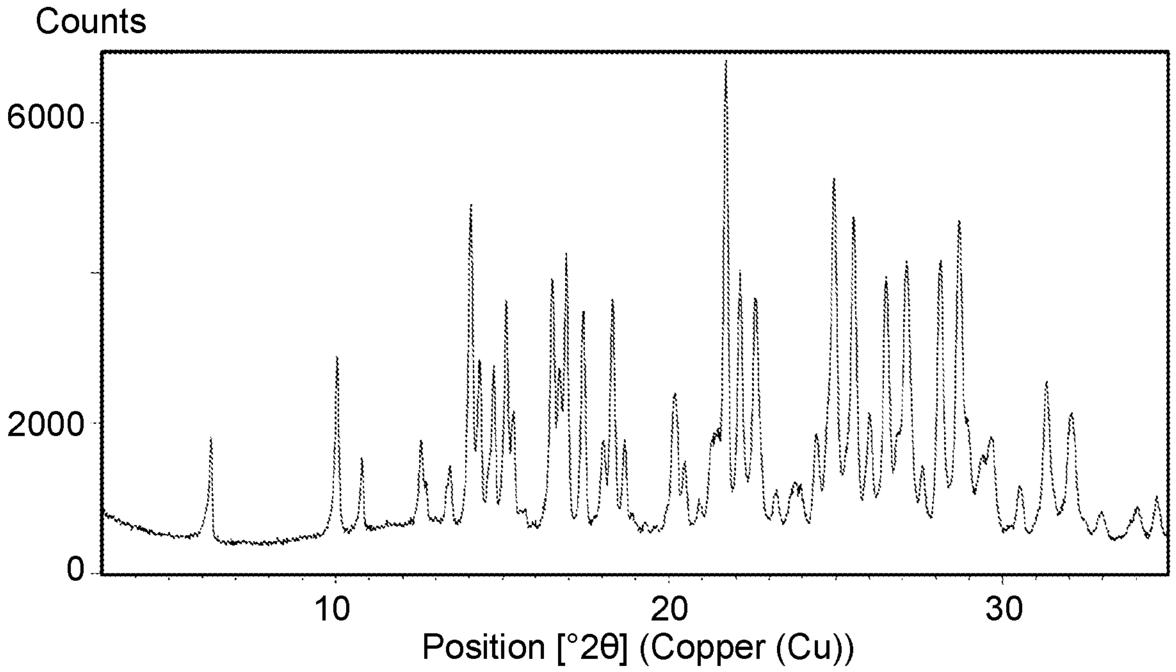
FIG. 38: XRPD Diffractogram of AP1189 Glutaric acid Pattern 1.

The present disclosure provides for a crystalline Form XXVII of AP1189 glutaric acid. Crystalline Form XXVII of AP1189 glutaric acid exhibits an XRPD diffractogram as shown in FIG. 38. One embodiment of the present disclosure provides for a crystalline Form XXVII of AP1189 glutaric acid exhibiting at least X-ray lines (2-theta values) in a powder diffraction pattern when measured using Cu $K_\alpha$ radiation at 14.1±0.2, 21.7±0.2, and 25.0±0.2. One embodiment provides for a crystalline Form XXVII of AP1189 glutaric acid further exhibiting one or more X-ray lines (2-theta values) in a powder diffraction pattern when measured using Cu $K_\alpha$ radiation selected from the group consisting of 16.9±0.2, 25.6±0.2, 27.1±0.2, 28.2±0.2, and 28.7±0.2. One embodiment of the present disclosure provides for a crystalline Form XXVII of AP1189 glutaric acid further exhibiting one or more X-ray lines (2-theta values) in a powder diffraction pattern when measured using Cu $K_\alpha$ radiation selected from the group consisting of 6.3±0.2, 10.1±0.2, 14.3±0.2, 14.7±0.2, 15.1±0.2, 17.4±0.2, 21.1±0.2, 22.6±0.2, and 26.5±0.2. One embodiment of the disclosure provides for a crystalline Form XXVII of AP1189 glutaric acid exhibiting an X-ray pattern (2-theta values) in a powder diffraction when measured using Cu $K_\alpha$ radiation according to FIG. 38.

One embodiment of the disclosure provides for a crystalline Form XXVII of AP1189 glutaric acid exhibiting one or more X-ray lines (2-theta values) in a powder diffraction pattern when measured using Cu $K_\alpha$ radiation selected from the group consisting of 6.3, 10.1, 10.8, 12.6, 12.7, 13.5, 14.1, 14.3, 14.7, 15.1, 15.3, 15.7, 16.5, 16.7, 16.9, 17.4, 18.0, 18.3, 18.7, 18.9, 19.3, 19.6, 20.1, 20.2, 20.5, 20.9, 21.3, 21.7, 22.1, 22.6, 23.2, 24.0, 24.4, 25.0, 25.6, 26.0, 26.5, 26.8, 27.1, 27.6, 28.2, 28.7, 29.0, 29.4, 29.7, 30.5, 31.3, 32.0, 33.0, and 34.1. One embodiment of the disclosure provides for a crystalline Form XXVII of AP1189 glutaric acid exhibiting one or more X-ray lines (2-theta values) in a powder diffraction pattern when measured using Cu $K_\alpha$ radiation selected from the group consisting of 6.3±0.2, 10.1±0.2, 10.8±0.2, 12.6±0.2, 12.7±0.2, 13.5±0.2, 14.1±0.2, 14.3±0.2, 14.7±0.2, 15.1±0.2, 15.3±0.2, 15.7±0.2, 16.5±0.2, 16.7±0.2, 16.9±0.2, 17.4±0.2, 18.0±0.2, 18.3±0.2, 18.7±0.2, 18.9±0.2, 19.3±0.2, 19.6±0.2, 20.1±0.2, 20.2±0.2, 20.5±0.2, 20.9±0.2, 21.3±0.2, 21.7±0.2, 22.1±0.2, 22.6±0.2, 23.2±0.2, 24.0±0.2, 24.4±0.2, 25.0±0.2, 25.6±0.2, 26.0±0.2, 26.5±0.2, 26.8±0.2, 27.1±0.2, 27.6±0.2, 28.2±0.2, 28.7±0.2, 29.0±0.2, 29.4±0.2, 29.7±0.2, 30.5±0.2, 31.3±0.2, 32.0±0.2, 33.0±0.2, and 34.1±0.2. It may be advantageous to identify the crystalline Form XXVII of AP1189 glutaric acid by X-ray lines (2-theta values) having a high relative intensity, and/or by characteristic X-ray lines. Thus, one embodiment of the present disclosure provides for a crystalline Form XXVII of AP1189 glutaric acid exhibiting one or more X-ray lines (2-theta values) in a powder diffraction pattern when measured using Cu $K_\alpha$ radiation selected from the group consisting of 6.3, 10.1, 14.1, 14.3, 14.7, 15.1, 16.9, 17.4, 21.7, 22.1, 22.6, 25.0, 25.6, 26.5, 27.1, 28.2, and 28.7. One embodiment of the present disclosure provides for a crystalline Form XXVII of AP1189 glutaric acid exhibiting one or more X-ray lines (2-theta values) in a powder diffraction pattern when measured using Cu $K_\alpha$ radiation selected from the group consisting of 6.3±0.2, 10.1±0.2, 14.1±0.2, 14.3±0.2, 14.7±0.2, 15.1±0.2, 16.9±0.2, 17.4±0.2, 21.7±0.2, 22.1±0.2, 22.6±0.2, 25.0±0.2, 25.6±0.2, 26.5±0.2, 27.1±0.2, 28.2±0.2, and 28.7±0.2. One embodiment of the present disclosure provides for a crystalline Form XXVII of AP1189 glutaric acid exhibiting one or more X-ray lines (2-theta values) in a powder diffraction pattern when measured using Cu $K_\alpha$ radiation selected from the group consisting of the 2-theta values in listed in Table 33.

AP1189 Glutaric Acid Form XXVIII

Figure 91:
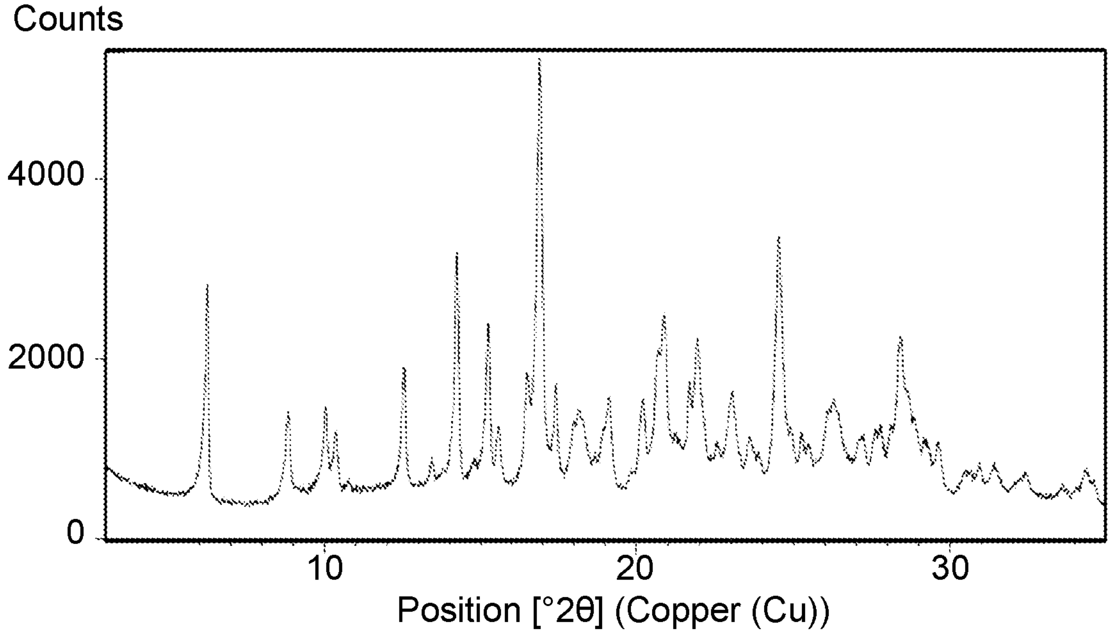
FIG. 91: XRPD Diffractogram of AP1189 Glutaric acid Pattern 4.

The present disclosure provides for a crystalline Form XXVIII of AP1189 glutaric acid. Crystalline Form XXVIII of AP1189 glutaric acid exhibits an XRPD diffractogram as shown in FIG. 91. One embodiment of the present disclosure provides for a crystalline Form XXVIII of AP1189 glutaric acid exhibiting at least X-ray lines (2-theta values) in a powder diffraction pattern when measured using Cu $K_\alpha$ radiation at 14.2±0.2, 16.9±0.2, and 24.5±0.2. One embodiment provides for a crystalline Form XXVIII of AP1189 glutaric acid further exhibiting one or more X-ray lines (2-theta values) in a powder diffraction pattern when measured using Cu $K_\alpha$ radiation selected from the group consisting of 6.3±0.2, 15.2±0.2, 20.9±0.2, and 21.9±0.2. One embodiment of the present disclosure provides for a crystalline Form XXVIII of AP1189 glutaric acid further exhibiting one or more X-ray lines (2-theta values) in a powder diffraction pattern when measured using Cu $K_\alpha$ radiation selected from the group consisting of 8.9±0.2, 10.1±0.2, 12.6±0.2, 17.4±0.2, 19.1±0.2, 20.6±0.2, and 28.4±0.2. One embodiment of the disclosure provides for a crystalline Form XXVIII of AP1189 glutaric acid exhibiting an X-ray pattern (2-theta values) in a powder diffraction when measured using Cu $K_\alpha$ radiation according to FIG. 91.

One embodiment of the disclosure provides for a crystalline Form XXVIII of AP1189 glutaric acid exhibiting one or more X-ray lines (2-theta values) in a powder diffraction pattern when measured using Cu $K_\alpha$ radiation selected from the group consisting of 6.3, 8.9, 10.1, 10.4, 10.7, 12.6, 13.4, 13.8, 14.2, 15.2, 15.6, 16.5, 16.9, 17.4, 18.2, 19.1, 19.8, 20.2, 20.6, 20.9, 21.7, 21.9, 22.5, 23.0, 23.6, 23.8, 24.5, 24.9, 25.3, 26.1, 27.2, 27.8, 28.4, 29.3, 29.6, 30.5, 31.0, 31.4, 32.4, 33.6, and 34.3. One embodiment of the disclosure provides for a crystalline Form XXVIII of AP1189 glutaric acid exhibiting one or more X-ray lines (2-theta values) in a powder diffraction pattern when measured using Cu $K_\alpha$ radiation selected from the group consisting of 6.3±0.2, 8.9±0.2, 10.1±0.2, 10.4±0.2, 10.7±0.2, 12.6±0.2, 13.4±0.2, 13.8±0.2, 14.2±0.2, 15.2±0.2, 15.6±0.2, 16.5±0.2, 16.9±0.2, 17.4±0.2, 18.2±0.2, 19.1±0.2, 19.8±0.2, 20.2±0.2, 20.6±0.2, 20.9±0.2, 21.7±0.2, 21.9±0.2, 22.5±0.2, 23.0±0.2, 23.6±0.2, 23.8±0.2, 24.5±0.2, 24.9±0.2, 25.3±0.2, 26.1±0.2, 27.2±0.2, 27.8±0.2, 28.4±0.2, 29.3±0.2, 29.6±0.2, 30.5±0.2, 31.0±0.2, 31.4±0.2, 32.4±0.2, 33.6±0.2, and 34.3±0.2. It may be advantageous to identify the crystalline Form XXVIII of AP1189 glutaric acid by X-ray lines (2-theta values) having a high relative intensity, and/or by characteristic X-ray lines. Thus, one embodiment of the present disclosure provides for a crystalline Form XXVIII of AP1189 glutaric acid exhibiting one or more X-ray lines (2-theta values) in a powder diffraction pattern when measured using Cu $K_\alpha$ radiation selected from the group consisting of 6.3, 8.9, 10.1, 12.6, 14.2, 15.2, 16.9, 17.4, 19.1, 20.6, 20.9, 21.9, 24.5, and 28.4. One embodiment of the present disclosure provides for a crystalline Form XXVIII of AP1189 glutaric acid exhibiting one or more X-ray lines (2-theta values) in a powder diffraction pattern when measured using Cu $K_\alpha$ radiation selected from the group consisting of 6.3±0.2, 8.9±0.2, 10.1±0.2, 12.6±0.2, 14.2±0.2, 15.2±0.2, 16.9±0.2, 17.4±0.2, 19.1±0.2, 20.6±0.2, 20.9±0.2, 21.9±0.2, 24.5±0.2, and 28.4±0.2. One embodiment of the present disclosure provides for a crystalline Form XXVIII of AP1189 glutaric acid exhibiting one or more X-ray lines (2-theta values) in a powder diffraction pattern when measured using Cu $K_\alpha$ radiation selected from the group consisting of the 2-theta values in listed in Table 34.

AP1189 Adipic Acid Form XXIX

Figure 39:
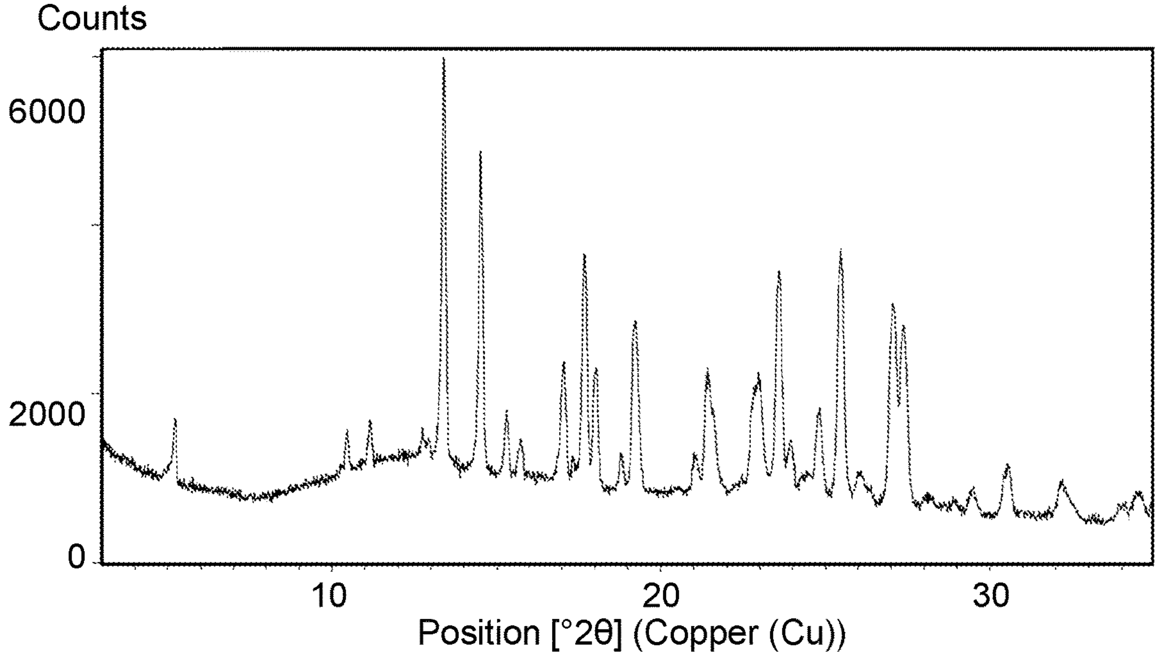
FIG. 39: XRPD Diffractogram of AP1189 Adipic acid Pattern 1.

The present disclosure provides for a crystalline Form XXIX of AP1189 adipic acid. Crystalline Form XXIX of AP1189 adipic acid exhibits an XRPD diffractogram as shown in FIG. 39. One embodiment of the present disclosure provides for a crystalline Form XXIX of AP1189 adipic acid exhibiting at least X-ray lines (2-theta values) in a powder diffraction pattern when measured using Cu $K_\alpha$ radiation at 13.4±0.2, 14.5±0.2, and 25.5±0.2. One embodiment provides for a crystalline Form XXIX of AP1189 adipic acid further exhibiting one or more X-ray lines (2-theta values) in a powder diffraction pattern when measured using Cu $K_\alpha$ radiation selected from the group consisting of 17.6±0.2, 23.5±0.2, 25.4±0.2, and 27.1±0.2. One embodiment of the present disclosure provides for a crystalline Form XXIX of AP1189 adipic acid further exhibiting one or more X-ray lines (2-theta values) in a powder diffraction pattern when measured using Cu $K_\alpha$ radiation selected from the group consisting of 5.2±0.2, 19.2±0.2, and 21.4±0.2. One embodiment of the disclosure provides for a crystalline Form XXIX of AP1189 adipic acid exhibiting an X-ray pattern (2-theta values) in a powder diffraction when measured using Cu $K_\alpha$ radiation according to FIG. 39.

One embodiment of the disclosure provides for a crystalline Form XXIX of AP1189 adipic acid exhibiting one or more X-ray lines (2-theta values) in a powder diffraction pattern when measured using Cu $K_\alpha$ radiation selected from the group consisting of 5.2, 10.5, 11.2, 12.7, 13.4, 14.5, 15.3, 15.8, 17.1, 17.6, 18.0, 18.8, 19.2, 20.5, 21.0, 21.4, 22.4, 22.8, 23.0, 23.5, 23.9, 24.4, 24.8, 25.4, 25.5, 26.1, 26.3, 27.1, 27.5, 28.1, 28.9, 29.5, 30.6, 32.2, 33.9, and 34.5. One embodiment of the disclosure provides for a crystalline Form XXIX of AP1189 adipic acid exhibiting one or more X-ray lines (2-theta values) in a powder diffraction pattern when measured using Cu $K_\alpha$ radiation selected from the group consisting of 5.2±0.2, 10.5±0.2, 11.2±0.2, 12.7±0.2, 13.4±0.2, 14.5±0.2, 15.3±0.2, 15.8±0.2, 17.1±0.2, 17.6±0.2, 18.0±0.2, 18.8±0.2, 19.2±0.2, 20.5±0.2, 21.0±0.2, 21.4±0.2, 22.4±0.2, 22.8±0.2, 23.0±0.2, 23.5±0.2, 23.9±0.2, 24.4±0.2, 24.8, 25.4, 25.5, 26.1, 26.3, 27.1, 27.5, 28.1, 28.9, 29.5, 30.6, 32.2, 33.9, and 34.5±0.2. It may be advantageous to identify the crystalline Form XXIX of AP1189 adipic acid by X-ray lines (2-theta values) having a high relative intensity, and/or by characteristic X-ray lines. Thus, one embodiment of the present disclosure provides for a crystalline Form XXIX of AP1189 adipic acid exhibiting one or more X-ray lines (2-theta values) in a powder diffraction pattern when measured using Cu $K_\alpha$ radiation selected from the group consisting of 5.2, 13.4, 14.5, 17.6, 19.2, 21.4, 23.5, 25.4, 25.5, and 27.1. One embodiment of the present disclosure provides for a crystalline Form XXIX of AP1189 adipic acid exhibiting one or more X-ray lines (2-theta values) in a powder diffraction pattern when measured using Cu $K_\alpha$ radiation selected from the group consisting of 5.2±0.2, 13.4±0.2, 14.5±0.2, 17.6±0.2, 19.2±0.2, 21.4±0.2, 23.5±0.2, 25.4±0.2, 25.5±0.2, and 27.1±0.2. One embodiment of the present disclosure provides for a crystalline Form XXIX of AP1189 adipic exhibiting one or more X-ray lines (2-theta values) in a powder diffraction pattern when measured using Cu $K_\alpha$ radiation selected from the group consisting of the 2-theta values in listed in Table 35.

Further Characterisation of Crystalline Forms

The salts of AP1189 provided herein may be further characterised by the onset temperatures they exhibit as assessed by differential scanning calorimetry.

Figure 8:
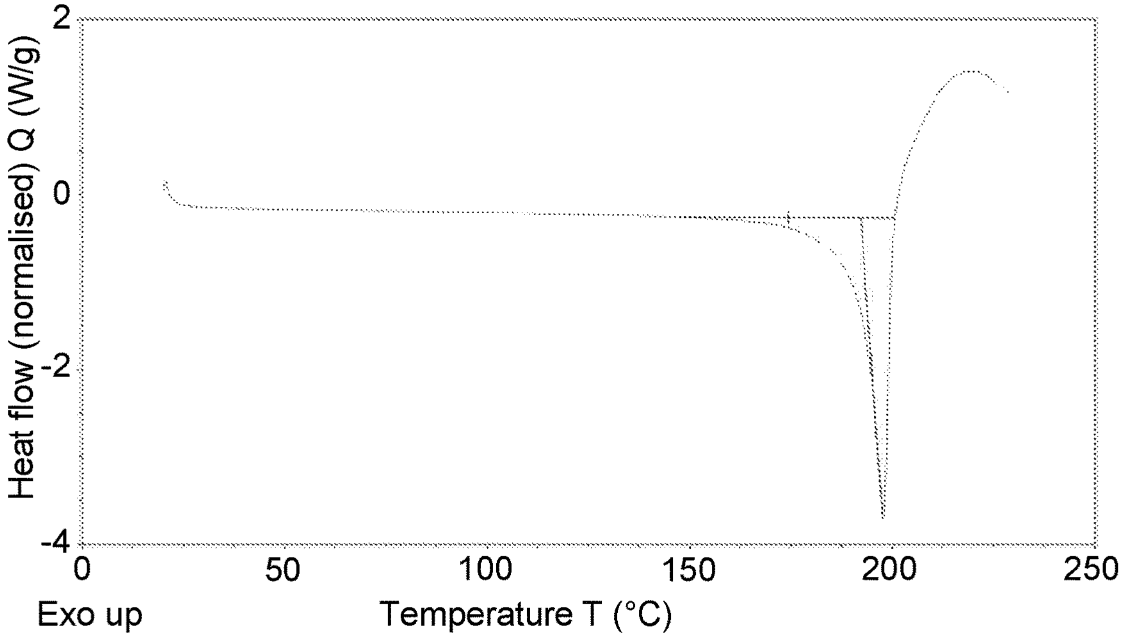
FIG. 8: DSC thermogram of AP1189 acetate Pattern 1 from acetonitrile. Peak temperature 197.86° C.; onset: 192.19° C.; enthalpy (normalised): 147.26 J/g.
Figure 9:
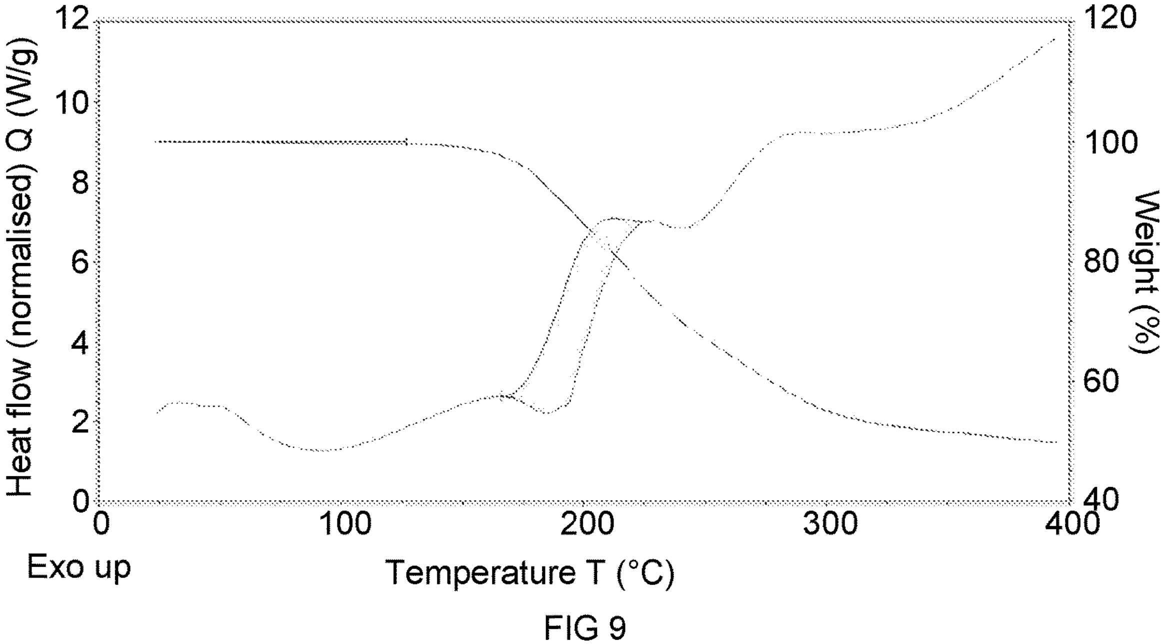
FIG. 9: TGA/DSC thermogram of AP1189 acetate Pattern 1 & 2 from 2-methyl THF. Peak temperature: 194.18° C.; onset: 171.54° C.; enthalpy (normalised): 475.77 J/g. Weight loss: 0.021 mg; weight percent loss: 0.478%.
Figure 10:
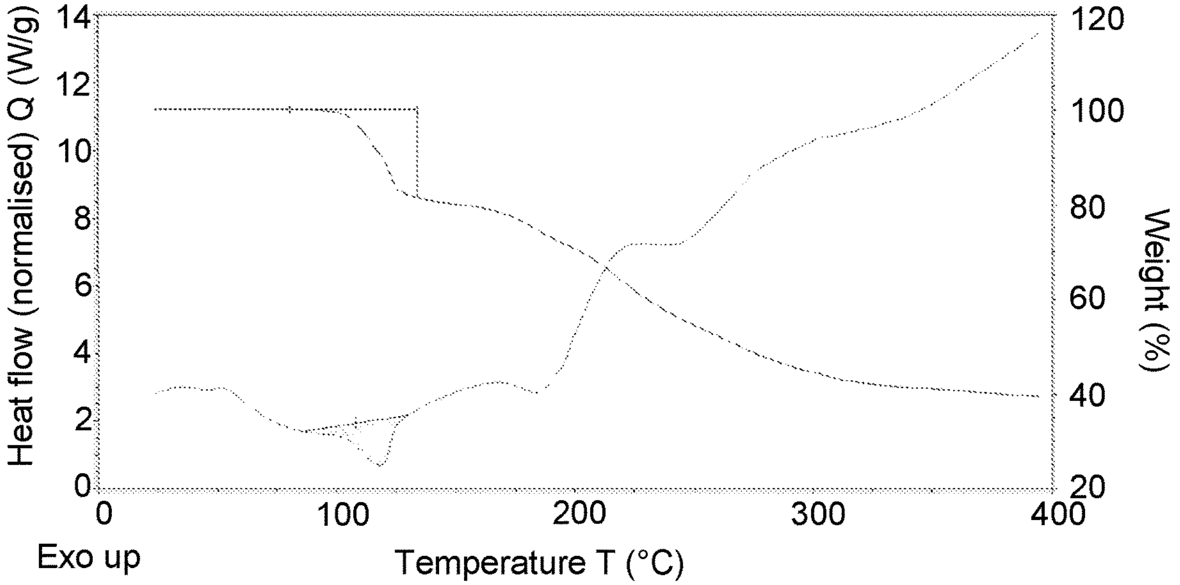
FIG. 10: TGA/DSC thermogram of AP1189 acetate Pattern 3 from THF. Peak temperature: 118.76° C.; onset: 100.62° C.; enthalpy (normalised): 138.49 J/g. First weight loss segment: weight loss: 0.002 mg; weight percent loss: 0.067%. Second weight loss segment: weight loss: 0.672 mg; weight percent loss: 18.610%.

One embodiment of the present disclosure provides for a crystalline Form A of AP1189 acetate exhibiting in differential scanning calorimetry an onset temperature between 185 and 199° C. One specific embodiment of the present disclosure provides a crystalline Form A of AP1189 acetate exhibiting in differential scanning calorimetry an onset temperature of substantially 192° C. In a further embodiment, the onset temperature is assessed using a heating rate of 10° C./min. One embodiment of the disclosure provides for a crystalline Form A of AP1189 acetate exhibiting in differential scanning calorimetry an onset temperature as shown in the examples herein, specifically example 4, and/or in the figures herein, specifically FIG. 8. One embodiment of the present disclosure provides a crystalline Form A of AP1189 acetate exhibiting a differential scanning calorimetry thermogram according to FIG. 8. One embodiment of the present disclosure provides for a crystalline Form A of AP1189 acetate exhibiting in differential scanning calorimetry an onset temperature falling within the interval 192±7° C., such as 192±6° C., such as 192±5° C., such as 192±4° C., such as 192±3° C., such as 192±2° C., such as 192±1° C.

Figure 13:
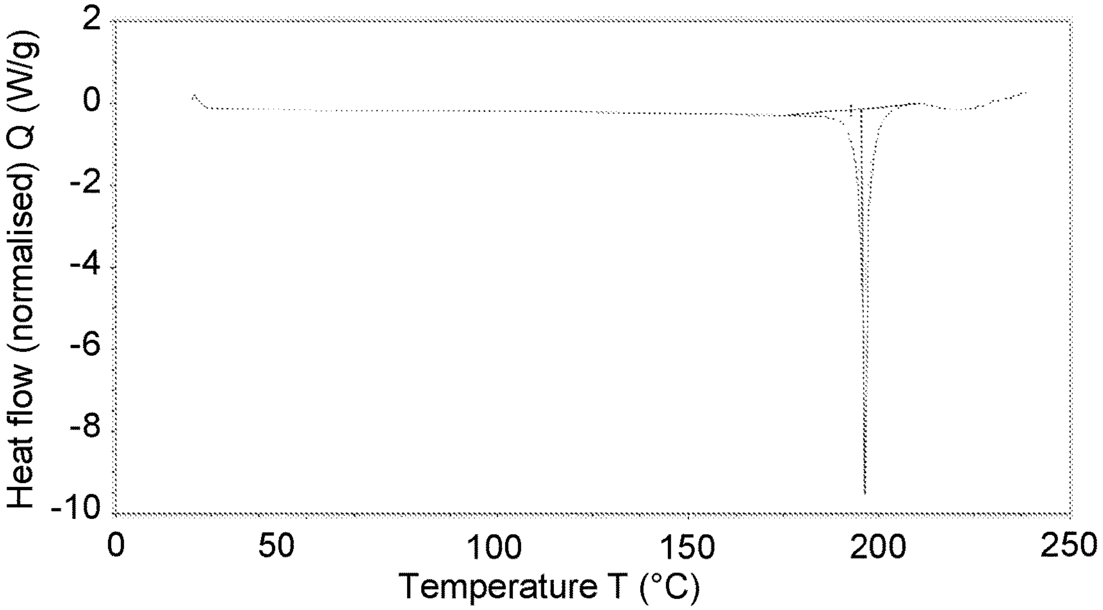
FIG. 13: DSC thermogram of AP1189 succinate Pattern 1 from IPA:water 90:10 v/v. Peak temperature: 196.27° C.; onset: 195.18° C.; enthalpy (normalised): 196.27 J/g.

One embodiment of the present disclosure provides for a crystalline Form B of AP1189 succinate exhibiting in differential scanning calorimetry an onset temperature between 187 and 201° C. One specific embodiment of the present disclosure provides a crystalline Form B of AP1189 succinate exhibiting in differential scanning calorimetry an onset temperature of substantially 194° C. In a further embodiment, the onset temperature is assessed using a heating rate of 10° C./min. One embodiment of the disclosure provides for a crystalline Form B of AP1189 succinate exhibiting in differential scanning calorimetry an onset temperature as shown in the examples herein, specifically example 4, and/or in the figures herein, specifically FIG. 13. One embodiment of the present disclosure provides a crystalline Form B of AP1189 succinate exhibiting a differential scanning calorimetry thermogram according to FIG. 13. One embodiment of the present disclosure provides for a crystalline Form B of AP1189 succinate exhibiting in differential scanning calorimetry an onset temperature falling within the interval 195±7° C., such as 195±6° C., such as 195±5° C., such as 1954° C., such as 1953° C., such as 195±2° C., such as 195±1° C.

Figure 11:
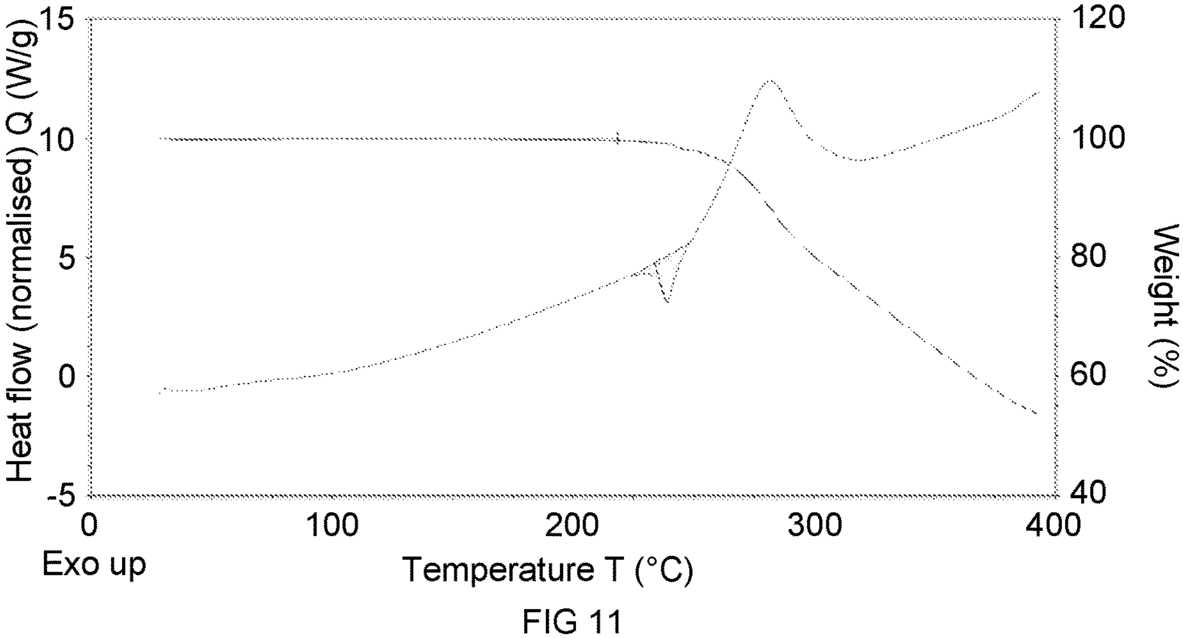
FIG. 11: TGA/DSC thermogram of AP1189 tosylate Pattern 1 from IPA:water 90:10 v/v after storage at 40° C. Peak temperature: 239.24° C.; onset: 233.75° C.; enthalpy (normalised): 99.785 J/g. Weight loss: 0.006 mg; weight percent loss: 0.330%.

One embodiment of the present disclosure provides for a crystalline Form C of AP1189 tosylate exhibiting in differential scanning calorimetry an onset temperature between 227 and 241° C. One specific embodiment of the present disclosure provides a crystalline Form C of AP1189 tosylate exhibiting in differential scanning calorimetry an onset temperature of substantially 234° C. In a further embodiment, the onset temperature is assessed using a heating rate of 10° C./min. One embodiment of the disclosure provides for a crystalline Form C of AP1189 tosylate exhibiting in differential scanning calorimetry an onset temperature as shown in the examples herein, specifically example 4, and/or in the figures herein, specifically FIG. 11. One embodiment of the present disclosure provides a crystalline Form C of AP1189 tosylate exhibiting a differential scanning calorimetry thermogram according to FIG. 11. One embodiment of the present disclosure provides for a crystalline Form C of AP1189 tosylate exhibiting in differential scanning calorimetry an onset temperature falling within the interval 234±7° C., such as 234±6° C., such as 234±5° C., such as 234±4° C., such as 234±3° C., such as 234±2° C., such as 234±1° C.

Figure 12:
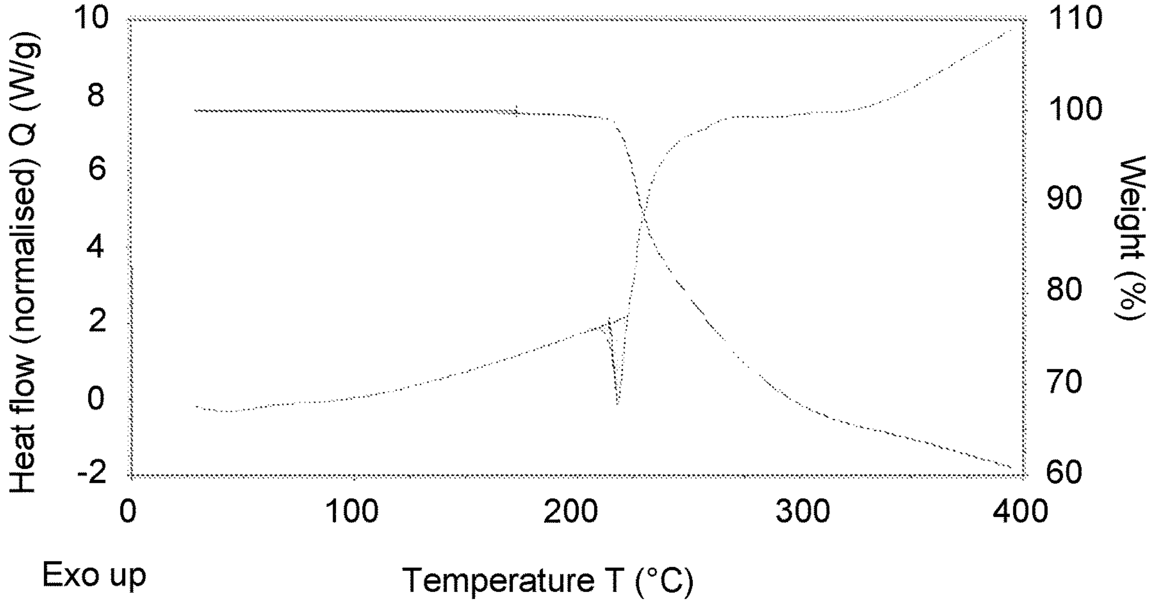
FIG. 12: TGA/DSC thermogram of AP1189 fumarate Pattern 1 from 2-propanol:water 90:10. Peak temperature: 218.27° C.; onset: 214.61° C.; enthalpy (normalised): 68.467 J/g. WE0.012 mg; weight percent loss: 0.319%.

One embodiment of the present disclosure provides for a crystalline Form D of AP1189 fumarate exhibiting in differential scanning calorimetry an onset temperature between 208 and 222° C. One specific embodiment of the present disclosure provides a crystalline Form D of AP1189 fumarate exhibiting in differential scanning calorimetry an onset temperature of substantially 215° C. In a further embodiment, the onset temperature is assessed using a heating rate of 10° C./min. One embodiment of the disclosure provides for a crystalline Form D of AP1189 fumarate exhibiting in differential scanning calorimetry an onset temperature as shown in the examples herein, specifically example 4, and/or in the figures herein, specifically FIG. 12. One embodiment of the present disclosure provides a crystalline Form D of AP1189 fumarate exhibiting a differential scanning calorimetry thermogram according to FIG. 12. One embodiment of the present disclosure provides for a crystalline Form D of AP1189 fumarate exhibiting in differential scanning calorimetry an onset temperature falling within the interval 215±7° C., such as 215±6° C., such as 215±5° C., such as 215±4° C., such as 215±3° C., such as 215±2° C., such as 215±1° C.

Certain salts disclosed herein exhibit more than one onset temperature, e.g. two onset temperatures. The salts may be characterised by either of their onset temperatures in isolation, or as a combination of onset temperatures.

Figure 40:
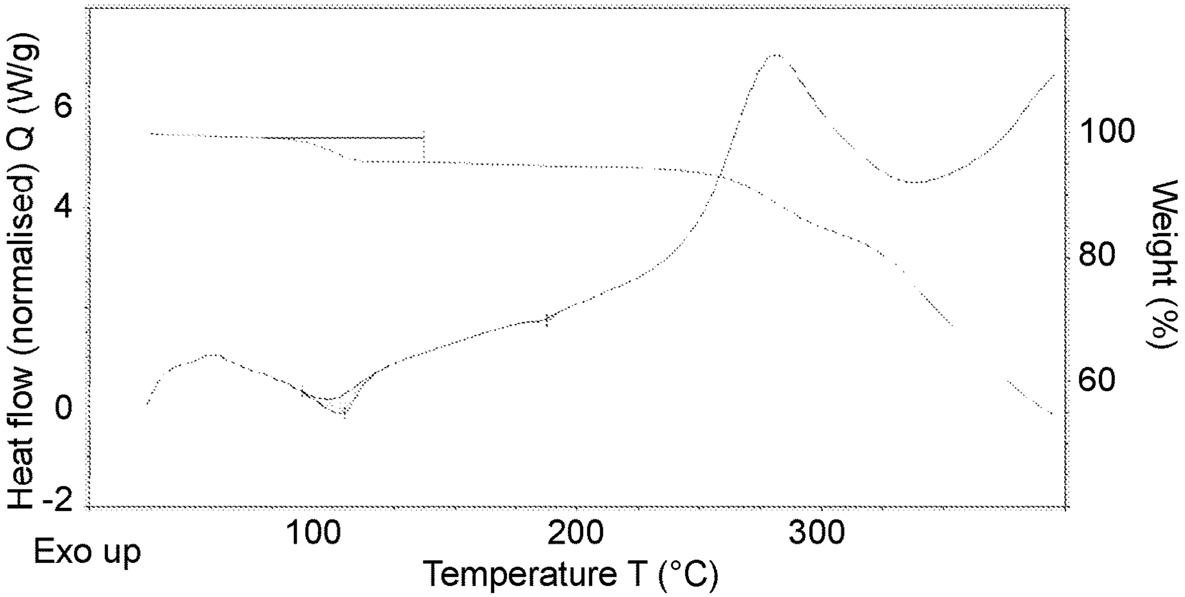
FIG. 40: TG/DSC thermogram of AP1189 Napadisylate Pattern 1. Weight loss: 0.1356 mg. Weight Percent Loss: 3.974%. Enthalpy (normalised): 29.422 J/g; Onset x: 87.38° C.; peak temperature: 104.76° C. Enthalpy (normalised): 1.8937 J/g; Peak temperature: 187.47° C.

One embodiment of the present disclosure provides for a crystalline Form III of AP1189 napadisylate exhibiting in differential scanning calorimetry an onset temperature between 80 and 94° C. One specific embodiment of the present disclosure provides a crystalline Form III of AP1189 napadisylate exhibiting in differential scanning calorimetry an onset temperature of substantially 87° C. In a further embodiment, the onset temperature is assessed using a heating rate of 10° C./min. One embodiment of the disclosure provides for a crystalline Form III of AP1189 napadisylate exhibiting in differential scanning calorimetry an onset temperature as shown in the examples herein, specifically example 4, and/or in the figures herein, specifically FIG. 40. One embodiment of the present disclosure provides a crystalline Form III of AP1189 napadisylate exhibiting a differential scanning calorimetry thermogram according to FIG. 40. One embodiment of the present disclosure provides for a crystalline Form III of AP1189 napadisylate exhibiting in differential scanning calorimetry an onset temperature falling within the interval 87±7° C., such as 87±6° C., such as 87±5° C., such as 874° C., such as 873° C., such as 87±2° C., such as 87±1° C.

One embodiment of the present disclosure provides for a crystalline Form III of AP1189 napadisylate exhibiting in differential scanning calorimetry an onset temperature between 180 and 194° C. One specific embodiment of the present disclosure provides a crystalline Form III of AP1189 napadisylate exhibiting in differential scanning calorimetry an onset temperature of substantially 187° C. In a further embodiment, the onset temperature is assessed using a heating rate of 10° C./min. One embodiment of the disclosure provides for a crystalline Form III of AP1189 napadisylate exhibiting in differential scanning calorimetry an onset temperature as shown in the examples herein, specifically example 4, and/or in the figures herein, specifically FIG. 40. One embodiment of the present disclosure provides a crystalline Form III of AP1189 napadisylate exhibiting a differential scanning calorimetry thermogram according to FIG. 40. One embodiment of the present disclosure provides for a crystalline Form III of AP1189 napadisylate exhibiting in differential scanning calorimetry an onset temperature falling within the interval 187±7° C., such as 187±6° C., such as 187±5° C., such as 187±4° C., such as 187±3° C., such as 187±2° C., such as 187±1° C.

Figure 81:
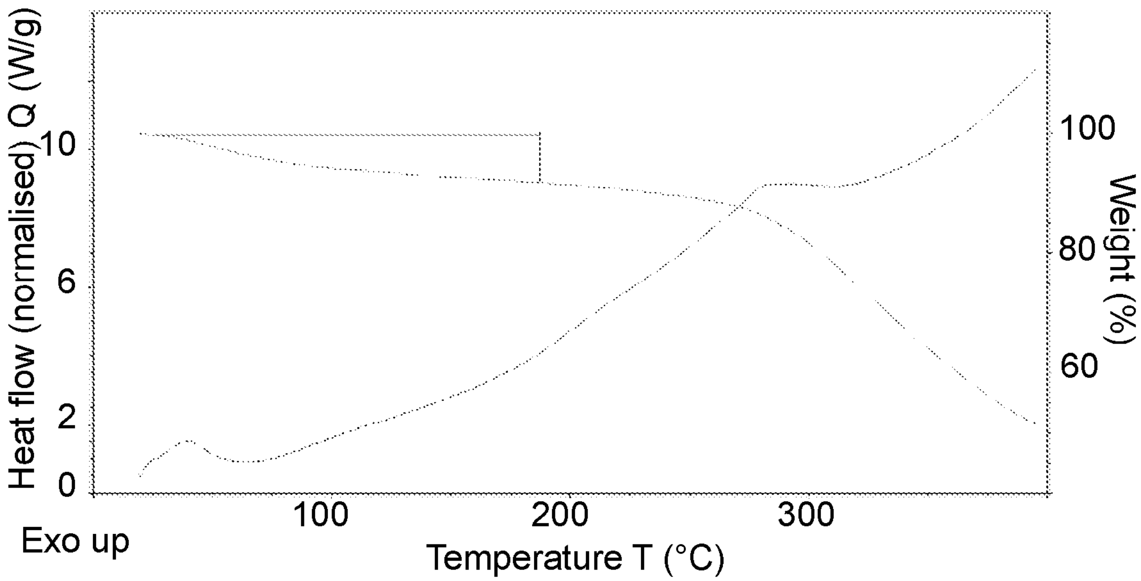
FIG. 81: TG/DSC thermogram of AP1189 Napadisylate Pattern 2. Weight Loss: 0.157 mg. Weight Percent Loss: 7.940%.

One embodiment of the disclosure provides for a crystalline Form IV of AP1189 napadisylate exhibiting in differential scanning calorimetry an onset temperature as shown in the examples herein, specifically example 4, and/or in the figures herein, specifically FIG. 81. One embodiment of the present disclosure provides a crystalline Form IV of AP1189 napadisylate exhibiting a differential scanning calorimetry thermogram according to FIG. 81.

Figure 41:
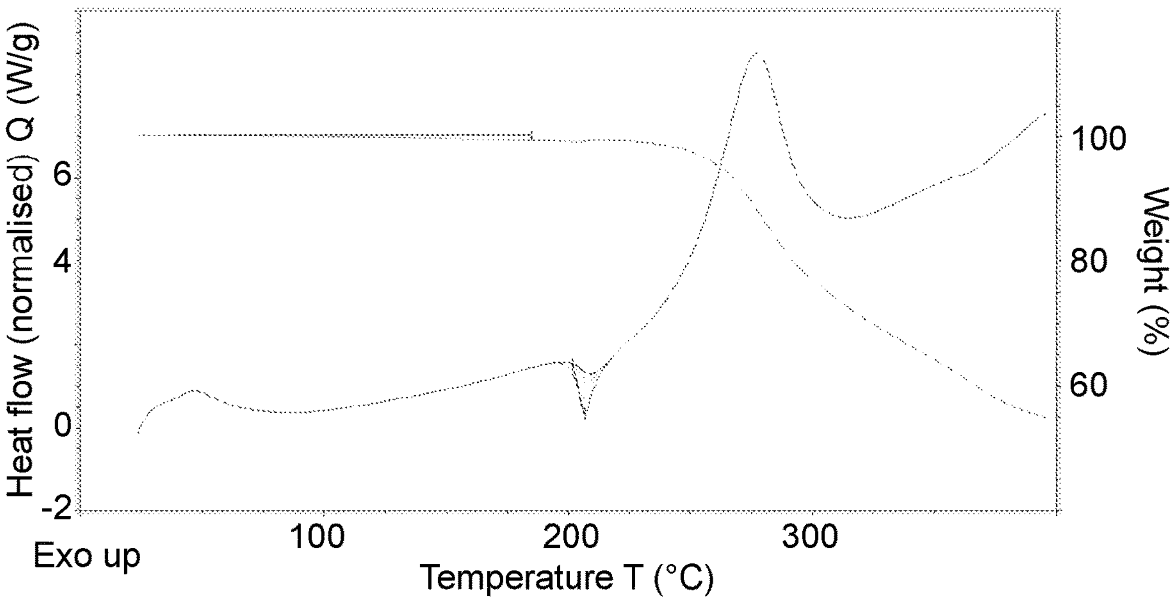
FIG. 41: TG/DSC thermogram of AP1189 Esylate Pattern 1. Weight Loss: 0.032 mg. Weight Percent Loss: 0.911%. Enthalpy (normalised): 42.119 J/g; Onset x: 201.95° C.; Peak temperature: 207.06° C.

One embodiment of the present disclosure provides for a crystalline Form V of AP1189 esylate exhibiting in differential scanning calorimetry an onset temperature between 200 and 214° C. One specific embodiment of the present disclosure provides a crystalline Form V of AP1189 esylate exhibiting in differential scanning calorimetry an onset temperature of substantially 207° C. In a further embodiment, the onset temperature is assessed using a heating rate of 10° C./min. One embodiment of the disclosure provides for a crystalline Form V of AP1189 esylate exhibiting in differential scanning calorimetry an onset temperature as shown in the examples herein, specifically example 4, and/or in the figures herein, specifically FIG. 41. One embodiment of the present disclosure provides a crystalline Form V of AP1189 esylate exhibiting a differential scanning calorimetry thermogram according to FIG. 41. One embodiment of the present disclosure provides for a crystalline Form V of AP1189 esylate exhibiting in differential scanning calorimetry an onset temperature falling within the interval 207±7° C., such as 207±6° C., such as 207±5° C., such as 207±4° C., such as 207±3° C., such as 207±2° C., such as 207±1° C.

Figure 82:
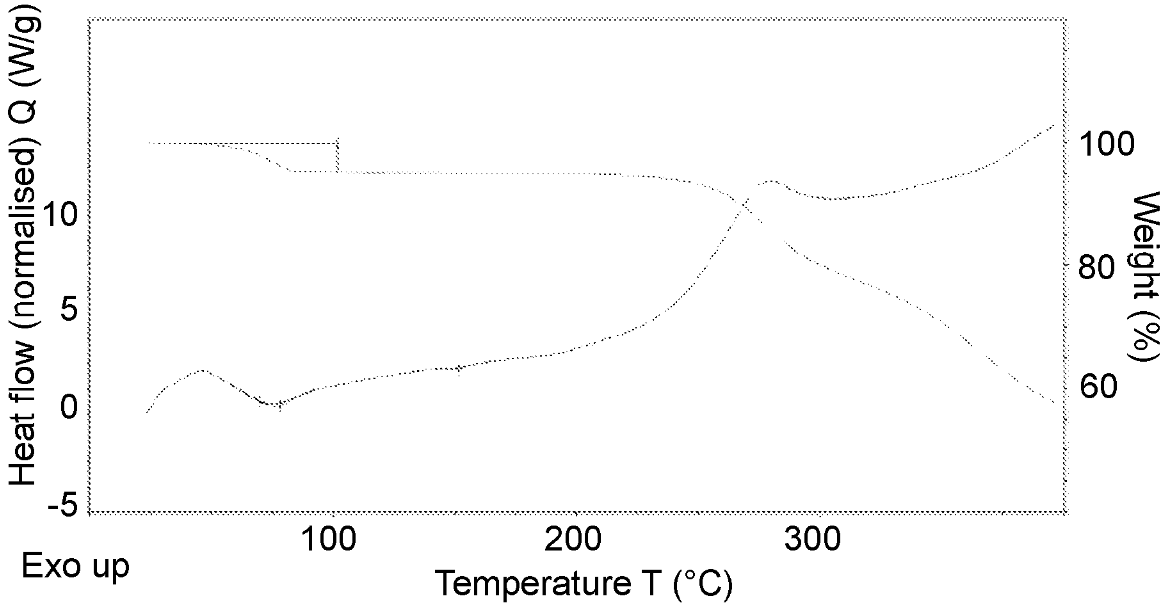
FIG. 82: TG/DSC thermogram of AP1189 Edisylate Pattern 1. Weight Loss: 0.082 mg. Weight Percent Loss: 4.634%. Enthalpy (normalised): 3.2707 J/g; Onset x: 69.98° C.; Peak temperature: 78.37° C. Enthalpy (normalised): 0.83635 J/g; Peak temperature: 151.31° C.

One embodiment of the present disclosure provides for a crystalline Form VI of AP1189 edisylate exhibiting in differential scanning calorimetry an onset temperature between 71 and 85° C. One specific embodiment of the present disclosure provides a crystalline Form VI of AP1189 edisylate exhibiting in differential scanning calorimetry an onset temperature of substantially 78° C. In a further embodiment, the onset temperature is assessed using a heating rate of 10° C./min. One embodiment of the disclosure provides for a crystalline Form VI of AP1189 edisylate exhibiting in differential scanning calorimetry an onset temperature as shown in the examples herein, specifically example 4, and/or in the figures herein, specifically FIG. 82. One embodiment of the present disclosure provides a crystalline Form VI of AP1189 edisylate exhibiting a differential scanning calorimetry thermogram according to FIG. 82. One embodiment of the present disclosure provides for a crystalline Form VI of AP1189 edisylate exhibiting in differential scanning calorimetry an onset temperature falling within the interval 78±7° C., such as 78±6° C., such as 78±5° C., such as 78±4° C., such as 78±3° C., such as 78±2° C., such as 78±1° C.

One embodiment of the present disclosure provides for a crystalline Form VI of AP1189 edisylate exhibiting in differential scanning calorimetry an onset temperature between 144 and 158° C. One specific embodiment of the present disclosure provides a crystalline Form VI of AP1189 edisylate exhibiting in differential scanning calorimetry an onset temperature of substantially 151° C. In a further embodiment, the onset temperature is assessed using a heating rate of 10° C./min. One embodiment of the disclosure provides for a crystalline Form VI of AP1189 edisylate exhibiting in differential scanning calorimetry an onset temperature as shown in the examples herein, specifically example 4, and/or in the figures herein, specifically FIG. 82. One embodiment of the present disclosure provides a crystalline Form VI of AP1189 edisylate exhibiting a differential scanning calorimetry thermogram according to FIG. 82. One embodiment of the present disclosure provides for a crystalline Form VI of AP1189 edisylate exhibiting in differential scanning calorimetry an onset temperature falling within the interval 151±7° C., such as 151±6° C., such as 151±5° C., such as 151±4° C., such as 151±3° C., such as 151±2° C., such as 151±1° C.

Figure 42:
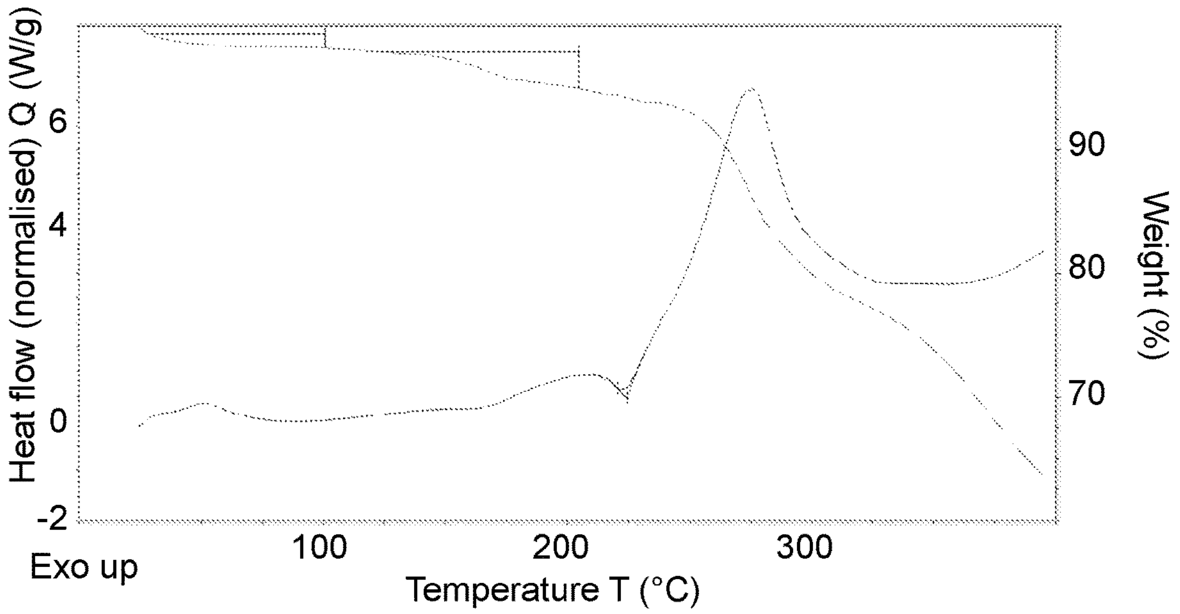
FIG. 42: TG/DSC thermogram of AP1189 Edisylate Pattern 2. Weight Loss: 0.061 mg. Weight Percent Loss: 1.175%. Weight Loss: 0.158 mg. Weight Percent Loss: 3.040%. Enthalpy (normalised): 3.1886 J/g; Onset x: 220.71° C.; Peak temperature: 224.57° C.

One embodiment of the present disclosure provides for a crystalline Form VII of AP1189 edisylate exhibiting in differential scanning calorimetry an onset temperature between 218 and 232° C. One specific embodiment of the present disclosure provides a crystalline Form VII of AP1189 edisylate exhibiting in differential scanning calorimetry an onset temperature of substantially 225° C. In a further embodiment, the onset temperature is assessed using a heating rate of 10° C./min. One embodiment of the disclosure provides for a crystalline Form VII of AP1189 edisylate exhibiting in differential scanning calorimetry an onset temperature as shown in the examples herein, specifically example 4, and/or in the figures herein, specifically FIG. 42. One embodiment of the present disclosure provides a crystalline Form VII of AP1189 edisylate exhibiting a differential scanning calorimetry thermogram according to FIG. 42. One embodiment of the present disclosure provides for a crystalline Form VII of AP1189 edisylate exhibiting in differential scanning calorimetry an onset temperature falling within the interval 225±7° C., such as 225±6° C., such as 225±5° C., such as 225±4° C., such as 225±3° C., such as 225±2° C., such as 225±1° C.

Figure 43:
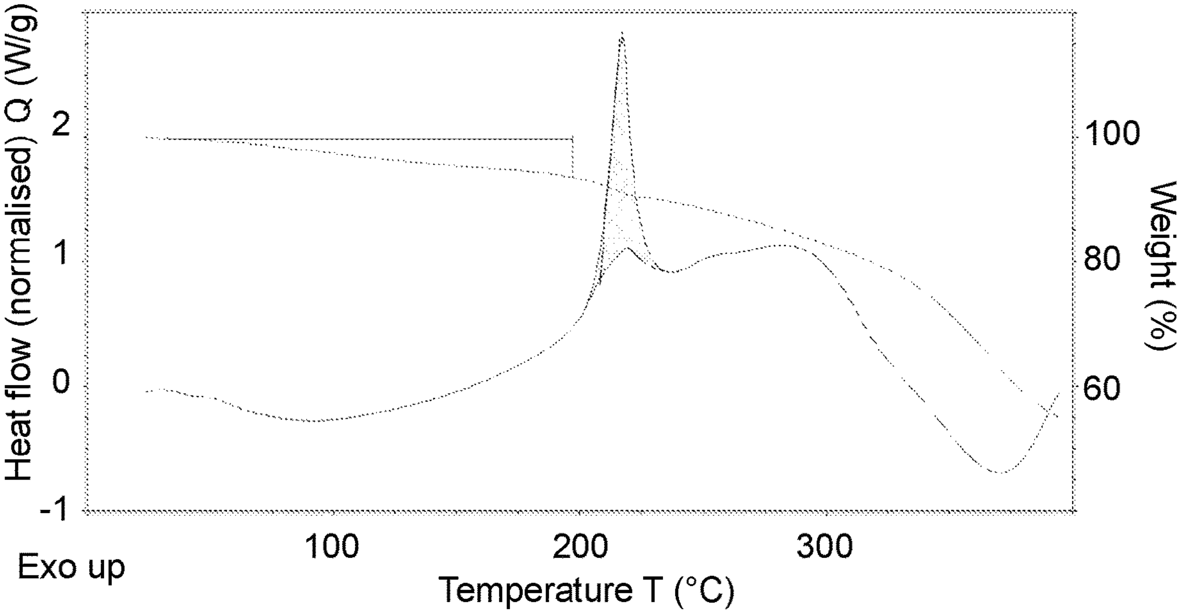
FIG. 43: TG/DSC thermogram of AP1189 Edisylate Pattern 4. Weight Loss: 1.463 mg. Weight Percent Loss: 6.372%. Enthalpy (normalised): 100.17 J/g. Onset x: 208.40° C.; Peak temperature: 217.37° C.

One embodiment of the present disclosure provides for a crystalline Form VIII of AP1189 edisylate exhibiting in differential scanning calorimetry an onset temperature between 201 and 215° C. One specific embodiment of the present disclosure provides a crystalline Form VIII of AP1189 edisylate exhibiting in differential scanning calorimetry an onset temperature of substantially 208° C. In a further embodiment, the onset temperature is assessed using a heating rate of 10° C./min. One embodiment of the disclosure provides for a crystalline Form VIII of AP1189 edisylate exhibiting in differential scanning calorimetry an onset temperature as shown in the examples herein, specifically example 4, and/or in the figures herein, specifically FIG. 43. One embodiment of the present disclosure provides a crystalline Form VIII of AP1189 edisylate exhibiting a differential scanning calorimetry thermogram according to FIG. 43. One embodiment of the present disclosure provides for a crystalline Form VIII of AP1189 edisylate exhibiting in differential scanning calorimetry an onset temperature falling within the interval 208±7° C., such as 208±6° C., such as 208±5° C., such as 208±4° C., such as 208±3° C., such as 208±2° C., such as 208±1° C.

Figure 44:
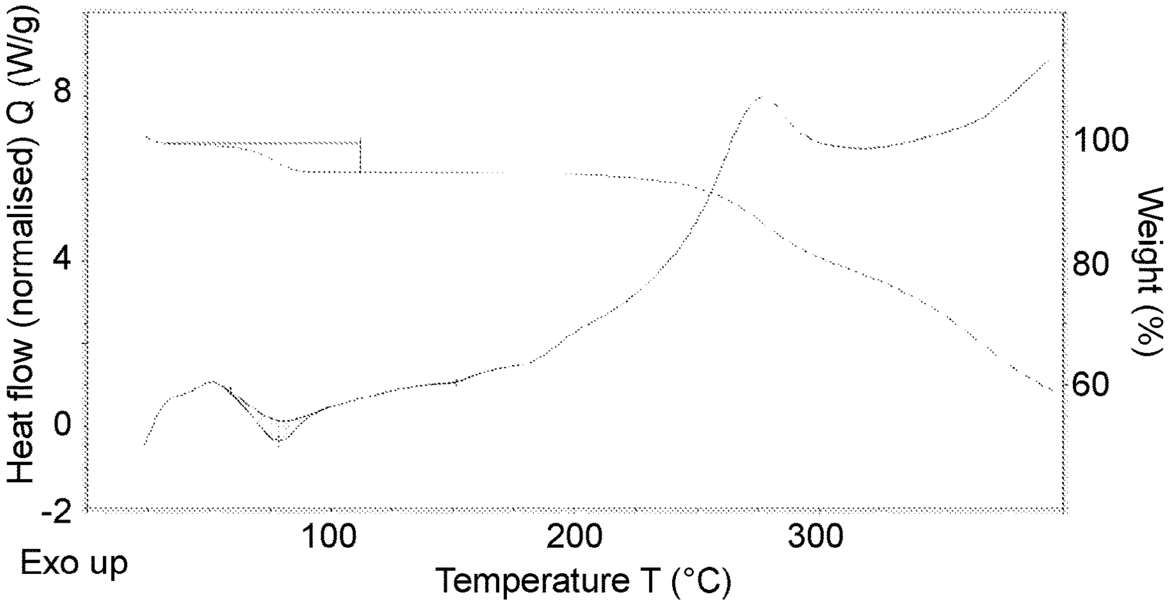
FIG. 44: TG/DSC thermogram of AP1189 Edisylate Pattern 5. Weight Loss: 0.120 mg. Weight Percent Loss: 4.701%. Enthalpy (normalised): 54.800 J/g; Onset x: 58.52° C.; Peak temperature: 78.51° C. Enthalpy (normalised): 0.93567 J/g; Onset x: Not found; Peak temperature: 151.11° C.

One embodiment of the present disclosure provides for a crystalline Form IX of AP1189 edisylate exhibiting in differential scanning calorimetry an onset temperature between 52 and 66° C. One specific embodiment of the present disclosure provides a crystalline Form IX of AP1189 edisylate exhibiting in differential scanning calorimetry an onset temperature of substantially 59° C. In a further embodiment, the onset temperature is assessed using a heating rate of 10° C./min. One embodiment of the disclosure provides for a crystalline Form IX of AP1189 edisylate exhibiting in differential scanning calorimetry an onset temperature as shown in the examples herein, specifically example 4, and/or in the figures herein, specifically FIG. 44. One embodiment of the present disclosure provides a crystalline Form IX of AP1189 edisylate exhibiting a differential scanning calorimetry thermogram according to FIG. 44. One embodiment of the present disclosure provides for a crystalline Form IX of AP1189 edisylate exhibiting in differential scanning calorimetry an onset temperature falling within the interval 59±7° C., such as 59±6° C., such as 59±5° C., such as 59±4° C., such as 59±3° C., such as 59±2° C., such as 59±1° C.

One embodiment of the present disclosure provides for a crystalline Form XI of AP1189 edisylate exhibiting in differential scanning calorimetry an onset temperature between 144 and 158° C. One specific embodiment of the present disclosure provides a crystalline Form IX of AP1189 edisylate exhibiting in differential scanning calorimetry an onset temperature of substantially 151° C. In a further embodiment, the onset temperature is assessed using a heating rate of 10° C./min. One embodiment of the disclosure provides for a crystalline Form IX of AP1189 edisylate exhibiting in differential scanning calorimetry an onset temperature as shown in the examples herein, specifically example 4, and/or in the figures herein, specifically FIG. 44. One embodiment of the present disclosure provides a crystalline Form IX of AP1189 edisylate exhibiting a differential scanning calorimetry thermogram according to FIG. 44. One embodiment of the present disclosure provides for a crystalline Form IX of AP1189 edisylate exhibiting in differential scanning calorimetry an onset temperature falling within the interval 151±7° C., such as 151±6° C., such as 151±5° C., such as 151±4° C., such as 151±3° C., such as 151±2° C., such as 151±1° C.

Figure 45:
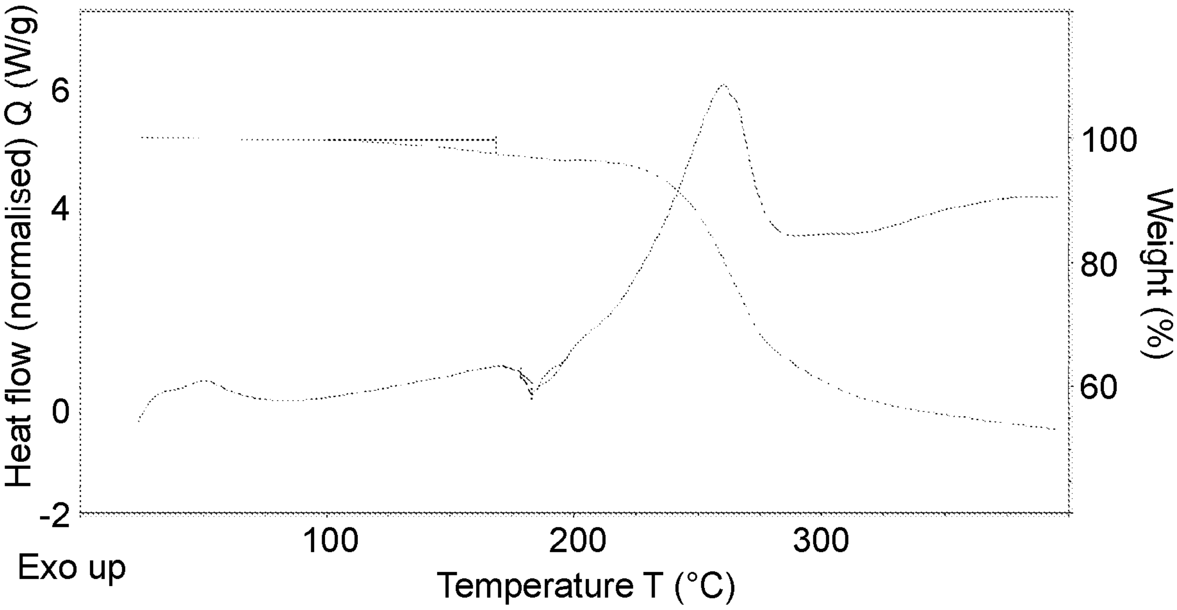
FIG. 45: TG/DSC thermogram of AP1189 Nitrate Pattern 1. Weight Loss: 0.095 mg. Weight Percent Loss: 2.139%. Enthalpy (normalised): 0.4851 J/g; Onset x: 178.54° C.; Peak temperature: 182.88° C.

One embodiment of the present disclosure provides for a crystalline Form X of AP1189 nitrate exhibiting in differential scanning calorimetry an onset temperature between 172 and 186° C. One specific embodiment of the present disclosure provides a crystalline Form X of AP1189 nitrate exhibiting in differential scanning calorimetry an onset temperature of substantially 179° C. In a further embodiment, the onset temperature is assessed using a heating rate of 10° C./min. One embodiment of the disclosure provides for a crystalline Form X of AP1189 nitrate exhibiting in differential scanning calorimetry an onset temperature as shown in the examples herein, specifically example 4, and/or in the figures herein, specifically FIG. 45. One embodiment of the present disclosure provides a crystalline Form X of AP1189 nitrate exhibiting a differential scanning calorimetry thermogram according to FIG. 45. One embodiment of the present disclosure provides for a crystalline Form X of AP1189 nitrate exhibiting in differential scanning calorimetry an onset temperature falling within the interval 179±7° C., such as 179±6° C., such as 179±5° C., such as 179±4° C., such as 179±3° C., such as 179±2° C., such as 179±1° C.

Figure 46:
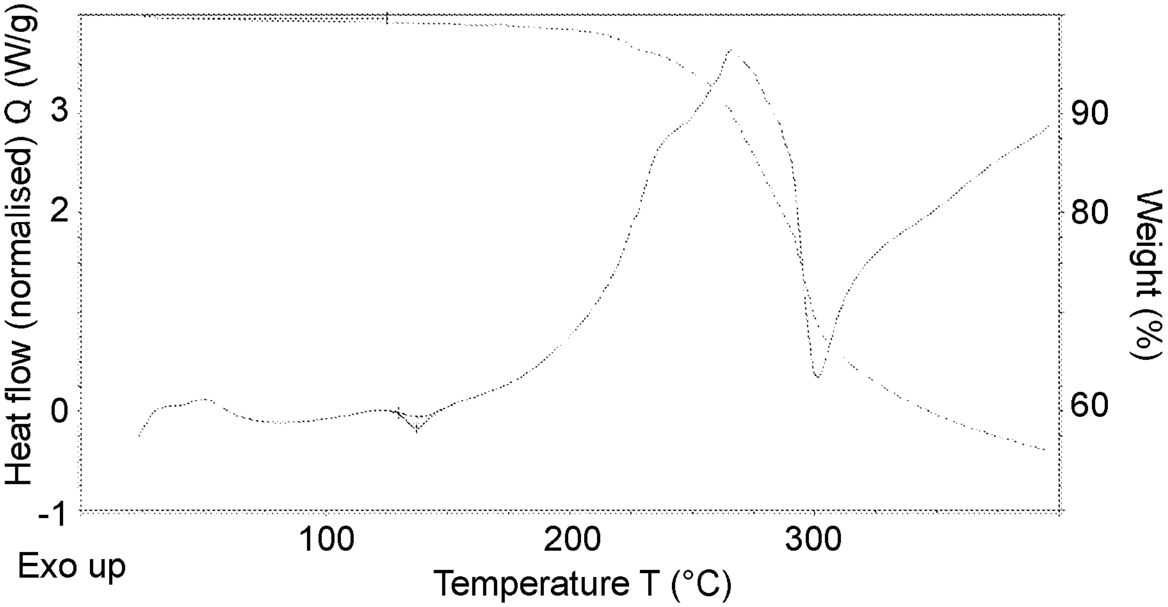
FIG. 46: TG/DSC thermogram of AP1189 Cyclamate Pattern 2. Weight Loss: 0.033 mg. Weight Percent Loss: 0.459%. Enthalpy (normalised): 6.4491 J/g; Onset x: 129.90° C.; Peak temperature: 137.27° C.

One embodiment of the present disclosure provides for a crystalline Form XI of AP1189 cyclamate exhibiting in differential scanning calorimetry an onset temperature between 123 and 137° C. One specific embodiment of the present disclosure provides a crystalline Form XI of AP1189 cyclamate exhibiting in differential scanning calorimetry an onset temperature of substantially 130° C. In a further embodiment, the onset temperature is assessed using a heating rate of 10° C./min. One embodiment of the disclosure provides for a crystalline Form XI of AP1189 cyclamate exhibiting in differential scanning calorimetry an onset temperature as shown in the examples herein, specifically example 4, and/or in the figures herein, specifically FIG. 46. One embodiment of the present disclosure provides a crystalline Form XI of AP1189 cyclamate exhibiting a differential scanning calorimetry thermogram according to FIG. 46. One embodiment of the present disclosure provides for a crystalline Form XI of AP1189 cyclamate exhibiting in differential scanning calorimetry an onset temperature falling within the interval 130±7° C., such as 130±6° C., such as 130±5° C., such as 130±4° C., such as 130±3° C., such as 130±2° C., such as 130±1° C.

Figure 47:
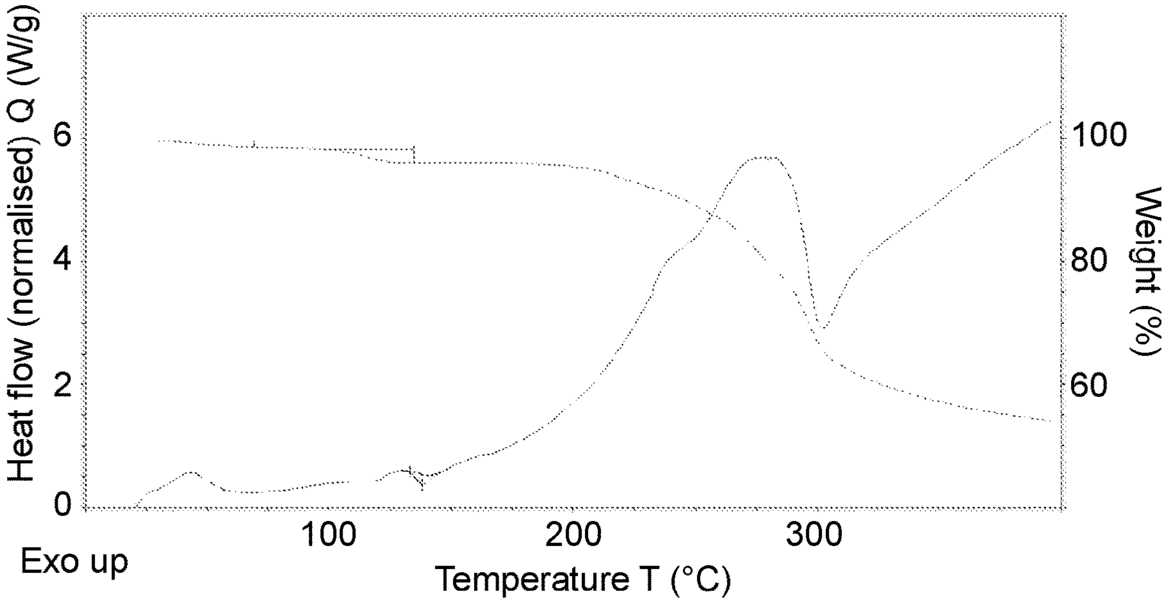
FIG. 47: TG/DSC thermogram of AP1189 Cyclamate Pattern 4. Weight Loss: 0.041 mg. Weight Percent Loss: 1.080%. Weight Loss: 0.088 mg. Weight Percent Loss: 2.337%. Enthalpy (normalised): 0.0143 J/g; Onset x: 133.07° C.; Peak temperature: 138.20° C.

One embodiment of the present disclosure provides for a crystalline Form XII of AP1189 cyclamate exhibiting in differential scanning calorimetry an onset temperature between 131 and 145° C. One specific embodiment of the present disclosure provides a crystalline Form XII of AP1189 cyclamate exhibiting in differential scanning calorimetry an onset temperature of substantially 138° C. In a further embodiment, the onset temperature is assessed using a heating rate of 10° C./min. One embodiment of the disclosure provides for a crystalline Form XII of AP1189 cyclamate exhibiting in differential scanning calorimetry an onset temperature as shown in the examples herein, specifically example 4, and/or in the figures herein, specifically FIG. 47. One embodiment of the present disclosure provides a crystalline Form XII of AP1189 cyclamate exhibiting a differential scanning calorimetry thermogram according to FIG. 47. One embodiment of the present disclosure provides for a crystalline Form XII of AP1189 cyclamate exhibiting in differential scanning calorimetry an onset temperature falling within the interval 138±7° C., such as 138±6° C., such as 138±5° C., such as 138±4° C., such as 138±3° C., such as 138±2° C., such as 138±1° C.

Figure 83:
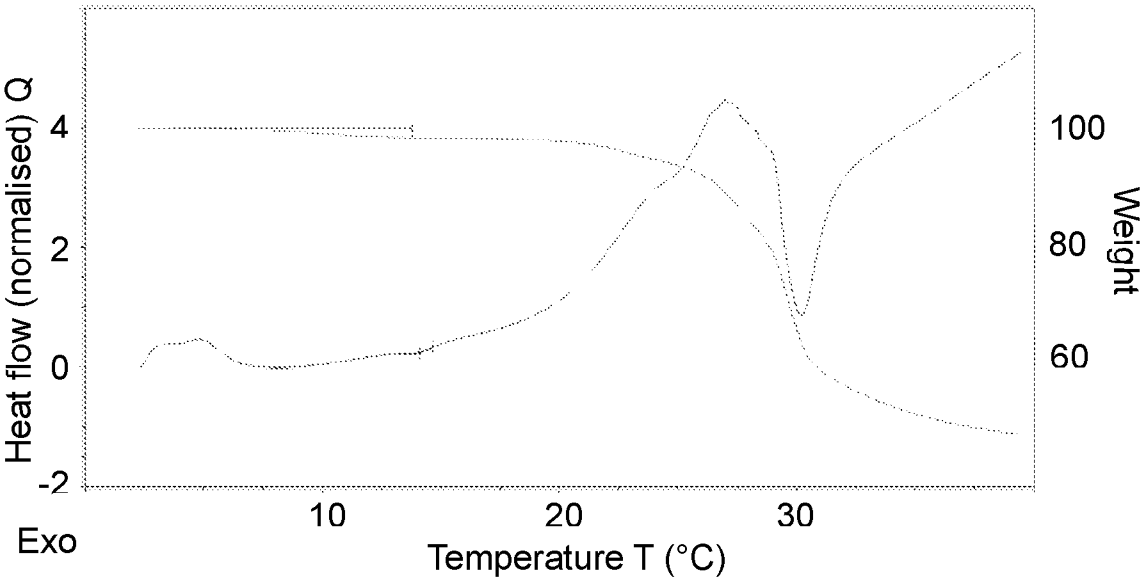
FIG. 83: TG/DSC thermogram of AP1189 Cyclamate Pattern 5. Weight Loss: 0.070 mg. Weight Percent Loss: 1.696%. Enthalpy (normalised): 0.68855 J/g; Onset x: 140.91° C.; Peak temperature: 146.39° C.

One embodiment of the present disclosure provides for a crystalline Form XIII of AP1189 cyclamate exhibiting in differential scanning calorimetry an onset temperature between 134 and 148° C. One specific embodiment of the present disclosure provides a crystalline Form XIII of AP1189 cyclamate exhibiting in differential scanning calorimetry an onset temperature of substantially 141° C. In a further embodiment, the onset temperature is assessed using a heating rate of 10° C./min. One embodiment of the disclosure provides for a crystalline Form XIII of AP1189 cyclamate exhibiting in differential scanning calorimetry an onset temperature as shown in the examples herein, specifically example 4, and/or in the figures herein, specifically FIG. 83. One embodiment of the present disclosure provides a crystalline Form XIII of AP1189 cyclamate exhibiting a differential scanning calorimetry thermogram according to FIG. 83. One embodiment of the present disclosure provides for a crystalline Form XIII of AP1189 cyclamate exhibiting in differential scanning calorimetry an onset temperature falling within the interval 141±7° C., such as 141±6° C., such as 141±5° C., such as 141±4° C., such as 141±3° C., such as 141±2° C., such as 141±1° C.

Figure 48:
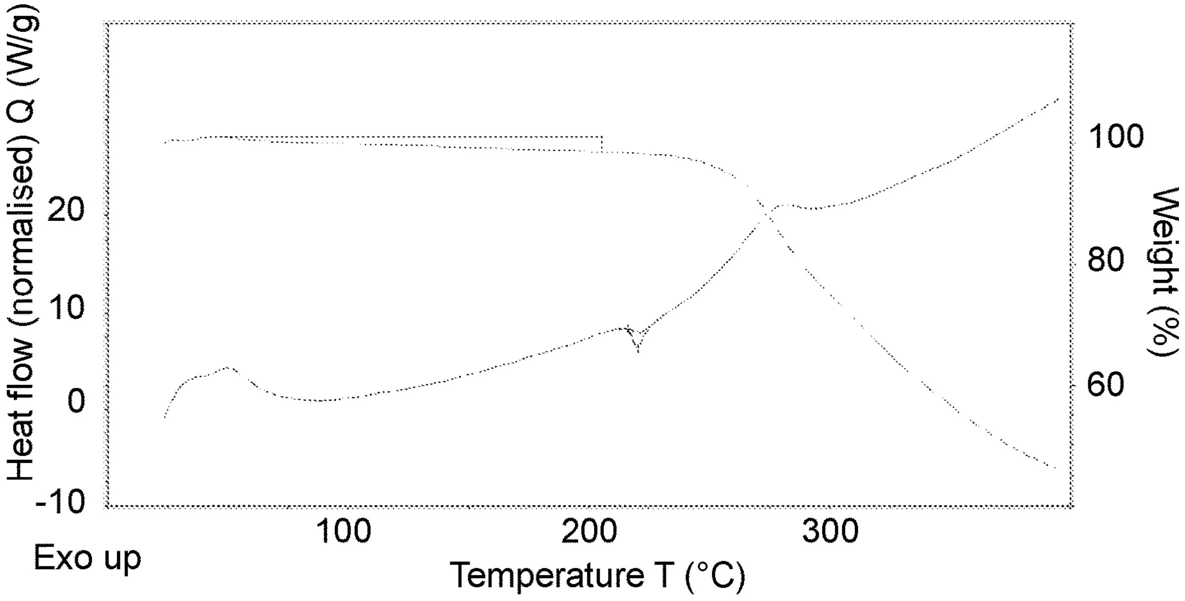
FIG. 48: TG/DSC thermogram of AP1189 Besylate Pattern 1. Weight Loss: 0.014 mg. Weight Percent Loss: 2.369%. Enthalpy (normalised): 48.524 J/g; Onset x: 216.45° C.; Peak temperature: 220.49° C.

One embodiment of the present disclosure provides for a crystalline Form XIV of AP1189 besylate exhibiting in differential scanning calorimetry an onset temperature between 219 and 223° C. One specific embodiment of the present disclosure provides a crystalline Form XIV of AP1189 besylate exhibiting in differential scanning calorimetry an onset temperature of substantially 216° C. In a further embodiment, the onset temperature is assessed using a heating rate of 10° C./min. One embodiment of the disclosure provides for a crystalline Form XIV of AP1189 besylate exhibiting in differential scanning calorimetry an onset temperature as shown in the examples herein, specifically example 4, and/or in the figures herein, specifically FIG. 48. One embodiment of the present disclosure provides a crystalline Form XIV of AP1189 besylate exhibiting a differential scanning calorimetry thermogram according to FIG. 48. One embodiment of the present disclosure provides for a crystalline Form XIV of AP1189 besylate exhibiting in differential scanning calorimetry an onset temperature falling within the interval 216±7° C., such as 216±6° C., such as 216±5° C., such as 216±4° C., such as 216±3° C., such as 216±2° C., such as 216±1° C.

Figure 49:
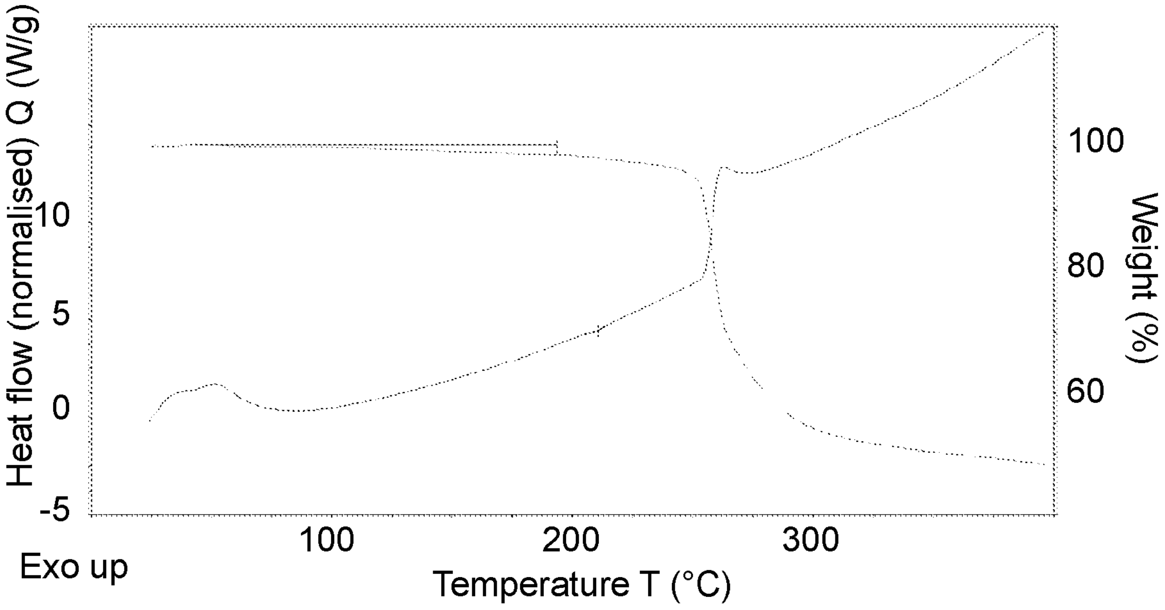
FIG. 49: TG/DSC thermogram of AP1189 Oxalate Pattern 1. Weight Loss: 0.023 mg. Weight Percent Loss: 1.665%. Enthalpy (normalised): 0.32686 J/g; Peak temperature: 210.52° C.

One embodiment of the present disclosure provides for a crystalline Form XV of AP1189 oxalate exhibiting in differential scanning calorimetry a peak temperature between 204 and 218° C. One specific embodiment of the present disclosure provides a crystalline Form XV of AP1189 oxalate exhibiting in differential scanning calorimetry a peal temperature of substantially 211° C. In a further embodiment, the peak temperature is assessed using a heating rate of 10° C./min. One embodiment of the disclosure provides for a crystalline Form XV of AP1189 oxalate exhibiting in differential scanning calorimetry a peak temperature as shown in the examples herein, specifically example 4, and/or in the figures herein, specifically FIG. 49. One embodiment of the present disclosure provides a crystalline Form XV of AP1189 oxalate exhibiting a differential scanning calorimetry thermogram according to FIG. 49. One embodiment of the present disclosure provides for a crystalline Form XV of AP1189 oxalate exhibiting in differential scanning calorimetry a peak temperature falling within the interval 211±7° C., such as 211±6° C., such as 211±5° C., such as 211±4° C., such as 211±3° C., such as 211±2° C., such as 211±1° C.

Figure 50:
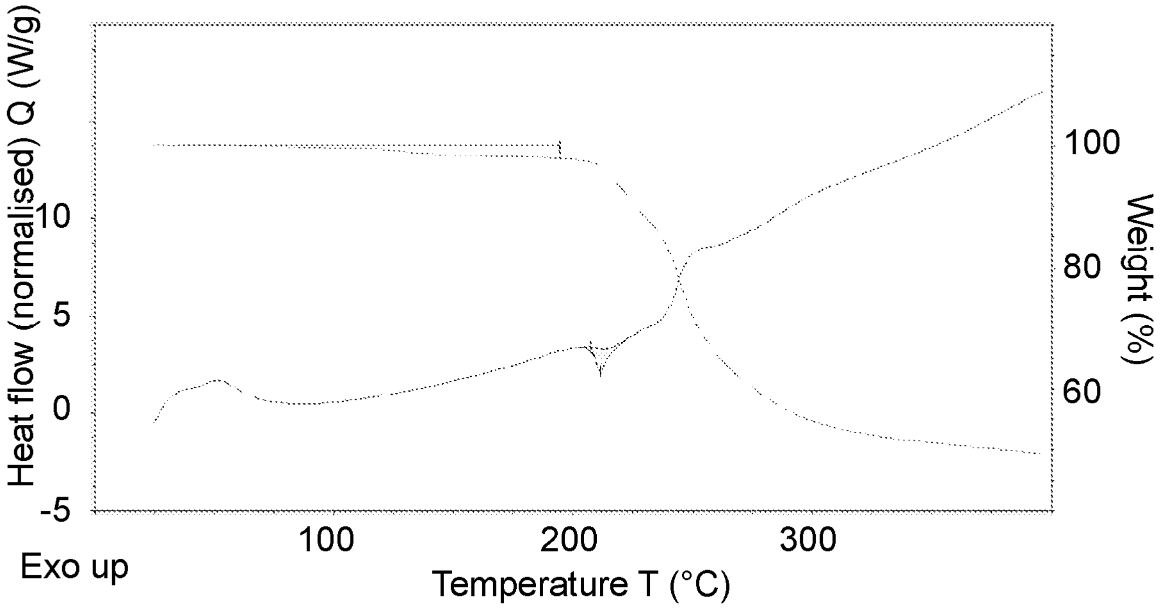
FIG. 50: TG/DSC thermogram of AP1189 Oxalate Pattern 2. Weight Loss. 0.035 mg. Weight Percent Loss: 2.156%. Enthalpy (normalised): 40.935 J/g; Onset x: 207.42° C.; Peak temperature: 211.50° C.

One embodiment of the present disclosure provides for a crystalline Form XVI of AP1189 oxalate exhibiting in differential scanning calorimetry an onset temperature between 200 and 214° C. One specific embodiment of the present disclosure provides a crystalline Form XVI of AP1189 oxalate exhibiting in differential scanning calorimetry an onset temperature of substantially 207° C. In a further embodiment, the onset temperature is assessed using a heating rate of 10° C./min. One embodiment of the disclosure provides for a crystalline Form XVI of AP1189 oxalate exhibiting in differential scanning calorimetry an onset temperature as shown in the examples herein, specifically example 4, and/or in the figures herein, specifically FIG. 50. One embodiment of the present disclosure provides a crystalline Form XVI of AP1189 oxalate exhibiting a differential scanning calorimetry thermogram according to FIG. 50. One embodiment of the present disclosure provides for a crystalline Form XVI of AP1189 oxalate exhibiting in differential scanning calorimetry an onset temperature falling within the interval 207±7° C., such as 207±6° C., such as 207±5° C., such as 207±4° C., such as 207±3° C., such as 207±2° C., such as 207±1° C.

Figure 51:
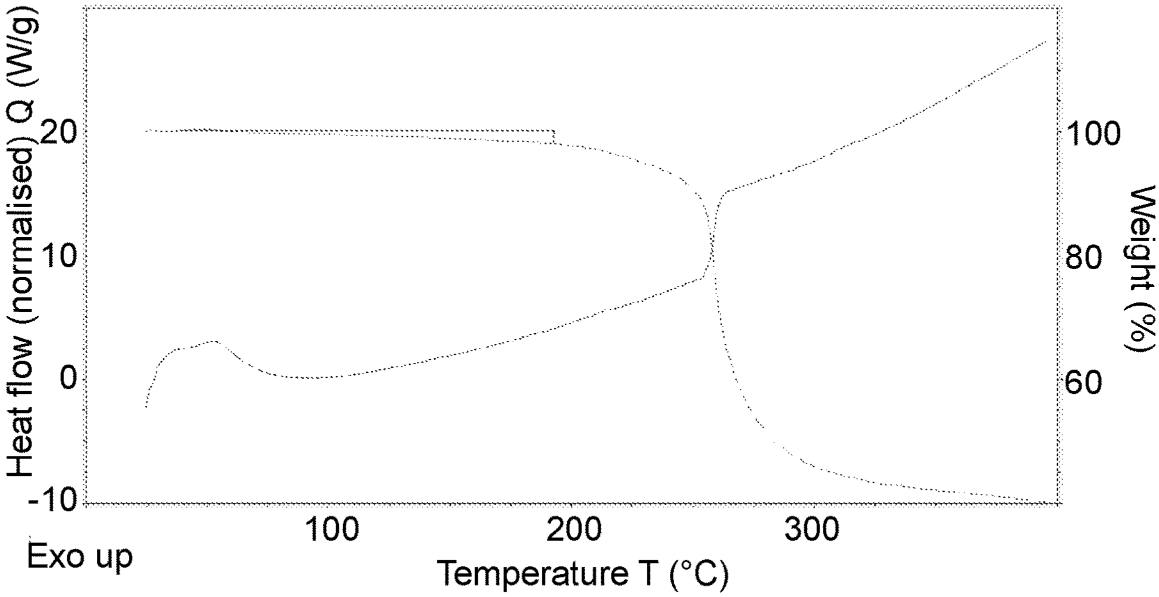
FIG. 51: TG/DSC thermogram of AP1189 Oxalate Pattern 4. Weight Loss: 0.016 mg. Weight Percent Loss: 2.164%.

One embodiment of the disclosure provides for a crystalline Form XVII of AP1189 oxalate exhibiting in differential scanning calorimetry an onset temperature as shown in the examples herein, specifically example 4, and/or in the figures herein, specifically FIG. 51. One embodiment of the present disclosure provides a crystalline Form XVII of AP1189 oxalate exhibiting a differential scanning calorimetry thermogram according to FIG. 51.

Figure 52:
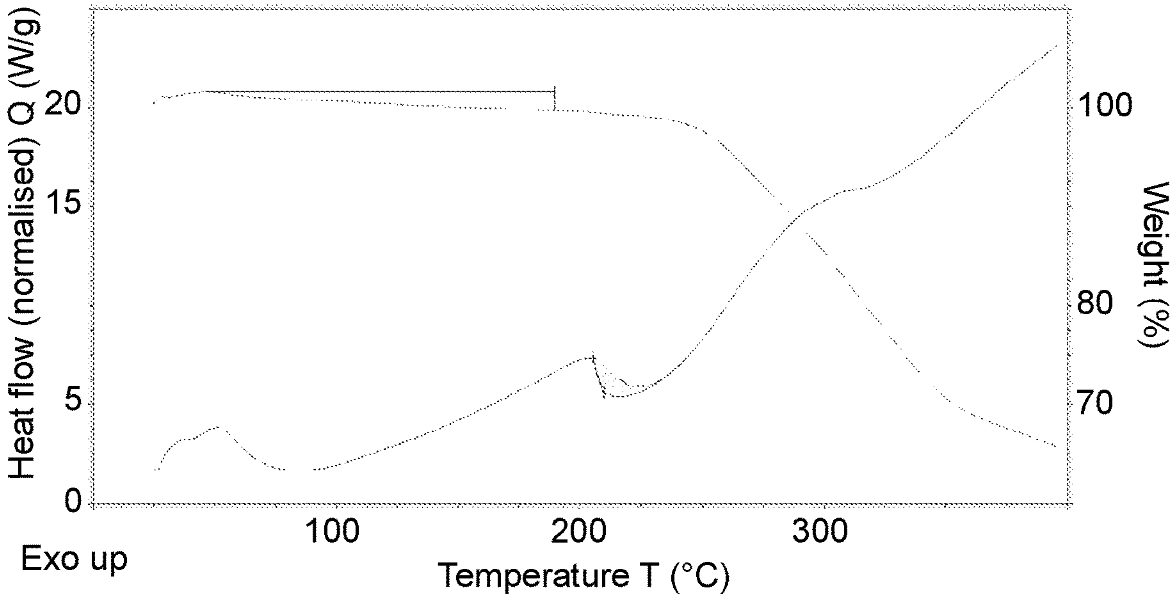
FIG. 52: TG/DSC thermogram of AP1189 (+)-Camphor-10-sulfonic acid Pattern 1. Weight Loss: 0.017 mg. Weight Percent Loss: 1.843%. Enthalpy (normalised): 107.65 J/g; Onset x: 205.38° C.; Peak temperature: 209.93° C.

One embodiment of the present disclosure provides for a crystalline Form XVIII of AP1189 (+)-camphor-10-sulfonic acid exhibiting in differential scanning calorimetry an onset temperature between 198 and 212° C. One specific embodiment of the present disclosure provides a crystalline Form XVIII of AP1189 (+)-camphor-10-sulfonic acid exhibiting in differential scanning calorimetry an onset temperature of substantially 205° C. In a further embodiment, the onset temperature is assessed using a heating rate of 10° C./min. One embodiment of the disclosure provides for a crystalline Form XVIII of AP1189 (+)-camphor-10-sulfonic acid exhibiting in differential scanning calorimetry an onset temperature as shown in the examples herein, specifically example 4, and/or in the figures herein, specifically FIG. 52. One embodiment of the present disclosure provides a crystalline Form XVIII of AP1189 (+)-camphor-10-sulfonic acid exhibiting a differential scanning calorimetry thermogram according to FIG. 52. One embodiment of the present disclosure provides for a crystalline Form XVIII of AP1189 (+)-camphor-10-sulfonic acid exhibiting in differential scanning calorimetry an onset temperature falling within the interval 205±7° C., such as 205±6° C., such as 205±5° C., such as 205±4° C., such as 205±3° C., such as 205±2° C., such as 205±1° C.

Figure 53:
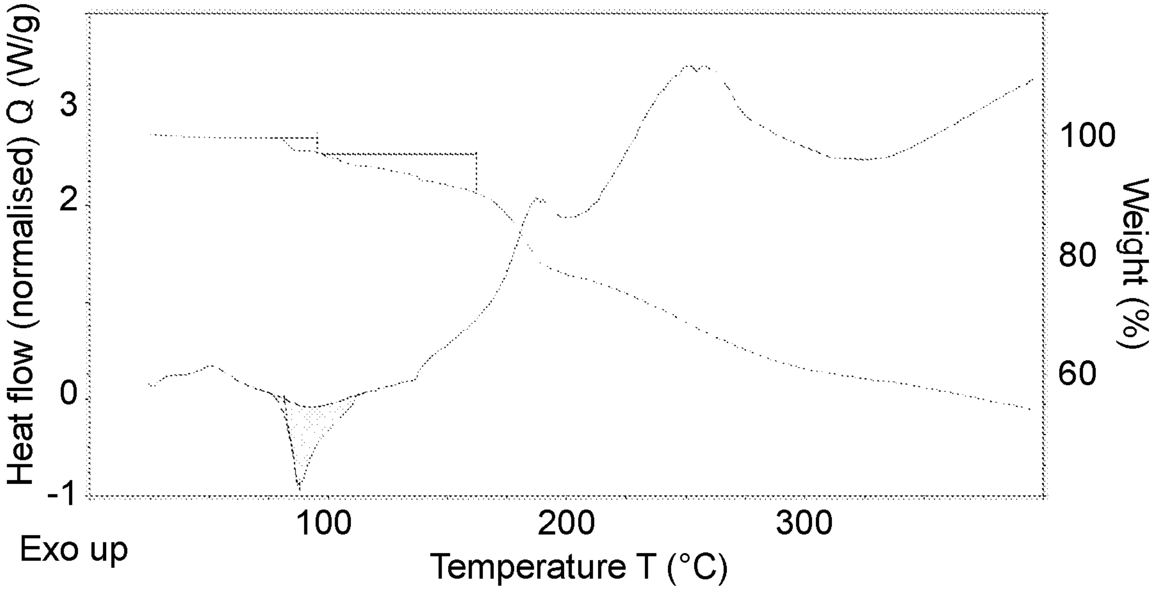
FIG. 53: TG/DSC thermogram of AP1189 Oxoglutarate Pattern 1. Weight Loss: 0.167 mg. Weight Percent Loss: 2.379%. Weight Loss: 0.462 mg. Weight Percent Loss: 6.588%. Enthalpy (normalised): 68.335 J/g. Onset x: 81.31° C. Peak temperature: 87.92° C.

One embodiment of the present disclosure provides for a crystalline Form XIX of AP1189 oxoglutarate exhibiting in differential scanning calorimetry an onset temperature between 74 and 88° C. One specific embodiment of the present disclosure provides a crystalline Form XIX of AP1189 oxoglutarate exhibiting in differential scanning calorimetry an onset temperature of substantially 81° C. In a further embodiment, the onset temperature is assessed using a heating rate of 10° C./min. One embodiment of the disclosure provides for a crystalline Form XIX of AP1189 oxoglutarate exhibiting in differential scanning calorimetry an onset temperature as shown in the examples herein, specifically example 4, and/or in the figures herein, specifically FIG. 53. One embodiment of the present disclosure provides a crystalline Form XIX of AP1189 oxoglutarate exhibiting a differential scanning calorimetry thermogram according to FIG. 53. One embodiment of the present disclosure provides for a crystalline Form XIX of AP1189 oxoglutarate exhibiting in differential scanning calorimetry an onset temperature falling within the interval 81±7° C., such as 81±6° C., such as 81±5° C., such as 81±4° C., such as 81±3° C., such as 81±2° C., such as 81±1° C.

Figure 54:
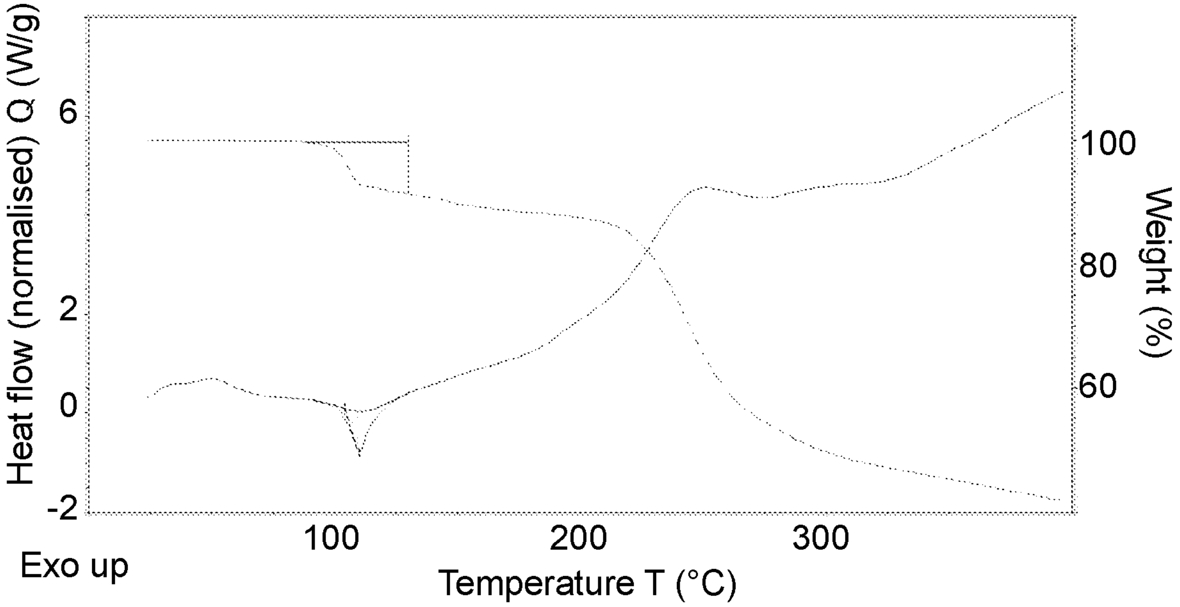
FIG. 54: TG/DSC thermogram of AP1189 DL-mandelic acid Pattern 2. Weight Loss: 0.424 mg. Weight Percent Loss: 8.372%. Enthalpy (normalised): 43.266 J/g; Onset x: 104.13° C.; Peak temperature: 110.06° C.

One embodiment of the present disclosure provides for a crystalline Form XX of AP1189 DL-mandelic acid exhibiting in differential scanning calorimetry an onset temperature between 103 and 117° C. One specific embodiment of the present disclosure provides a crystalline Form XX of AP1189 DL-mandelic acid exhibiting in differential scanning calorimetry an onset temperature of substantially 110° C. In a further embodiment, the onset temperature is assessed using a heating rate of 10° C./min. One embodiment of the disclosure provides for a crystalline Form XX of AP1189 DL-mandelic acid exhibiting in differential scanning calorimetry an onset temperature as shown in the examples herein, specifically example 4, and/or in the figures herein, specifically FIG. 54. One embodiment of the present disclosure provides a crystalline Form XX of AP1189 DL-mandelic acid exhibiting a differential scanning calorimetry thermogram according to FIG. 54. One embodiment of the present disclosure provides for a crystalline Form XX of AP1189 DL-mandelic acid exhibiting in differential scanning calorimetry an onset temperature falling within the interval 110±7° C., such as 110±6° C., such as 110±5° C., such as 110±4° C., such as 1103° C., such as 1102° C., such as 110±1° C.

Figure 55:
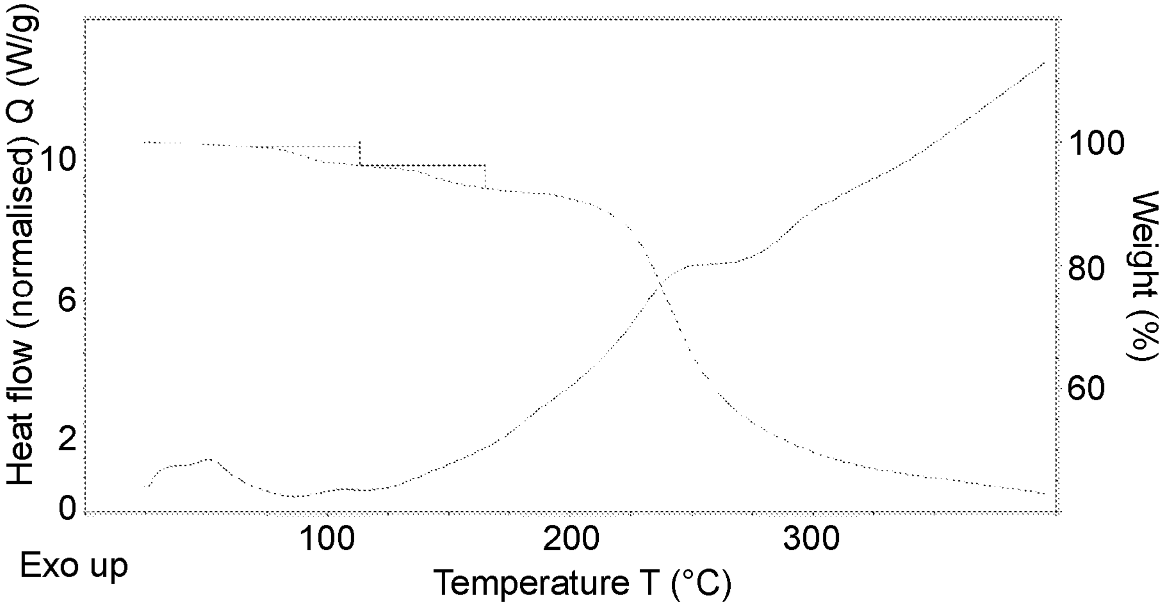
FIG. 55: TG/DSC thermogram of AP1189 DL-mandelic acid Pattern 3. Weight Los: 0.066 mg. Weight Percent Loss: 3.021%. Weight Loss: 0.081 mg. Weight Percent Loss: 3.698%.

One embodiment of the disclosure provides for a crystalline Form XXI of AP1189 mandelic acid exhibiting in differential scanning calorimetry an onset temperature as shown in the examples herein, specifically example 4, and/or in the figures herein, specifically FIG. 55. One embodiment of the present disclosure provides a crystalline Form XXI of AP1189 mandelic acid exhibiting a differential scanning calorimetry thermogram according to FIG. 55.

Figure 56:
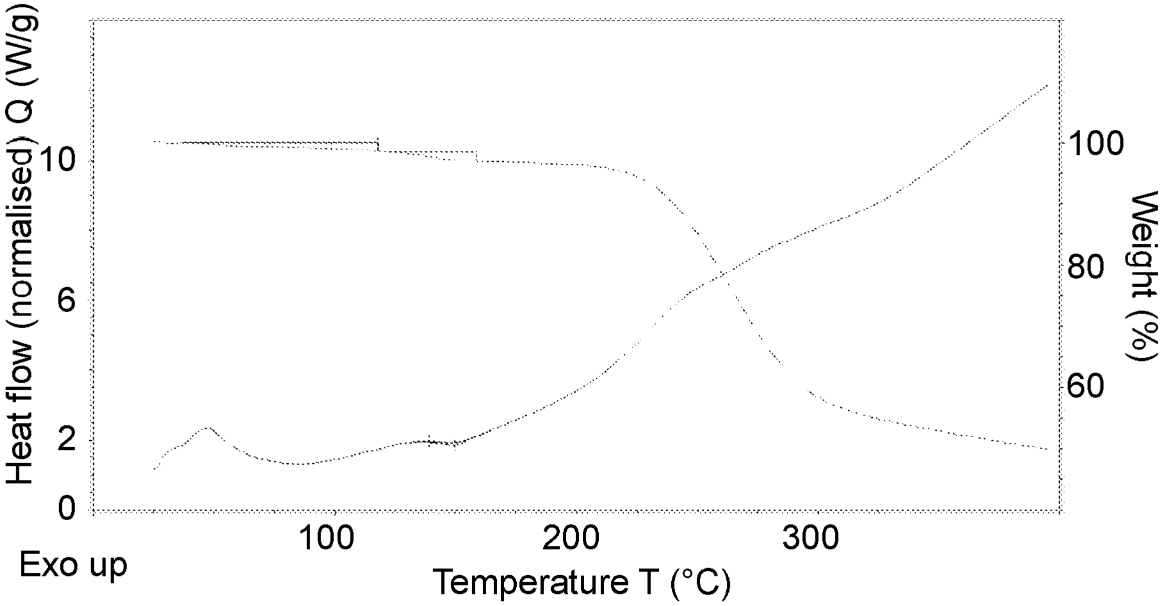
FIG. 56: TG/DSC thermogram of AP1189 Hippuric acid Pattern 1. Weight Loss: 0.022 mg. Weight Percent Loss: 1.294%. Weight Loss: 0.026 mg. Weight Percent Loss: 1.495%. Enthalpy (normalised): 4.7263 J/g; Onset x: 138.92° C.; Peak temperature: 149.72° C.

One embodiment of the present disclosure provides for a crystalline Form XXII of AP1189 hippuric acid exhibiting in differential scanning calorimetry an onset temperature between 132 and 146° C. One specific embodiment of the present disclosure provides a crystalline Form XXII of AP1189 hippuric acid exhibiting in differential scanning calorimetry an onset temperature of substantially 139° C. In a further embodiment, the onset temperature is assessed using a heating rate of 10° C./min. One embodiment of the disclosure provides for a crystalline Form XXII of AP1189 hippuric acid exhibiting in differential scanning calorimetry an onset temperature as shown in the examples herein, specifically example 4, and/or in the figures herein, specifically FIG. 56. One embodiment of the present disclosure provides a crystalline Form XXII of AP1189 hippuric acid exhibiting a differential scanning calorimetry thermogram according to FIG. 56. One embodiment of the present disclosure provides for a crystalline Form XXII of AP1189 hippuric acid exhibiting in differential scanning calorimetry an onset temperature falling within the interval 139±7° C., such as 139±6° C., such as 139±5° C., such as 139±4° C., such as 1393° C., such as 1392° C., such as 139±1° C.

Figure 84:
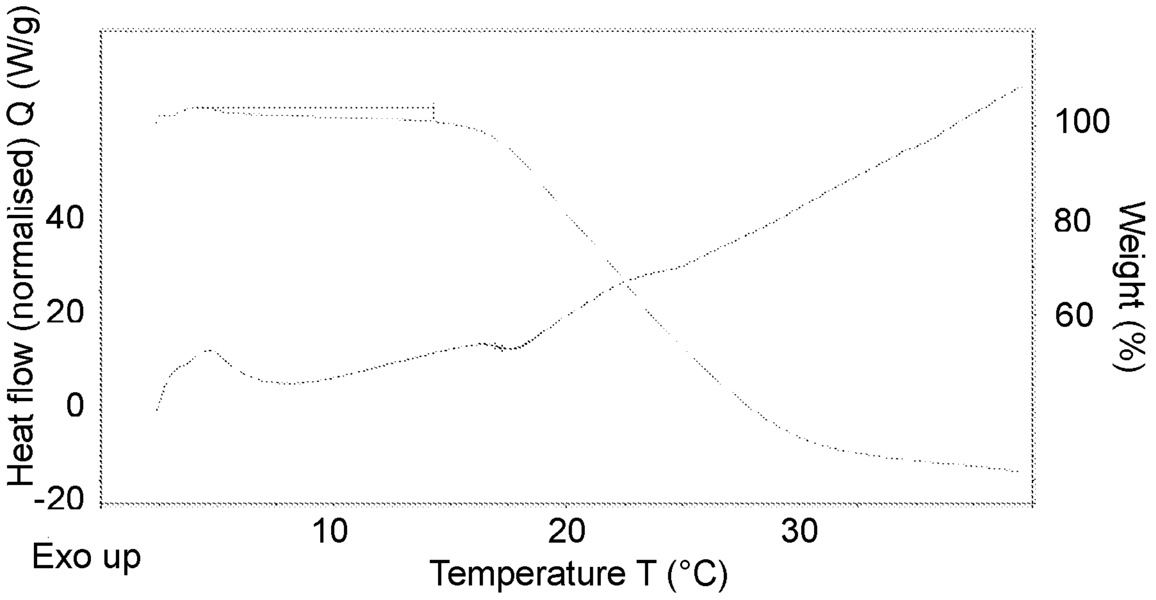
FIG. 84: TG/DSC thermogram of AP1189 Formic acid Pattern 1. Weight Loss: 0.008 mg. Weight Percent Loss: 3.049%. Enthalpy (normalised): 7.5282 J/g; Onset x: 169.12° C.; Peak temperature: 171.97° C.

One embodiment of the present disclosure provides for a crystalline Form XXIII of AP1189 formate exhibiting in differential scanning calorimetry an onset temperature between 162 and 176° C. One specific embodiment of the present disclosure provides a crystalline Form XIII of AP1189 formate exhibiting in differential scanning calorimetry an onset temperature of substantially 169° C. In a further embodiment, the onset temperature is assessed using a heating rate of 10° C./min. One embodiment of the disclosure provides for a crystalline Form XXIII of AP1189 formate exhibiting in differential scanning calorimetry an onset temperature as shown in the examples herein, specifically example 4, and/or in the figures herein, specifically FIG. 84. One embodiment of the present disclosure provides a crystalline Form XXIII of AP1189 formate exhibiting a differential scanning calorimetry thermogram according to FIG. 84. One embodiment of the present disclosure provides for a crystalline Form XXIII of AP1189 formate exhibiting in differential scanning calorimetry an onset temperature falling within the interval 169±7° C., such as 169±6° C., such as 169±5° C., such as 1694° C., such as 1693° C., such as 169±2° C., such as 169±1° C.

Figure 85:
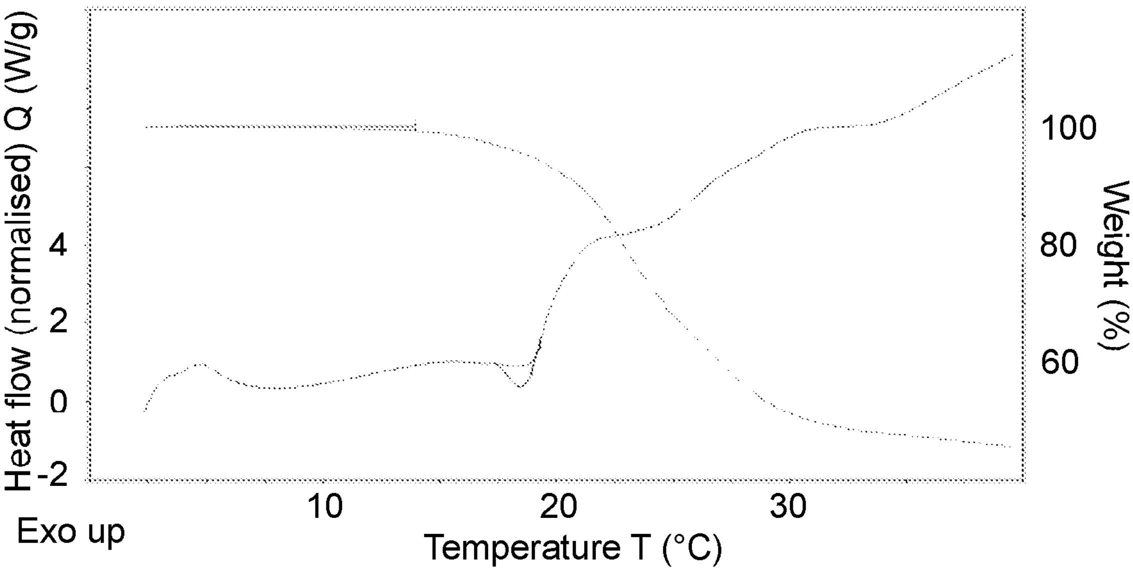
FIG. 85: TG/DSC thermogram of AP1189 DL-Lactic acid Pattern 1. Weight Loss: 0.026 mg. Weight Percent Loss: 0.859%. Enthalpy (normalised): 31.499 J/g. Onset x: 189.47° C. Peak temperature: 192.80° C.

One embodiment of the present disclosure provides for a crystalline Form XXIV of AP1189 DL-lactic acid exhibiting in differential scanning calorimetry an onset temperature between 182 and 196° C. One specific embodiment of the present disclosure provides a crystalline Form XXIV of AP1189 DL-lactic acid exhibiting in differential scanning calorimetry an onset temperature of substantially 189° C. In a further embodiment, the onset temperature is assessed using a heating rate of 10° C./min. One embodiment of the disclosure provides for a crystalline Form XXIV of AP1189 DL-lactic acid exhibiting in differential scanning calorimetry an onset temperature as shown in the examples herein, specifically example 4, and/or in the figures herein, specifically FIG. 85. One embodiment of the present disclosure provides a crystalline Form XXIV of AP1189 DL-lactic acid exhibiting a differential scanning calorimetry thermogram according to FIG. 85. One embodiment of the present disclosure provides for a crystalline Form XXIV of AP1189 DL-lactic acid exhibiting in differential scanning calorimetry an onset temperature falling within the interval 189±7° C., such as 189±6° C., such as 189±5° C., such as 189±4° C., such as 189±3° C., such as 189±2° C., such as 189±1° C.

Figure 86:
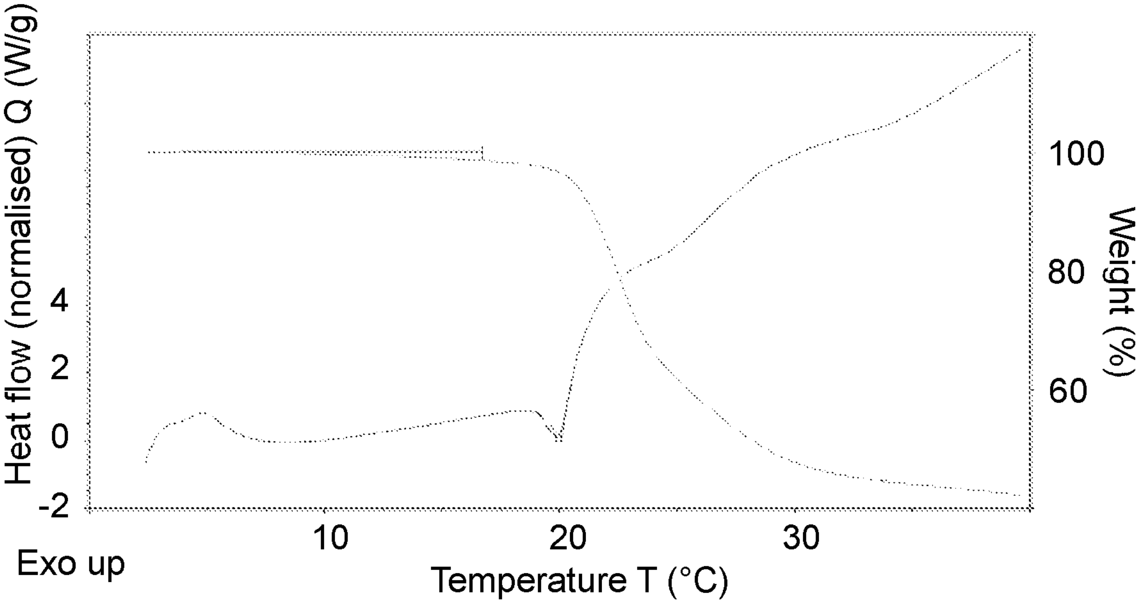
FIG. 86: TG/DSC thermogram of AP1189 DL-Lactic acid Pattern 1. Weight Loss: 0.034 mg. Weight Percent Loss: 1.476%. Enthalpy (normalised): 2.2523 J/g; Onset x: 198.48° C.; Peak temperature: 200.63° C.

One embodiment of the present disclosure provides for a crystalline Form XXV of AP1189 DL-lactic acid exhibiting in differential scanning calorimetry an onset temperature between 191 and 205° C. One specific embodiment of the present disclosure provides a crystalline Form XXV of AP1189 DL-lactic acid exhibiting in differential scanning calorimetry an onset temperature of substantially 198° C. In a further embodiment, the onset temperature is assessed using a heating rate of 10° C./min. One embodiment of the disclosure provides for a crystalline Form XXV of AP1189 DL-lactic acid exhibiting in differential scanning calorimetry an onset temperature as shown in the examples herein, specifically example 4, and/or in the figures herein, specifically FIG. 86. One embodiment of the present disclosure provides a crystalline Form XXV of AP1189 DL-lactic acid exhibiting a differential scanning calorimetry thermogram according to FIG. 86. One embodiment of the present disclosure provides for a crystalline Form XXV of AP1189 DL-lactic acid exhibiting in differential scanning calorimetry an onset temperature falling within the interval 198±7° C., such as 198±6° C., such as 198±5° C., such as 198±4° C., such as 198±3° C., such as 198±2° C., such as 198±1° C.

Figure 87:
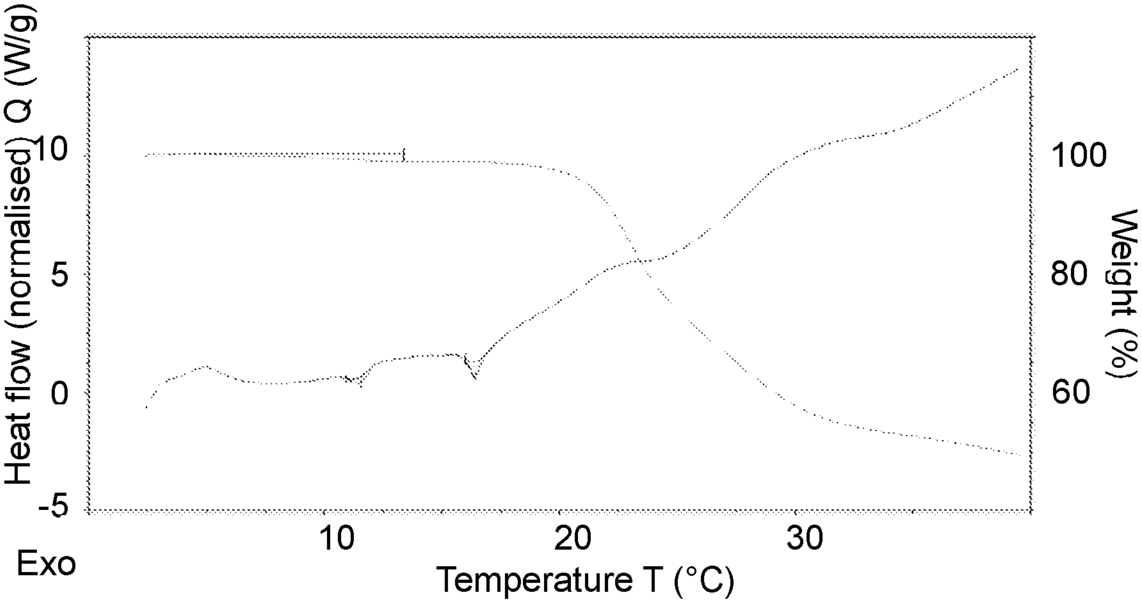
FIG. 87: TG/DSC thermogram of AP1189 Glutaric acid Pattern 1. Weight Loss: 0.27 mg. Weight Percent Loss: 1.256%. Enthalpy (normalised): 0.0964 J/g; Onset x: 109.24° C.; Peak temperature: 115.31° C. Enthalpy (normalised): 16.647 J/g; Onset x: 159.93° C.; Peak temperature: 164.02° C.

One embodiment of the present disclosure provides for a crystalline Form XXVI of AP1189 glutaric acid exhibiting in differential scanning calorimetry an onset temperature between 102 and 116° C. One specific embodiment of the present disclosure provides a crystalline Form XXVI of AP1189 glutaric acid exhibiting in differential scanning calorimetry an onset temperature of substantially 109° C. In a further embodiment, the onset temperature is assessed using a heating rate of 10° C./min. One embodiment of the disclosure provides for a crystalline Form XXVI of AP1189 glutaric acid exhibiting in differential scanning calorimetry an onset temperature as shown in the examples herein, specifically example 4, and/or in the figures herein, specifically FIG. 87. One embodiment of the present disclosure provides a crystalline Form XXVI of AP1189 glutaric acid exhibiting a differential scanning calorimetry thermogram according to FIG. 87. One embodiment of the present disclosure provides for a crystalline Form XXVI of AP1189 glutaric acid exhibiting in differential scanning calorimetry an onset temperature falling within the interval 109±7° C., such as 109±6° C., such as 109±5° C., such as 109±4° C., such as 109±3° C., such as 109±2° C., such as 109±1° C.

One embodiment of the present disclosure provides for a crystalline Form XXVI of AP1189 glutaric acid exhibiting in differential scanning calorimetry an onset temperature between 153 and 167° C. One specific embodiment of the present disclosure provides a crystalline Form XXVI of AP1189 glutaric acid exhibiting in differential scanning calorimetry an onset temperature of substantially 160° C. In a further embodiment, the onset temperature is assessed using a heating rate of 10° C./min. One embodiment of the disclosure provides for a crystalline Form XXVI of AP1189 glutaric acid exhibiting in differential scanning calorimetry an onset temperature as shown in the examples herein, specifically example 4, and/or in the figures herein, specifically FIG. 87. One embodiment of the present disclosure provides a crystalline Form XXVI of AP1189 glutaric acid exhibiting a differential scanning calorimetry thermogram according to FIG. 87. One embodiment of the present disclosure provides for a crystalline Form XXVI of AP1189 glutaric acid exhibiting in differential scanning calorimetry an onset temperature falling within the interval 160±7° C., such as 160±6° C., such as 160±5° C., such as 160±4° C., such as 160±3° C., such as 160±2° C., such as 160±1° C.

Figure 88:
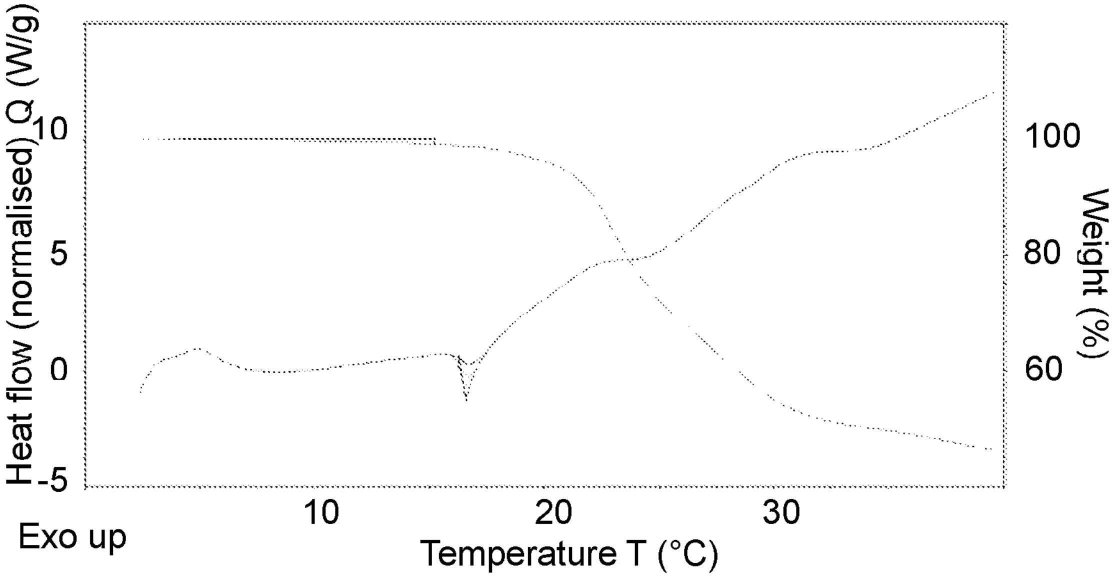
FIG. 88: TG/DSC thermogram of AP1189 Glutaric acid Pattern 2. Weight Loss: 0.019 mg. Weight Percent Loss: 1.001%. Enthalpy (normalised): 48.550 J/g; Onset x: 162.77° C.; Peak temperature: 165.94° C.

One embodiment of the present disclosure provides for a crystalline Form XXVII of AP1189 glutaric acid exhibiting in differential scanning calorimetry an onset temperature between 156 and 170° C. One specific embodiment of the present disclosure provides a crystalline Form XXVII of AP1189 glutaric acid exhibiting in differential scanning calorimetry an onset temperature of substantially 163° C. In a further embodiment, the onset temperature is assessed using a heating rate of 10° C./min. One embodiment of the disclosure provides for a crystalline Form XXVII of AP1189 glutaric acid exhibiting in differential scanning calorimetry an onset temperature as shown in the examples herein, specifically example 4, and/or in the figures herein, specifically FIG. 88. One embodiment of the present disclosure provides a crystalline Form XXVII of AP1189 glutaric acid exhibiting a differential scanning calorimetry thermogram according to FIG. 88. One embodiment of the present disclosure provides for a crystalline Form XXVII of AP1189 glutaric acid exhibiting in differential scanning calorimetry an onset temperature falling within the interval 163±7° C., such as 163±6° C., such as 163±5° C., such as 163±4° C., such as 163±3° C., such as 163±2° C., such as 163±1° C.

Figure 89:
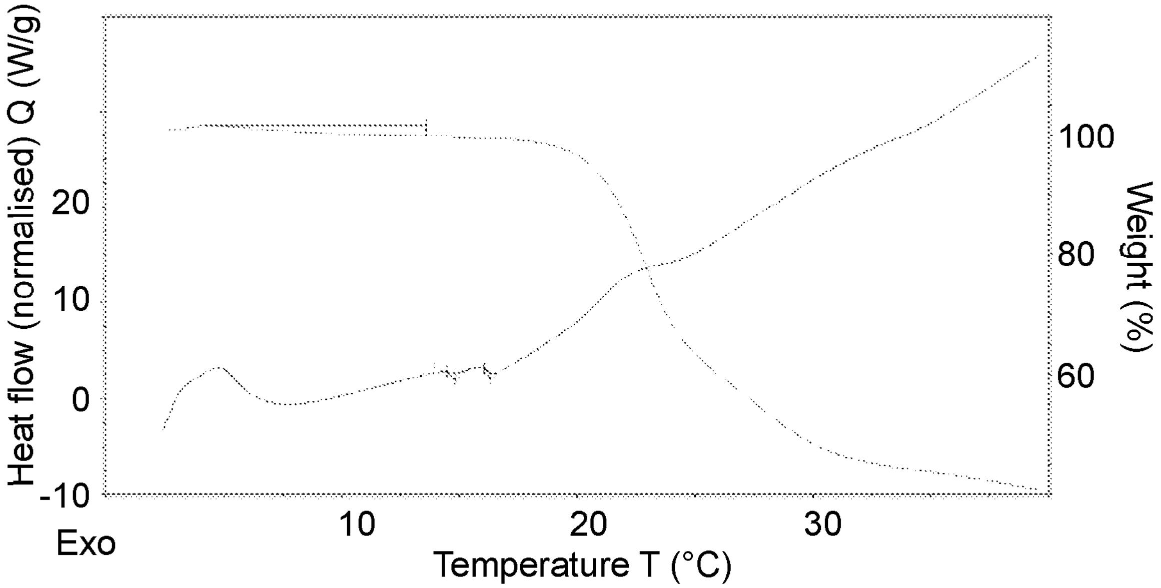
FIG. 89: TG/DSC thermogram of AP1189 Glutaric acid Pattern 4. Weight Loss: 0.010 mg. Weight Percent Loss: 1.764%. Enthalpy (normalised): 18.475 J/g; Onset x: 114.55° C.; Peak temperature: 148.15° C. Enthalpy (normalised): 10.102 J/g; Onset x: 160.45° C.; Peak temperature: 163.28° C.

One embodiment of the present disclosure provides for a crystalline Form XXVIII of AP1189 glutaric acid exhibiting in differential scanning calorimetry an onset temperature between 138 and 152° C. One specific embodiment of the present disclosure provides a crystalline Form XXVIII of AP1189 glutaric acid exhibiting in differential scanning calorimetry an onset temperature of substantially 145° C. In a further embodiment, the onset temperature is assessed using a heating rate of 10° C./min. One embodiment of the disclosure provides for a crystalline Form XXVIII of AP1189 glutaric acid exhibiting in differential scanning calorimetry an onset temperature as shown in the examples herein, specifically example 4, and/or in the figures herein, specifically FIG. 89. One embodiment of the present disclosure provides a crystalline Form XXVIII of AP1189 glutaric acid exhibiting a differential scanning calorimetry thermogram according to FIG. 89. One embodiment of the present disclosure provides for a crystalline Form XXVIII of AP1189 glutaric acid exhibiting in differential scanning calorimetry an onset temperature falling within the interval 145±7° C., such as 145±6° C., such as 145±5° C., such as 145±4° C., such as 145±3° C., such as 145±2° C., such as 145±1° C.

One embodiment of the present disclosure provides for a crystalline Form XXVIII of AP1189 glutaric acid exhibiting in differential scanning calorimetry an onset temperature between 153 and 167° C. One specific embodiment of the present disclosure provides a crystalline Form XXVIII of AP1189 glutaric acid exhibiting in differential scanning calorimetry an onset temperature of substantially 160° C. In a further embodiment, the onset temperature is assessed using a heating rate of 10° C./min. One embodiment of the disclosure provides for a crystalline Form XXVIII of AP1189 glutaric acid exhibiting in differential scanning calorimetry an onset temperature as shown in the examples herein, specifically example 4, and/or in the figures herein, specifically FIG. 89. One embodiment of the present disclosure provides a crystalline Form XXVIII of AP1189 glutaric acid exhibiting a differential scanning calorimetry thermogram according to FIG. 89. One embodiment of the present disclosure provides for a crystalline Form XXVIII of AP1189 glutaric acid exhibiting in differential scanning calorimetry an onset temperature falling within the interval 160±7° C., such as 160±6° C., such as 160±5° C., such as 160±4° C., such as 160±3° C., such as 160±2° C., such as 160±1° C.

Figure 90:
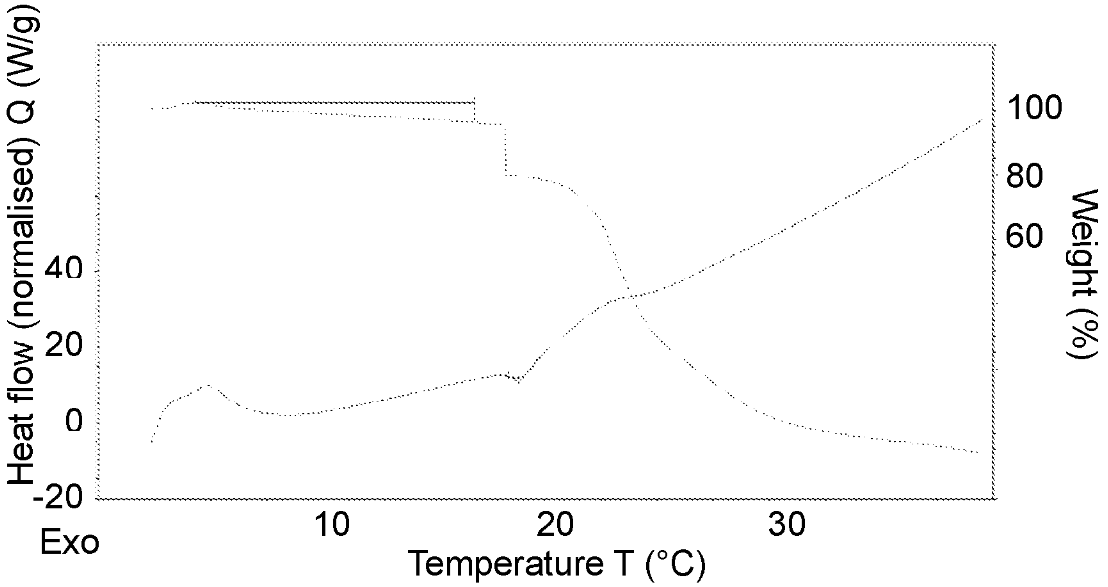
FIG. 90: TG/DSC thermogram of AP1189 Adipic acid Pattern 1. Weight Loss: 0.015 mg. Weight Percent Loss: 6.117%. Enthalpy (normalised): 12.428 J/g. Onset x: 183.34° C.; Peak temperature: 187.98° C.

One embodiment of the present disclosure provides for a crystalline Form XXIX of AP1189 adipic acid exhibiting in differential scanning calorimetry an onset temperature between 176 and 190° C. One specific embodiment of the present disclosure provides a crystalline Form XXIX of AP1189 adipic acid exhibiting in differential scanning calorimetry an onset temperature of substantially 183° C. In a further embodiment, the onset temperature is assessed using a heating rate of 10° C./min. One embodiment of the disclosure provides for a crystalline Form XXIX of AP1189 adipic acid exhibiting in differential scanning calorimetry an onset temperature as shown in the examples herein, specifically example 4, and/or in the figures herein, specifically FIG. 90. One embodiment of the present disclosure provides a crystalline Form XXIX of AP1189 adipic acid exhibiting a differential scanning calorimetry thermogram according to FIG. 90. One embodiment of the present disclosure provides for a crystalline Form XXIX of AP1189 adipic acid exhibiting in differential scanning calorimetry an onset temperature falling within the interval 183±7° C., such as 183±6° C., such as 183±5° C., such as 183±4° C., such as 183±3° C., such as 183±2° C., such as 183±1° C.

The salts of AP1189 disclosed herein may be further identified by their FT-IR spectra. FT-IR spectra may be obtained as outlined in Example 13. FT-IR are reported in peaks corresponding to specific wavenumbers given in $cm^{-1}$. While the peaks are given herein with some degree of certainty, it is to be construed that the accuracy of an FT-IR measurement is typically ±1, ±2, or ±3 $cm^{-1}$. Accordingly, any peak reported herein is to be interpreted as having an accuracy of ±1, 2, or ±3 $cm^{-1}$.

Figure 57:
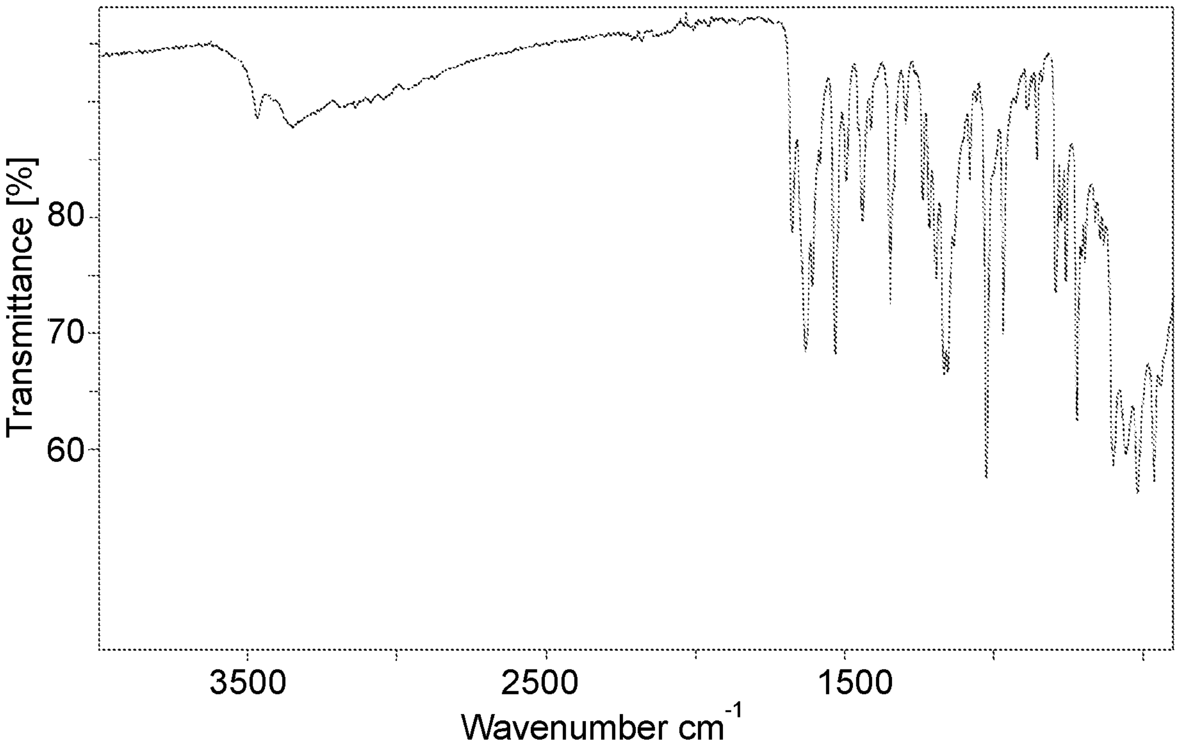
FIG. 57: FT-IR Spectrum of AP1189 Napadisylate Pattern 1.

One embodiment of the present disclosure provides for a crystalline Form III of AP1189 napadisylate having an FT-IR as shown in FIG. 57. One embodiment of the present disclosure provides for a crystalline Form III of AP1189 napadisylate having in an FT-IR spectrum peaks as shown in Table 45.

Figure 58:
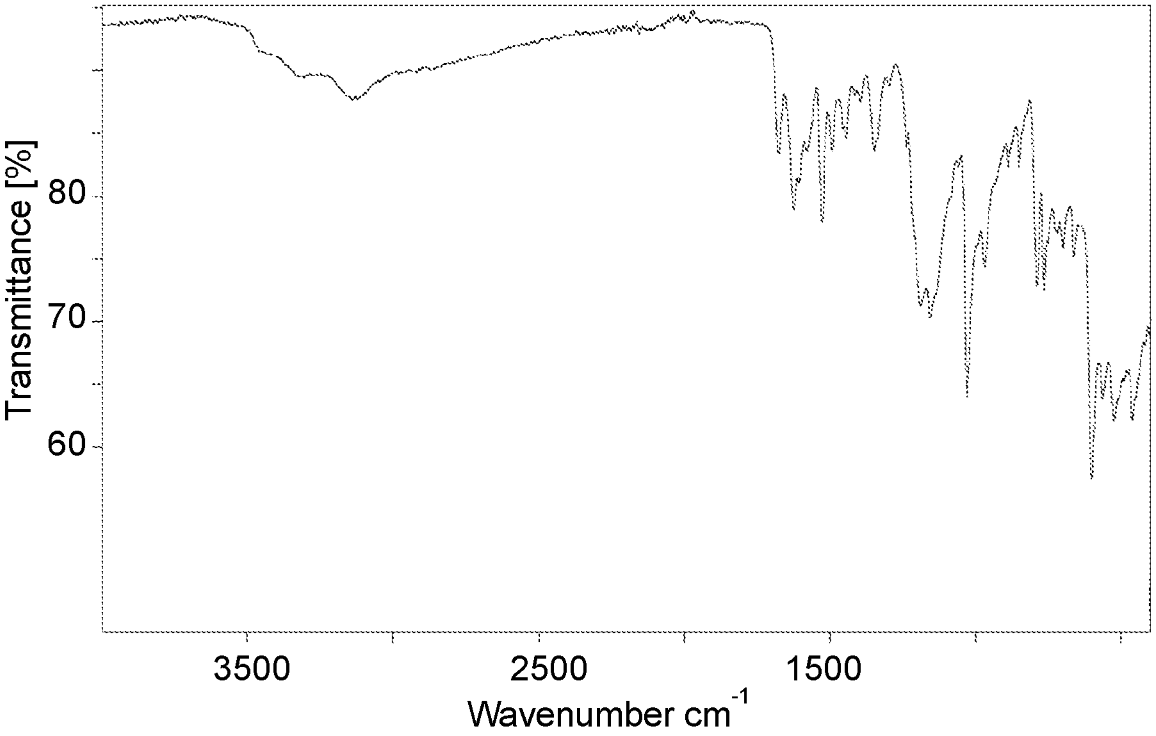
FIG. 58: FT-IR Spectrum of AP1189 Napadisylate Pattern 2.

One embodiment of the present disclosure provides for a crystalline Form IV of AP1189 napadisylate having an FT-IR as shown in FIG. 58. One embodiment of the present disclosure provides for a crystalline Form IV of AP1189 napadisylate having in an FT-IR spectrum peaks as shown in Table 46.

Figure 59:
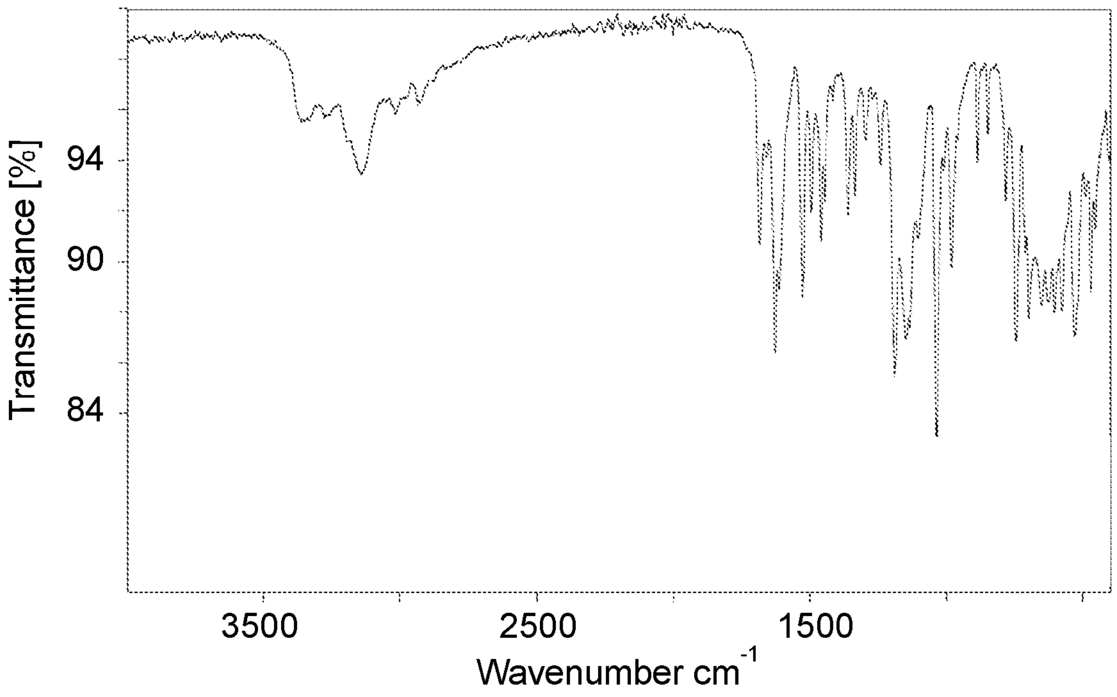
FIG. 59: FT-IR Spectrum of AP1189 Esylate Pattern 1.

One embodiment of the present disclosure provides for a crystalline Form V of AP1189 esylate having an FT-IR as shown in FIG. 59. One embodiment of the present disclosure provides for a crystalline Form V of AP1189 esylate having in an FT-IR spectrum peaks as shown in Table 47.

Figure 60:
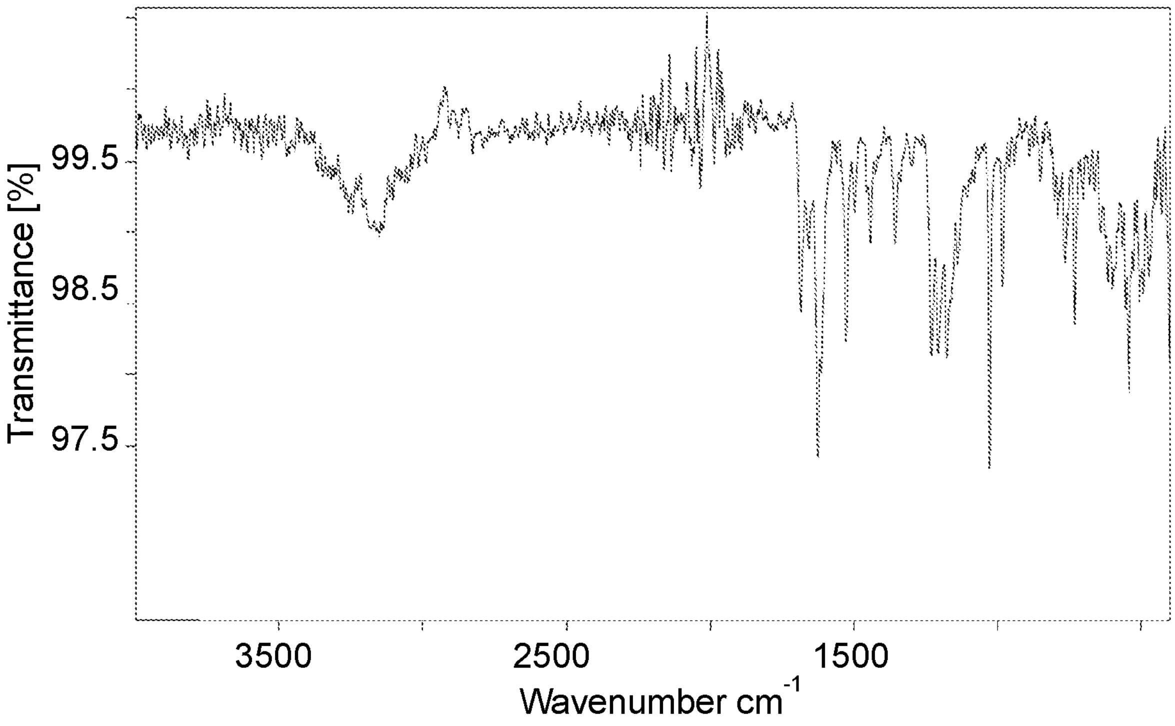
FIG. 60: FT-IR Spectrum of AP1189 Edisylate Pattern 2.

One embodiment of the present disclosure provides for a crystalline Form VII of AP1189 edisylate having an FT-IR as shown in FIG. 60. One embodiment of the present disclosure provides for a crystalline Form VII of AP1189 edisylate having in an FT-IR spectrum peaks as shown in Table 48.

Figure 61:
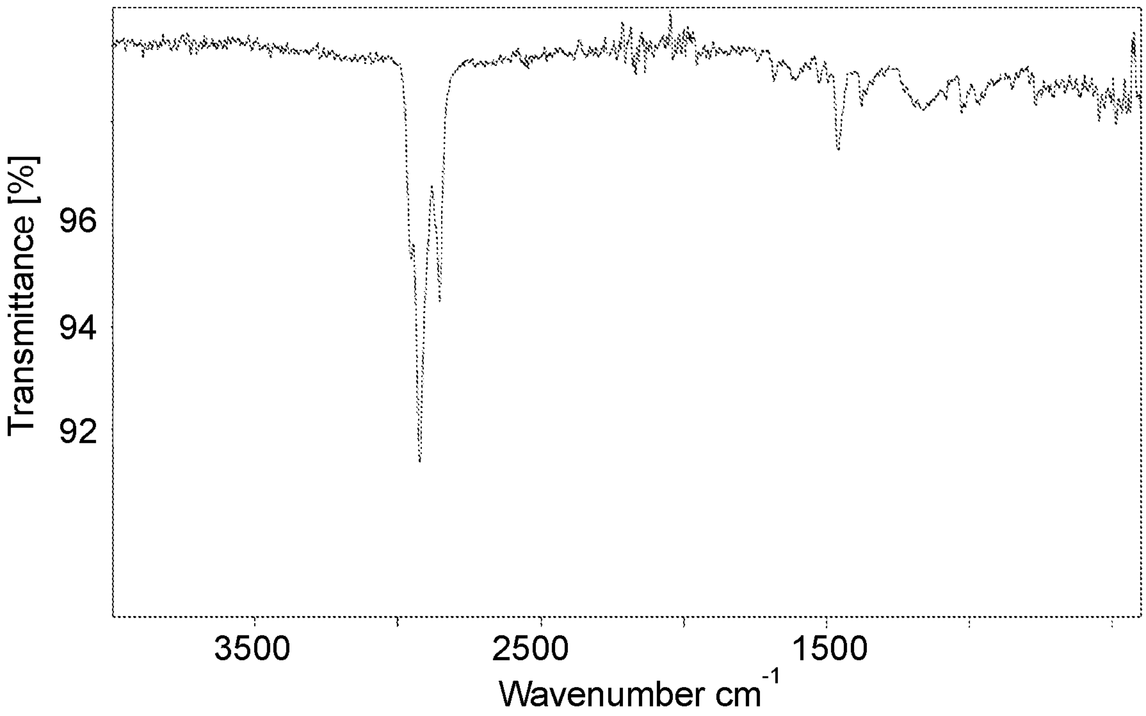
FIG. 61: FT-IR Spectrum of AP1189 Edisylate Pattern 4.

One embodiment of the present disclosure provides for a crystalline Form VIII of AP1189 edisylate having an FT-IR as shown in FIG. 61. One embodiment of the present disclosure provides for a crystalline Form VIII of AP1189 edisylate having in an FT-IR spectrum peaks as shown in Table 49.

Figure 62:
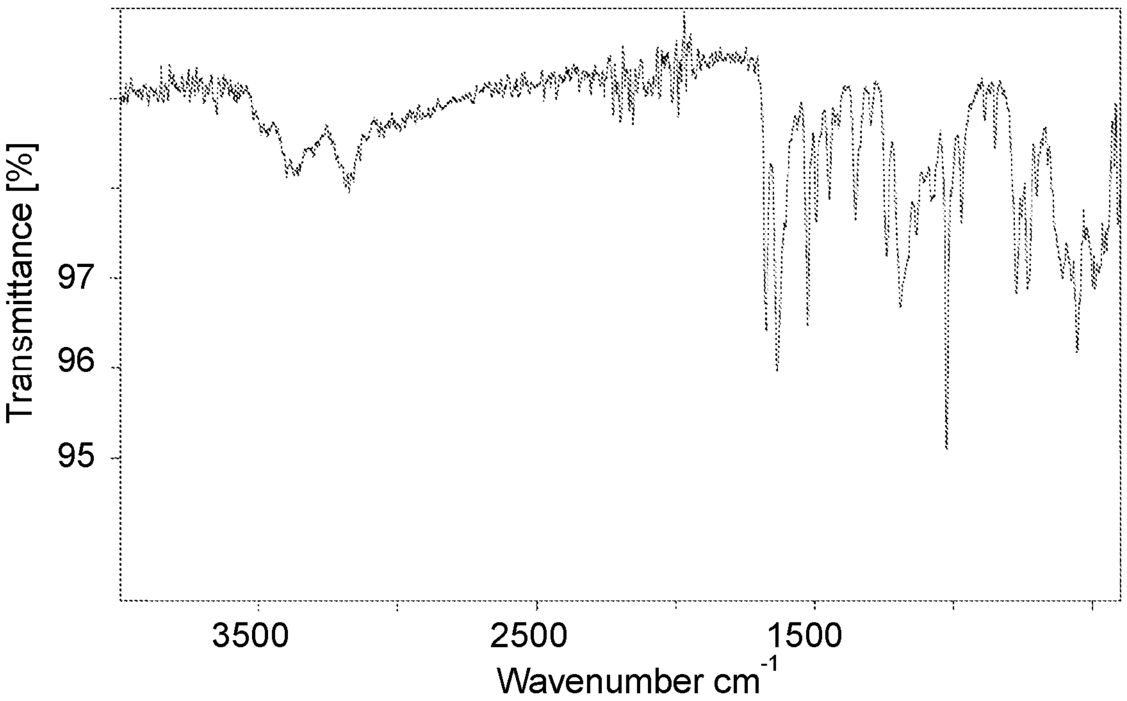
FIG. 62: FT-IR Spectrum of AP1189 Edisylate Pattern 5.

One embodiment of the present disclosure provides for a crystalline Form IX of AP1189 edisylate having an FT-IR as shown in FIG. 62. One embodiment of the present disclosure provides for a crystalline Form IX of AP1189 edisylate having in an FT-IR spectrum peaks as shown in Table 50.

Figure 63:
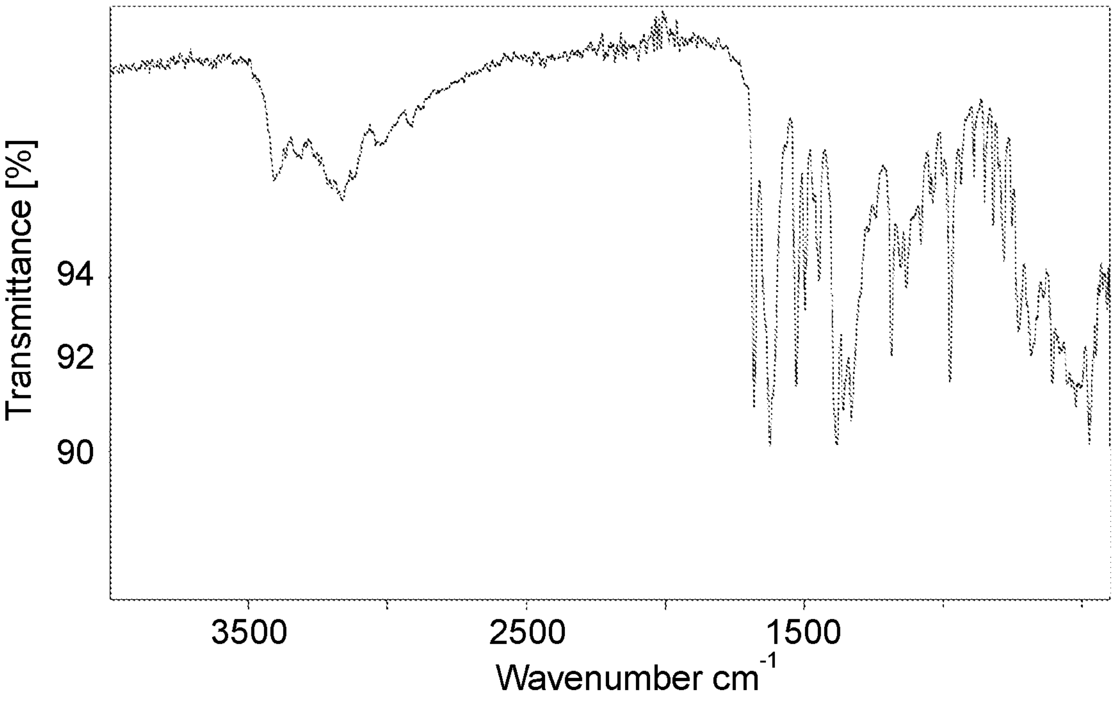
FIG. 63: FT-IR Spectrum of AP1189 Nitrate Pattern 1.

One embodiment of the present disclosure provides for a crystalline Form X of AP1189 nitrate having an FT-IR as shown in FIG. 63. One embodiment of the present disclosure provides for a crystalline Form X of AP1189 nitrate having in an FT-IR spectrum peaks as shown in Table 51.

Figure 64:
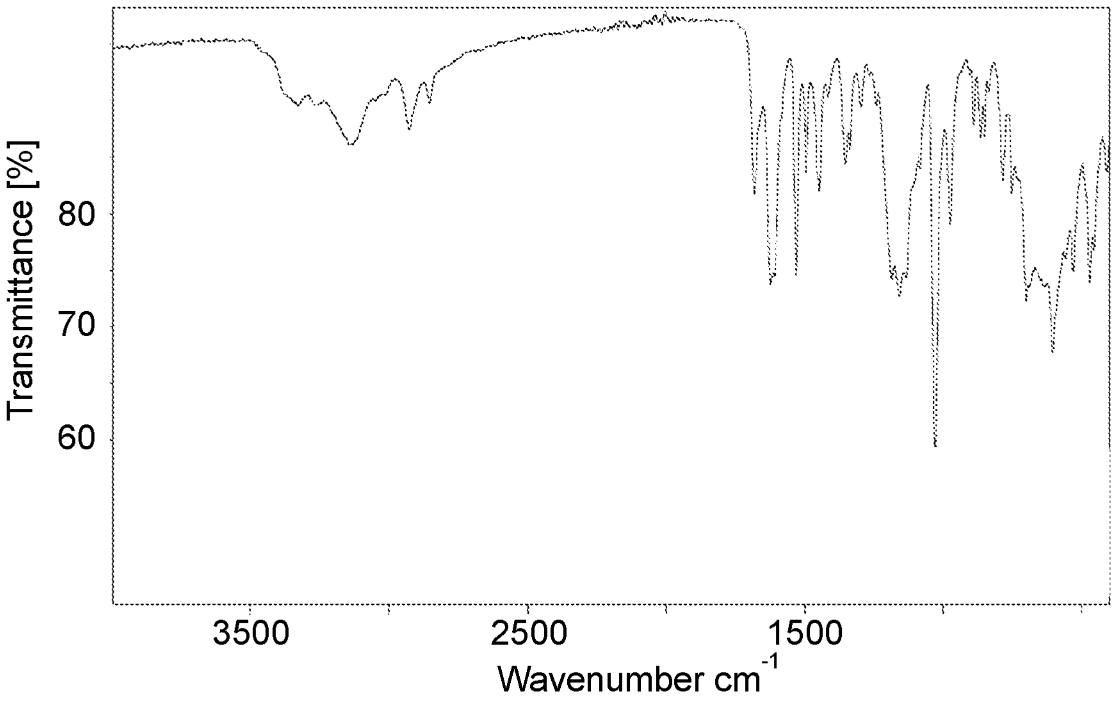
FIG. 64: FT-IR Spectrum of AP1189 Cyclamate Pattern 2.

One embodiment of the present disclosure provides for a crystalline Form XI of AP1189 cyclamate having an FT-IR as shown in FIG. 64. One embodiment of the present disclosure provides for a crystalline Form XI of AP1189 cyclamate having in an FT-IR spectrum peaks as shown in Table 52.

Figure 65:
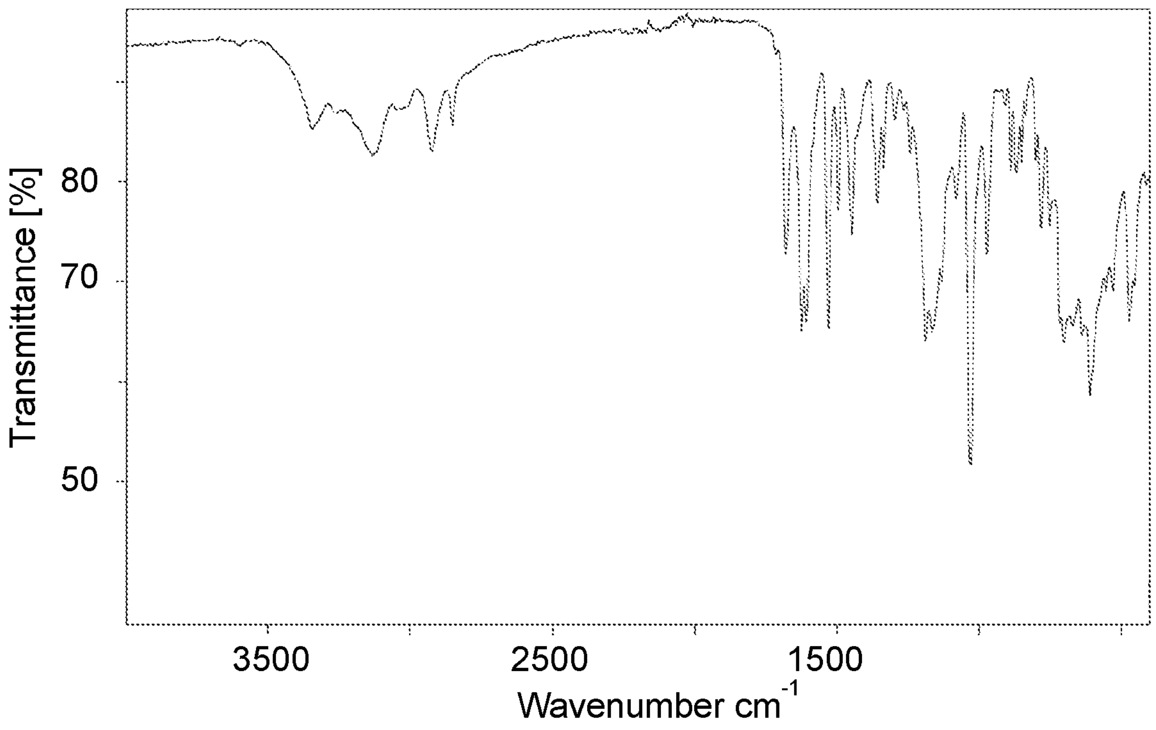
FIG. 65: FT-IR Spectrum of AP1189 Cyclamate Pattern 4.

One embodiment of the present disclosure provides for a crystalline Form XII of AP1189 cyclamate having an FT-IR as shown in FIG. 65. One embodiment of the present disclosure provides for a crystalline Form XII of AP1189 cyclamate having in an FT-IR spectrum peaks as shown in Table 53.

Figure 66:
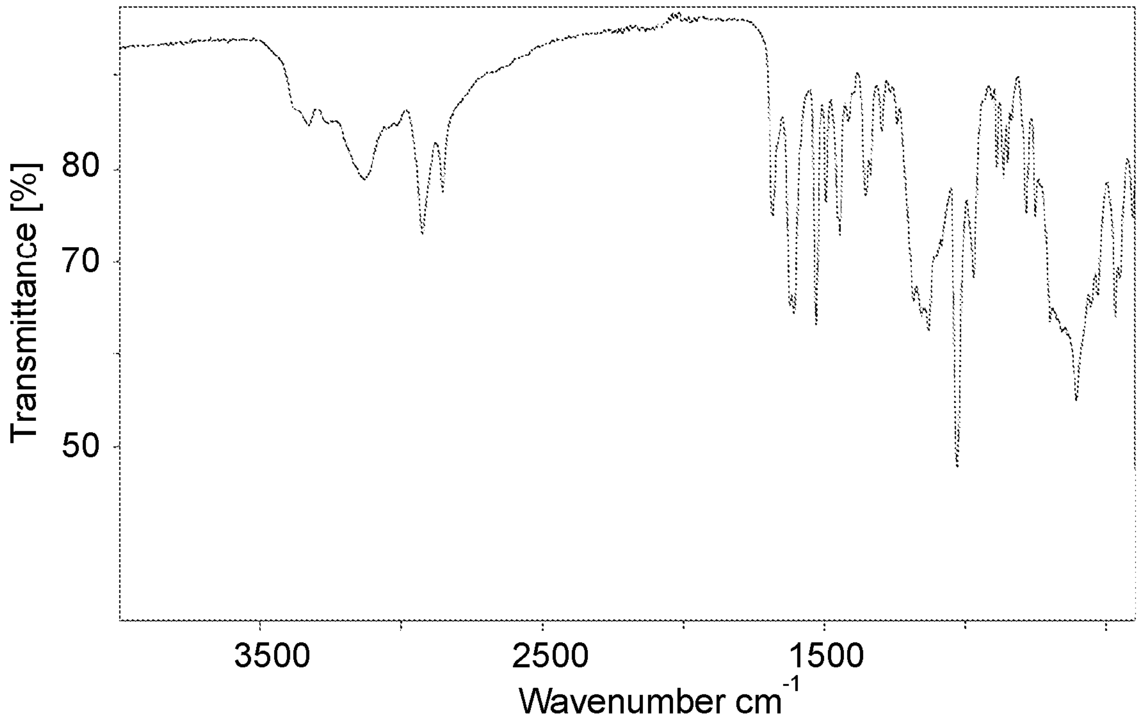
FIG. 66: FT-IR Spectrum of AP1189 Cyclamate Pattern 5.

One embodiment of the present disclosure provides for a crystalline Form XIII of AP1189 cyclamate having an FT-IR as shown in FIG. 66. One embodiment of the present disclosure provides for a crystalline Form XIII of AP1189 cyclamate having in an FT-IR spectrum peaks as shown in Table 54.

Figure 67:
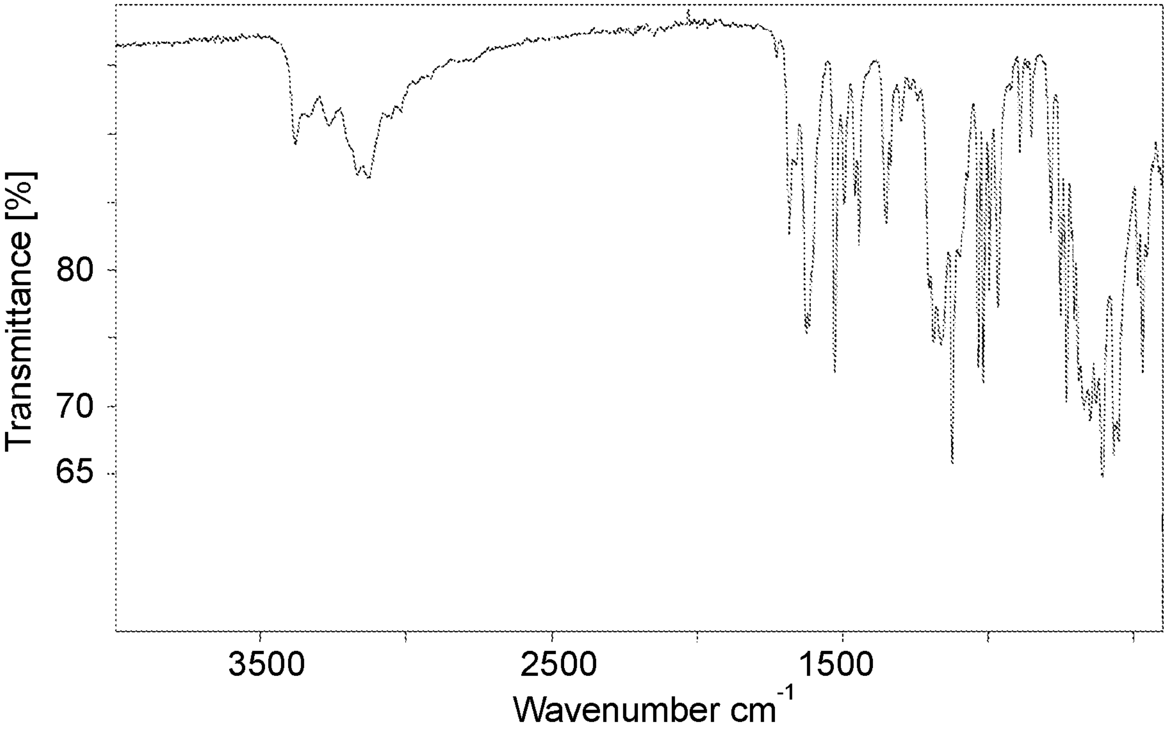
FIG. 67: FT-IR Spectrum of AP1189 Besylate Pattern 1.

One embodiment of the present disclosure provides for a crystalline Form XIV of AP1189 besylate having an FT-IR as shown in FIG. 67. One embodiment of the present disclosure provides for a crystalline Form XIV of AP1189 besylate having in an FT-IR spectrum peaks as shown in Table 55.

Figure 68:
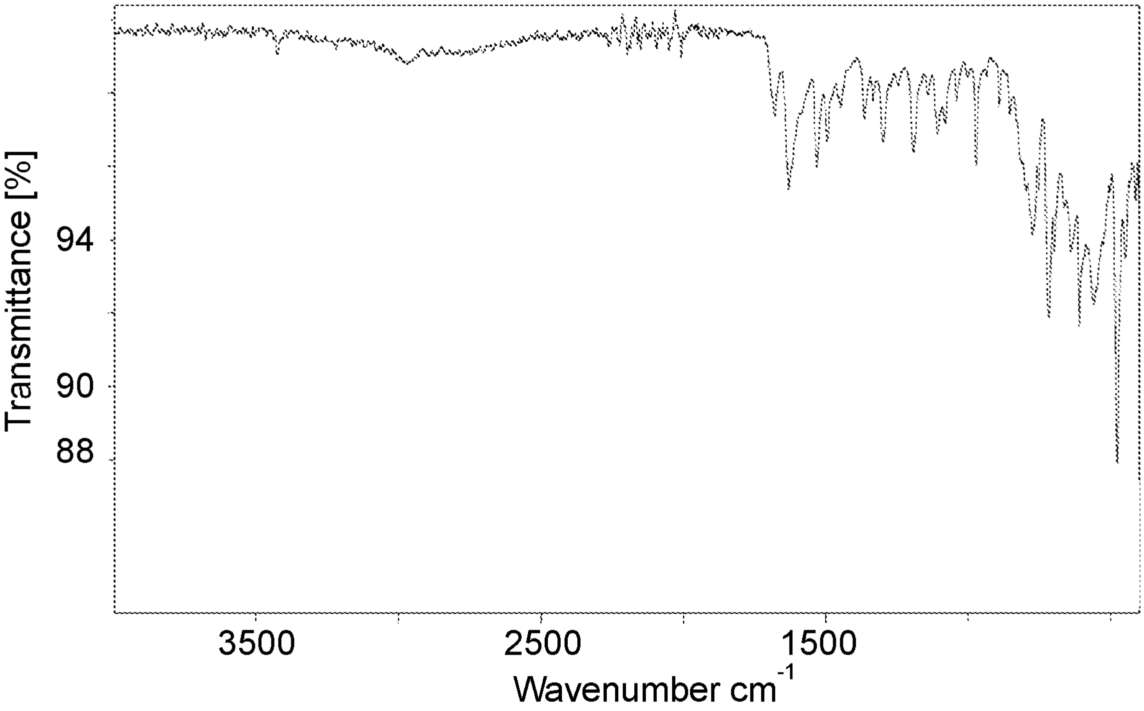
FIG. 68: FT-IR Spectrum of AP1189 Oxalate Pattern 1.

One embodiment of the present disclosure provides for a crystalline Form XV of AP1189 oxalate having an FT-IR as shown in FIG. 68. One embodiment of the present disclosure provides for a crystalline Form XV of AP1189 oxalate having in an FT-IR spectrum peaks as shown in Table 56.

Figure 69:
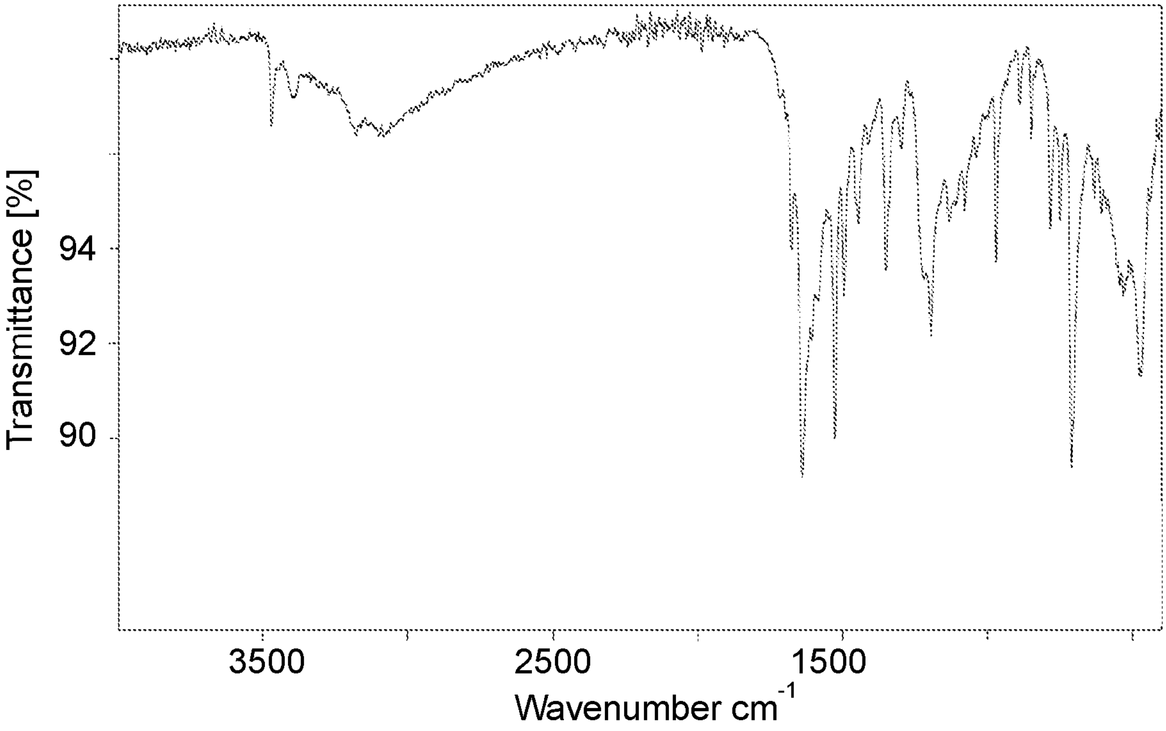
FIG. 69: FT-IR Spectrum of AP1189 Oxalate Pattern 2.

One embodiment of the present disclosure provides for a crystalline Form XVI of AP1189 oxalate having an FT-IR as shown in FIG. 69. One embodiment of the present disclosure provides for a crystalline Form XVI of AP1189 oxalate having in an FT-IR spectrum peaks as shown in Table 57.

Figure 70:
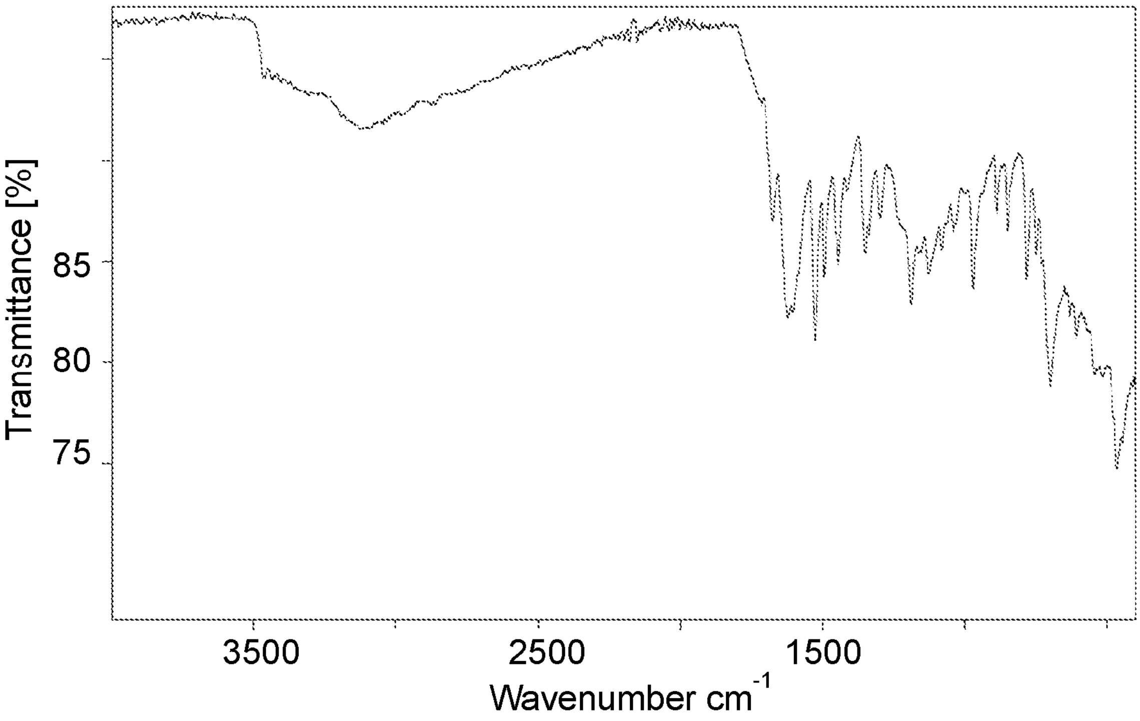
FIG. 70: FT-IR Spectrum of AP1189 Oxalate Pattern 4.

One embodiment of the present disclosure provides for a crystalline Form XVII of AP1189 oxalate having an FT-IR as shown in FIG. 70. One embodiment of the present disclosure provides for a crystalline Form XVII of AP1189 oxalate having in an FT-IR spectrum peaks as shown in Table 58.

Figure 71:
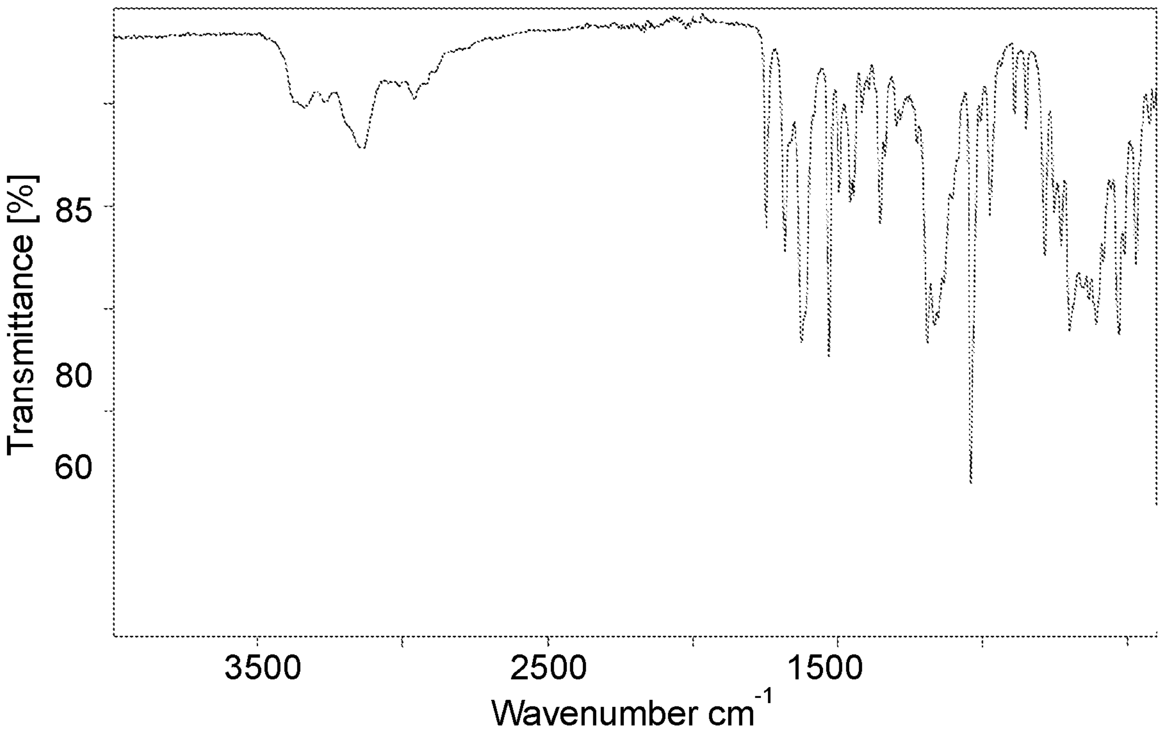
FIG. 71: FT-IR Spectrum of AP1189 (+)-Camphor-10-sulfonic acid Pattern 1.

One embodiment of the present disclosure provides for a crystalline Form XVIII of AP1189 (+)-camphor-10-sulfonic acid having an FT-IR as shown in FIG. 71. One embodiment of the present disclosure provides for a crystalline Form XVIII of AP1189 (+)-camphor-10-sulfonic acid having in an FT-IR spectrum peaks as shown in Table 59.

Figure 72:
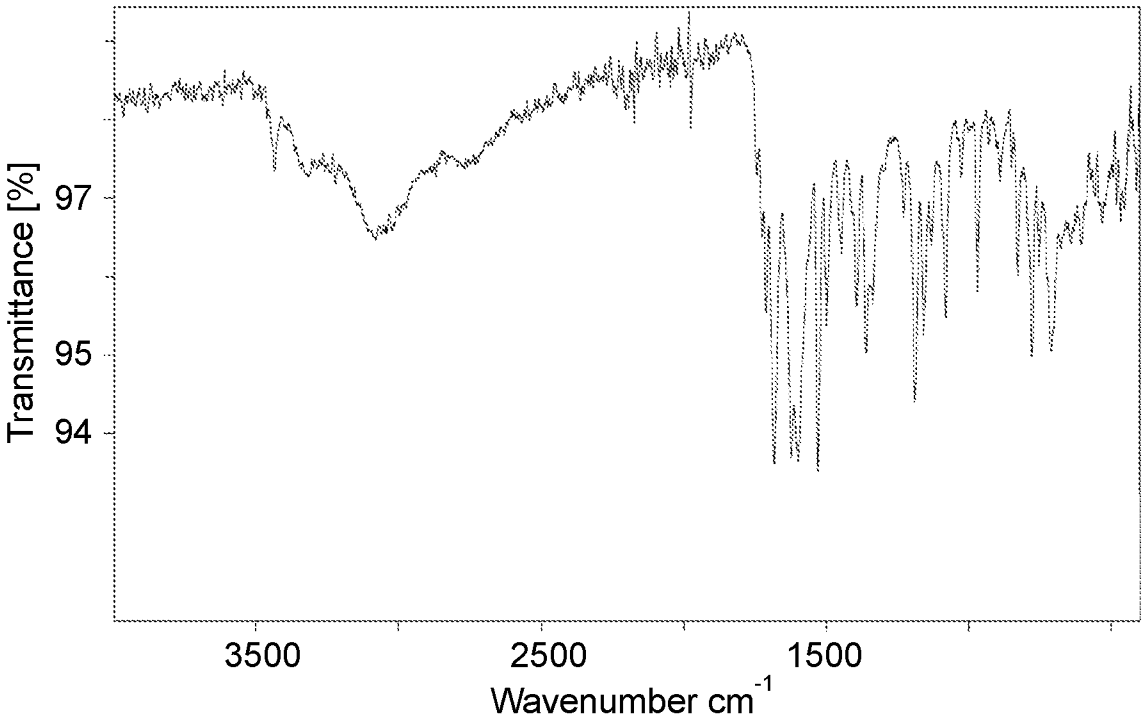
FIG. 72: FT-IR Spectrum of AP1189 Oxoglutarate Pattern 1.

One embodiment of the present disclosure provides for a crystalline Form XIX of AP1189 oxoglutarate having an FT-IR as shown in FIG. 72. One embodiment of the present disclosure provides for a crystalline Form XIX of AP1189 oxoglutarate having in an FT-IR spectrum peaks as shown in Table 60.

Figure 73:
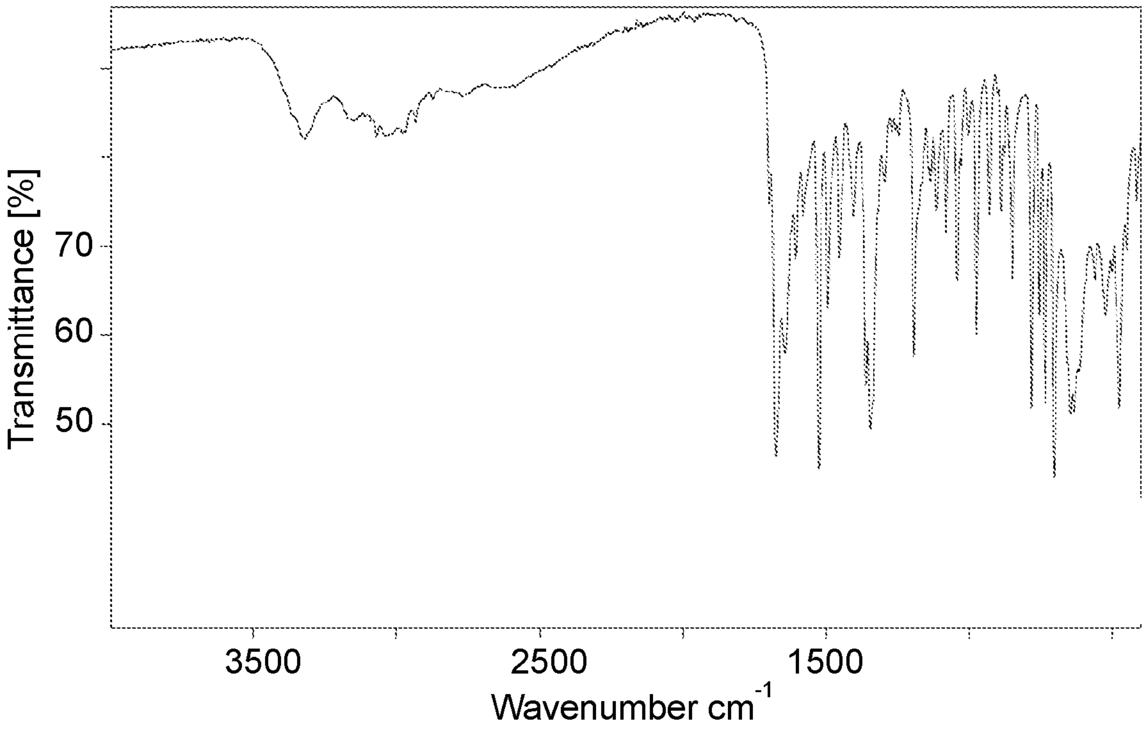
FIG. 73: FT-IR Spectrum of AP1189 DL-mandelic acid Pattern 2.

One embodiment of the present disclosure provides for a crystalline Form XX of AP1189 DL-mandelic acid having an FT-IR as shown in FIG. 73. One embodiment of the present disclosure provides for a crystalline Form XX of AP1189 DL-mandelic acid having in an FT-IR spectrum peaks as shown in Table 61.

Figure 74:
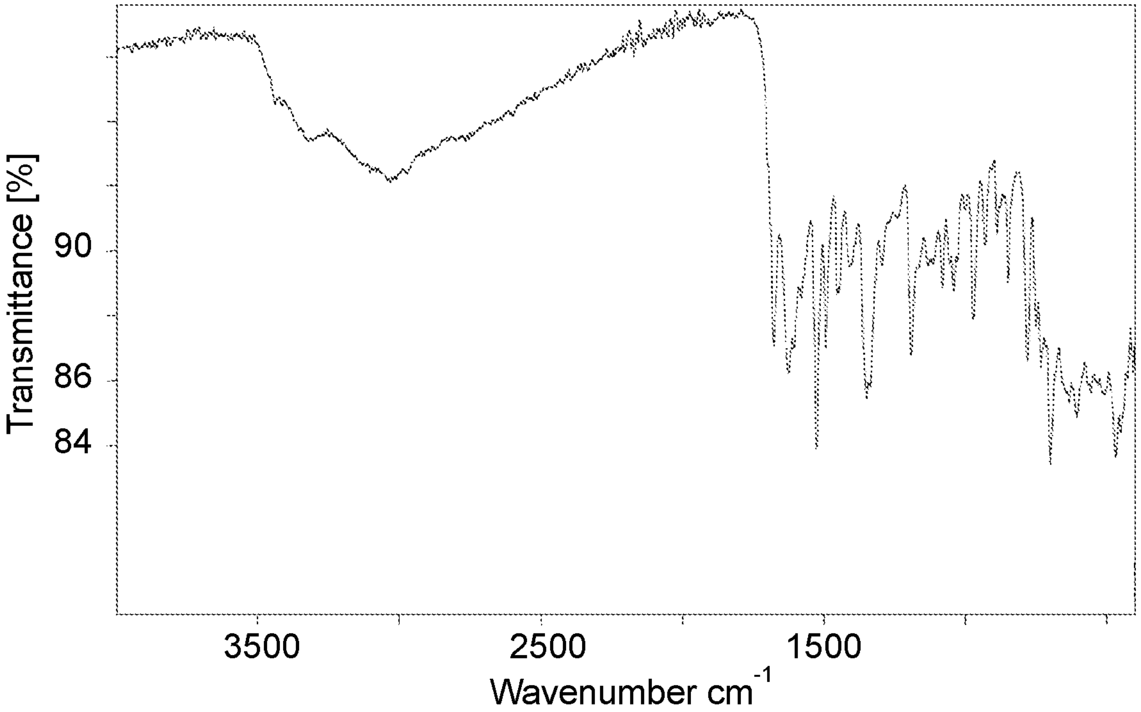
FIG. 74: FT-IR Spectrum of AP1189 DL-mandelic acid Pattern 3.

One embodiment of the present disclosure provides for a crystalline Form XXI of AP1189 DL-mandelic acid having an FT-IR as shown in FIG. 74. One embodiment of the present disclosure provides for a crystalline Form XXI of AP1189 DL-mandelic acid having in an FT-IR spectrum peaks as shown in Table 62.

Figure 75:
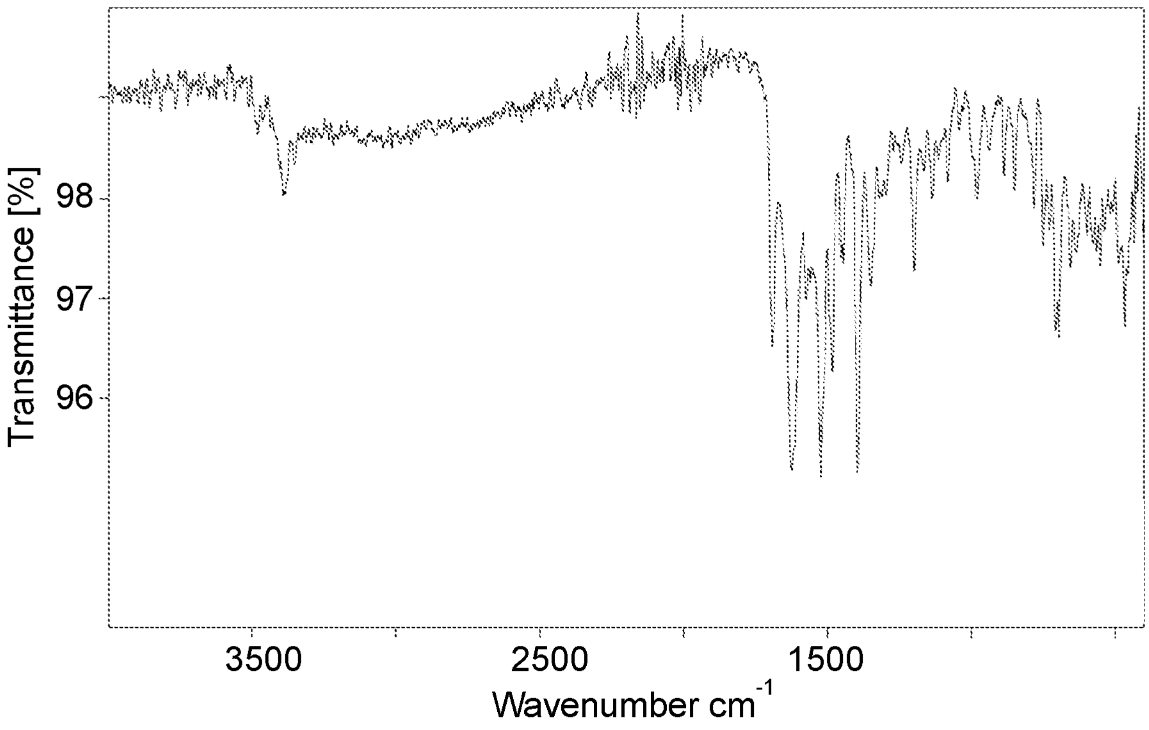
FIG. 75: FT-IR Spectrum of AP1189 Hippuric acid Pattern 1.

One embodiment of the present disclosure provides for a crystalline Form XXII of AP1189 hippuric acid having an FT-IR as shown in FIG. 75. One embodiment of the present disclosure provides for a crystalline Form XXII of AP1189 hippuric acid having in an FT-IR spectrum peaks as shown in Table 63.

Figure 76:
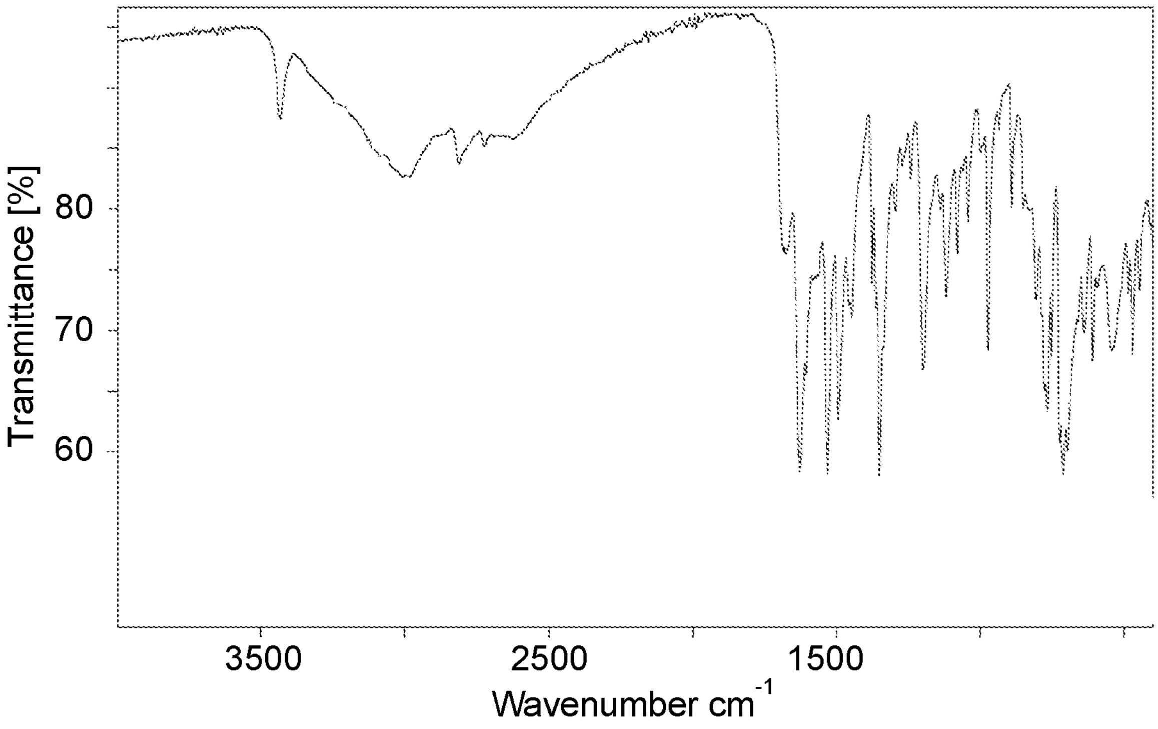
FIG. 76: FT-IR Spectrum of AP1189 Formic acid Pattern 1.

One embodiment of the present disclosure provides for a crystalline Form XXIII of AP1189 formate having an FT-IR as shown in FIG. 76. One embodiment of the present disclosure provides for a crystalline Form XXIII of AP1189 formate having in an FT-IR spectrum peaks as shown in Table 64.

Figure 77:
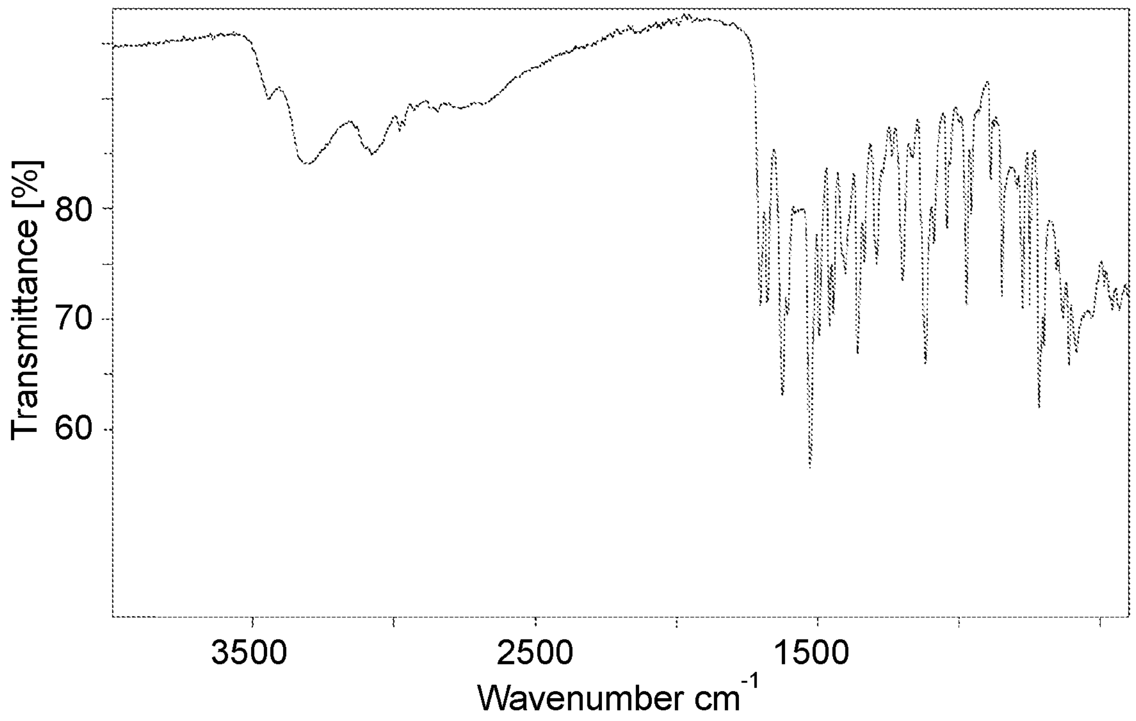
FIG. 77: FT-IR Spectrum of AP1189 DL-Lactic acid Pattern 1.

One embodiment of the present disclosure provides for a crystalline Form XXIV of AP1189 DL-lactic acid having an FT-IR as shown in FIG. 77. One embodiment of the present disclosure provides for a crystalline Form XXIV of AP1189 DL-lactic acid having in an FT-IR spectrum peaks as shown in Table 65.

Figure 78:
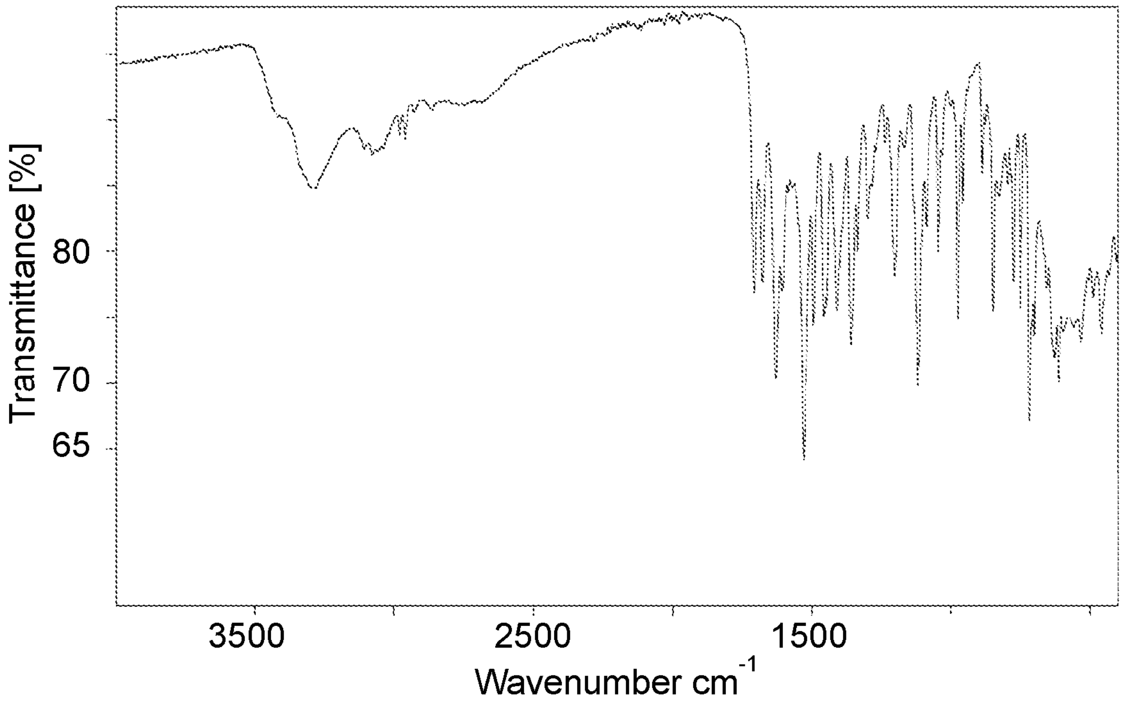
FIG. 78: FT-IR Spectrum of AP1189 DL-Lactic acid Pattern 1.

One embodiment of the present disclosure provides for a crystalline Form XXV of AP1189 DL-lactic acid having an FT-IR as shown in FIG. 78. One embodiment of the present disclosure provides for a crystalline Form XXV of AP1189 DL-lactic acid having in an FT-IR spectrum peaks as shown in Table 66.

Figure 79:
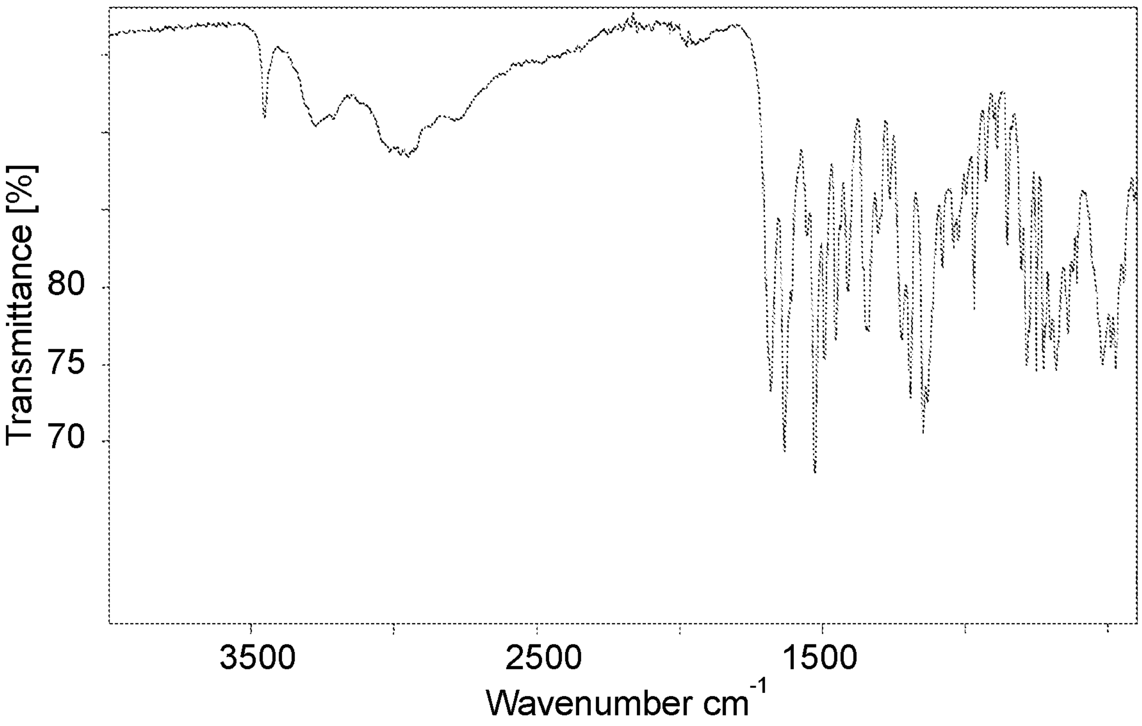
FIG. 79: FT-IR Spectrum of AP1189 Glutaric acid Pattern 1.

One embodiment of the present disclosure provides for a crystalline Form XXVI of AP1189 glutaric acid having an FT-IR as shown in FIG. 79. One embodiment of the present disclosure provides for a crystalline Form XXVI of AP1189 glutaric acid having in an FT-IR spectrum peaks as shown in Table 67.

Figure 80:
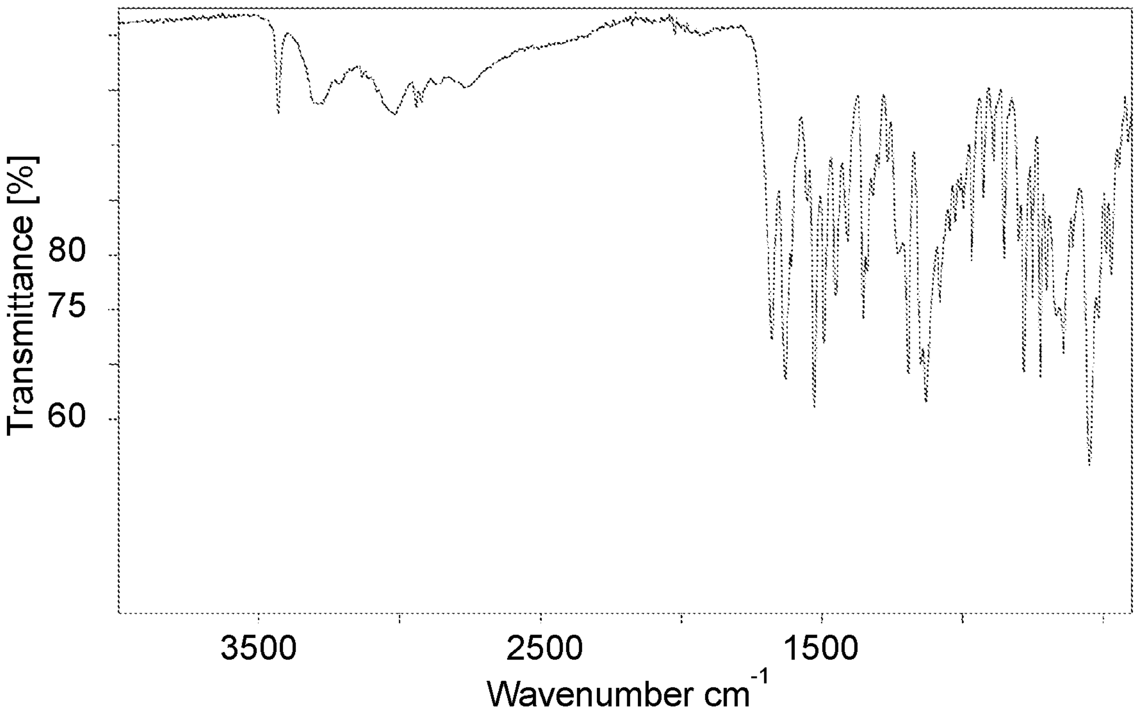
FIG. 80: FT-IR Spectrum of AP1189 Glutaric acid Pattern 2.

One embodiment of the present disclosure provides for a crystalline Form XXVII of AP1189 glutaric acid having an FT-IR as shown in FIG. 80. One embodiment of the present disclosure provides for a crystalline Form XXVII of AP1189 glutaric acid having in an FT-IR spectrum peaks as shown in Table 68.

Figure 92:
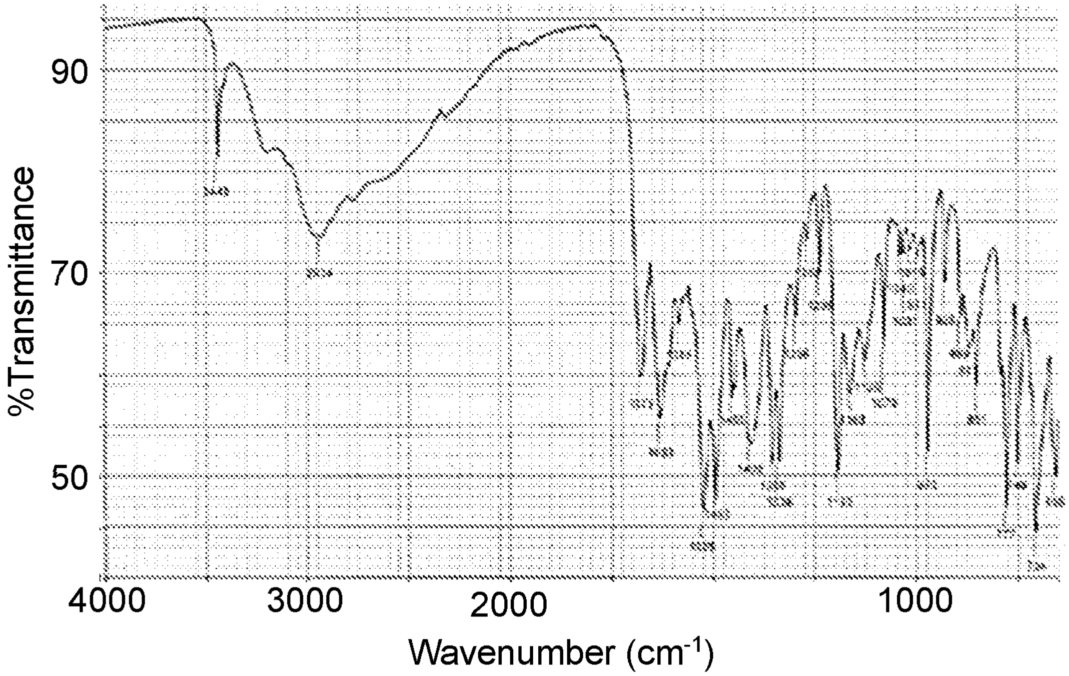
FIG. 92: IR spectrum of AP1189 acetate Pattern 1.

One embodiment of the present disclosure provides for a crystalline Form A of AP1189 acetic acid having an IR spectrum as shown in FIG. 92.

Properties of Crystalline Forms

The present disclosure provides salts of AP1189 having higher solubility. It is to be construed that when solubility is discussed in the context of the present disclosure, solubility in aqueous solution is preferably meant. In one embodiment of the disclosure, solubility is in aqueous medium. Specifically, as shown in the examples herein, the crystalline Form A of AP1189 acetate was found to have a high solubility at pH 1.2. Likewise, crystalline Form B of AP1189 succinate was found to have a higher solubility at pH 1.2-1.3. It is an object of the present disclosure to provide salts of AP1189 having a high solubility at low pH, as this improves in vivo uptake of AP1189 after administration to a subject, such as oral administration to a subject.

High solubility of AP1189 salts is not a given, as is shown in the examples herein. For example, both AP1189 tosylate and AP1189 fumarate were found to have low solubility at low pH, e.g. pH 1.2-1.3.

One embodiment of the present disclosure provides for a salt of AP1189 having a solubility at pH 1.2 of at least 10 mM, such as least 15 mM, such as at least 20 mM, such as at least 25 mM, such as at least 30 mM, such as at least 35 mM.

One embodiment of the present disclosure provides for a crystalline Form A of AP1189 acetate having a solubility at pH 1.2 of at least 100 mM, such as at least 110 mM, such as at least 120 mM.

One embodiment of the present disclosure provides for a crystalline Form B of AP1189 succinate having a solubility at pH 1.2 of at least 20 mM, such as at least 25 mM, such as at least 30 mM, such as at least 35 mM.

The solubility of a compound may be assessed by adding a surplus of the compound to a volume of solvent such that some of the compound is not dissolved, then isolating the non-dissolved compound and measuring the amount. The solubility of a compound may alternatively be assessed by adding a surplus of the compound to a volume of solvent such that some of the compound is not dissolved, and then measure the amount of compound in solution. Measuring the amount of compound in solution may be done using any suitable method, such as HPLC, titration, or spectrometry.

Methods for Preparing AP1189 Salts

Salts of AP1189 may be prepared as disclosed herein.

One embodiment of the present disclosure provides for a method of producing AP1189 acetate of crystalline Form A, said method comprising:

i. mixing AP1189 and acetic acid in a solvent to form a mixture; and
ii. isolating the AP1189 acetate of crystalline Form A from said mixture.

As used herein, "mixture" can mean a solution or a slurry of one or more solids in a solvent or mixture of solvents. In one embodiment of the disclosure, the mixture is a solution, where the solute or solutes are substantially fully dissolved. In one embodiment, the mixture is a slurry, wherein one or more solutes are only partly dissolved, and the remaining part or parts of the solute or solutes are not dissolved.

One embodiment of the present disclosure provides for a method for producing AP1189 acetate of crystalline Form A, said method comprising:

i. mixing AP1189 and acetate salt in a solvent to form a mixture; and
ii. isolating the AP1189 acetate of crystalline Form A from said mixture.

In one embodiment, the acetate salt is ammonium acetate or a metal acetate salt such as sodium acetate, lithium acetate, magnesium acetate, potassium acetate, or calcium acetate.

In one embodiment, the method further comprises adding an acid in step i, such as an organic acid or a mineral acid.

One embodiment of the disclosure provides for a method for producing AP1189 acetate of crystalline Form A, said method comprising:

i. mixing AP1189 acetate in a solvent to form a composition; and
ii. isolating the AP1189 acetate of crystalline Form A from said composition.

In one embodiment, such method is effective in converting AP1189 acetate not of crystalline Form A to AP1189 acetate of crystalline Form A.

As used herein, "composition" can mean a solution or a slurry of one solid in a solvent or mixture of solvents. In one embodiment of the disclosure, the composition is a solution, where the solute is substantially fully dissolved. In one embodiment, the composition is a slurry, wherein the solute is only partly dissolved, and the remaining part of the solute is not dissolved. The composition may further comprise one or more other agents or reagents which may be dissolved or may be only partly dissolved. Such other agents includes, but are not limited to, surfactants, detergents, acids, bases, sugars, salts, biomolecules, bioactive agents, and other excipients such as pharmaceutical excipients.

This present disclosure also relates to non-solid compositions, e.g. liquid compositions, gel compositions, pastes, creams, or ointments prepared from the crystalline forms disclosed herein. One embodiment provides for a liquid composition, gel composition, paste, cream, or ointment prepared from a crystalline form disclosed herein. One specific embodiment provides for a liquid composition prepared from a crystalline form disclosed herein and a solvent. In a specific embodiment, the solvent is aqueous. In one embodiment, the present disclosure provides for a method of preparing a liquid composition, a gel composition, a paste, a cream, or an ointment, said method comprising mixing a crystalline form disclosed herein and one or more additional agents. One specific embodiment provides for a method of preparing a liquid composition, said method comprising mixing a crystalline form disclosed herein and a solvent. In a further embodiment, the solvent is aqueous.

One embodiment of the disclosure provides for a method for producing N-{3-[1-(2-nitrophenyl)-1H-pyrrol-2-yl]-allylidene}-aminoguanidinium acetate of crystalline Form A, said method comprising:

i. mixing 3-[1-(2-nitrophenyl)-1-H-pyrrole-2-yl]-propanal, amino guanidine or a salt thereof, and acetic acid or a salt thereof in a solvent, and ii. isolating the N-{3-[1-(2-nitrophenyl)-1H-pyrrol-2-yl]-allylidene}-aminoguanidinium acetate of crystalline Form A from said composition.

Any one of the above agents of step i may be generated from a precursor in situ.

One embodiment of the present disclosure provides for a method for producing N-{3-[1-(2-nitrophenyl)-1H-pyrrol-2-yl]-allylidene}-aminoguanidinium acetate of crystalline Form A, said method comprising:

i. providing N-{3-[1-(2-nitrophenyl)-1H-pyrrol-2-yl]-allylidene}-aminoguanidine or an N-{3-[1-(2-nitrophenyl)-1H-pyrrol-2-yl]-allylidene}-aminoguanidinium salt, ii. introducing acetate as a counter ion using ion exchange, and iii. isolating N-{3-[1-(2-nitrophenyl)-1H-pyrrol-2-yl]-allylidene}-aminoguanidinium acetate of crystalline Form A.

One embodiment of the present disclosure provides for a method of producing AP1189 succinate of crystalline Form B, said method comprising:

i. mixing AP1189 and succinic acid in a solvent to form a mixture; and ii. isolating the AP1189 succinate of crystalline Form B from the mixture.

One embodiment of the present disclosure provides for a method of producing AP1189 succinate of crystalline Form B, said method comprising:

i. mixing a AP1189 salt and succinic acid in a solvent to form a mixture, and ii. isolating the AP1189 succinate of crystalline Form B from the mixture.

One embodiment of the present disclosure provides for a method for producing the N-{3-[1-(2-nitrophenyl)-1H-pyrrol-2-yl]-allylidene}-aminoguanidinium succinate of crystalline Form B, said method comprising:

i. mixing 3-[1-(2-nitrophenyl)-1-H-pyrrole-2-yl]-propanal, amino guanidine or a salt thereof, and succinic acid or a salt thereof in a solvent, and ii. isolating the N-{3-[1-(2-nitrophenyl)-1H-pyrrol-2-yl]-allylidene}-aminoguanidinium succinate of crystalline Form B from said composition.

Any one of the above agents of step i may be generated from a precursor in situ.

One embodiment of the present disclosure provides for a method for producing the N-{3-[1-(2-nitrophenyl)-1H-pyrrol-2-yl]-allylidene}-aminoguanidinium succinate of crystalline Form B, said method comprising:

i. providing N-{3-[1-(2-nitrophenyl)-1H-pyrrol-2-yl]-allylidene}-aminoguanidine or an N-{3-[1-(2-nitrophenyl)-1H-pyrrol-2-yl]-allylidene}-aminoguanidinium salt, ii. introducing succinate as a counter ion using ion exchange, and iii. isolating N-{3-[1-(2-nitrophenyl)-1H-pyrrol-2-yl]-allylidene}-aminoguanidinium succinate of crystalline Form B.

In one embodiment of the present disclosure, the solvent is a protic or a polar aprotic solvent. In one embodiment, the solvent is selected from the group consisting of 1,4-dioxane, methanol, ethanol, 1-propanol, 2-propanol, acetone, acetonitrile, anisole, isopropyl acetate, methylethyl ketone, water, and ethyl acetate.

In one embodiment of the present disclosure, the mixture or the composition is heated at least once before the isolating step. In one embodiment, the mixture or the composition is heated and cooled in cycles before the isolation step. In one embodiment, the mixture or the composition is heated and cooled in cycles for up to 72 hours before the isolating step. In one embodiment the mixture or the composition is heated and cooled in cycles for 15 min to 72 hours before the isolating step. In one embodiment, one cycle comprises heating the mixture or the composition to at least a first threshold temperature, maintaining the temperature above said first threshold temperature for a first duration, then cooling the mixture or the composition to below a second threshold temperature and maintaining the temperature below said second threshold temperature for a second duration. In one embodiment of the present disclosure, the cycle is carried out 1 to 200 times. In one embodiment of the present disclosure, the first threshold temperature is 30° C., such as 35° C., such as 40° C., such as 45° C., such as 50° C., such as 55° C., such as 60° C., such as 65° C., such as 70° C., such as 75° C., such as 80° C. In one embodiment of the present disclosure, the second threshold temperature is 30° C., such as 25° C., such as 20° C., such as 15° C., such as 10° C., such as 7° C., such as 5° C. In one embodiment of the present disclosure, the first and/or the second duration is 1 to 2 min, such as 2 to 5 min, such as 5 to 10 min, such as 10 to 20 min, such as 20 to 30 min, such as 30 to 40 min, such as 40 to 50 min, such as 50 to 60 min, such as 1 hour to 1.5 hours, such as 1.5 to 2 hours, such as 2 to 3 hours, such as 3 to 4 hours, such as 4 to 5 hours, such as 5 to 6 hours, such as 6 to 7 hours, such as 7 to 8 hours. In one embodiment, the first and the second durations are the same. In one embodiment, the first and the second durations are different. In one embodiment, the first duration is different or the same for each cycle. In one embodiment, the second duration is different or the same for each cycle.

In one embodiment, heating is to about 40° C.

In one embodiment, cooling is to about 20° C.

In one embodiment, the method further comprises a step of adding an anti-solvent to the mixture or the composition before the isolation step. In one embodiment, the anti-solvent is a non-polar aprotic solvent. In one embodiment, the anti-solvent is selected from the group consisting of tert-butyl methyl ether, THF, and acetone, and mixtures comprising tert-butyl methyl ether, THF, or acetone. In one embodiment of the present disclosure, the anti-solvent is water.

Isolation of crystals may be carried out using an appropriate means. In one embodiment of the disclosure, the isolation is carried out using filtration, centrifugation, and/or evaporation of the solvent or solvents. In one embodiment, a slow evaporation method is utilised. In one embodiment, a fast evaporation method is utilised. In one embodiment, the evaporation is carried out using spray drying. In one embodiment, the evaporation is carried out using fluid bed drying, freeze drying, vacuum drying, tumble drying, rotary evaporation, and/or thin-film evaporation. In one embodiment, the drying is carried out using a conductive (contact) dryer, including tray dryers, rotary cone dryers, tumble dryers, and paddle dryers. In one further embodiment, the drying is carried out using a carrier gas.

In one embodiment of the present disclosure, one or more pKa values, such as at least one pKa, of the corresponding acid to the counter ion of the AP1189 salt is about equal to or lower than the pKa value of succinic acid and/or acetic acid. By way of example, "the corresponding acid to the counter ion of the AP1189 fumarate" is fumaric acid. The pKa value of acetic acid is 4.756. The pKa value corresponding to the first acid dissociation of succinic acid is 4.2. The pKa value corresponding to the second acid dissociation of succinic acid is 5.6. Accordingly, in one embodiment, the pKa value of the corresponding acid to the counter ion of the AP1189 salt is about equal to or lower than 4.756. In another embodiment, the pKa value of the corresponding acid to the counter ion of the AP1189 salt is about equal to or lower than 4.2 and/or 5.6.

One embodiment of the present disclosure provides for a crystalline Form A of AP1189 acetate produced by the method as disclosed herein.

One embodiment of the present disclosure provides for a crystalline Form B of AP1189 succinate produced by the method as disclosed herein.

One embodiment of the present disclosure provides for a method of producing crystalline Form A of AP1189 acetate as disclosed herein, wherein the method further comprises adding a seed crystal of crystalline Form A of AP1189 acetate before the isolation step. One embodiment of the present disclosure provides for a method of producing crystalline Form B of AP1189 succinate as disclosed herein, wherein the method further comprises adding a seed crystal of crystalline Form B of AP1189 succinate before the isolation step.

Pharmaceutical Compositions

One embodiment of the disclosure provides for a pharmaceutical composition comprising the crystalline Form A of AP1189 acetate as disclosed herein and a pharmaceutically acceptable excipient.

One embodiment of the disclosure provides for a pharmaceutical composition comprising the crystalline Form B of AP1189 succinate as disclosed herein and a pharmaceutically acceptable excipient.

In some embodiments there is provided an oral formulation, a pharmaceutical composition, or unit dosage form comprising the crystalline Form A of AP1189 acetate as disclosed herein or the crystalline Form B of AP1189 succinate as disclosed herein.

One embodiment provides for a pharmaceutical composition as disclosed herein, wherein the pharmaceutical composition is formulated for oral administration. Such composition may be in the form of a tablet or a capsule.

One embodiment of the disclosure provides for a method of preparing a pharmaceutical composition comprising mixing the crystalline Form A of AP1189 acetate with a pharmaceutically acceptable excipient.

One embodiment of the disclosure provides for a method of preparing a pharmaceutical composition comprising mixing the crystalline Form B of AP1189 succinate with a pharmaceutically acceptable excipient.

One embodiment of the disclosure provides for the crystalline Form A of AP1189 acetate, the crystalline Form B of AP1189 succinate, or the pharmaceutical composition as disclosed herein for use in medicine. One embodiment of the present disclosure provides for the crystalline Form A of AP1189 acetate, the crystalline Form B of AP1189 succinate, or the pharmaceutical composition as disclosed herein, for use in the treatment of a kidney disease such as proteinuria, a cardiovascular disease, an arthritic disease, or a viral infection.

One embodiment of the present disclosure provides for a method of treating a disease or disorder in a subject in need thereof, said method comprising administering crystalline Form A of AP1189 acetate, crystalline Form B of AP1189 succinate, or the pharmaceutical composition as disclosed herein, to a subject in need thereof. In one further embodiment, the disease or disorder is selected from the list consisting of a kidney disease such as proteinuria, a cardiovascular disease, an arthritic disease, or a viral infection.

One embodiment of the present disclosure provides for a use of the crystalline Form A of AP1189 acetate or the crystalline Form B of AP1189 succinate, or the pharmaceutical composition as disclosed herein for the manufacture of a medicament for treatment of a disease or disorder.

Medical Use

It is an aspect of the present disclosure to provide a pharmaceutical formulation, such as an oral formulation, comprising the crystalline Form A of AP1189 acetate as disclosed herein or the crystalline Form B of AP1189 succinate as disclosed herein, for use in the treatment of a disease or disorder.

In some embodiments, the disease or disorder is selected from the group consisting of a kidney disease, an arthritic disease, a viral disease or disorder, and a cardiovascular disease and/or atherosclerosis.

Kidney Disease

It is an aspect of the present disclosure to provide a pharmaceutical formulation such as an oral formulation, a pharmaceutical composition, or unit dosage form according to the present disclosure for use in treating or preventing a kidney disease.

Also disclosed is a method of treating or preventing a kidney disease in a subject in need thereof, wherein the subject is administered a therapeutically effect amount of the oral formulation, pharmaceutical composition, or unit dosage form of the present disclosure.

Also disclosed is the use of an oral formulation, pharmaceutical composition, or unit dosage form according to the present disclosure for use in the manufacture of a medicament for the treatment or prevention of a kidney disease.

In some embodiments of the present disclosure there is provided an oral formulation, such as a solid oral formulation, comprising the crystalline form A of AP1189 acetate or the crystalline Form B of AP1189 succinate, and at least one pharmaceutically acceptable excipient, as disclosed herein, for use in treating or preventing a kidney disease.

In some embodiments said kidney disease present with proteinuria. In some embodiments said kidney disease is a proteinuric kidney disease.

In some embodiments said kidney disease is a glomerular disease

In some embodiments said kidney disease is nephrotic syndrome (glomerulonephrosis).

In some embodiments said kidney disease is primary nephrotic syndrome (primary glomerulonephrosis).

In some embodiments said primary nephrotic syndrome is membranous glomerulonephritis (MGN) (or membranous nephropathy (MN)).

In some embodiments said primary nephrotic syndrome is focal segmental glomerulosclerosis (FSGS).

In some embodiments said primary nephrotic syndrome is membranoproliferative glomerulonephritis (MPGN) (mesangiocapillary glomerulonephritis).

In some embodiments said membranoproliferative glomerulonephritis (MPGN) is selected from Type 1 MPGN and Type 2 MPGN.

In some embodiments said primary nephrotic syndrome is rapidly progressive glomerulonephritis (RPGN) (crescentic GN).

In some embodiments said primary nephrotic syndrome is minimal change disease (MCD).

In some embodiments said kidney disease is secondary nephrotic syndrome (secondary glomerulonephrosis).

In some embodiments said secondary nephrotic syndrome is caused by an underlying autoimmune disease, an underlying cancer disease, an underlying genetic disorder, or by an underlying disease selected from the group consisting of: Systemic lupus erythematosus (SLE), Diabetic nephropathy, Sarcoidosis, Sjögren's syndrome, Amyloidosis, Multiple myeloma, Vasculitis, Cancer and Genetic disorders (such as congenital nephrotic syndrome).

In some embodiments said secondary nephrotic syndrome is caused by Diabetic nephropathy, by an infection, such as a urinary tract infection, such as an infection selected from the group consisting of HIV, syphilis, hepatitis such as hepatitis A, B and C, post-streptococcal infection, urinary schistosomiasis and Ebola. In some embodiments said secondary nephrotic syndrome is drug-induced.

In some embodiments said kidney disease is an inflammatory kidney disease.

In some embodiments said kidney disease is glomerulonephritis (GN). In some embodiments said glomerulonephritis is selected from the group consisting of IgA nephropathy (Berger's disease), IgM nephropathy, Post-infectious glomerulonephritis and Thin basement membrane disease.

In some embodiment said kidney disease is idiopathic membranous nephropathy (iMN).

In some embodiments there is provided an oral formulation, a pharmaceutical composition, or unit dosage form according to the present disclosure for use in treating or preventing idiopathic membranous nephropathy (iMN).

Arthritic Disease

It is as aspect of the present disclosure to provide an oral formulation, a pharmaceutical composition, or unit dosage form according to the present disclosure for use in treating or preventing an arthritic disease.

Also disclosed is a method of treating or preventing an arthritic disease in a subject in need thereof, wherein the subject is administered a therapeutically effect amount of the oral formulation, pharmaceutical composition, or unit dosage form of the present disclosure.

Also disclosed is the use of an oral formulation, pharmaceutical composition, or unit dosage form according to the present disclosure for use in the manufacture of a medicament for the treatment or prevention of an arthritic disease.

In some embodiments of the present disclosure there is provided an oral formulation, such as a solid oral formulation, comprising the crystalline Form A of AP1189 acetate or crystalline Form B of AP1189 succinate, and at least one pharmaceutically acceptable excipient, as disclosed herein, for use in treating or preventing an arthritic disease.

In one embodiment the arthritic disease is an autoimmune disease and/or an inflammatory disease that presents with joint inflammation.

In one embodiment, the arthritic disease is selected from the group consisting of inflammatory arthritis, degenerative arthritis, metabolic arthritis, reactive arthritis and infectious arthritis.

In one embodiment, the arthritic disease is inflammatory arthritis.

In one embodiment, the inflammatory arthritis is selected from the group consisting of Rheumatoid Arthritis (RA), Psoriatic Arthritis, and Ankylosing Spondylitis.

In one embodiment, the inflammatory arthritis is Rheumatoid Arthritis (RA).

In one embodiment, the rheumatoid arthritis is severe active RA (CDAI>22). In one embodiment, the rheumatoid arthritis is RA with a CDAI>22.

In one embodiment, the rheumatoid arthritis is RA with a DAS28 score of above 5.1.

In one embodiment, the rheumatoid arthritis is juvenile rheumatoid arthritis (JRA).

In one embodiment, the degenerative arthritis is osteoarthritis.

In one embodiment, the metabolic arthritis is gouty arthritis.

In one embodiment, the reactive and/or infectious arthritis is arthritis associated with infection with one or more of Hepatitis C, *Chlamydia*, gonorrhoea, *salmonella* or *shigella*.

In one embodiment the arthritic disease is arthritis as part of a systemic inflammatory disease.

In one embodiment, the arthritis as part of a systemic inflammatory disease, such as an inflammatory disease selected from the group consisting of systemic lupus erythematosus, mixed connective tissue disease, Still's disease, and Polymyalgia Rheumatica.

In some embodiments there is provided an oral formulation, a pharmaceutical composition, or unit dosage form according to the present disclosure for use in treating or preventing rheumatoid arthritis.

In some embodiments there is provided an oral formulation, a pharmaceutical composition, or unit dosage form according to the present disclosure in combination with MTX (methotrexate) for use in treating or preventing rheumatoid arthritis.

In some embodiments there is provided an oral formulation, a pharmaceutical composition, or unit dosage form according to the present disclosure, alone or in combination with MTX (methotrexate), for use in treating or preventing rheumatoid arthritis in patients with an inappropriate response to MTX (such as patients with a reduced response to MTX treatment, such as an MTX non-responder).

Viral Disease or Disorder

It is as aspect of the present disclosure to provide an oral formulation, a pharmaceutical composition, or unit dosage form according to the present disclosure for use in treating or preventing a viral disease or disorder.

Also disclosed is a method of treating or preventing a viral disease or disorder in a subject in need thereof, wherein the subject is administered a therapeutically effect amount of the oral formulation, pharmaceutical composition, or unit dosage form of the present disclosure.

Also disclosed is the use of an oral formulation, pharmaceutical composition, or unit dosage form according to the present disclosure for use in the manufacture of a medicament for the treatment or prevention of a viral disease or disorder.

In some embodiments of the present disclosure there is provided an oral formulation, such as a solid oral formulation, comprising a pharmaceutically acceptable salt of AP1189, such as AP1189 acetate or AP1189 succinate, and at least one pharmaceutically acceptable excipient, as disclosed herein, for use in treating or preventing a viral disease or disorder.

In some embodiments said viral disease or disorder is a symptomatic viral disease or disorder.

In some embodiments said viral disease or disorder is a symptomatic viral disease or disorder with inflammation, such as hyperinflammation.

In some embodiments said viral disease or disorder is a symptomatic viral disease or disorder with inflammation, such as hyperinflammation, in one or more organs.

Inflammation in one or more organs may also be referred to as local inflammation.

In some embodiments said one or more organs are selected from the group consisting of lungs, the respiratory tract, kidney, liver, pancreas, spleen, exocrine glands, endocrine glands, lymph nodes, brain, heart, muscles, bone marrow, skin, skeleton, bladder, reproduction organs including the phallopian tubes, eye, ear, vascular system, the gastrointestinal tract including small intestines, colon, rectum, canalis analis and the prostate gland.

In some embodiments said viral disease or disorder is inflammatory viral diseases or disorders.

In some embodiments said viral disease or disorder is a viral respiratory infection, such as a viral lower respiratory infection.

In some embodiments said viral disease or disorder is viral respiratory diseases or disorders.

In some embodiments said viral disease or disorder is viral diseases or disorders of the lung.

In some embodiments said viral disease or disorder is viral diseases or disorders with inflammation in the respiratory system, such as in the lungs and/or respiratory tract.

In some embodiments said viral disease or disorder is viral diseases or disorders with one or more respiratory symptoms. In one embodiment said one or more respiratory symptoms are selected from the group consisting of cough, dry cough, dyspnea, impaired oxygenation, respiratory illness, respiratory dysfunction, respiratory failure, respiratory syndrome and acute respiratory disease (ARD).

In some embodiments said viral disease or disorder is severe disease. Severe disease present with dyspnoea, increased respiratory frequency, reduced blood oxygen saturation and/or lung infiltrates.

In some embodiments said viral disease or disorder is critical disease. Critical disease present with respiratory failure, septic shock, and/or multiple organ dysfunction (MOD) or multiple organ failure (MOF).

In some embodiments said viral disease or disorder is viral pneumonia.

In some embodiments said viral disease or disorder is viral bronchiolitis.

In some embodiments said viral disease or disorder is viral diseases or disorders with respiratory failure.

In some embodiments said viral disease or disorder is acute respiratory distress syndrome (ARDS).

In some embodiments said viral disease or disorder is viral acute respiratory distress syndrome (ARDS).

In some embodiments said viral disease or disorder is symptomatic COVID-19 with acute respiratory distress syndrome (ARDS).

In some embodiments there is provided an oral formulation, a pharmaceutical composition, or unit dosage form according to the present disclosure for use in treating or preventing ARDS, such as viral ARDS.

In some embodiments said viral disease or disorder is viral diseases and disorders with systemic inflammatory distress syndrome (SIDS) and/or sepsis.

In some embodiments said viral disease or disorder is viral diseases and disorders with pulmonary insufficiency.

In some embodiments said viral disease or disorder is viral diseases or disorders with cytokine release syndrome (CRS) and/or a cytokine storm (hypercytokinemia).

In some embodiments said viral disease or disorder is caused by a viral infection selected from the group consisting of Severe Acute Respiratory Syndrome CoronaVirus 2 (SARS-CoV-2), often referred to as the COVID-19 virus; SARS-CoV, MERS-CoV, the dengue virus and influenza virus (including Type A, Type B and Type C).

Cardiovascular Disease and/or Atherosclerosis

It is as aspect of the present disclosure to provide an oral formulation, a pharmaceutical composition, or unit dosage form according to the present disclosure for use in treating or preventing a cardiovascular disease and/or atherosclerosis.

Also disclosed is a method of treating or preventing a cardiovascular disease and/or atherosclerosis in a subject in need thereof, wherein the subject is administered a therapeutically effect amount of the oral formulation, pharmaceutical composition, or unit dosage form of the present disclosure.

Also disclosed is the use of an oral formulation, pharmaceutical composition, or unit dosage form according to the present disclosure for use in the manufacture of a medicament for the treatment or prevention of a cardiovascular disease and/or atherosclerosis.

In some embodiments of the present disclosure there is provided an oral formulation, such as a solid oral formulation, comprising the crystalline Form A of AP1189 acetate as disclosed herein or the crystalline Form B of AP1189 succinate as disclosed herein, and at least one pharmaceutically acceptable excipient, as disclosed herein, for use in treating or preventing a cardiovascular disease and/or atherosclerosis.

In some embodiments said cardiovascular disease is selected from the group consisting of coronary artery diseases (CAD) such as angina and myocardial infarction (commonly known as a heart attack); stroke, heart failure, hypertensive heart disease, rheumatic heart disease, cardiomyopathy, abnormal heart rhythms, congenital heart disease, valvular heart disease, carditis, aortic aneurysms, peripheral artery disease, vascular disease, thromboembolic disease, and venous thrombosis.

In some embodiments said cardiovascular disease is atherosclerotic cardiovascular disease.

In some embodiments said atherosclerotic cardiovascular disease is selected from the group consisting of coronary artery disease, stroke (cerebrovascular disease), and peripheral artery disease.

In some embodiments said cardiovascular disease is vascular inflammation.

Systemic Inflammatory Disorders

It is as aspect of the present disclosure to provide an oral formulation, a pharmaceutical composition, or unit dosage form according to the present disclosure for use in treating or preventing a systemic inflammatory disorder.

Also disclosed is a method of treating or preventing a systemic inflammatory disorder in a subject in need thereof, wherein the subject is administered a therapeutically effective amount of the oral formulation, pharmaceutical composition, or unit dosage form of the present disclosure.

Also disclosed is the use of an oral formulation, pharmaceutical composition, or unit dosage form according to the present disclosure for use in the manufacture of a medicament for the treatment or prevention of a systemic inflammatory disorder.

In some embodiments of the present disclosure there is provided an oral formulation, such as a solid oral formulation, comprising the crystalline Form A of AP1189 acetate as disclosed herein or the crystalline Form B of AP1189 succinate, and at least one pharmaceutically acceptable excipient, as disclosed herein, for use in treating or preventing a systemic inflammatory disorder.

Systemic disorders with possible involvement of the nervous system include a variety of diseases with presumed inflammatory and autoimmune pathomechanisms, among them Behçet disease, sarcoidosis, systemic lupus erythematosus, juvenile idiopathic arthritis, scleroderma, and Sjögren syndrome. This disease group encompasses systemic inflammatory disorders with a genetically defined dysregulation of the innate immune system as well as systemic autoimmune disorders characterized by alterations of the adaptive immunity such as autoantibodies and autoreactive T cells.

In some embodiments said systemic inflammatory disorder is an autoimmune disorder.

In some embodiments said systemic inflammatory disorder is selected from the group consisting of Behçet disease, sarcoidosis, systemic lupus erythematosus, juvenile idiopathic arthritis, scleroderma, Sjögren syndrome, myositis including dermamyositis and polymyositis, vasculitis, giant cell arteritis, ankylosing spondylitis, polymyalgia rheumatic and psoriatic arthritis.

EXAMPLES

Example 1: Formation of Salts

From the Reaction Yielding N-{3-[1-(2-nitrophenyl)-1H-pyrrol-2-yl]-allylidene}-aminoguanidine An acid is added as a slurry or solution in a protic or polar aprotic solvent to a heated slurry or solution of 3-[1-(2-nitrophenyl)-1-H-pyrrole-2-yl]-propanal and aminoguanidine or a salt thereof in a protic or polar aprotic solvent. The resulting mixture is heated and stirred, preferably until completion of the reaction, before cooled and optionally an anti-solvent, such as a non-polar aprotic solvent, is added. The resulting salt is isolated by conventional methods, such as filtration, centrifugation, evaporation of the solvents, including spray drying.

From Free Base

An acid is added (such as an excess of said acid) as a slurry or solution in a protic or polar aprotic solvent to a slurry of N-{3-[1-(2-nitrophenyl)-1H-pyrrol-2-yl]-allylidene}-aminoguanidine in a protic or polar aprotic solvent. The resulting mixture is heated and cooled in cycles between 15 min and 72 hours, before cooled and optionally an anti-solvent, such as a non-polar aprotic solvent, is added. The resulting salt is isolated by conventional methods, such as filtration, centrifugation, evaporation of the solvents, including spray drying.

From Another Salt

This method is feasible if the corresponding acid to the counterion is stronger in the salt formed. An excess of an acid is added as a slurry or solution in a protic or polar aprotic solvent to a slurry of N-{3-[1-(2-nitrophenyl)-1H-pyrrol-2-yl]-allylidene}-aminoguanidinium salt in a protic or polar aprotic solvent. The resulting mixture is heated and cooled in cycles between 15 min and 72 hours, before cooled and optionally an anti-solvent, such as a non-polar aprotic solvent, is added. The resulting salt is isolated by conventional methods, such as filtration, centrifugation, or evaporation of the solvents, including spray drying.

Exemplary Procedure for Formation of Acetate Salt 0.9 equivalent of acetic acid was slowly whilst stirring added to 3-[1-(2-nitrophenyl)-1-H-pyrrole-2-yl]-propanal and aminoguanidine hydrogen carbonate in ethanol. Heated at 50-55° C. for 1 hour before additional 0.11 equivalent acetic acid was added and the mixture was heated to reflux for at least 2 hours. The suspension was cooled to 60° C. before tert-butyl methyl ether was added. Cooled and kept at 2-5° C. for 10-16 hours. Filtered and washed with tert-butyl methyl ether, before recrystallized from ethanol.

The procedure produces a polymorph of AP1189 acetate salt corresponding to XRPD pattern 1.

Exemplary Procedure for Formation of Succinate Salt of AP1189

2-propanol:water 90:10 v/v was added to AP1189 acetate to prepare a slurry. 2-propanol:water 90:10 v/v was added to 1.1 equivalents of succinic acid. The counterion slurry was added to the acetate salt slurry. Temperature cycling was carried out between ambient and 40° C. for ca. 18 h with 4 hour hold periods at ambient temperature and 4 hour hold periods at 40° C. The entire slurry was then isolated by Buchner filtration and washed with deionised water. The solids were dried under vacuum at ambient.

The procedure produced a polymorph of AP1189 succinate salt corresponding to XRPD pattern 1.

Salt Break of Freebase AP1189

Ethyl acetate and 1 M sodium bicarbonate was added to AP1190 acetate to create a biphasic mixture. The mixture was transferred to a separating funnel and the aqueous phase was removed. The organic phase was washed with water. The organic phase was dried with sodium sulphate. The solvent of the organic phase was removed by rotary evaporation.

The procedure produced AP1189 freebase as a solid.

Example 2: Polymorphism Assessment for AP1189 Acetate Salt

Methods

A polymorphism assessment was carried out in order to identify alternate polymorphs of AP1189 acetate: AP1189 acetate was dissolved in 1,4-dioxane-water and lyophilized to obtain an amorphous solid. Aliquots were suspended in the specific solvents and heated in temperature cycles between ambient and 40° C. for 3 days, before being isolated by filtration.

Results

Table 2 outlines the results of the polymorphism study. Acetate Pattern 1 was obtained from 8 solvent systems. A mixture of Pattern 1 and 2 was obtained from 8 solvent systems. Pattern 3 was obtained from THF. Extended temperature cycling for a further 3 days for the acetate Pattern 1 and 2 mixture from ethyl acetate resulted in conversion to acetate Pattern 1.

TABLE 2

Results from polymorphism study.

| Solvent or solvent system | XRPD analysis |
|---|---|
| 1,4-Dioxane | Pattern 1 |
| 1-Butanol | Gum |
| 1-Propanol | Gum |
| 2-Methyl THF | Pattern 1 and 2 |
| 2-Propanol | Pattern 1 |
| 90% 2-Propanol:10% Water (% v/v) | Gum |
| Acetone | Pattern 1 |
| Acetonitrile | Pattern 1 |
| Anisole | Pattern 1 |
| Dichloromethane | Pattern 1 and 2 |
| Di-isopropyl ether | Gum |
| 3% Dimethylsulfoxide:97% THF (% v/v) | Solution |
| Ethanol | Gum |
| Ethyl Acetate | Pattern 1 and 2* |
| Heptane | Pattern 1 and 2 |
| Isopropyl Acetate | Pattern 1 |
| 11% Methanol:89% t-BME (% v/v) | Gum |
| Methylethyl Ketone | Pattern 1 |

TABLE 2-continued

| Results from polymorphism study. | |
|---|---|
| Solvent or solvent system | XRPD analysis |
| Methylisobutyl Ketone | Pattern 1 and 2 |
| 14% N,N'-Dimethylacetamide:86% t-BME (% v/v) | Pattern 1 and 2 |
| tert-Butyl methyl ether | Pattern 1 and 2 |
| Tetrahydrofuran | Pattern 3 |
| Toluene | Pattern 1 and 2 |
| Water | Pattern 1 |

*Extended temperature cycling for a further 3 days for the acetate Pattern 1 and 2 mixture from ethyl acetate resulted in conversion to acetate Pattern 1.

Conclusion

The polymorphism study for AP1189 acetate revealed three different polymorphs, corresponding to XRPD Pattern 1, Pattern 1 and 2 (i.e. Pattern 2 as a mixture with Pattern 1), and Pattern 3.

Example 3: X-Ray Powder Diffraction

Methods

XRPD analysis was carried out on a PANalytical X'pert pro with PIXcel detector (128 channels), scanning the samples between 3 and 35° 2θ. The material was gently ground (where required) to release any agglomerates and loaded onto a multi-well plate with Kapton or Mylar polymer film to support the sample. The multi-well plate was then placed into the diffractometer and analysed using Cu K radiation ($\alpha1\lambda$=1.54060 Å; $\alpha2$=1.54443 Å; β=1.39225 Å; $\alpha1$:$\alpha2$ ratio=0.5) running in transmission mode (step size 0.0130° 2θ, step time 18.87 s) using 40 kV/40 mA generator settings.

Results

AP1189 Acetate Form A

The XRPD diffractogram for AP1189 acetate salt Pattern 1 crystallised from acetonitrile is shown in FIG. 1. The corresponding XRPD diffractogram peak list for acetate Pattern 1 is shown in Table 3.

TABLE 3

XRPD diffractogram peak list for acetate Pattern 1 from acetonitrile.

| Pos. [°2θ] | Height [cts] | FWHM Left [°2θ] | d-spacing [Å] | Rel. Int. [%] |
|---|---|---|---|---|
| 6.0782 | 61.99 | 0.0768 | 14.54111 | 3.01 |
| **11.4999** | **376.76** | **0.0768** | **7.69497** | **18.27** |
| **11.7129** | **266.97** | **0.0895** | **7.55551** | **12.94** |
| 12.1877 | 173.70 | 0.0895 | 7.26219 | 8.42 |
| **12.9668** | **297.55** | **0.0512** | **6.82756** | **14.43** |
| **15.4892** | **966.17** | **0.0512** | **5.72091** | **46.85** |
| **15.6424** | **2062.40** | **0.0768** | **5.66523** | **100.00** |
| 15.8752 | 681.44 | 0.0768 | 5.58267 | 33.04 |
| **16.2455** | **289.74** | **0.0640** | **5.45625** | **14.05** |
| 18.3417 | 132.31 | 0.0640 | 4.83712 | 6.42 |
| 18.5685 | 91.14 | 0.0768 | 4.77856 | 4.42 |
| **19.5716** | **316.98** | **0.0895** | **4.53584** | **15.37** |
| **20.0451** | **546.76** | **0.1023** | **4.42976** | **26.51** |
| 20.5722 | 265.47 | 0.1151 | 4.31743 | 12.87 |
| **21.1229** | **532.99** | **0.1151** | **4.20611** | **25.84** |
| 21.5003 | 272.41 | 0.0895 | 4.13312 | 13.21 |
| 21.8494 | 142.83 | 0.0895 | 4.06787 | 6.93 |
| 22.3320 | 305.94 | 0.0895 | 3.98103 | 14.83 |
| **23.5498** | **1324.22** | **0.1279** | **3.77786** | **64.21** |
| **24.7752** | **1187.85** | **0.1151** | **3.59371** | **57.60** |
| 25.7239 | 208.72 | 0.1279 | 3.46328 | 10.12 |
| **26.9625** | **1300.30** | **0.1151** | **3.30693** | **63.05** |
| 27.4977 | 285.23 | 0.0768 | 3.24378 | 13.83 |
| 28.1563 | 198.27 | 0.0895 | 3.16939 | 9.61 |
| 28.5405 | 90.88 | 0.1279 | 3.12758 | 4.41 |

TABLE 3-continued

XRPD diffractogram peak list for acetate Pattern 1 from acetonitrile.

| Pos. [°2θ] | Height [cts] | FWHM Left [°2θ] | d-spacing [Å] | Rel. Int. [%] |
|---|---|---|---|---|
| 30.2113 | 66.51 | 0.1023 | 2.95832 | 3.22 |
| 30.7262 | 58.06 | 0.1279 | 2.90991 | 2.82 |
| 31.2143 | 198.84 | 0.0768 | 2.86551 | 9.64 |
| 32.2538 | 40.40 | 0.2047 | 2.77549 | 1.96 |
| 32.8859 | 29.42 | 0.1535 | 2.72357 | 1.43 |
| 33.4037 | 43.22 | 0.2047 | 2.68254 | 2.10 |
| 34.3356 | 17.97 | 0.2047 | 2.61183 | 0.87 |

Characteristic peaks are indicated in bold.

Indexed unit cell data: a [Å] 7.8; b [Å] 15.1; c [Å] 20.7; alpha [°] 73.6; beta [°] 80.5; gamma [°] 86.5; volume [$Å^3$] 2311.8.

AP1189 Acetate Form I

The XRPD diffractogram for AP1189 acetate salt Pattern 1 and 2 crystallised from ethyl acetate is shown in FIG. 2. The corresponding XRPD diffractogram peak list for acetate salt Pattern 1 and 2 is shown in Table 4.

TABLE 4

XRPD diffractogram peak list for acetate Pattern 1 and 2 from ethyl acetate.

| Pos. [°2θ] | Height [cts] | FWHM Left [°2θ] | d-spacing [Å] | Rel. Int. [%] |
|---|---|---|---|---|
| 3.2635 | 158.25 | 0.6140 | 27.07331 | 6.65 |
| 5.7636 | 129.03 | 0.0512 | 15.33407 | 5.42 |
| **11.5242** | **491.32** | **0.1023** | **7.67882** | **20.64** |
| **11.7039** | **436.17** | **0.0640** | **7.56130** | **18.32** |
| 12.1439 | 260.95 | 0.1023 | 7.28832 | 10.96 |
| **12.9022** | **494.37** | **0.0895** | **6.86160** | **20.76** |
| 14.7250 | 397.68 | 0.0768 | 6.01607 | 16.70 |
| **14.9424** | **1114.74** | **0.1279** | **5.92902** | **46.82** |
| **15.3955** | **2380.95** | **0.0768** | **5.75554** | **100.00** |
| **15.6099** | **1481.01** | **0.0640** | **5.67694** | **62.20** |
| 15.8562 | 467.40 | 0.0895 | 5.58931 | 19.63 |
| 16.2700 | 306.75 | 0.1279 | 5.44809 | 12.88 |
| 16.4491 | 241.34 | 0.0768 | 5.38917 | 10.14 |
| 16.7354 | 143.36 | 0.1023 | 5.29761 | 6.02 |
| **18.0224** | **665.00** | **0.0895** | **4.92210** | **27.93** |
| 18.3450 | 141.43 | 0.0768 | 4.83626 | 5.94 |
| 18.5587 | 133.47 | 0.0768 | 4.78105 | 5.61 |
| 18.9146 | 118.41 | 0.0895 | 4.69189 | 4.97 |
| 19.5667 | 272.77 | 0.1279 | 4.53697 | 11.46 |
| **19.9482** | **633.37** | **0.0624** | **4.44737** | **26.60** |
| **19.9955** | **663.36** | **0.0384** | **4.44065** | **27.86** |
| 20.1366 | 348.13 | 0.0640 | 4.40985 | 14.62 |
| 20.4922 | 248.29 | 0.1535 | 4.33412 | 10.43 |
| **21.0979** | **338.62** | **0.1279** | **4.21103** | **14.22** |
| **21.4992** | **410.08** | **0.1023** | **4.13333** | **17.22** |
| **21.7757** | **380.77** | **0.1279** | **4.08146** | **15.99** |
| **22.4413** | **550.91** | **0.0768** | **3.96190** | **23.14** |
| 22.7456 | 183.39 | 0.1023 | 3.90958 | 7.70 |
| 23.2063 | 330.75 | 0.1279 | 3.83300 | 13.89 |
| **23.5430** | **2355.44** | **0.1279** | **3.77893** | **98.93** |
| **24.2404** | **2157.44** | **0.1151** | **3.67177** | **90.61** |
| **24.7492** | **788.30** | **0.1023** | **3.59742** | **33.11** |
| 25.3486 | 189.70 | 0.0768 | 3.51371 | 7.97 |
| 25.7030 | 227.22 | 0.1023 | 3.46606 | 9.54 |
| 26.5363 | 135.18 | 0.0768 | 3.35907 | 5.68 |
| **26.9149** | **1479.12** | **0.1407** | **3.31268** | **62.12** |
| 27.5238 | 407.92 | 0.1023 | 3.24076 | 17.13 |
| 28.1364 | 363.05 | 0.0512 | 3.17158 | 15.25 |
| 28.6315 | 98.86 | 0.1535 | 3.11786 | 4.15 |
| 28.9219 | 125.28 | 0.1023 | 3.08720 | 5.26 |
| 30.1919 | 39.10 | 0.1535 | 2.96018 | 1.64 |
| 30.6694 | 51.02 | 0.2558 | 2.91516 | 2.14 |
| 31.1058 | 142.84 | 0.1279 | 2.87525 | 6.00 |
| 32.3303 | 18.51 | 0.2047 | 2.76910 | 0.78 |

TABLE 4-continued

XRPD diffractogram peak list for acetate Pattern 1 and 2 from ethyl acetate.

| Pos. [°2θ] | Height [cts] | FWHM Left [°2θ] | d-spacing [Å] | Rel. Int. [%] |
|---|---|---|---|---|
| 33.2416 | 39.67 | 0.3070 | 2.69524 | 1.67 |
| 33.8884 | 21.89 | 0.2047 | 2.64527 | 0.92 |

Characteristic peaks are indicated in bold.

AP1189 Acetate Form II

The XRPD diffractogram for AP1189 acetate salt Pattern 3 crystallised from THF is shown in FIG. 3. The corresponding XRPD diffractogram peak list for acetate salt Pattern 3 is shown in Table 5.

TABLE 5

XRPD diffractogram peak list for acetate Pattern 3 from THF.

| Pos. [°2θ] | Height [cts] | FWHM Left [°2θ] | d-spacing [Å] | Rel. Int. [%] |
|---|---|---|---|---|
| 7.4087 | 420.49 | 0.1023 | 11.93253 | 11.02 |
| **7.5476** | **521.50** | **0.0640** | **11.71324** | **13.67** |
| **9.3630** | **615.90** | **0.0895** | **9.44578** | **16.15** |
| 10.2795 | 148.14 | 0.0768 | 8.60560 | 3.88 |
| 10.3817 | 145.57 | 0.0640 | 8.52114 | 3.82 |
| **12.7834** | **3086.55** | **0.0768** | **6.92512** | **80.93** |
| 12.8920 | 1547.27 | 0.0384 | 6.86699 | 40.57 |
| **13.2514** | **3226.07** | **0.0895** | **6.68157** | **84.58** |
| 13.5704 | 569.08 | 0.0512 | 6.52520 | 14.92 |
| **14.1812** | **647.30** | **0.0768** | **6.24549** | **16.97** |
| 14.8366 | 334.40 | 0.1279 | 5.97104 | 8.77 |
| 15.1355 | 499.98 | 0.0384 | 5.85381 | 13.11 |
| **15.3087** | **614.19** | **0.1023** | **5.78798** | **16.10** |
| 15.5117 | 478.34 | 0.0895 | 5.71268 | 12.54 |
| **16.0316** | **1497.51** | **0.0895** | **5.52858** | **39.26** |
| 16.3925 | 709.43 | 0.1023 | 5.40763 | 18.60 |
| **17.0466** | **862.25** | **0.1023** | **5.20159** | **22.61** |
| 17.2943 | 190.95 | 0.0768 | 5.12765 | 5.01 |
| 17.6910 | 274.54 | 0.0895 | 5.01355 | 7.20 |
| 18.2222 | 208.88 | 0.0895 | 4.86857 | 5.48 |
| 18.4583 | 387.60 | 0.0640 | 4.80685 | 10.16 |
| **18.8043** | **1265.02** | **0.1407** | **4.71917** | **33.17** |
| 19.5046 | 902.38 | 0.0895 | 4.55128 | 23.66 |
| **19.6774** | **1113.67** | **0.0640** | **4.51170** | **29.20** |
| 19.7852 | 1009.94 | 0.0512 | 4.48735 | 26.48 |
| **20.2727** | **758.58** | **0.1023** | **4.38054** | **19.89** |
| **21.1079** | **3814.09** | **0.1023** | **4.20907** | **100.00** |
| **21.4406** | **1810.10** | **0.1023** | **4.14449** | **47.46** |
| **21.8531** | **1509.72** | **0.1151** | **4.06719** | **39.58** |
| **22.0123** | **1816.88** | **0.0895** | **4.03813** | **47.64** |
| 22.3192 | 771.07 | 0.1535 | 3.98330 | 20.22 |
| **22.7104** | **1217.98** | **0.0895** | **3.91555** | **31.93** |
| **23.0558** | **2438.93** | **0.1151** | **3.85768** | **63.95** |
| 23.3224 | 694.42 | 0.0768 | 3.81417 | 18.21 |
| 23.6146 | 902.32 | 0.1279 | 3.76763 | 23.66 |
| 23.9023 | 235.45 | 0.1023 | 3.72293 | 6.17 |
| 24.5581 | 544.77 | 0.0768 | 3.62499 | 14.28 |
| 25.0512 | 717.52 | 0.0768 | 3.55474 | 18.81 |
| 25.4354 | 261.30 | 0.2047 | 3.50191 | 6.85 |
| 26.0711 | 205.72 | 0.1023 | 3.41795 | 5.39 |
| 26.6312 | 908.25 | 0.0780 | 3.34455 | 23.81 |
| 26.6726 | 949.13 | 0.0512 | 3.34222 | 24.88 |
| 26.9412 | 646.78 | 0.1279 | 3.30951 | 16.96 |
| 27.2272 | 315.93 | 0.0895 | 3.27539 | 8.28 |
| 27.6284 | 279.23 | 0.1535 | 3.22872 | 7.32 |
| 27.8687 | 183.38 | 0.1023 | 3.20144 | 4.81 |
| 28.3712 | 268.31 | 0.1791 | 3.14586 | 7.03 |
| 28.6345 | 398.22 | 0.1023 | 3.11753 | 10.44 |
| 29.3348 | 503.54 | 0.0640 | 3.04468 | 13.20 |
| 29.7178 | 312.61 | 0.1023 | 3.00631 | 8.20 |
| 30.2079 | 657.53 | 0.1535 | 2.95865 | 17.24 |
| 30.5905 | 188.33 | 0.0768 | 2.92251 | 4.94 |
| 30.9427 | 286.22 | 0.1791 | 2.89004 | 7.50 |
| 31.9648 | 186.60 | 0.1279 | 2.79992 | 4.89 |

TABLE 5-continued

XRPD diffractogram peak list for acetate Pattern 3 from THF.

| Pos. [°2θ] | Height [cts] | FWHM Left [°2θ] | d-spacing [Å] | Rel. Int. [%] |
|---|---|---|---|---|
| 33.1436 | 281.81 | 0.1535 | 2.70299 | 7.39 |
| 33.6247 | 136.29 | 0.1535 | 2.66540 | 3.57 |
| 34.5747 | 173.57 | 0.128 | 2.59431 | 4.55 |

Characteristic peaks are indicated in bold.

Indexed unit cell data: a [Å] 12.5; b [Å] 12.7; c [Å] 20.9; alpha [°] 76.0; beta [°] 73.1; gamma [°] 86.6; volume [$Å^3$] 3074.1.

AP1189 Tosylate Form C

The XRPD diffractogram for AP1189 tosylate salt Pattern 1 crystallised from methanol is shown in FIG. 4. The corresponding XRPD diffractogram peak list for tosylate salt Pattern 1 is shown in Table 6.

TABLE 6

XRPD diffractogram peak list for tosylate Pattern 1 from methanol.

| Pos. [°2θ] | Height [cts] | FWHM Left [°2θ] | d-spacing [Å] | Rel. Int. [%] |
|---|---|---|---|---|
| **7.95280** | **565.46** | **0.0768** | **11.11733** | **13.44** |
| **9.42330** | **1279.54** | **0.0895** | **9.38555** | **30.41** |
| **9.96040** | **1509.46** | **0.0895** | **8.88062** | **35.88** |
| 10.76630 | 133.52 | 0.0768 | 8.21756 | 3.17 |
| 12.07190 | 246.37 | 0.0640 | 7.33164 | 5.86 |
| 12.31920 | 203.44 | 0.0640 | 7.18500 | 4.84 |
| **13.44230** | **2110.32** | **0.0895** | **6.58708** | **50.16** |
| 14.09060 | 1043.18 | 0.0768 | 6.28546 | 24.80 |
| **14.49790** | **4207.16** | **0.1023** | **6.10978** | **100.00** |
| **15.28210** | **833.29** | **0.1023** | **5.79797** | **19.81** |
| 15.70980 | 713.17 | 0.0895 | 5.64106 | 16.95 |
| **15.98490** | **2747.52** | **0.1023** | **5.54462** | **65.31** |
| **16.74560** | **1838.99** | **0.1023** | **5.29441** | **43.71** |
| **17.55870** | **1963.25** | **0.1535** | **5.05103** | **46.66** |
| **19.15130** | **708.39** | **0.1151** | **4.63442** | **16.84** |
| **19.79500** | **1554.81** | **0.1023** | **4.48515** | **36.96** |
| 20.01010 | 1455.65 | 0.1151 | 4.43743 | 34.60 |
| 20.74200 | 698.27 | 0.1023 | 4.28247 | 16.60 |
| **20.98000** | **3263.54** | **0.1279** | **4.23443** | **77.57** |
| **21.34790** | **1658.88** | **0.1279** | **4.16229** | **39.43** |
| 22.02470 | 407.91 | 0.1151 | 4.03589 | 9.70 |
| 22.38540 | 763.27 | 0.0640 | 3.97167 | 18.14 |
| 22.65840 | 400.17 | 0.0384 | 3.92442 | 9.51 |
| 22.83650 | 258.14 | 0.0768 | 3.89421 | 6.14 |
| 23.14460 | 310.98 | 0.1279 | 3.84307 | 7.39 |
| 23.55690 | 160.13 | 0.1279 | 3.77674 | 3.81 |
| 24.05140 | 646.06 | 0.1023 | 3.70020 | 15.36 |
| 24.29100 | 327.31 | 0.1023 | 3.66424 | 7.78 |
| **25.15830** | **4097.87** | **0.1151** | **3.53984** | **97.40** |
| **25.43100** | **1927.26** | **0.1151** | **3.50250** | **45.81** |
| 25.70240 | 416.16 | 0.1023 | 3.46613 | 9.89 |
| 26.05180 | 374.86 | 0.1023 | 3.42043 | 8.91 |
| 26.65210 | 421.78 | 0.1791 | 3.34474 | 10.03 |
| 27.13070 | 158.43 | 0.1535 | 3.28682 | 3.77 |
| 27.66440 | 258.67 | 0.0895 | 3.22461 | 6.15 |
| 28.07950 | 526.46 | 0.0895 | 3.17788 | 12.51 |
| 29.04430 | 391.90 | 0.1023 | 3.07448 | 9.32 |
| 29.24250 | 336.72 | 0.0384 | 3.05409 | 8.00 |
| 29.88270 | 587.69 | 0.1023 | 2.99009 | 13.97 |
| 30.28370 | 319.89 | 0.2303 | 2.95141 | 7.60 |
| 30.67120 | 509.33 | 0.1535 | 2.91500 | 12.11 |
| 31.39270 | 66.82 | 0.2047 | 2.84963 | 1.59 |
| 32.74010 | 194.37 | 0.1279 | 2.73537 | 4.62 |
| 33.15360 | 274.41 | 0.1791 | 2.70220 | 6.52 |
| 33.52400 | 157.80 | 0.1791 | 2.67318 | 3.75 |
| 34.06450 | 185.09 | 0.1279 | 2.63200 | 4.40 |
| 34.63470 | 112.70 | 0.1535 | 2.58996 | 2.68 |

Characteristic peaks are indicated in bold.

AP1189 Fumarate Form D

The XRPD diffractogram for AP1189 fumarate salt Pattern 1 crystallised from isopropylalcohol:water 90:10 v/v is shown in FIG. 5. The corresponding XRPD diffractogram peak list for fumarate salt Pattern 1 from isopropylalcohol: water 90:10 v/v is shown in Table 7.

TABLE 7

XRPD diffractogram peak list for fumarate Pattern 1 from isopropylalcohol:water 90:10 v/v.

| Pos. [°2θ] | Height [cts] | FWHM Left [°2θ] | d-spacing [Å] | Rel. Int. [%] |
|---|---|---|---|---|
| 8.6209 | 310.50 | 0.0640 | 10.25719 | 6.33 |
| **9.2296** | **1873.51** | **0.0895** | **9.58209** | **38.22** |
| 10.2345 | 347.27 | 0.0640 | 8.64332 | 7.08 |
| **10.5354** | **852.43** | **0.0640** | **8.39713** | **17.39** |
| **10.9191** | **1388.14** | **0.0768** | **8.10292** | **28.32** |
| **11.4728** | **2930.97** | **0.0895** | **7.71311** | **59.80** |
| **11.8926** | **2170.42** | **0.0895** | **7.44176** | **44.28** |
| 13.3718 | 346.23 | 0.0512 | 6.62169 | 7.06 |
| **15.7963** | **1426.98** | **0.1023** | **5.61039** | **29.11** |
| 16.0311 | 849.53 | 0.0895 | 5.52872 | 17.33 |
| 16.3575 | 561.06 | 0.1023 | 5.41913 | 11.45 |
| 16.5708 | 474.42 | 0.0768 | 5.34985 | 9.68 |
| 17.2941 | 531.10 | 0.0640 | 5.12771 | 10.84 |
| **17.5600** | **3319.60** | **0.1023** | **5.05067** | **67.73** |
| 18.1912 | 548.58 | 0.0895 | 4.87682 | 11.19 |
| 18.5329 | 529.75 | 0.0512 | 4.78765 | 10.81 |
| **18.6734** | **794.04** | **0.0895** | **4.75195** | **16.20** |
| **19.4122** | **1637.66** | **0.1023** | **4.57272** | **33.41** |
| 19.5565 | 1187.94 | 0.0512 | 4.53932 | 24.24 |
| 19.7714 | 359.40 | 0.0640 | 4.49046 | 7.33 |
| 20.5917 | 692.05 | 0.0512 | 4.31338 | 14.12 |
| **21.1710** | **4901.56** | **0.1279** | **4.19667** | **100.00** |
| 21.3706 | 1056.31 | 0.0768 | 4.15791 | 21.55 |
| **21.9494** | **2839.37** | **0.1407** | **4.04957** | **57.93** |
| 22.6944 | 230.40 | 0.1023 | 3.91828 | 4.70 |
| 23.0753 | 363.82 | 0.0895 | 3.85446 | 7.42 |
| **23.4284** | **1295.19** | **0.1407** | **3.79716** | **26.42** |
| **23.8881** | **2543.55** | **0.1535** | **3.72511** | **51.89** |
| **24.5122** | **1525.50** | **0.1535** | **3.63167** | **31.12** |
| 24.7719 | 401.96 | 0.0768 | 3.59418 | 8.20 |
| 25.0387 | 542.09 | 0.1151 | 3.55649 | 11.06 |
| 26.0822 | 1360.04 | 0.1279 | 3.41652 | 27.75 |
| **26.3417** | **4606.74** | **0.1407** | **3.38345** | **93.99** |
| 26.9772 | 178.54 | 0.0900 | 3.30243 | 3.64 |
| 27.5829 | 462.97 | 0.1023 | 3.23395 | 9.45 |
| 27.9868 | 874.09 | 0.1023 | 3.18819 | 17.83 |
| 28.5342 | 442.65 | 0.1151 | 3.12826 | 9.03 |
| 28.7849 | 321.79 | 0.1023 | 3.10159 | 6.57 |
| 29.1336 | 199.54 | 0.1279 | 3.06525 | 4.07 |
| 29.5204 | 318.82 | 0.0640 | 3.02597 | 6.50 |
| 29.9470 | 467.63 | 0.0895 | 2.98382 | 9.54 |
| 30.2812 | 204.98 | 0.1535 | 2.95165 | 4.18 |
| 30.9714 | 1155.91 | 0.1404 | 2.88504 | 23.58 |
| 31.0214 | 1083.09 | 0.0624 | 2.88766 | 22.10 |
| 31.5455 | 443.03 | 0.2808 | 2.83383 | 9.04 |
| 31.9500 | 514.93 | 0.0780 | 2.79887 | 10.51 |
| 32.4106 | 193.90 | 0.1872 | 2.76014 | 3.96 |
| 33.0815 | 204.69 | 0.1248 | 2.70568 | 4.18 |
| 33.5275 | 415.89 | 0.0936 | 2.67070 | 8.48 |
| 34.2307 | 89.28 | 0.1872 | 2.61743 | 1.82 |
| 34.7358 | 407.34 | 0.0468 | 2.58051 | 8.31 |

Characteristic peaks are indicated in bold.

AP1189 Succinate Form B

The XRPD diffractogram for AP1189 succinate salt Pattern 1 crystallised from isopropanol:water 90:10 v/v is shown in FIG. 6. The corresponding XRPD diffractogram peak list for succinate salt Pattern 1 is shown in Table 8.

TABLE 8

XRPD diffractogram peak list for succinate Pattern 1 from isopropanol:water 90:10 v/v.

| Pos. [°2θ] | Height [cts] | FWHM Left [°2θ] | d-spacing [Å] | Rel. Int. [%] |
|---|---|---|---|---|
| **5.4069** | **986.93** | **0.0640** | **16.34500** | **48.23** |
| **9.7178** | **2046.18** | **0.0768** | **9.10169** | **100.00** |
| **12.2493** | **579.97** | **0.0895** | **7.22581** | **28.34** |
| 12.6625 | 194.49 | 0.0768 | 6.99096 | 9.50 |
| **13.3815** | **1060.24** | **0.0895** | **6.61688** | **51.82** |
| 13.6088 | 85.82 | 0.0768 | 6.50687 | 4.19 |
| **15.7849** | **670.53** | **0.1023** | **5.61442** | **32.77** |
| **16.2820** | **940.26** | **0.1023** | **5.44410** | **45.95** |
| 18.0910 | 90.94 | 0.1023 | 4.90360 | 4.44 |
| 18.6109 | 131.29 | 0.1023 | 4.76776 | 6.42 |
| 18.9143 | 81.96 | 0.0895 | 4.69198 | 4.01 |
| **19.5146** | **976.30** | **0.1023** | **4.54897** | **47.71** |
| 19.8650 | 251.71 | 0.0895 | 4.46952 | 12.30 |
| 21.1182 | 76.58 | 0.1279 | 4.20703 | 3.74 |
| **21.7806** | **623.87** | **0.0624** | **4.07718** | **30.49** |
| 21.8237 | 575.40 | 0.0468 | 4.07934 | 28.12 |
| 21.9659 | 346.03 | 0.0624 | 4.04321 | 16.91 |
| 22.1773 | 283.42 | 0.1092 | 4.00514 | 13.85 |
| 22.3520 | 227.12 | 0.0936 | 3.97423 | 11.10 |
| **22.7669** | **1214.56** | **0.1404** | **3.90274** | **59.36** |
| 23.4039 | 80.68 | 0.1560 | 3.79793 | 3.94 |
| 23.7400 | 51.39 | 0.0936 | 3.74492 | 2.51 |
| 24.6205 | 235.25 | 0.1092 | 3.61295 | 11.50 |
| 24.9667 | 183.96 | 0.0624 | 3.56363 | 8.99 |
| 25.2780 | 236.68 | 0.1404 | 3.52044 | 11.57 |
| 26.0672 | 79.01 | 0.1872 | 3.41562 | 3.86 |
| 26.2812 | 115.48 | 0.0936 | 3.38830 | 5.64 |
| **26.7189** | **1090.24** | **0.1404** | **3.33377** | **53.28** |
| 27.4666 | 226.04 | 0.0936 | 3.24470 | 11.05 |
| **28.5058** | **649.21** | **0.1560** | **3.12872** | **31.73** |
| 29.0947 | 167.43 | 0.1560 | 3.06673 | 8.18 |
| 29.4393 | 71.92 | 0.1560 | 3.03161 | 3.51 |
| 30.0230 | 19.05 | 0.3744 | 2.97398 | 0.93 |
| 31.5076 | 74.16 | 0.1560 | 2.83715 | 3.62 |
| 32.3204 | 158.75 | 0.2496 | 2.76763 | 7.76 |
| 32.7195 | 60.07 | 0.1248 | 2.73478 | 2.94 |
| 33.5540 | 65.22 | 0.1872 | 2.66865 | 3.19 |
| 34.1457 | 52.21 | 0.5616 | 2.62374 | 2.55 |

Characteristic peaks are indicated in bold.

AP1189 Napadisylate Form III

The XRPD diffractogram for AP1189 napadisylate salt Pattern 1 crystallised from 2-propanol:water 90:10% v/v is shown in FIG. 14. The corresponding XRPD diffractogram peak list for napadisylate salt Pattern 1 is shown in Table 9.

TABLE 9

XRPD diffractogram peak list for napadisylate Pattern 1 from 2-propanol:water 90:10% v/v.

| Pos. [°2θ] | d-spacing [Å] | Height [cts] | Rel. Int. [%] |
|---|---|---|---|
| **7.5504** | **11.70884** | **689.5** | **18.85** |
| **10.7197** | **8.2532** | **944.25** | **25.82** |
| **12.3794** | **7.1502** | **1041.08** | **28.46** |
| **13.4473** | **6.58465** | **1775.32** | **48.54** |
| 13.9776 | 6.33602 | 516.26 | 14.11 |
| **15.0881** | **5.87208** | **1507.82** | **41.22** |
| **15.5452** | **5.70043** | **1428.49** | **39.06** |
| 17.1935 | 5.15749 | 578.34 | 15.81 |
| 18.2562 | 4.8596 | 147.08 | 4.02 |
| 18.7653 | 4.72888 | 105.22 | 2.88 |
| 19.2562 | 4.60944 | 116.02 | 3.17 |
| 20.3308 | 4.36815 | 344.81 | 9.43 |
| 21.3564 | 4.16064 | 180.29 | 4.93 |
| 21.7571 | 4.08153 | 255.62 | 6.99 |
| **22.1571** | **4.01206** | **3657.63** | **100** |
| **22.8309** | **3.89516** | **1110.18** | **30.35** |
| **23.4703** | **3.79047** | **1179.36** | **32.24** |
| 24.3345 | 3.65778 | 425.24 | 11.63 |
| 24.904 | 3.57542 | 341.67 | 9.34 |

TABLE 9-continued

XRPD diffractogram peak list for napadisylate Pattern 1 from 2-propanol:water 90:10% v/v.

| Pos. [°2θ] | d-spacing [Å] | Height [cts] | Rel. Int. [%] |
|---|---|---|---|
| 25.3384 | 3.5151 | 356.8 | 9.76 |
| **26.817** | **3.32455** | **2133.99** | **58.34** |
| 27.1283 | 3.28439 | 217.11 | 5.94 |
| 27.6015 | 3.22914 | 261.56 | 7.15 |
| **27.9744** | **3.18957** | **1458.18** | **39.87** |
| 28.5214 | 3.12964 | 329.01 | 9.00 |
| 28.9049 | 3.08898 | 129.88 | 3.55 |
| 29.4676 | 3.03126 | 159.64 | 4.36 |
| 29.9117 | 2.98727 | 132.26 | 3.62 |
| 30.4558 | 2.93512 | 173.56 | 4.75 |
| 31.3597 | 2.85019 | 60.18 | 1.65 |
| 31.8567 | 2.80918 | 261.91 | 7.16 |
| 32.5624 | 2.74989 | 58.95 | 1.61 |
| 33.4807 | 2.67654 | 56.16 | 1.54 |

Characteristic peaks are indicated in bold.

AP1189 Napadisylate Form IV

The XRPD diffractogram for AP1189 napadisylate salt Pattern 2 crystallised from THF is shown in FIG. 15. The corresponding XRPD diffractogram peak list for napadisylate salt Pattern 2 is shown in Table 10.

TABLE 10

XRPD diffractogram peak list for napadisylate Pattern 2 from THF.

| Pos. [°2θ] | d-spacing [Å] | Height [cts] | Rel. Int. [%] |
|---|---|---|---|
| **5.4286** | **16.27965** | **346.5** | **79.53** |
| 6.5128 | 13.56063 | 14.65 | 3.36 |
| 7.4311 | 11.89657 | 47.58 | 10.92 |
| **8.5219** | **10.37613** | **163.19** | **37.46** |
| 10.0575 | 8.7878 | 35.75 | 8.21 |
| **10.8271** | **8.17155** | **104.41** | **23.97** |
| 11.3074 | 7.81909 | 58.98 | 13.54 |
| 12.0655 | 7.32943 | 70.52 | 16.19 |
| **12.5500** | **7.05339** | **242.28** | **55.61** |
| **13.1311** | **6.7425** | **159.5** | **36.61** |
| **15.5722** | **5.6906** | **435.67** | **100** |
| 16.2658 | 5.44496 | 141.14 | 32.4 |
| 16.6142 | 5.33158 | 109.83 | 25.21 |
| **18.3509** | **4.83472** | **301.22** | **69.14** |
| 19.0496 | 4.65509 | 92.9 | 21.32 |
| **19.4848** | **4.55586** | **195.31** | **44.83** |
| **19.8774** | **4.46675** | **193.35** | **44.38** |
| 20.2585 | 4.37995 | 158.03 | 36.27 |
| **21.0620** | **4.21813** | **219.31** | **50.34** |
| **22.0067** | **4.03915** | **314.65** | **72.22** |
| **22.7195** | **3.91401** | **259.61** | **59.59** |
| **23.3676** | **3.8069** | **367.37** | **84.32** |
| **24.1961** | **3.67839** | **303.55** | **69.67** |
| **25.1931** | **3.53212** | **169.22** | **38.84** |
| **25.8383** | **3.44821** | **292.44** | **67.13** |
| 26.8947 | 3.31512 | 155.27 | 35.64 |
| 30.4999 | 2.92856 | 25.88 | 5.94 |

Characteristic peaks are indicated in bold.

AP1189 Esylate Form V

The XRPD diffractogram for AP1189 esylate salt Pattern 1 crystallised from methylethyl ketone is shown in FIG. 16. The corresponding XRPD diffractogram peak list for esylate salt Pattern 1 is shown in Table 11.

TABLE 11

XRPD diffractogram peak list for esylate Pattern 1 from methylethyl ketone.

| Pos. [°2θ] | d-spacing [Å] | Height [cts] | Rel. Int. [%] |
|---|---|---|---|
| **8.4696** | **10.44008** | **96.34** | **47.64** |
| 9.813 | **9.01365** | **125.06** | **61.84** |
| **10.4203** | **8.48969** | **99.32** | **49.11** |
| 11.331 | 7.80283 | 29.09 | 14.39 |
| 11.5369 | 7.66404 | 26.98 | 13.34 |
| 12.9606 | 6.82518 | 30.38 | 15.02 |
| 14.3275 | 6.17693 | 62.18 | 30.75 |
| **14.5301** | **6.09631** | **200.81** | **99.29** |
| **15.3453** | **5.77425** | **76.71** | **37.93** |
| **16.5381** | **5.36036** | **202.23** | **100** |
| **18.639** | **4.76065** | **175.44** | **86.75** |
| **19.7148** | **4.50323** | **125.45** | **62.03** |
| **20.1181** | **4.41384** | **174.51** | **86.29** |
| 20.9895 | 4.22902 | 74.36 | 36.77 |
| 21.1237 | 4.20595 | 83.32 | 41.2 |
| **21.9184** | **4.05521** | **76.71** | **37.93** |
| **22.4735** | **3.9563** | **80.84** | **39.97** |
| 23.9411 | 3.71699 | 58.21 | 28.78 |
| 25.514 | 3.48841 | 36.26 | 17.93 |
| **26.0564** | **3.41702** | **74.49** | **36.83** |
| 26.4224 | 3.3705 | 46.97 | 23.23 |
| **26.7682** | **3.3305** | **111.98** | **55.37** |
| 27.5072 | 3.24 | 35.01 | 17.31 |
| 29.7173 | 3.00387 | 10.74 | 5.31 |
| 31.4122 | 2.84555 | 22.93 | 11.34 |
| 32.1715 | 2.7801 | 16.17 | 8.00 |
| 33.501 | 2.67275 | 24.35 | 12.04 |

Characteristic peaks are indicated in bold.

AP1189 Edisylate Form VI

The XRPD diffractogram for AP1189 edisylate salt Pattern 1 crystallised from 2-Propanol:water (80:20% v/v) is shown in FIG. 17. The corresponding XRPD diffractogram peak list for edisylate salt Pattern 1 is shown in Table 12.

TABLE 12

XRPD diffractogram peak list for edisylate Pattern 1 from 2-Propanol:water (80:20 %v/v).

| Pos. [°2θ] | d-spacing [Å] | Height [cts] | Rel. Int. [%] |
|---|---|---|---|
| **4.7606** | **18.56231** | **1152.22** | **94.52** |
| **9.5373** | **9.27355** | **445.57** | **36.55** |
| **10.8586** | **8.14796** | **233.5** | **19.16** |
| 11.603 | 7.62679 | 126.33 | 10.36 |
| **12.7876** | **6.92285** | **908.15** | **74.5** |
| **14.2703** | **6.2067** | **250.78** | **20.57** |
| **15.2286** | **5.81822** | **339.82** | **27.88** |
| **16.4938** | **5.37466** | **1218.96** | **100** |
| 16.976 | 5.21876 | 97.95 | 8.04 |
| **17.8605** | **4.96636** | **561.86** | **46.09** |
| **18.5957** | **4.77162** | **419.86** | **34.44** |
| 19.1831 | 4.62683 | 215.67 | 17.69 |
| 20.2602 | 4.38322 | 273.24 | 22.42 |
| **21.4287** | **4.14676** | **516.36** | **42.36** |
| 22.4944 | 3.95267 | 481.25 | 39.48 |
| **23.4349** | **3.79612** | **624.9** | **51.27** |
| **24.4775** | **3.63674** | **376.83** | **30.91** |
| 25.2503 | 3.52716 | 478.62 | 39.26 |
| 25.4765 | 3.49346 | 234.8 | 19.26 |
| 26.4673 | 3.36767 | 160.37 | 13.16 |
| **27.167** | **3.28251** | **506.76** | **41.57** |
| 28.0417 | 3.17944 | 76.44 | 6.27 |
| 29.4833 | 3.02968 | 120.53 | 9.89 |
| 29.7204 | 3.00357 | 71.2 | 5.84 |
| 30.1891 | 2.96045 | 157.41 | 12.91 |
| 30.9905 | 2.88569 | 105.44 | 8.65 |

TABLE 12-continued

XRPD diffractogram peak list for edisylate Pattern 1 from 2-Propanol:water (80:20 %v/v).

| Pos. [°2θ] | d-spacing [Å] | Height [cts] | Rel. Int. [%] |
|---|---|---|---|
| 32.5886 | 2.74774 | 59.41 | 4.87 |
| 33.3411 | 2.68743 | 98.37 | 8.07 |
| 34.2969 | 2.61252 | 25.44 | 2.09 |

Characteristic peaks are indicated in bold.

AP1189 Edisylate Form VII

The XRPD diffractogram for AP1189 edisylate salt Pattern 2 crystallised from methylethyl ketone is shown in FIG. 18. The corresponding XRPD diffractogram peak list for edisylate salt Pattern 2 is shown in Table 13.

TABLE 13

XRPD diffractogram peak list for edisylate Pattern 2 from methylethyl ketone.

| Pos. [°2θ] | d-spacing [Å] | Height [cts] | Rel. Int. [%] |
|---|---|---|---|
| **6.0662** | **14.56989** | **1499.14** | **71.99** |
| 10.0241 | 8.82426 | 358.32 | 17.21 |
| **11.7435** | **7.53586** | **730.04** | **35.06** |
| **12.0936** | **7.31848** | **994.92** | **47.78** |
| **12.7392** | **6.94906** | **586** | **28.14** |
| 14.1325 | 6.26692 | 281.25 | 13.51 |
| **15.7281** | **5.63457** | **2082.36** | **100** |
| 16.2886 | 5.43741 | 73.51 | 3.53 |
| 17.6463 | 5.02614 | 139.37 | 6.69 |
| 17.9369 | 4.94129 | 119.4 | 5.73 |
| 18.3429 | 4.83683 | 256.13 | 12.3 |
| **19.2641** | **4.60756** | **739.74** | **35.52** |
| **20.1215** | **4.41311** | **922.85** | **44.32** |
| 20.893 | 4.25186 | 304.45 | 14.62 |
| **21.7546** | **4.08539** | **1293.59** | **62.12** |
| 22.3549 | 3.97702 | 230.14 | 11.05 |
| 22.7399 | 3.91055 | 531.54 | 25.53 |
| **23.6495** | **3.76216** | **1405.44** | **67.49** |
| 24.2528 | 3.66992 | 299.01 | 14.36 |
| 24.825 | 3.58662 | 279.37 | 13.42 |
| 25.1151 | 3.54584 | 413 | 19.83 |
| 25.7826 | 3.45553 | 230.5 | 11.07 |
| 26.5375 | 3.35893 | 317.73 | 15.26 |
| 27.0339 | 3.29837 | 200.04 | 9.61 |
| 27.4795 | 3.2432 | 119.71 | 5.75 |
| 28.2254 | 3.16178 | 267.76 | 12.86 |
| 28.6125 | 3.11988 | 326.38 | 15.67 |
| 29.6505 | 3.01298 | 123.96 | 5.95 |
| 30.5784 | 2.92363 | 141.58 | 6.8 |
| 31.2303 | 2.86408 | 184.2 | 8.85 |
| 31.8981 | 2.80331 | 50.64 | 2.43 |
| 32.4213 | 2.76154 | 98.58 | 4.73 |
| 32.8959 | 2.72277 | 69.53 | 3.34 |
| 33.53 | 2.6705 | 24.94 | 1.2 |
| 34.1437 | 2.6239 | 13.62 | 0.65 |

Characteristic peaks are indicated in bold.

AP1189 Edisylate Form VIII

The XRPD diffractogram for AP1189 edisylate salt Pattern 4 crystallised from THF is shown in FIG. 19. The corresponding XRPD diffractogram peak list for edisylate salt Pattern 4 is shown in Table 14.

TABLE 14

XRPD diffractogram peak list for edisylate Pattern 4 from THF.

| Pos. [°2θ] | d-spacing [Å] | Height [cts] | Rel. Int. [%] |
|---|---|---|---|
| **6.4465** | **13.71127** | **191.95** | **14.27** |
| 9.9098 | 8.92585 | 71.5 | 5.32 |
| **12.145** | **7.28767** | **583.39** | **43.38** |

TABLE 14-continued

XRPD diffractogram peak list for edisylate Pattern 4 from THF.

| Pos. [°2θ] | d-spacing [Å] | Height [cts] | Rel. Int. [%] |
|---|---|---|---|
| 12.4961 | 7.07778 | 129.05 | 9.6 |
| **12.9954** | **6.81261** | **368.87** | **27.43** |
| 14.0381 | 6.30364 | 112.5 | 8.37 |
| **15.4892** | **5.72092** | **1344.79** | **100** |
| 17.7793 | 4.98886 | 229.27 | 17.05 |
| 18.2552 | 4.85583 | 85.69 | 6.37 |
| 18.6687 | 4.75313 | 171.63 | 12.76 |
| 19.5432 | 4.53863 | 215.92 | 16.06 |
| 20.0215 | 4.43494 | 373.31 | 27.76 |
| **20.6977** | **4.29155** | **760.34** | **56.54** |
| **21.672** | **4.10076** | **591.86** | **44.01** |
| 22.2098 | 3.99935 | 256.17 | 19.05 |
| 23.123 | 3.84661 | 356.78 | 26.53 |
| 24.1173 | **3.69023** | **405.74** | **30.17** |
| **25.23** | **3.52996** | **365.37** | **27.17** |
| 25.6746 | 3.46695 | 126.18 | 9.38 |
| 27.0992 | 3.29057 | 76.34 | 5.68 |
| 27.9198 | 3.19305 | 16.88 | 1.26 |
| 30.6998 | 2.91235 | 54.54 | 4.06 |
| 31.0943 | 2.87391 | 70.76 | 5.26 |
| 31.6385 | 2.82571 | 50.08 | 3.72 |
| 34.4866 | 2.59859 | 31.14 | 2.32 |

Characteristic peaks are indicated in bold.

AP1189 Edisylate Form IX

The XRPD diffractogram for AP1189 edisylate salt Pattern 5 crystallised from 2-Propanol:water (80:20% v/v) is shown in FIG. 20. The corresponding XRPD diffractogram peak list for edisylate salt Pattern 5 is shown in Table 15.

TABLE 15

XRPD diffractogram peak list for edisylate Pattern 5 from 2-Propanol:water (80:20 % v/v).

| Pos. [°2θ] | d-spacing [Å] | Height [cts] | Rel. Int. [%] |
|---|---|---|---|
| **4.4981** | **19.645** | **792.29** | **100** |
| **8.987** | **9.84018** | **198.33** | **25.03** |
| 11.701 | 7.55689 | 88.54 | 11.17 |
| **12.1573** | **7.28032** | **254.63** | **32.14** |
| 12.3685 | 7.15054 | 124.48 | 15.71 |
| 13.098 | 6.75385 | 29.04 | 3.67 |
| **15.4882** | **5.7213** | **274.49** | **34.64** |
| **16.703** | **5.30781** | **484.11** | **61.1** |
| 17.3062 | 5.11992 | 85.77 | 10.83 |
| **18.0377** | **4.91797** | **183.23** | **23.13** |
| 19.9018 | 4.46133 | 148.72 | 18.77 |
| 20.3543 | 4.36316 | 157.85 | 19.92 |
| 21.0548 | 4.21606 | 86.99 | 10.98 |
| 21.9589 | 4.04782 | 136.42 | 17.22 |
| 22.8828 | 3.88644 | 218 | 27.51 |
| **24.6983** | **3.60472** | **418.6** | **52.83** |
| 26.7569 | 3.33188 | 87.66 | 11.06 |
| 28.3461 | 3.14859 | 42.09 | 5.31 |

Characteristic peaks are indicated in bold.

AP1189 Nitrate Form X

The XRPD diffractogram for AP1189 nitrate salt Pattern 1 crystallised from THF is shown in FIG. 21. The corresponding XRPD diffractogram peak list for nitrate salt Pattern 1 is shown in Table 16.

TABLE 16

XRPD diffractogram peak list for nitrate Pattern 1 from THF.

| Pos. [°2θ] | d-spacing [Å] | Height [cts] | Rel. Int. [%] |
|---|---|---|---|
| **3.726** | **23.71408** | **179.91** | **19.17** |
| **7.5467** | **11.71468** | **136.08** | **14.5** |

TABLE 16-continued

XRPD diffractogram peak list for nitrate Pattern 1 from THF.

| Pos. [°2θ] | d-spacing [Å] | Height [cts] | Rel. Int. [%] |
|---|---|---|---|
| **11.8592** | **7.46261** | **408.46** | **43.52** |
| **12.4917** | **7.08616** | **368.75** | **39.29** |
| 13.0853 | 6.76599 | 242.4 | 25.83 |
| **14.712** | **6.02134** | **295.86** | **31.53** |
| **15.2583** | **5.80697** | **522.07** | **55.63** |
| 16.9052 | 5.24478 | 238.58 | 25.42 |
| **17.7422** | **4.99921** | **322.64** | **34.38** |
| **18.1478** | **4.88837** | **288.49** | **30.74** |
| 18.7034 | 4.74047 | 109.88 | 11.71 |
| 19.6432 | 4.51949 | 198.86 | 21.19 |
| **21.3874** | **4.15468** | **938.45** | **100** |
| 22.9764 | 3.87083 | 226.32 | 24.12 |
| 24.1196 | 3.68989 | 348.22 | 37.11 |
| **25.1008** | **3.54782** | **430.13** | **45.83** |
| 26.6187 | 3.34886 | 432.7 | 46.11 |
| **27.7139** | **3.21896** | **372.36** | **39.68** |
| 29.5135 | 3.02665 | 108.41 | 11.55 |
| 31.6588 | 2.82629 | 101.37 | 10.8 |

Characteristic peaks are indicated in bold.

AP1189 Cyclamate Form XI

The XRPD diffractogram for AP1189 cyclamate salt Pattern 2 crystallised from THF is shown in FIG. 22. The corresponding XRPD diffractogram peak list for cyclamate salt Pattern 2 is shown in Table 17.

TABLE 17

XRPD diffractogram peak list for cyclamate Pattern 2 from THF.

| Pos. [°2θ] | d-spacing [Å] | Height [cts] | Rel. Int. [%] |
|---|---|---|---|
| **3.1621** | **27.94165** | **179.59** | **22.76** |
| 5.2127 | 16.95363 | 87.48 | 11.09 |
| **7.0019** | **12.62477** | **789.01** | **100** |
| 10.3525 | 8.5451 | 123.07 | 15.6 |
| **11.2896** | **7.83785** | **208.18** | **26.39** |
| 11.8811 | 7.44278 | 58.65 | 7.43 |
| **13.7568** | **6.4372** | **370.07** | **46.9** |
| 14.1759 | 6.24266 | 73.01 | 9.25 |
| **15.2643** | **5.8047** | **355.29** | **45.03** |
| **15.6888** | **5.64858** | **426.88** | **54.1** |
| 16.2658 | 5.44496 | 134.02 | 16.99 |
| 17.5752 | 5.04633 | 231.81 | 29.38 |
| 18.5197 | 4.78707 | 90.13 | 11.42 |
| 19.1685 | 4.6303 | 187.78 | 23.8 |
| 20.0509 | 4.4285 | 273.46 | 34.66 |
| **20.7048** | **4.29009** | **321.46** | **40.74** |
| **21.4639** | **4.14005** | **317.94** | **40.3** |
| **21.7871** | **4.07598** | **242.18** | **30.69** |
| 22.0945 | 4.01997 | 146.05 | 18.51 |
| 22.7092 | 3.91253 | 125.64 | 15.92 |
| 23.4403 | 3.79526 | 148.21 | 18.78 |
| 25.2406 | 3.52849 | 143 | 18.12 |
| 26.0048 | 3.42651 | 115.43 | 14.63 |
| 27.7815 | 3.21128 | 54.76 | 6.94 |

Characteristic peaks are indicated in bold.

AP1189 Cyclamate Form XII

The XRPD diffractogram for AP1189 cyclamate salt Pattern 4 crystallised from acetone is shown in FIG. 23. The corresponding XRPD diffractogram peak list for cyclamate salt Pattern 4 is shown in Table 18.

TABLE 18

XRPD diffractogram peak list for cyclamate Pattern 4 from acetone.

| Pos. [°2θ] | d-spacing [Å] | Height [cts] | Rel. Int. [%] |
|---|---|---|---|
| 6.2906 | 14.05077 | 102.71 | 26.16 |
| **7.3357** | **12.05109** | **335.85** | **85.54** |
| 9.3353 | 9.4659 | 8.68 | 2.21 |
| **11.3095** | **7.82408** | **86.03** | **21.91** |
| 12.7131 | 6.95747 | 47.33 | 12.05 |
| **13.1319** | **6.74211** | **97.06** | **24.72** |
| 14.7863 | 5.98632 | 106.38 | 27.09 |
| **15.3435** | **5.77491** | **392.64** | **100** |
| **16.2948** | **5.43987** | **164.44** | **41.88** |
| **16.8716** | **5.25516** | **128.27** | **32.67** |
| **17.8941** | **4.95711** | **338.3** | **86.16** |
| **19.0531** | **4.65811** | **184.82** | **47.07** |
| 19.3468 | 4.58425 | 98.78 | 25.16 |
| 20.1366 | 4.40984 | 126.64 | 32.25 |
| **21.9846** | **4.04315** | **195.66** | **49.83** |
| **22.655** | **3.92501** | **157.07** | **40** |
| 24.0828 | 3.69238 | 90.63 | 23.08 |
| 24.7776 | 3.59337 | 97.12 | 24.74 |
| 25.779 | 3.45315 | 28.08 | 7.15 |
| 27.1015 | 3.28757 | 6.68 | 1.7 |
| 29.0272 | 3.07624 | 38.61 | 9.83 |

Characteristic peaks are indicated in bold.

AP1189 Cyclamate Form XIII

The XRPD diffractogram for AP1189 cyclamate salt Pattern 5 crystallised from THF is shown in FIG. 24. The corresponding XRPD diffractogram peak list for cyclamate salt Pattern 5 is shown in Table 19.

TABLE 19

XRPD diffractogram peak list for cyclamate Pattern 5 from THF.

| Pos. [°2θ] | d-spacing [Å] | Height [cts] | Rel. Int. [%] |
|---|---|---|---|
| 3.3077 | 26.69018 | 8.98 | 0.58 |
| **5.5967** | **15.7911** | **187.14** | **12.03** |
| **6.4474** | **13.70936** | **956.81** | **61.52** |
| **7.1491** | **12.36521** | **828.98** | **53.3** |
| 7.588 | 11.65099 | 39.91 | 2.57 |
| **8.517** | **10.38213** | **485.85** | **31.24** |
| 9.4338 | 9.36732 | 140.49 | 9.03 |
| 9.8762 | 8.95612 | 582.21 | 37.44 |
| 10.2304 | 8.64685 | 266.94 | 17.16 |
| **10.4969** | **8.42791** | **570.75** | **36.7** |
| 10.9495 | 8.08048 | 182.36 | 11.73 |
| 11.6202 | 7.61559 | 281.21 | 18.08 |
| 11.8805 | 7.4431 | 57.72 | 3.71 |
| 12.3095 | 7.19065 | 168.44 | 10.83 |
| **13.0658** | **6.77606** | **629.6** | **40.48** |
| 13.3285 | 6.64308 | 706.95 | 45.46 |
| 13.7029 | 6.46239 | 245.66 | 15.8 |
| 14.1105 | 6.27663 | 180.03 | 11.58 |
| **14.6296** | **6.05509** | **1139.54** | **73.27** |
| **15.2647** | **5.80454** | **1555.19** | **100** |
| **16.2222** | **5.46402** | **565.52** | **36.36** |
| **16.6625** | **5.32062** | **949.92** | **61.08** |
| 17.4798 | 5.06945 | 169.19 | 10.88 |
| **18.4631** | **4.80561** | **1460.84** | **93.93** |
| **18.7365** | **4.73609** | **1201.35** | **77.25** |
| **19.8483** | **4.47324** | **1059.17** | **68.11** |
| 20.2298 | 4.38973 | 770.27 | 49.53 |
| 20.5681 | 4.3183 | 571.09 | 36.72 |
| 21.0659 | 4.21388 | −403.55 | −25.95 |
| 21.1423 | 4.20229 | 606.37 | 38.99 |
| 21.346 | 4.1592 | 442.84 | 28.47 |
| 21.6546 | 4.10402 | 389.75 | 25.06 |
| 22.0577 | 4.02991 | 385.89 | 24.81 |
| 22.5829 | 3.93737 | 598.47 | 38.48 |
| 22.8215 | 3.89352 | 314.13 | 20.2 |
| 23.6665 | 3.75949 | 387.36 | 24.91 |
| 24.1076 | 3.69169 | 372.97 | 23.98 |
| 24.8773 | 3.5792 | 301.43 | 19.38 |
| 25.1001 | 3.54498 | 361.41 | 23.24 |

TABLE 19-continued

XRPD diffractogram peak list for cyclamate Pattern 5 from THF.

| Pos. [°2θ] | d-spacing [Å] | Height [cts] | Rel. Int. [%] |
|---|---|---|---|
| 25.7105 | 3.46506 | 300.34 | 19.31 |
| **26.2315** | **3.39741** | **512.24** | **32.94** |
| **26.9513** | **3.30828** | **549.96** | **35.36** |
| 27.7471 | 3.21519 | 196.84 | 12.66 |
| 28.6818 | 3.10992 | 34.66 | 2.23 |
| 29.4102 | 3.03453 | 16.29 | 1.05 |
| 29.9519 | 2.98088 | 42.78 | 2.75 |
| 30.844 | 2.89907 | 51.86 | 3.33 |
| 31.6221 | 2.82948 | 75.34 | 4.84 |
| 32.3706 | 2.76575 | 66.76 | 4.29 |
| 33.6225 | 2.66558 | 27.56 | 1.77 |

Characteristic peaks are indicated in bold.

AP1189 Besylate Form XIV

The XRPD diffractogram for AP1189 besylate salt Pattern 1 crystallised from 2-Propanol:water 80:20% v/v is shown in FIG. 25. The corresponding XRPD diffractogram peak list for besylate salt Pattern 1 is shown in Table 20.

TABLE 20

XRPD diffractogram peak list for besylate Pattern 1 from 2-Propanol:water 80:20% v/v. Characteristic peaks are indicated in bold.

| **Pos. [°2θ]** | **d-spacing [Å]** | **Height [cts]** | **Rel. Int. [%]** |
|---|---|---|---|
| 3.2175 | 27.46024 | 62.4 | 1.8 |
| **8.3275** | **10.61794** | **225.23** | **6.49** |
| **9.0111** | **9.81393** | **198.54** | **5.72** |
| 9.9442 | 8.89498 | 282.36 | 8.14 |
| 10.7688 | 8.21566 | 502.34 | 14.48 |
| **11.2282** | **7.88052** | **765.63** | **22.07** |
| **12.9603** | **6.83095** | **1879.15** | **54.16** |
| 13.1459 | 6.73493 | 2421.9 | 69.8 |
| **15.0755** | **5.87695** | **3469.81** | **100** |
| 15.9809 | 5.54599 | 542.33 | 15.63 |
| **16.4072** | **5.40284** | **568.66** | **16.39** |
| 16.6812 | 5.31472 | 255.6 | 7.37 |
| 17.2775 | 5.13261 | 246.45 | 7.1 |
| 18.0701 | 4.90514 | 144.29 | 4.16 |
| **18.3074** | **4.84612** | **830.57** | **23.94** |
| **18.6991** | **4.74549** | **548.41** | **15.81** |
| 18.9774 | 4.67651 | 338.15 | 9.75 |
| 19.4439 | 4.56536 | 154.45 | 4.45 |
| **19.9239** | **4.45643** | **1750.81** | **50.46** |
| 20.252 | 4.38496 | 383.72 | 11.06 |
| 20.8939 | 4.24817 | 111.11 | 3.2 |
| 21.2688 | 4.17759 | 274.85 | 7.92 |
| 21.6759 | 4.10004 | 975.93 | 28.13 |
| 22.0414 | 4.02953 | 110.44 | 3.18 |
| 22.7796 | 3.90382 | 519.42 | 14.97 |
| 23.1205 | 3.84703 | 470.89 | 13.57 |
| 23.5722 | 3.77431 | 700.52 | 20.19 |
| 24.8029 | 3.58976 | 481.62 | 13.88 |
| 25.0701 | 3.54917 | 168.35 | 4.85 |
| 25.4203 | 3.50395 | 642.92 | 18.53 |
| 26.268 | 3.39277 | 2290.5 | 66.01 |
| 26.4692 | 3.36743 | 1015.25 | 29.26 |
| 27.1415 | 3.28553 | 372.17 | 10.73 |
| 28.1081 | 3.17471 | 152.82 | 4.4 |
| 28.5473 | 3.12686 | 199.35 | 5.75 |
| 29.8458 | 2.99371 | 178.8 | 5.15 |
| 30.4198 | 2.93852 | 180.23 | 5.19 |
| 31.1212 | 2.87387 | 102.11 | 2.94 |
| 32.0148 | 2.79567 | 64.16 | 1.85 |
| 33.1565 | 2.70197 | 130.3 | 3.76 |
| 34.1106 | 2.62636 | 20.78 | 0.6 |

AP1189 Oxalate Form XV

The XRPD diffractogram for AP1189 oxalate salt Pattern 1 crystallised from 2-Propanol:water 80:20% v/v is shown in FIG. 26. The corresponding XRPD diffractogram peak list for oxalate salt Pattern 1 is shown in Table 21.

TABLE 21

XRPD diffractogram peak list for oxalate Pattern 1 from 2-Propanol:water 80:20% v/v. Characteristic peaks are indicated in bold.

| **Pos. [°2θ]** | **d-spacing [Å]** | **Height [cts]** | **Rel. Int. [%]** |
|---|---|---|---|
| **7.2467** | **12.19886** | **450.79** | **12.92** |
| **10.7644** | **8.21907** | **1408.52** | **40.37** |
| 12.1117 | 7.30758 | 459.79 | 13.18 |
| **13.8551** | **6.39177** | **2142.95** | **61.42** |
| 14.5121 | 6.10385 | 746.59 | 21.4 |
| 15.0495 | 5.88706 | 2731.17 | 78.28 |
| **15.6303** | **5.66959** | **1938.29** | **55.55** |
| 16.4777 | 5.37988 | 392.84 | 11.26 |
| 16.813 | 5.27334 | 908.28 | 26.03 |
| 17.3104 | 5.12291 | 635.74 | 18.22 |
| 18.2079 | 4.87238 | 433.56 | 12.43 |
| 18.4636 | 4.80547 | 727.13 | 20.84 |
| **19.46** | **4.56161** | **3187.27** | **91.35** |
| 20.0756 | 4.42311 | 1393.22 | 39.93 |
| **21.6762** | **4.09998** | **1576.06** | **45.17** |
| 22.9254 | 3.87931 | 1254.01 | 35.94 |
| **23.2534** | **3.82534** | **3284.1** | **94.13** |
| **23.789** | **3.74041** | **2446.77** | **70.13** |
| 24.2503 | 3.67029 | 918.98 | 26.34 |
| 24.7678 | 3.59477 | 612.09 | 17.54 |
| **25.8167** | **3.45105** | **3489.04** | **100** |
| 27.0213 | 3.29987 | 560.44 | 16.06 |
| 27.9092 | 3.19688 | 158.4 | 4.54 |
| 28.5985 | 3.12137 | 374.56 | 10.74 |
| 29.2965 | 3.04605 | 218.5 | 6.26 |
| 29.7343 | 3.00468 | 369.86 | 10.6 |
| 30.1941 | 2.95996 | 331 | 9.49 |
| 32.2394 | 2.7744 | 121.27 | 3.48 |
| 32.8731 | 2.72461 | 547.75 | 15.7 |

AP1189 Oxalate Form XVI

The XRPD diffractogram for AP189 oxalate salt Pattern 2 crystallised from acetone is shown in FIG. 27. The corresponding XRPD diffractogram peak list for oxalate salt Pattern 2 is shown in Table 22.

TABLE 22

XRPD diffractogram peak list for oxalate Pattern 2 from acetone. Characteristic peaks are indicated in bold.

| **Pos. [°2θ]** | **d-spacing [Å]** | **Height [cts]** | **Rel. Int. [%]** |
|---|---|---|---|
| **9.4812** | **9.32829** | **213.07** | **10.76** |
| **11.2719** | **7.85012** | **650.76** | **32.86** |
| 12.1183 | 7.30367 | 220.43 | 11.13 |
| 13.0908 | 6.75757 | 112.09 | 5.66 |
| 13.9612 | 6.34341 | 478.29 | 24.15 |
| 15.2544 | 5.80845 | 324.46 | 16.39 |
| **15.898** | **5.57471** | **1338.77** | **67.61** |
| 16.4116 | 5.4014 | 416.06 | 21.01 |
| **17.1359** | **5.1747** | **1606.29** | **81.12** |
| **17.9059** | **4.95387** | **1980.2** | **100** |
| 18.9149 | 4.69182 | 528.99 | 26.71 |
| **19.5773** | **4.53453** | **1768.33** | **89.3** |
| 20.0364 | 4.43166 | 1097.18 | 55.41 |
| **21.2196** | **4.18715** | **1066.83** | **53.87** |
| 22.0167 | 4.03734 | 440.36 | 22.24 |
| 22.6679 | 3.9228 | 1185.33 | 59.86 |
| 23.0104 | 3.86518 | 733.85 | 37.06 |
| **23.3684** | **3.80677** | **872.51** | **44.06** |
| **24.1748** | **3.68159** | **1377.48** | **69.56** |
| **24.3941** | **3.64898** | **1473.07** | **74.39** |
| 24.7636 | 3.59536 | 607.76 | 30.69 |
| **25.3618** | **3.51191** | **1006.2** | **50.81** |
| 25.7384 | 3.45851 | 366.83 | 18.52 |
| 26.3029 | 3.38835 | 461.15 | 23.29 |
| **27.3315** | **3.26312** | **1359.3** | **68.64** |

TABLE 22-continued

| XRPD diffractogram peak list for oxalate Pattern 2 from acetone. Characteristic peaks are indicated in bold. | | | |
|---|---|---|---|
| **Pos. [°2θ]** | **d-spacing [Å]** | **Height [cts]** | **Rel. Int. [%]** |
| 28.43 | 3.13949 | 406.26 | 20.52 |
| 29.8952 | 2.98887 | 274.54 | 13.86 |
| 30.4479 | 2.93586 | 457.22 | 23.09 |
| 31.2648 | 2.861 | 142.51 | 7.2 |
| 32.1862 | 2.78117 | 104.33 | 5.27 |
| 33.3237 | 2.68879 | 132.12 | 6.67 |
| 33.8688 | 2.64675 | 154.16 | 7.79 |
| 34.2555 | 2.61776 | 191.52 | 9.67 |
| 34.8614 | 2.5715 | 107.77 | 5.44 |

AP1189 Oxalate Form XVII

The XRPD diffractogram for AP1189 oxalate salt Pattern 4 crystallised from THF is shown in FIG. 28. The corresponding XRPD diffractogram peak list for oxalate salt Pattern 4 is shown in Table 23.

TABLE 23

| XRPD diffractogram peak list for oxalate Pattern 4 from THF. Characteristic peaks are indicated in bold. | | | |
|---|---|---|---|
| **Pos. [°2θ]** | **d-spacing [Å]** | **Height [cts]** | **Rel. Int. [%]** |
| **6.3181** | **13.98948** | **2384.52** | **98.7** |
| 8.1738 | 10.81722 | 70.4 | 2.91 |
| **10.5526** | **8.38352** | **2415.83** | **100** |
| **11.7369** | **7.54012** | **942.41** | **39.01** |
| **12.3228** | **7.18288** | **950.21** | **39.33** |
| 12.5733 | 7.04032 | 282.57 | 11.7 |
| 12.875 | 6.87604 | 519.84 | 21.52 |
| 13.2362 | 6.68366 | 89.53 | 3.71 |
| **14.0559** | **6.3009** | **588.24** | **24.35** |
| 14.2029 | 6.23602 | 569.99 | 23.59 |
| 15.8039 | 5.6077 | 284.16 | 11.76 |
| 16.0669 | 5.51651 | 324.39 | 13.43 |
| 17.0726 | 5.19374 | 809.18 | 33.5 |
| 17.7878 | 4.98649 | 345.64 | 14.31 |
| **18.4337** | **4.81321** | **1051.56** | **43.53** |
| 19.0388 | 4.65772 | 111.88 | 4.63 |
| 19.2304 | 4.61554 | 251.01 | 10.39 |
| **19.7672** | **4.4914** | **1361.5** | **56.36** |
| 20.2529 | 4.38479 | 312.67 | 12.94 |
| 20.6597 | 4.29935 | 413.55 | 17.12 |
| 20.9554 | 4.23934 | 722.78 | 29.92 |
| 21.3823 | 4.15566 | 252.83 | 10.47 |
| 21.7977 | 4.07739 | 397.86 | 16.47 |
| 21.9785 | 4.04091 | 211.05 | 8.74 |
| 22.2699 | 3.992 | 329.34 | 13.63 |
| 22.6213 | 3.93077 | 878.11 | 36.35 |
| 23.2335 | 3.82856 | 349.11 | 14.45 |
| **23.517** | **3.78305** | **702.57** | **29.08** |
| **23.7795** | **3.74188** | **1071.63** | **44.36** |
| 24.4105 | 3.64656 | 424.2 | 17.56 |
| 24.7951 | 3.58791 | 104.42 | 4.32 |
| 25.4426 | 3.50094 | 211.14 | 8.74 |
| 25.8594 | 3.44545 | 657.65 | 27.22 |
| 26.0571 | 3.41975 | 541.52 | 22.42 |
| 26.5554 | 3.35393 | 72.07 | 2.98 |
| 27.1137 | 3.28884 | 147.15 | 6.09 |
| 27.5269 | 3.24041 | 139.31 | 5.77 |
| 27.8473 | 3.20119 | 46.04 | 1.91 |
| 28.3054 | 3.15302 | 258.71 | 10.71 |
| 28.6747 | 3.11068 | 101.9 | 4.22 |
| 29.0198 | 3.07701 | 115.18 | 4.77 |
| **30.0442** | **2.97439** | **642.27** | **26.59** |
| 31.1015 | 2.87565 | 58.92 | 2.44 |
| 33.0328 | 2.7118 | 49.68 | 2.06 |
| 33.6771 | 2.66138 | 64.96 | 2.69 |
| 34.2549 | 2.61563 | 22.71 | 0.94 |

AP1189 (+)-Camphor-10-Sulfonic Acid Form XVIII

The XRPD diffractogram for AP1189 (+)-camphor-10-sulfonic acid salt Pattern 1 crystallised from 2-Propanol:water 80:20% v/v is shown in FIG. 29. The corresponding XRPD diffractogram peak list for (+)-camphor-10-sulfonic acid salt Pattern 1 is shown in Table 24.

TABLE 24

| XRPD diffractogram peak list for (+)-Camphor-10-sulfonic acid Pattern 1 from 2-Propanol:water 80:20% v/v. Characteristic peaks are indicated in bold. | | | |
|---|---|---|---|
| **Pos. [°2θ]** | **d-spacing [Å]** | **Height [cts]** | **Rel. Int. [%]** |
| 5.1412 | 17.18901 | 74.2 | 4.85 |
| **6.54** | **13.51547** | **654.67** | **42.8** |
| 7.6658 | 11.53287 | 63.53 | 4.15 |
| 9.3718 | 9.43695 | 250.57 | 16.38 |
| 9.8668 | 8.96463 | 153.81 | 10.06 |
| 10.402 | 8.50455 | 214.98 | 14.05 |
| 10.9801 | 8.05138 | 117.55 | 7.69 |
| **11.5235** | **7.67925** | **673.45** | **44.03** |
| 12.2098 | 7.2431 | 124.1 | 8.11 |
| **12.9822** | **6.81949** | **581.07** | **37.99** |
| **13.6946** | **6.46629** | **561.07** | **36.68** |
| 13.9583 | 6.34474 | 251.61 | 16.45 |
| 14.345 | 6.16946 | 118.72 | 7.76 |
| **14.788** | **5.99059** | **1529.62** | **100** |
| 15.5959 | 5.67733 | 160.54 | 10.5 |
| **15.8762** | **5.5777** | **338.29** | **22.12** |
| **16.1184** | **5.49898** | **574.21** | **37.54** |
| 17.2105 | 5.15243 | 315.7 | 20.64 |
| 18.131 | 4.89288 | 262.31 | 17.15 |
| 18.3504 | 4.83086 | 148.91 | 9.73 |
| **18.8333** | **4.71198** | **392.27** | **25.64** |
| **19.7635** | **4.49224** | **398.89** | **26.08** |
| **21.0597** | **4.21859** | **535.54** | **35.01** |
| 21.5101 | 4.13126 | 268.38 | 17.55 |
| 22.2216 | 3.99725 | 162.99 | 10.66 |
| 22.7338 | 3.91158 | 214.89 | 14.05 |
| 23.1598 | 3.8374 | 165.06 | 10.79 |
| 23.8376 | 3.7329 | 280.8 | 18.36 |
| 25.0641 | 3.55295 | 203.63 | 13.31 |
| 25.6703 | 3.47039 | 163.36 | 10.68 |
| 26.0558 | 3.41992 | 103.35 | 6.76 |
| 27.1796 | 3.28102 | 169.26 | 11.07 |
| 28.7362 | 3.10673 | 78.1 | 5.11 |
| 30.0563 | 2.97322 | 53.81 | 3.52 |
| 31.5327 | 2.8373 | 32.12 | 2.1 |

AP1189 Oxoglutarate Form XIX

The XRPD diffractogram for AP1189 oxoglutarate salt Pattern 1 crystallised from acetone is shown in FIG. 30. The corresponding XRPD diffractogram peak list for oxoglutarate salt Pattern 1 is shown in Table 25.

TABLE 25

| XRPD diffractogram peak list for oxoglutarate Pattern 1 from acetone. Characteristic peaks are indicated in bold. | | | |
|---|---|---|---|
| **Pos. [°2θ]** | **d-spacing [Å]** | **Height [cts]** | **Rel. Int. [%]** |
| **9.1083** | **9.70943** | **477.95** | **11.66** |
| **10.7459** | **8.23315** | **495.72** | **12.1** |
| 11.7595 | 7.51943 | 326.29 | 7.96 |
| 11.9888 | 7.38223 | 1205.72 | 29.42 |
| **12.8261** | **6.90214** | **1716.69** | **41.89** |
| **13.2196** | **6.69755** | **1567** | **38.24** |
| **13.3525** | **6.63121** | **2125.73** | **51.88** |
| 13.8276 | 6.39912 | 275.65 | 6.73 |
| 14.0138 | 6.31972 | 404.29 | 9.87 |
| 15.9327 | 5.56267 | 304.57 | 7.43 |
| **16.4363** | **5.39333** | **2897.8** | **70.72** |
| **16.8348** | **5.26657** | **4097.71** | **100** |
| 17.0851 | 5.18996 | 2766.55 | 67.51 |
| 17.9377 | 4.94515 | 772.63 | 18.86 |
| 18.2986 | 4.84842 | 340.41 | 8.31 |

TABLE 25-continued

XRPD diffractogram peak list for oxoglutarate Pattern 1 from acetone. Characteristic peaks are indicated in bold.

| Pos. [°2θ] | d-spacing [Å] | Height [cts] | Rel. Int. [%] |
|---|---|---|---|
| 19.4963 | 4.5532 | 718.78 | 17.54 |
| 20.0696 | 4.42442 | 924.41 | 22.56 |
| **20.8084** | **4.26896** | **1505.3** | **36.74** |
| **21.6016** | **4.11397** | **3079.97** | **75.16** |
| 21.9908 | 4.04204 | 800.41 | 19.53 |
| 22.9225 | 3.87981 | 615.58 | 15.02 |
| **23.4067** | **3.80062** | **3422.59** | **83.52** |
| **23.6024** | **3.76956** | **3716.86** | **90.71** |
| **24.0809** | **3.69267** | **1988.14** | **48.52** |
| **24.1593** | **3.69001** | **1705.36** | **41.62** |
| 25.7946 | 3.4511 | 992.25 | 24.21 |
| **26.5255** | **3.35764** | **3336.34** | **81.42** |
| **26.9122** | **3.31026** | **3545.15** | **86.52** |
| 27.4146 | 3.25073 | 816.47 | 19.93 |
| 27.8612 | 3.19962 | 818.49 | 19.97 |
| 28.8582 | 3.09132 | 551.01 | 13.45 |
| 29.9137 | 2.9846 | 238.13 | 5.81 |
| 30.337 | 2.94391 | 890.96 | 21.74 |
| 30.8796 | 2.8934 | 536.6 | 13.1 |
| 32.2965 | 2.76963 | 570.06 | 13.91 |
| 32.6262 | 2.74239 | 457.46 | 11.16 |
| 33.1486 | 2.70036 | 572.75 | 13.98 |
| 33.8402 | 2.64673 | 328.06 | 8.01 |
| 34.6933 | 2.58358 | 456.51 | 11.14 |

AP1189 DL-Mandelic Acid Form XX

The XRPD diffractogram for AP1189 DL-mandelic acid salt Pattern 2 crystallised from methylethyl ketone is shown in FIG. 31. The corresponding XRPD diffractogram peak list for DL-mandelic acid salt Pattern 2 is shown in Table 26.

TABLE 26

XRPD diffractogram peak list for DL-mandelic acid Pattern 2 from methylethyl ketone. Characteristic peaks are indicated in bold.

| Pos. [°2θ] | d-spacing [Å] | Height [cts] | Rel. Int. [%] |
|---|---|---|---|
| **5.3278** | **16.58759** | **1845** | **55.02** |
| **9.5789** | **9.23344** | **2024.97** | **60.39** |
| **9.968** | **8.87386** | **2381.68** | **71.02** |
| 10.6699 | 8.28474 | 231.21 | 6.89 |
| 10.8512 | 8.15348 | 328.99 | 9.81 |
| 11.7447 | 7.53513 | 368.64 | 10.99 |
| 12.0395 | 7.35127 | 603.48 | 18.00 |
| **12.3648** | **7.15856** | **1003.51** | **29.92** |
| **13.3371** | **6.63884** | **1307.90** | **39.00** |
| 13.9345 | 6.35027 | 169.90 | 5.07 |
| **14.7843** | **5.99208** | **2603.01** | **77.62** |
| 15.304 | 5.78972 | 241.37 | 7.2 |
| **16.0411** | **5.52532** | **758.96** | **22.63** |
| **16.8321** | **5.26741** | **1019.62** | **30.41** |
| 17.0395 | 5.19944 | 178.31 | 5.32 |
| 17.3113 | 5.12267 | 830.26 | 24.76 |
| 17.6081 | 5.03696 | 738.87 | 22.03 |
| **17.9246** | **4.94873** | **1940.47** | **57.87** |
| 18.5095 | 4.79366 | 874.43 | 26.08 |
| **19.1041** | **4.64578** | **2097.59** | **62.55** |
| 19.7677 | 4.49129 | 625.71 | 18.66 |
| 20.2411 | 4.3873 | 503.03 | 15.00 |
| 20.6976 | 4.29157 | 616.33 | 18.38 |
| **21.2349** | **4.18417** | **1247.47** | **37.20** |
| **21.4535** | **4.14203** | **2057.15** | **61.34** |
| 21.8113 | 4.07152 | 163.21 | 4.87 |
| 22.8944 | 3.88451 | 381.11 | 11.36 |
| **24.1665** | **3.68283** | **2677.35** | **79.84** |
| 24.5371 | 3.62805 | 739.38 | 22.05 |
| **24.7981** | **3.59044** | **1227.19** | **36.60** |
| **25.4748** | **3.49658** | **3353.42** | **100** |
| 26.3652 | 3.38048 | 266.48 | 7.95 |
| 26.885 | 3.31630 | 824.52 | 24.59 |

TABLE 26-continued

XRPD diffractogram peak list for DL-mandelic acid Pattern 2 from methylethyl ketone. Characteristic peaks are indicated in bold.

| Pos. [°2θ] | d-spacing [Å] | Height [cts] | Rel. Int. [%] |
|---|---|---|---|
| 27.1313 | 3.28675 | 532.22 | 15.87 |
| 27.5018 | 3.24331 | 648.76 | 19.35 |
| 28.0542 | 3.18068 | 402.6 | 12.01 |
| 28.3699 | 3.14600 | 228.01 | 6.80 |
| 29.6695 | 3.01110 | 302.57 | 9.02 |
| 30.3377 | 2.94628 | 551.12 | 16.43 |
| 31.2069 | 2.86617 | 280.40 | 8.36 |
| 32.3828 | 2.76473 | 130.17 | 3.88 |
| 32.7924 | 2.73113 | 272.61 | 8.13 |
| 33.0937 | 2.70695 | 199.35 | 5.94 |
| 33.4812 | 2.67650 | 153.52 | 4.58 |
| 34.3739 | 2.60901 | 154.65 | 4.61 |
| 34.6967 | 2.58333 | 89.00 | 2.65 |

AP1189 DL-Mandelic Acid Form XXI

The XRPD diffractogram for AP1189 DL-mandelic acid salt Pattern 3 crystallised from acetone is shown in FIG. 32. The corresponding XRPD diffractogram peak list for DL-mandelic acid salt Pattern 3 is shown in Table 27.

TABLE 27

XRPD diffractogram peak list for DL-mandelic acid Pattern 3 from acetone. Characteristic peaks are indicated in bold.

| Pos. [°2θ] | d-spacing [Å] | Height [cts] | Rel. Int. [%] |
|---|---|---|---|
| **5.3893** | **16.39843** | **4912.28** | **88.86** |
| **9.7591** | **9.06332** | **3991.44** | **72.2** |
| **10.0419** | **8.80866** | **5528.14** | **100** |
| 11.2198 | 7.88644 | 781.77 | 14.14 |
| 11.5373 | 7.66373 | 229.46 | 4.15 |
| 11.7936 | 7.504 | 1004.79 | 18.18 |
| **12.6722** | **6.98565** | **1846.06** | **33.39** |
| **13.5326** | **6.54335** | **2579.7** | **46.66** |
| 14.3544 | 6.17052 | 699.64 | 12.66 |
| 15.0397 | 5.89088 | 1043.83 | 18.88 |
| 15.4731 | 5.72682 | 1523.04 | 27.55 |
| 15.6775 | 5.65264 | 1495.79 | 27.06 |
| 15.8208 | 5.59712 | 378.04 | 6.84 |
| **16.5687** | **5.35053** | **3283.44** | **59.39** |
| 17.1736 | 5.16342 | 1270.64 | 22.98 |
| **18.1157** | **4.89697** | **3148.28** | **56.95** |
| 19.5677 | 4.53675 | 762.3 | 13.79 |
| 20.2232 | 4.39116 | 892.62 | 16.15 |
| 20.6533 | 4.30067 | 1765.5 | 31.94 |
| **21.1402** | **4.20269** | **2967.73** | **53.68** |
| **21.7114** | **4.09342** | **2549.07** | **46.11** |
| 22.5571 | 3.94182 | 860.51 | 15.57 |
| 23.255 | 3.82508 | 1053.7 | 19.06 |
| 23.5888 | 3.77171 | 2097.93 | 37.95 |
| **24.5508** | **3.62604** | **5283.58** | **95.58** |
| **25.3869** | **3.50849** | **2895.23** | **52.37** |
| 26.0622 | 3.41909 | 1624.06 | 29.38 |
| 27.0317 | 3.29589 | 972.29 | 17.59 |
| 27.2552 | 3.27209 | 1730.57 | 31.3 |
| 28.664 | 3.11439 | 405.06 | 7.33 |
| 28.9743 | 3.08174 | 371.42 | 6.72 |
| 29.8399 | 2.99429 | 436.53 | 7.9 |
| 30.4007 | 2.94032 | 770.85 | 13.94 |
| 30.6937 | 2.91051 | 239.34 | 4.33 |
| 31.1806 | 2.86854 | 293.27 | 5.31 |
| 32.8239 | 2.72858 | 186.18 | 3.37 |
| 33.4914 | 2.67571 | 336.08 | 6.08 |
| 33.9645 | 2.63951 | 205.17 | 3.71 |
| 34.5199 | 2.59831 | 222.06 | 4.02 |

AP1189 Hippuric Acid Form XXII

The XRPD diffractogram for AP1189 hippuric acid salt Pattern 1 crystallised from methylethyl ketone is shown in FIG. 33. The corresponding XRPD diffractogram peak list for hippuric acid salt Pattern 1 is shown in Table 28.

TABLE 28

XRPD diffractogram peak list for hippuric acid Pattern 1 from methylethyl ketone. Characteristic peaks are indicated in bold.

| Pos. [°2θ] | d-spacing [Å] | Height [cts] | Rel. Int. [%] |
|---|---|---|---|
| 8.6143 | 10.25659 | 113.08 | 8.83 |
| **9.598** | **9.21503** | **527.96** | **41.23** |
| 9.8144 | 9.00493 | 260.1 | 20.31 |
| **10.8895** | **8.12492** | **928.65** | **72.51** |
| **11.4793** | **7.70874** | **893.63** | **69.78** |
| 11.7567 | 7.52125 | 410.35 | 32.04 |
| 12.6953 | 6.97294 | 640.66 | 50.03 |
| 13.255 | 6.67974 | 664.76 | 51.91 |
| 13.8253 | 6.40018 | 374.81 | 29.27 |
| 14.1095 | **6.27188** | **395.92** | **30.92** |
| **14.4273** | **6.13954** | **822.58** | **64.23** |
| **14.8688** | **5.95818** | **960.42** | **74.99** |
| **15.5334** | **5.70474** | **717.01** | **55.99** |
| 16.3714 | 5.4101 | 289.13 | 22.58 |
| 17.4516 | 5.08178 | 564.67 | 44.09 |
| **18.0621** | **4.91136** | **797.05** | **62.24** |
| 19.4664 | 4.55635 | 312.87 | 24.43 |
| **20.0768** | **4.42284** | **1099.31** | **85.84** |
| 20.686 | 4.29394 | 945.98 | 73.87 |
| 20.9823 | 4.23046 | 638.13 | 49.83 |
| 21.989 | 4.04236 | 1034.88 | 80.81 |
| 22.3837 | 3.97197 | 1097 | 85.66 |
| 22.781 | 3.90358 | 958.14 | 74.82 |
| 23.1141 | 3.84489 | 610.08 | 47.64 |
| **24.0708** | **3.69726** | **1280.66** | **100** |
| **24.489** | **3.63506** | **1255.08** | **98.00** |
| 25.2989 | 3.5205 | 684.15 | 53.42 |
| 25.7814 | 3.45569 | 537.56 | 41.98 |
| 27.1059 | 3.28976 | 557.88 | 43.56 |
| 28.072 | 3.17871 | 304.59 | 23.78 |
| 29.1378 | 3.06482 | 381.24 | 29.77 |

AP1189 Formic Acid Form XXIII

The XRPD diffractogram for AP1189 formate salt Pattern 1 crystallised from acetone is shown in FIG. 34. The corresponding XRPD diffractogram peak list for formate salt Pattern 1 is shown in Table 29.

TABLE 29

XRPD diffractogram peak list for formate Pattern 1 from acetone. Characteristic peaks are indicated in bold.

| Pos. [°2θ] | d-spacing [Å] | Height [cts] | Rel. Int. [%] |
|---|---|---|---|
| 7.3974 | 11.95078 | 545.69 | 3.73 |
| 10.3677 | 8.53261 | 1240.38 | 8.47 |
| 10.6166 | 8.33313 | 1104.27 | 7.54 |
| **12.1932** | **7.25896** | **1192.4** | **8.14** |
| **13.2943** | **6.66011** | **12637.58** | **86.28** |
| 14.1263 | 6.26963 | 1121.3 | 7.66 |
| **15.0608** | **5.88266** | **14646.45** | **100** |
| 15.2423 | 5.81303 | 2665.72 | 18.2 |
| 16.7797 | 5.28372 | 2633.7 | 17.98 |
| **17.3341** | **5.11595** | **8220.13** | **56.12** |
| 17.9963 | 4.92918 | 2302.64 | 15.72 |
| 18.4846 | 4.80007 | 7429.09 | 50.72 |
| 18.7509 | 4.73248 | 7824.4 | 53.42 |
| **18.9261** | **4.68908** | **7877.5** | **53.78** |
| 19.1184 | 4.64235 | 4567.83 | 31.19 |
| **20.5992** | **4.31184** | **5415.68** | **36.98** |
| 20.8504 | 4.26047 | 1014.98 | 6.93 |
| 21.3519 | 4.1615 | 596.99 | 4.08 |
| **21.845** | **4.06867** | **8642.95** | **59.01** |
| 22.3365 | 3.98024 | 835.56 | 5.7 |
| 22.5988 | 3.93464 | 2569.5 | 17.54 |
| **22.7594** | **3.90723** | **4206.51** | **28.72** |
| 23.1395 | 3.84391 | 843.2 | 5.76 |

TABLE 29-continued

XRPD diffractogram peak list for formate Pattern 1 from acetone. Characteristic peaks are indicated in bold.

| Pos. [°2θ] | d-spacing [Å] | Height [cts] | Rel. Int. [%] |
|---|---|---|---|
| **23.6272** | **3.76566** | **8913.09** | **60.85** |
| 24.0258 | 3.70408 | 3919.64 | 26.76 |
| 24.5257 | 3.6297 | 1772.27 | 12.1 |
| 24.8627 | 3.58126 | 2985.77 | 20.39 |
| **25.5562** | **3.48562** | **11808.59** | **80.62** |
| 26.7988 | 3.32676 | 1871.33 | 12.78 |
| 27.1478 | 3.28479 | 5298.04 | 36.17 |
| 27.555 | 3.23716 | 1232.48 | 8.41 |
| 28.1048 | 3.17508 | 688.88 | 4.7 |
| 28.5576 | 3.12575 | 1537.8 | 10.5 |
| **28.8538** | **3.09433** | **3072.99** | **20.98** |
| **29.2239** | **3.05598** | **2924.78** | **19.97** |
| 30.4606 | 2.93468 | 795.57 | 5.43 |
| 30.8589 | 2.8977 | 822.88 | 5.62 |
| 31.6975 | 2.82292 | 355.5 | 2.43 |
| 32.2437 | 2.77634 | 361.16 | 2.47 |
| 32.676 | 2.74059 | 1050.97 | 7.18 |
| 33.0782 | 2.70818 | 1100.1 | 7.51 |
| 34.0175 | 2.63552 | 712.7 | 4.87 |

AP1189 DL-Lactic Acid Form XXIV

The XRPD diffractogram for AP1189 DL-lactic acid salt Pattern 1 crystallised from acetone is shown in FIG. 35. The corresponding XRPD diffractogram peak list for L-lactic acid salt Pattern 1 is shown in Table 30.

TABLE 30

XRPD diffractogram peak list for L-lactic acid Pattern 1 from acetone. Characteristic peaks are indicated in bold.

| Pos. [°2θ] | d-spacing [Å] | Height [cts] | Rel. Int. [%] |
|---|---|---|---|
| **3.8307** | **23.06604** | **3178.24** | **47.86** |
| **7.6777** | **11.51498** | **1767.12** | **26.61** |
| **9.8772** | **8.95518** | **6641.34** | **100** |
| **11.9193** | **7.42511** | **4378.1** | **65.92** |
| 13.5622 | 6.52914 | 518.09 | 7.8 |
| 14.0188 | 6.31748 | 708.8 | 10.67 |
| 14.2103 | 6.2328 | 605.57 | 9.12 |
| 14.6766 | 6.03078 | 123.41 | 1.86 |
| **15.409** | **5.75051** | **1357.73** | **20.44** |
| 15.7676 | 5.62053 | 469.6 | 7.07 |
| 18.0461 | 4.91568 | 554.63 | 8.35 |
| 18.2556 | 4.85976 | 852 | 12.83 |
| 18.6623 | 4.75475 | 897.72 | 13.52 |
| 19.2881 | 4.60186 | 483.92 | 7.29 |
| 19.8255 | 4.47833 | 386.24 | 5.82 |
| 20.1676 | 4.40313 | 1223.74 | 18.43 |
| 20.4033 | 4.3528 | 919.15 | 13.84 |
| 20.6573 | 4.29984 | 1559.52 | 23.48 |
| 20.8905 | 4.25237 | 990.19 | 14.91 |
| 21.3526 | 4.16138 | 1157.33 | 17.43 |
| 21.646 | 4.10562 | 908.23 | 13.68 |
| 22.3961 | 3.96979 | 855.37 | 12.88 |
| 22.6249 | 3.93017 | 939.37 | 14.14 |
| **22.971** | **3.87172** | **2321.73** | **34.96** |
| 23.2857 | 3.82011 | 441.69 | 6.65 |
| 23.7043 | 3.75359 | 592.41 | 8.92 |
| **23.9203** | **3.72017** | **1448.41** | **21.81** |
| **25.3489** | **3.51366** | **1592.32** | **23.98** |
| 25.8516 | 3.44647 | 814.66 | 12.27 |
| **27.4586** | **3.24831** | **2881.16** | **43.38** |
| 27.8125 | 3.20777 | 443.85 | 6.68 |
| 28.5067 | 3.13122 | 1135.06 | 17.09 |
| 28.663 | 3.1145 | 927.83 | 13.97 |
| 29.5915 | 3.01635 | 53.45 | 0.8 |
| 29.9951 | 2.97668 | 37.42 | 0.56 |
| 30.429 | 2.93765 | 222.79 | 3.35 |
| 31.4341 | 2.84598 | 106.84 | 1.61 |

TABLE 30-continued

| XRPD diffractogram peak list for L-lactic acid Pattern 1 from acetone. Characteristic peaks are indicated in bold. | | | |
|---|---|---|---|
| **Pos. [°2θ]** | **d-spacing [Å]** | **Height [cts]** | **Rel. Int. [%]** |
| 31.8482 | 2.8099 | 177.22 | 2.67 |
| 33.0644 | 2.70928 | 164.9 | 2.48 |
| 33.6444 | 2.66389 | 179.49 | 2.7 |

AP1189 DL-Lactic Acid Form XXV

The XRPD diffractogram for AP1189 DL-lactic acid salt Pattern 1 crystallised from 2-propanol:water 80:20% v/v is shown in FIG. 36. The corresponding XRPD diffractogram peak list for DL-lactic acid salt Pattern 1 is shown in Table 31.

TABLE 31

| XRPD diffractogram peak list for DL-lactic acid Pattern 1 from 2-propanol:water 80:20% v/v. Characteristic peaks are indicated in bold. | | | |
|---|---|---|---|
| **Pos. [°2θ]** | **d-spacing [Å]** | **Height [cts]** | **Rel. Int. [%]** |
| **3.8162** | **23.15347** | **1804.22** | **34.05** |
| **7.6494** | **11.55762** | **1162.58** | **21.94** |
| **9.8321** | **8.9962** | **5298.36** | **100** |
| 11.8679 | **7.45715** | **3991.73** | **75.34** |
| 13.6586 | 6.48328 | 804.02 | 15.17 |
| 14.1081 | 6.27769 | 790.27 | 14.92 |
| 14.2862 | 6.19986 | 766.33 | 14.46 |
| **15.3333** | **5.77875** | **955.8** | **18.04** |
| 15.8231 | 5.60095 | 461.73 | 8.71 |
| 18.161 | 4.88484 | 815.96 | 15.4 |
| 18.5718 | 4.77771 | 802.78 | 15.15 |
| 19.2085 | 4.62076 | 490.09 | 9.25 |
| 19.7509 | 4.49507 | 401.86 | 7.58 |
| 20.5233 | 4.32761 | 965.62 | 18.22 |
| 20.9608 | 4.23826 | 1332.56 | 25.15 |
| 21.282 | 4.17503 | 639.09 | 12.06 |
| 21.5473 | 4.12421 | 839.68 | 15.85 |
| 22.4898 | 3.95019 | 262.35 | 4.95 |
| 22.6827 | 3.92028 | 577.78 | 10.9 |
| 22.8882 | 3.88554 | 782.98 | 14.78 |
| **23.2724** | **3.82226** | **1405.85** | **26.53** |
| 23.5751 | 3.77386 | 564.88 | 10.66 |
| **23.8954** | **3.72399** | **1240.54** | **23.41** |
| 25.0342 | 3.55417 | 184.12 | 3.48 |
| **25.5625** | **3.48479** | **1065.01** | **20.1** |
| 26.0731 | 3.41769 | 771.57 | 14.56 |
| **27.6295** | **3.2286** | **1820.33** | **34.36** |
| 28.6694 | 3.11382 | 923.63 | 17.43 |
| 29.3516 | 3.04046 | 87.68 | 1.65 |
| 29.6094 | 3.01458 | 79.61 | 1.5 |
| 29.8349 | 2.9923 | 57.71 | 1.09 |
| 30.216 | 2.95542 | 62.38 | 1.18 |
| 30.6416 | 2.91775 | 94.23 | 1.78 |
| 31.5599 | 2.83492 | 87.33 | 1.65 |
| 31.9945 | 2.79739 | 92.91 | 1.75 |
| 34.1244 | 2.62751 | 173.05 | 3.27 |

AP1189 Glutaric Acid Form XXVI

The XRPD diffractogram for AP1189 glutaric acid salt Pattern 1 crystallised from acetone is shown in FIG. 37. The corresponding XRPD diffractogram peak list for glutaric acid salt Pattern 1 is shown in Table 32.

TABLE 32

| XRPD diffractogram peak list for glutaric acid Pattern 1 from acetone. | | | |
|---|---|---|---|
| Pos. [°2θ] | d-spacing [Å] | Height [cts] | Rel. Int. [%] |
| **3.2187** | **27.45066** | **1273.8** | **44.98** |
| 6.2662 | 14.10535 | 91.37 | 3.23 |
| **8.2746** | **10.68563** | **2609.46** | **92.15** |
| **8.6516** | **10.22081** | **1050.19** | **37.08** |
| 9.8059 | 9.02016 | 1139.11 | 40.22 |
| 10.0791 | 8.76902 | 223.29 | 7.89 |
| 10.4696 | 8.44977 | 349.34 | 12.34 |
| **12.8461** | **6.89144** | **1821.76** | **64.33** |
| 13.6255 | 6.49895 | 355.14 | 12.54 |
| **14.3832** | **6.15823** | **1410.65** | **49.81** |
| **15.0994** | **5.86773** | **1435.45** | **50.69** |
| **15.8515** | **5.59098** | **2831.89** | **100** |
| **16.2437** | **5.45684** | **1350.34** | **47.68** |
| 17.0593 | 5.19775 | 800.86 | 28.28 |
| 17.4716 | 5.07602 | 467.92 | 16.52 |
| 17.9619 | 4.93854 | 515.41 | 18.2 |
| 18.3427 | 4.83288 | 132.32 | 4.67 |
| **19.0191** | **4.66636** | **1161.13** | **41** |
| **19.7618** | **4.49262** | **942.09** | **33.27** |
| 20.1675 | 4.40316 | 327.58 | 11.57 |
| 20.5267 | 4.32691 | 479.36 | 16.93 |
| 21.0323 | 4.22402 | 514.69 | 18.17 |
| 21.4391 | 4.14478 | 927.37 | 32.75 |
| 21.7032 | 4.09494 | 1737.14 | 61.34 |
| **21.9433** | **4.05068** | **2661.11** | **93.97** |
| 23.0149 | 3.86444 | 761.72 | 26.9 |
| 23.6232 | 3.76629 | 871.91 | 30.79 |
| 24.1144 | 3.69067 | 335.65 | 11.85 |
| 24.5213 | 3.62734 | 178.61 | 6.31 |
| 24.9925 | 3.56296 | 523.88 | 18.5 |
| 26.0019 | 3.42689 | 608.37 | 21.48 |
| 26.47 | 3.36733 | 449.64 | 15.88 |
| **27.108** | **3.28951** | **1957.29** | **69.12** |
| 27.6238 | 3.22926 | 659.12 | 23.28 |
| 28.1734 | 3.1675 | 497.17 | 17.56 |
| **28.8455** | **3.09521** | **1331.98** | **47.04** |
| **29.4794** | **3.03008** | **690.69** | **24.39** |
| 30.5566 | 2.92567 | 279.74 | 9.88 |
| 31.4382 | 2.84561 | 247.41 | 8.74 |
| 32.3422 | 2.76811 | 174.16 | 6.15 |
| 33.8394 | 2.64898 | 126.9 | 4.48 |

Characteristic peaks are indicated in bold.

AP1189 Glutaric Acid Form XXVII

The XRPD diffractogram for AP1189 glutaric acid salt Pattern 2 crystallised from methylethyl ketone is shown in FIG. 38. The corresponding XRPD diffractogram peak list for glutaric acid salt Pattern 2 is shown in Table 33.

TABLE 33

| XRPD diffractogram peak list for glutaric acid Pattern 2 from methylethyl ketone. | | | |
|---|---|---|---|
| Pos. [°2θ] | d-spacing [Å] | Height [cts] | Rel. Int. [%] |
| **6.2713** | **14.09393** | **1348.45** | **21.68** |
| **10.0606** | **8.79234** | **2465.26** | **39.64** |
| 10.7964 | 8.19475 | 1055.44 | 16.97 |
| 12.5578 | 7.04898 | 1369.87 | 22.03 |
| 12.7174 | 6.96091 | 816.87 | 13.14 |
| 13.4536 | 6.5816 | 976.38 | 15.7 |
| **14.0559** | **6.30088** | **4576.13** | **73.58** |
| **14.3305** | **6.18077** | **2421.41** | **38.94** |
| **14.7434** | **6.00859** | **2331.2** | **37.48** |
| **15.1147** | **5.86181** | **3300.67** | **53.07** |
| 15.3445 | 5.77454 | 1725.44 | 27.74 |
| 15.6849 | 5.64529 | 297.83 | 4.79 |
| 16.5052 | 5.37099 | 3574.38 | 57.47 |
| 16.7069 | 5.30659 | 2329.22 | 37.45 |
| **16.9302** | **5.23709** | **3892.59** | **62.59** |
| **17.4284** | **5.08848** | **3107.29** | **49.96** |
| 18.0004 | 4.92807 | 1304.54 | 20.98 |

TABLE 33-continued

XRPD diffractogram peak list for glutaric acid Pattern 2 from methylethyl ketone.

| Pos. [°2θ] | d-spacing [Å] | Height [cts] | Rel. Int. [%] |
|---|---|---|---|
| 18.3123 | 4.84484 | 3268.21 | 52.55 |
| 18.6803 | 4.7502 | 1268.95 | 20.4 |
| 18.9049 | 4.6904 | 348.68 | 5.61 |
| 19.2764 | 4.60083 | 230.03 | 3.7 |
| 19.6067 | 4.52407 | 213.08 | 3.43 |
| 20.1361 | 4.4063 | 1951.43 | 31.38 |
| 20.2103 | 4.4012 | 1852.93 | 29.79 |
| 20.4529 | 4.33876 | 1029.79 | 16.56 |
| 20.9143 | 4.24407 | 525.31 | 8.45 |
| 21.2592 | 4.17598 | 1295.43 | 20.83 |
| **21.6882** | **4.09434** | **6219.02** | **100** |
| **22.1229** | **4.01487** | **3700.13** | **59.5** |
| **22.5809** | **3.93447** | **3263.88** | **52.48** |
| 23.1992 | 3.83097 | 666.23 | 10.71 |
| 23.9542 | 3.71192 | 738.95 | 11.88 |
| 24.3918 | 3.64631 | 1342.56 | 21.59 |
| **24.9548** | **3.56529** | **4913.53** | **79.01** |
| **25.5599** | **3.48226** | **4269.78** | **68.66** |
| 25.9989 | 3.42444 | 1726.37 | 27.76 |
| **26.5216** | **3.35813** | **3601.16** | **57.91** |
| 26.8383 | 3.3192 | 1448.36 | 23.29 |
| **27.1448** | **3.28242** | **3733.35** | **60.03** |
| 27.6013 | 3.22916 | 1037 | 16.67 |
| **28.1593** | **3.16643** | **3739.98** | **60.14** |
| **28.7121** | **3.10671** | **4338.65** | **69.76** |
| 28.9792 | 3.07869 | 1514.53 | 24.35 |
| 29.3573 | 3.03989 | 1131.3 | 18.19 |
| 29.7049 | 3.0051 | 1374.88 | 22.11 |
| 30.5161 | 2.92703 | 742.83 | 11.94 |
| 31.3096 | 2.85464 | 2126.37 | 34.19 |
| 32.0253 | 2.79246 | 1658.17 | 26.66 |
| 32.9797 | 2.71379 | 391.9 | 6.3 |
| 34.0663 | 2.62968 | 459.08 | 7.38 |

Characteristic peaks are indicated in bold.

AP1189 Glutaric Acid Form XXVIII

The XRPD diffractogram for AP1189 glutaric acid salt Pattern 4 crystallised from acetone is shown in FIG. 91 The corresponding XRPD diffractogram peak list for glutaric acid salt Pattern 4 is shown in Table 34.

TABLE 34

XRPD diffractogram peak list for glutaric acid Pattern 4 from acetone.

| Pos. [°2θ] | d-spacing [Å] | Height [cts] | Rel. Int. [%] |
|---|---|---|---|
| **6.2649** | **14.10824** | **2317.26** | **45.92** |
| **8.856** | **9.98546** | **1016.84** | **20.15** |
| **10.0581** | **8.79456** | **1068.48** | **21.17** |
| 10.3774 | 8.52465 | 827.42 | 16.4 |
| 10.7078 | 8.25549 | 282.03 | 5.59 |
| **12.5708** | **7.04173** | **1531.07** | **30.34** |
| 13.4458 | 6.58542 | 495.2 | 9.81 |
| 13.8282 | 6.39883 | 372.75 | 7.39 |
| **14.2416** | **6.21914** | **2854.8** | **56.57** |
| **15.238** | **5.81468** | **2052.8** | **40.68** |
| 15.5797 | 5.6879 | 878.27 | 17.4 |
| 16.4839 | 5.37788 | 1494.63 | 29.62 |
| **16.8787** | **5.25296** | **5046.34** | **100** |
| **17.4128** | **5.09303** | **1366.17** | **27.07** |
| 18.1957 | 4.87561 | 1005.32 | 19.92 |
| **19.1108** | **4.64417** | **1212.63** | **24.03** |
| 19.7816 | 4.48446 | 372.75 | 7.39 |
| 20.1893 | 4.39845 | 1158.28 | 22.95 |
| **20.6392** | **4.30358** | **1641.43** | **32.53** |
| **20.9102** | **4.24841** | **1980.44** | **39.25** |
| 21.6891 | 4.09756 | 1391.84 | 27.58 |
| **21.9308** | **4.05295** | **1854.79** | **36.76** |
| 22.5489 | 3.94324 | 675.52 | 13.39 |
| 23.0328 | 3.86147 | 1238.92 | 24.55 |

TABLE 34-continued

XRPD diffractogram peak list for glutaric acid Pattern 4 from acetone.

| Pos. [°2θ] | d-spacing [Å] | Height [cts] | Rel. Int. [%] |
|---|---|---|---|
| 23.5993 | 3.77005 | 740.75 | 14.68 |
| 23.8463 | 3.72846 | 584.45 | 11.58 |
| **24.536** | **3.6282** | **3003.71** | **59.52** |
| 24.949 | 3.56907 | 820.3 | 16.26 |
| 25.2746 | 3.52382 | 778.83 | 15.43 |
| 26.0869 | 3.41591 | 1010.15 | 20.02 |
| 27.1988 | 3.27874 | 738.77 | 14.64 |
| 27.8279 | 3.20604 | 827.7 | 16.4 |
| **28.372** | **3.14577** | **1720.94** | **34.1** |
| 29.2659 | 3.04917 | 634.85 | 12.58 |
| 29.631 | 3.01492 | 674.74 | 13.37 |
| 30.5003 | 2.93095 | 356.34 | 7.06 |
| 30.9655 | 2.88797 | 448.36 | 8.88 |
| 31.4367 | 2.84574 | 415.64 | 8.24 |
| 32.4495 | 2.7592 | 328.32 | 6.51 |
| 33.6052 | 2.66691 | 196.33 | 3.89 |
| 34.3331 | 2.61202 | 366.12 | 7.26 |

Characteristic peaks are indicated in bold.

AP1189 Adipic Acid Form XXIX

The XRPD diffractogram for AP1189 adipic acid salt Pattern 1 crystallised from 2-Propanol:water 80:20% v/v is shown in FIG. 39. The corresponding XRPD diffractogram peak list for adipic acid salt Pattern 1 is shown in Table 35.

TABLE 35

XRPD diffractogram peak list for adipic acid Pattern 2 from 2-Propanol:water 80:20 % v/v.

| Pos. [°2θ] | d-spacing [Å] | Height [cts] | Rel. Int. [%] |
|---|---|---|---|
| **5.2288** | **16.9012** | **374.38** | **14.26** |
| 10.4544 | 8.46204 | 332.6 | 12.67 |
| 11.1721 | 7.92002 | 402.89 | 15.35 |
| 12.7447 | 6.94605 | 331.3 | 12.62 |
| **13.3934** | **6.61103** | **2624.96** | **100** |
| **14.5087** | **6.10526** | **2071.88** | **78.93** |
| 15.3038 | 5.78982 | 468.09 | 17.83 |
| 15.7578 | 5.62399 | 302.36 | 11.52 |
| 17.0607 | 5.19734 | 820.45 | 31.26 |
| **17.6454** | **5.0264** | **1305.13** | **49.72** |
| 18.0415 | 4.91694 | 783.53 | 29.85 |
| 18.794 | 4.72173 | 270.99 | 10.32 |
| **19.157** | **4.63306** | **977.8** | **37.25** |
| 20.5149 | 4.32579 | 76.13 | 2.9 |
| 21.0048 | 4.22949 | 277.16 | 10.56 |
| **21.389** | **4.15438** | **746.25** | **28.43** |
| 22.3725 | 3.97063 | 121.59 | 4.63 |
| 22.751 | 3.90866 | 583.38 | 22.22 |
| 22.996 | 3.86757 | 720.73 | 27.46 |
| **23.5265** | **3.78155** | **1287.83** | **49.06** |
| 23.9413 | 3.71696 | 408.65 | 15.57 |
| 24.4366 | 3.63972 | 198.1 | 7.55 |
| 24.8265 | 3.58641 | 586.6 | 22.35 |
| **25.3953** | **3.50735** | **1334.01** | **50.82** |
| **25.5279** | **3.48943** | **1466.02** | **55.85** |
| 26.0524 | 3.42035 | 225.22 | 8.58 |
| 26.2942 | 3.38664 | 103.24 | 3.93 |
| **27.0894** | **3.29173** | **1235.27** | **47.06** |
| 27.4729 | 3.24665 | 840.7 | 32.03 |
| 28.0693 | 3.17637 | 83.67 | 3.19 |
| 28.9363 | 3.08315 | 67.85 | 2.58 |
| 29.4981 | 3.0282 | 169.21 | 6.45 |
| 30.5878 | 2.92275 | 295.43 | 11.25 |
| 32.1777 | 2.78189 | 215.64 | 8.21 |
| 33.9424 | 2.64118 | 87.52 | 3.33 |
| 34.5436 | 2.59658 | 170.22 | 6.48 |

Characteristic peaks are indicated in bold.

Conclusion

X-Ray Powder Diffraction Data was Collected for a Selection of Different AP1189 Salts.

Example 4: Thermogravimetric Analysis/Differential Scanning Calorimetry and Differential Scanning Calorimetry Methods For the TGA/DSC assessment, approximately, 5-10 mg of material was added into a pre-tared open aluminium pan, loaded into a TA Instruments Discovery SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the sample purge gas, at a flow rate of 200 $cm^3$/min.

For the DSC assessment, approximately, 1-5 mg of material was weighed into an aluminium DSC pan and sealed non-hermetically with an aluminium lid. The sample pan was then loaded into a TA Instruments Discovery DSC 2500 differential scanning calorimeter equipped with a RC90 cooler. The sample and reference were heated to 230° C. or 240° C. at a scan rate of 10° C./min and the resulting heat flow response monitored. The sample was re-cooled to 20° C. and then reheated again to 230° C. or 240° C. all at 10° C./min. Nitrogen was used as the purge gas, at a flow rate of 50 $cm^3$/min.

Results

Results from the TGA/DSC and DSC assessments are shown in Table 36.

TABLE 36

TGA/DSC (*) and DSC (**) data for AP1189 salts.

| Counter ion | Solvent | TGA/DSC or DSC results |
|---|---|---|
| Acetic Acid | Acetonitrile. Pattern 1 | Endothermic onset 192° C. (**) |
| Acetic Acid | Ethyl acetate, Pattern 1 + 2 | Endothermic onset 172° C. (*) Note: Thermal data generated on 2-MeTHF sample. |
| Acetic Acid | THF, Pattern 3 | Endothermic onset 101° C. (*) |
| p-Toluenesulfonic acid | 2-propanol:water 90:10 v/v/methanol, Pattern 1 | Endothermic onset 234° C. (*) |
| Fumaric acid | 2-propanol:water 90:10 v/v, Pattern 1 | Endothermic onset 215° C. (*) |
| Succinic acid | 2-propanol:water 90:10 v/v | Endothermic onset 195° C. (*) |
| Napadisylate pattern 1 | 2-propanol:water 90:10 % v/v | $1^{st}$ onset 87° C. (*)<br>$2^{nd}$ onset 187° C. (*) |
| Esylate pattern 1 | methylethyl ketone | Onset 207° C. (*) |
| Edisylate pattern 1 | 2-Propanol:water (80:20 % v/v) | $1^{st}$ onset 78° C. (*)<br>$2^{nd}$ onset 151° C. (*) |
| Edisylate pattern 2 | methylethyl ketone | Onset 225° C. (*) |
| Edisylate pattern 4 | THF | Onset 208 ° (*) |
| Edisylate pattern 5 | 2-Propanol:water (80:20 % v/v) | $1^{st}$ onset 59° C. (*)<br>$2^{nd}$ onset 151° C. (*) |
| Nitrate pattern 1 | THF | Onset 179° C. (*) |
| Cyclamate pattern 2 | THF | Onset 130° C. (*) |
| Cyclamate pattern 4 | acetone | Onset 138° C. (*) |
| Cyclamate pattern 5 | THF | Onset 141° C. (*) |
| Besylate pattern 1 | 2-Propanol:water 80:20 % v/v | Onset 216° C. (*) |
| Oxalate pattern 1 | 2-Propanol:water 80:20 % v/v | Peak 211° C. (*) |
| Oxalate pattern 2 | acetone | Onset 207° C. (*) |
| (+)-Camphor-10-sulfonic acid pattern 1 | 2-Propanol:water 80:20 % v/v | Onset 205° C. (*) |
| Oxoglutarate pattern 1 | acetone | Onset 81° C. (*) |
| DL-mandelic acid pattern 2 | methylethyl ketone | Onset 110° C. (*) |
| Hippuric acid pattern 1 | methylethyl ketone | Onset 139° C. (*) |
| Formic acid pattern 1 | acetone | Onset 169° C. (*) |
| L-Lactic acid pattern 1 | acetone | Onset 189° C. (*) |
| DL-Lactic acid pattern 1 | 2-propanol:water 80:20 % v/v | Onset 198° C. (*) |
| Glutaric acid pattern 1 | acetone | $1^{st}$ onset 109° C. (*)<br>$2^{nd}$ onset 160° C. (*) |
| Glutaric acid pattern 2 | methylethyl ketone | Onset 163° C. (*) |
| Glutaric acid pattern 4 | acetone | $1^{st}$ onset 145° C. (*)<br>$2^{nd}$ onset 160° C. (*) |
| Adipic acid pattern 1 | 2-Propanol:water 80:20 % v/v | Onset 183° C. (*) |

Example 5: Nuclear Magnetic Resonance

Methods

NMR experiments were performed on a Bruker AVIIIHD spectrometer equipped with a DCH or PRODIGY cryoprobe operating at 500.12 or 500.23 MHz for protons. Experiments were performed in deuterated DMSO and each sample was prepared to ca. 10 mM concentration.

Results

Chemical shifts and integration of $^1$H-NMR signals from AP1189 salts are given in Table 37.

TABLE 37

Chemical shifts and integration of $^1$H-NMR signals from AP1189 salts. In DMSO-$d_6$.

| AP1189 Salt | $^1$H-NMR data Chemical shift (ppm) | Integration |
|---|---|---|
| Acetic Acid | 8.16 | 1.00 |
| | 7.89 | 1.04 |
| | 7.78 | 1.05 |
| | 7.63 | 2.04 |
| | 6.99 | 1.00 |
| | 6.65 | 1.07 |
| | 6.48 | 1.20 |
| | 6.30 | 1.72 |
| | 6.21 | 2.31 |
| | 4.04 | 0.28 |
| | 3.64 | 0.40 |
| | 3.57 | 1.32 |
| | 1.98 | 0.30 |
| | 1.84 | 2.98 |
| | 1.26 | 0.54 |
| | 1.17 | 0.18 |
| | 0.87 | 0.09 |
| p-Toluenesulfonic acid | 11.07 | 0.97 |
| | 8.16 | 1.00 |
| | 7.92 | 1.08 |
| | 7.82 | 1.08 |
| | 7.74 | 1.09 |
| | 7.66 | 1.11 |
| | 7.49 | 2.32 |
| | 7.37 | 3.26 |
| | 7.15 | 3.29 |
| | 6.80 | 1.05 |
| | 6.59 | 1.11 |
| | 6.34 | 2.04 |
| | 2.28 | 3.18 |
| | 2.04 | 0.16 |
| | 1.87 | 0.05 |
| | 1.27 | 0.77 |
| | 0.85 | 0.11 |
| Fumaric acid | 13.34 | 1.42 |
| | 8.17 | 1.00 |
| | 7.90 | 1.37 |
| | 7.80 | 1.18 |
| | 7.73 | 1.14 |
| | 7.65 | 1.23 |
| | 7.08 | 0.92 |
| | 6.76 | 0.90 |
| | 6.52 | 0.91 |
| | 6.46 | 1.73 |
| | 6.41 | 0.94 |
| | 6.33 | 0.92 |
| | 2.09 | 0.17 |
| | 1.90 | 0.01 |
| | 1.24 | 0.16 |
| Succinic acid | 13.80 | 1.02 |
| | 8.17 | 1.00 |
| | 7.90 | 1.05 |
| | 7.79 | 1.08 |
| | 7.67 | 2.06 |
| | 7.05 | 1.47 |
| | 6.93 | 3.12 |
| | 6.71 | 1.06 |
| | 6.50 | 2.11 |

TABLE 37-continued

Chemical shifts and integration of $^1$H-NMR signals from AP1189 salts. In DMSO-$d_6$.

| AP1189 Salt | $^1$H-NMR data Chemical shift (ppm) | Integration |
|---|---|---|
| | 6.29 | 0.98 |
| | 3.77 | 0.14 |
| | 2.33 | 4.10 |
| | 1.88 | 0.06 |
| | 1.23 | 0.32 |
| | 1.04 | 0.29 |
| | 0.84 | 0.06 |

AP1189 napadisylate pattern 2:0.7543 (11.0629); 2.557 (8.8634); 1 (8.1806); 2.6217 (7.941); 0.974 (7.9028); 1.0037 (7.7975); 0.8754 (7.739); 1.0347 (7.656); 3.5752 (7.4103); 0.8399 (7.096); 0.7845 (6.7841); 0.7859 (6.5499); 1.5389 (6.3551); 2.0976 (1.764).

AP1189 esylate pattern 1:1 (11.2407); 1.0302 (8.1724); 1.0864 (7.9088); 1.1096 (7.7985); 1.0938 (7.7285); 1.1564 (7.6532); 3.1799 (7.5066); 1.0215 (7.0896); 1.0396 (6.7843); 1.0711 (6.5428); 2.0916 (6.3686); 2.2641 (2.4374); 3.2592 (1.0734).

AP1189 edisylate pattern 1:0.9389 (11.1051); 1 (8.1816); 1.1764 (7.915); 1.2168 (7.8057); 1.0864 (7.7419); 1.1486 (7.66119); 4.2764 (7.4823); 1.1528 (7.1064); 1.0797 (6.7887); 1.1652 (6.5561); 1.941 (6.3703); 3.1838 (2.6499).

AP1189 edisylate pattern 2:1 (8.1754); 1.0457 (7.9043); 1.055 (7.7933); 1.0496 (7.7126); 1.0385 (7.6399); 3.6468 (7.2657); 1.0648 (7.074); 1.0135 (6.758); 1.0489 (6.5107); 2.0588 (6.3692); 1.8314 (2.6762); 0.4358 (1.8961).

AP1189 edisylate pattern 4:0.9704 (11.1726); 0.3728 (8.6189); 1 (8.1889); 1.0879 (7.9082); 1.1163 (7.8048); 1.1018 (7.7262); 1.2479 (7.649); 3.9613 (7.4808); 1.239 (7.081); 1.0035 (6.7776); 0.9982 (6.5529); 1.9363 (6.364); 5.8322 (2.7036); 0.3181 (1.9026); 2.3234 (1.7578).

AP1189 edisylate pattern 5:1 (11.1488); 1.0198 (8.1751); 1.0482 (7.9077); 1.0504 (7.7991); 1.0194 (7.7345); 1.0616 (7.6536); 3.4068 (7.4789); 0.9855 (7.0894); 1.0035 (6.7829); 1.0279 (6.5554); 2.0024 (6.3682); 2.1727 (2.6737).

AP1189 nitrate pattern 1:0.855 (11.0579); 1 (8.1758); 1.1992 (7.9089); 1.1124 (7.8009); 1.1028 (7.7426); 1.1063 (7.6607); 3.1664 (7.4236); 0.9762 (7.0947); 0.9159 (6.7819); 0.9574 (6.5523); 1.984 (6.3525); 0.3361 (2.0666); 0.2449 (1.909); 0.3598 (0.9061).

AP1189 cyclamate pattern 2:0.8634 (11.3476); 1 (8.1712); 1.0915 (7.9119); 1.0957 (7.7968); 1.0703 (7.7201); 1.1419 (7.6556); 3.5247 (7.5221); 1.0013 (7.0879); 1.0173 (6.7856); 1.0326 (6.5094); 2.0216 (6.3759); 1.0084 (2.8695); 0.0439 (2.0639); 2.0563 (1.889); 2.0597 (1.599); 1.0453 (1.4747); 2.129 (1.157); 3.1001 (1.0312); 0.0716 (0.9069).

AP1189 cyclamate pattern 4:0.9437 (11.3653); 1 (8.1707); 1.0501 (7.9029); 1.0542 (7.7958); 1.0598 (7.7205); 1.0888 (7.6517); 3.4746 (7.4706); 0.9954 (7.0905); 1.0072 (6.7896); 1.0321 (6.5128); 1.994 (6.3726); 1.0213 (2.877); 0.7166 (1.909); 1.9717 (1.8707); 2.0065 (1.5967); 0.9909 (1.4832); 2.0949 (1.1546); 3.0111 (1.037).

AP1189 besylate pattern 1:0.8981 (11.0474); 1 (8.1732); 1.0646 (7.9073); 1.077 (7.8033); 1.0818 (7.7354); 1.0947 (7.6588); 2.0107 (7.5938); 3.1874 (7.4508); 3.2895 (7.3107); 1.0376 (7.0824); 1.0335 (6.7775); 1.0395 (6.5391); 2.042 (6.3614); 0.081 (1.9071); 0.1755 (1.0388).

AP1189 oxalate pattern 1:1 (8.1532); 1.0304 (7.8871); 1.0453 (7.7725); 1.0065 (7.681); 1.0478 (7.6319); 2.9399 (7.1515); 1.1976 (7.0314); 1.0234 (6.7175); 2.04 (6.4104); 1.014 (6.3244); 0.105 (1.0377).

AP1189 oxalate pattern 2:1 (8.1689); 1.0959 (7.902); 1.0853 (7.7878); 1.2373 (7.7194); 1.4553 (7.6482); 2.6457 (7.5415); 0.988 (7.0686); 1.0003 (6.7689); 2.0665 (6.4477); 0.9929 (6.3465); 0.063 (2.0968).

AP1189 oxalate pattern 4:1 (8.1515); 1.0445 (7.8892); 1.0462 (7.7742); 1.0282 (7.6758); 1.0219 (7.6301); 2.6642 (7.1097); 1.2483 (7.024); 1.0034 (6.7159); 2.0859 (6.3975); 0.997 (6.3192); 0.1217 (1.7624).

AP1189 (+)-camphor-10-sulfonic acid pattern 1:0.8814 (11.1521); 1 (8.1744); 1.0627 (7.9089); 1.0996 (7.8055); 1.0638 (7.7356); 1.114 (7.6573); 3.3236 (7.4351); 1.012 (7.0913); 1.0191 (6.7741); 1.0391 (6.5267); 2.0264 (6.3743); 1.0414 (2.8818); 1.35 (2.661); 1.381 (2.3787); 1.0478 (2.2319); 1.0068 (1.9412); 0.0876 (1.9105); 0.9801 (1.8546); 1.1612 (1.7889); 2.1252 (1.276); 3.0996 (1.0314); 3.0831 (0.7379).

AP1189 oxoglutarate pattern 1:1 (8.1669); 1.8014 (7.8993); 1.5121 (7.7883); 1.1804 (7.7205); 1.0352 (7.6395); 0.9369 (7.0709); 0.9511 (6.7756); 0.9802 (6.5257); 1.8945 (6.3703); 2.0183 (2.7771); 2.0935 (2.3762); 3.775 (2.0831); 0.2799 (1.9065).

AP1189 DL-mandelic acid pattern 2:1 (8.1765); 1.1357 (7.9075); 1.1573 (7.8014); 2.282 (7.658); 2.4615 (7.373); 2.4095 (7.2395); 1.2411 (7.1718); 1.0362 (7.0527); 0.9926 (6.7419); 2.2546 (6.4249); 0.9906 (6.3355); 1.1242 (4.6566); 1.9165 (2.4309); 2.6899 (2.0752); 2.7184 (0.9137).

AP1189 DL-mandelic acid pattern 3:1 (8.1719); 1.0907 (7.8985); 1.1332 (7.7964); 2.0988 (7.6516); 3.1244 (7.3791); 1.5978 (7.3108); 2.5396 (7.2455); 1.2963 (7.173); 1.0635 (7.0434); 0.9514 (6.7353); 2.2616 (6.418); 0.9986 (6.3312); 1.0491 (4.6436); 1.5842 (2.0853); 0.9834 (1.8978); 0.3683 (0.9089).

AP1189 hippuric acid pattern 1:0.7548 (13.5715); 1.1969 (8.3963); 1 (8.16); 1.0703 (7.8863); 2.3929 (7.8433); 1.087 (7.7812); 1.0158 (7.6668); 1.0966 (7.633); 1.3863 (7.5276); 2.6135 (7.4589); 1.2686 (7.0294); 1.028 (6.7102); 1.0111 (6.4352); 0.9644 (6.3695); 1.0492 (6.3181); 2.4392 (3.7385); 0.3539 (2.0654); 0.4149 (1.8873); 0.3571 (0.9132).

AP1189 formic acid pattern 1:1.0292 (8.2978); 1 (8.1572); 1.11 (7.8919); 1.1402 (7.7789); 2.0493 (7.6393); 1.4368 (7.0232); 1.0484 (6.6976); 1.0843 (6.4271); 0.8414 (6.3563); 1.3615 (6.315).

AP189 L-lactic acid pattern 1:1 (8.1477); 1.0199 (7.8914); 1.0281 (7.7688); 1.016 (7.6355); 0.912 (7.5871); 0.8946 (6.9724); 0.9739 (6.6292); 0.9826 (6.4603); 1.1694 (6.2913); 2.0197 (6.1996); 3.1739 (1.8746).

AP1189 DL-lactic acid pattern 1:1 (8.162); 1.0734 (7.8983); 1.089 (7.7857); 1.1388 (7.6686); 0.8544 (7.6311); 3.8862 (7.0181); 1.0121 (6.703); 1.8676 (6.4245); 1.4225 (6.3346); 1.1312 (3.8217); 3.4204 (1.1735).

AP1189 glutaric acid pattern 1:1 (8.1619); 1.2231 (7.8898); 1.2238 (7.7746); 2.2688 (7.6176); 1.1544 (6.9851); 1.1233 (6.6576); 2.5919 (6.4392); 2.628 (6.2658); 5.0598 (2.1953); 0.155 (2.0861); 2.5366 (1.6883).

AP1189 glutaric acid pattern 2:1 (8.1501); 1.0837 (7.8878); 1.0944 (7.7738); 2.0793 (7.6257); 1.07 (6.9923); 1.5227 (6.6621); 1.5132 (6.44); 2.1718 (6.286); 4.2751 (2.1788); 0.1721 (1.8732); 2.132 (1.677); 0.0775 (0.9072).

AP1189 glutaric acid pattern 4:1 (8.1477); 1.0427 (7.889); 1.0498 (7.7725); 2.067 (7.6188); 1.0236 (6.9887); 1.0425 (6.6531); 4.4525 (6.4277); 2.3299 (6.2728); 4.2147 (2.1823); 2.0993 (1.6841).

AP1189 adipic acid pattern 1:1 (8.1534); 1.0731 (7.889); 1.1078 (7.7765); 2.1422 (7.6374); 1.3346 (7.0193); 1.1785 (6.6987); 1.078 (6.4364); 2.1349 (6.3344); 0.3194 (3.7674); 6.2668 (2.1336); 1.1285 (1.8523); 6.2972 (1.4746); 1.5977 (1.0395).

Conclusion

Chemical shift values and integration of peaks corresponds to the expected salts.

Example 6: Solubility of AP1189 and its Salts

Methods

The solubility of AP1189 acetate (XRPD pattern 1), fumarate (XRPD pattern 1), and succinate (XRDP pattern 1) salts were assessed in 0.5 M buffer solutions having pH of 1.2 and 4.5.

Results

The results of the study are shown in tables 38a and 38b for 0.5 M and 0.2 M buffers, respectively. Table 38c shows the solubility of further AP1189 salts.

For the 0.5 M buffers, the highest solubility was observed for acetate Pattern 1. Higher solubility was observed for succinate Pattern 1 compared with fumarate Pattern 1. XRPD analysis showed acetate Pattern 1 remained at pH 4.5. At pH 1.2 for the acetate, a likely HCl salt (assigned as HCl Pattern 1) was formed. Succinic acid was obtained from the succinate Pattern 1 experiment at pH 1.2. The free succinic acid in the residual solids may indicate that the system was not saturated with respect to the API and the solubility may be higher than that reported.

TABLE 38a

Thermodynamic solubility results using 0.5 M buffers

| Test compound | Buffer | Initial pH | 24 h pH | Solubility (mM freebase) |
|---|---|---|---|---|
| Acetate Salt | pH 1.2 | 4.06 → 1.16 | 3.73 → 1.24 | 243.85 |
| Pattern 1 (Form A) | pH 4.5 | 4.60 | 4.60 | 1.05 |
| Fumarate | pH 1.2 | 1.46 → 1.19 | 1.23 | 7.84 |
| Salt Pattern 1 (Form D) | pH 4.5 | 4.55 | 4.50 | 1.64 |
| Succinate | pH 1.2 | 2.06 → 1.30 | 2.23 → 1.26 | 98.20 |
| Salt Pattern 1 (Form B) | pH 4.5 | 4.58 | 4.54 | 1.71 |

TABLE 38b

Thermodynamic solubility results using 0.2 M buffers

| Test compound | Buffer | Initial pH | 24 h pH | Salt or freebase input concentration (mM) | Solubility at 24 h (mM freebase) |
|---|---|---|---|---|---|
| Acetate | pH 1.2 | 3.74 → 1.24 | 3.44 → 1.23 | 210* | 134.10 |
| salt | pH 4.5 | 4.52 | 4.54 | 74 | 2.23 |
| | pH 6.8 | 6.85 | 6.81 | 69 | 1.18 |

TABLE 38b-continued

Thermodynamic solubility results using 0.2 M buffers

| Test compound | Buffer | Initial pH | 24 h pH | Salt or freebase input concentration (mM) | Solubility at 24 h (mM freebase) |
|---|---|---|---|---|---|
| Tosylate | pH 1.2 | 1.22 | 1.26 | 31 | 0.31 |
| Salt | pH 4.5 | 4.91 → 4.45 | 4.47 | 34 | 0.17 |
| | pH 6.8 | 6.77 | 6.87 | 30 | —‡ |
| Fumarate | pH 1.2 | 1.35 → 1.18 | 1.29 | 38 | 10.90 |
| Salt | pH 4.5 | 4.47 | 4.48 | 39 | 2.73 |
| | pH 6.8 | 6.61 → 11.24 → 6.84 | 6.65 → 6.74 | 39 | 0.86 |
| Succinate | pH 1.2 | 1.62 → 1.21 | 1.36 → 1.26 | 89* | >36.26** |
| Salt | pH 4.5 | 4.48 | 4.56 | 36 | 4.26 |
| | pH 6.8 | 6.61 → 6.80 | 6.42 → 7.03 → 6.82 | 41 | 0.78 |

→: pH adjusted using hydrochloric acid or sodium hydroxide

*: Estimated input concentration

**: Fully soluble, input material was not sufficient to maintain a slurry

‡: Not detected

For pH 1.2 succinate experiments there was insufficient available material at the time of experiment to maintain a suspension.

TABLE 38c

Solubility of additional AP1189 salts

| AP1189 salt form | Solubility HCl/KCl Buffer 0.5 M pH 1.2 | Salt form crystallised from |
|---|---|---|
| Napadisylate (Form III, IV) | <15 mM | 2-propanol:water 90:10 % v/v (Form III) or THF (Form IV) |
| Esylate (Form V) | <15 mM | methylethyl ketone |
| Edisylate (Form VII) | <15 mM | methylethyl ketone |
| Nitrate (Form X) | — | THF |
| Cyclamate (Form XI, XII) | <15 mM | THF (Form XI) or acetone (Form XII) |
| Besylate (Form XIV) | ≥15 to <50 mM | 2-Propanol:water 80:20 % v/v |
| Oxalate (Form XV, XVI, XVII) | <15 mM | 2-Propanol:water 80:20 % v/v (Form XV) or acetone (Form XVI) or THF (Form XVII) |
| (+)-Camphor-10-sulfonic acid (Form XVIII) | <15 mM | 2-Propanol:water 80:20 % v/v |
| Oxoglutarate (Form XIX) | ≥15 to <50 mM | acetone |
| DL-Mandelic acid (Form XX) | ≥50 mM | methylethyl ketone |
| Hippuric acid (Form XXII) | ≥50 mM | methylethyl ketone |
| Formic acid (Form XXIII) | ≥15 to <50 mM | acetone |
| L-Lactic acid (Form XXIV) | ≥50 mM | acetone |
| DL-Lactic acid (Form XXV) | ≥15 to <50 mM | 2-propanol:water 80:20 % v/v |
| Glutaric acid (Form XXVI) | ≥15 to <50 mM | acetone |
| Adipic acid (Form XXIX) | ≥15 to <50 mM | 2-Propanol:water 80:20 % v/v |

Conclusion

The test compounds exhibited remarkably different solubilities, especially at low pH. Specifically, the acetate and succinate salts showed high solubility at pH 1.2, indicating the potential for using these compounds in applications where a high solubility at low pH is desirable.

Example 7: Polymorph Study of AP1189 Succinate

Materials and Methods

Approximately 300 mg of the received succinate salt was added to 14 mL vials. The required volume of the appropriate solvent system was added to each vial, and the experiments were stirred at 70-73° C. until complete dissolution was achieved. The experiments were then cooled to 68° C., and seeded with AP1189 succinate. 5 to 15% seed load was used. The experiments were stirred at 68° C. for another 1 h to allow for equilibration. The experiments were then cooled to 5° C. at 0.1° C./min, and stirred at 5° C. until isolation. The experiments (slurries) were vacuum filtered, and the cakes were each washed with 3 mL of the respective input solvent system (precooled at 5° C.). The solids were analysed by XRPD to check the polymorphic form. The remainder of the solids were druid under vacuum at ambient for ca. 3 days. The dried solids were characterised. The concentrations of the recovered mother liquors and was were determined by HPLC.

Results

Both damp and dried crystallised solids were consistent with Pattern 1 of the succinate salt. Table 39 summarises the findings of the study.

TABLE 39 results from polymorph study for AP1189 succinate. Succ. Patt. 1 is succinate Pattern 1.

| | Yield (%) | | Purity (% area) | | XRPD | |
|---|---|---|---|---|---|---|
| Solvent system | Isolated | HPLC | Solid | ML | Damp | Dried |
| 1-Propanol:water 50:50 v/v % | 67.7 | 82.9 | 96.52 | 80.94 | Succ. Patt. 1 | Succ. Patt. 1 |

TABLE 39-continued results from polymorph study for AP1189 succinate. Succ. Patt. 1 is succinate Pattern 1.

| | Yield (%) | | Purity (% area) | | XRPD | |
|---|---|---|---|---|---|---|
| Solvent system | Isolated | HPLC | Solid | ML | Damp | Dried |
| 2-Propanol:water 50:50 v/v % | 71.3 | 84.7 | 96.21 | 83.59 | Succ. Patt. 1 | Succ. Patt. 1 |
| Ethanol:water 75:25 v/v % | 65.9 | 74.3 | 96.22 | 88.75 | Succ. Patt. 1 | Succ. Patt. 1 |
| Ethanol:water 50:50 v/v % | 76.3 | 86.5 | 96.17 | 83.98 | Succ. Patt. 1 | Succ. Patt. 1 |

Conclusion

AP1189 succinate exhibiting the crystal form of Pattern 1 was obtained using various crystallisation conditions.

Example 8: Polymorph Study of AP1189 Succinate

Materials and Methods

Approximately 300 mg of AP1189 was added to 20 mL vials. The required volume of the appropriate solvent system was added to each vial, and the experiments were stirred at 65-69° C. The experiments were then cooled to 55° C., and seeded with AP1189 succinate. 2% seed load was used. The experiments were stirred at 55° C. for another 1 h to allow for equilibration. The experiments were then cooled to 5° C. at 0.1° C./min, and stirred at 5° C. After ca. 18 h of stirring at 5° C., 200 μL aliquot of each slurry was extracted and centrifuged using 0.2 μm nylon tubes. The isolated solids were dried under vacuum at ambient and analysed by HPLC (purity). The concentration and purity of the mother liquors were also determined by HPLC. To the remainder of the experiments, anti-solvent addition was carried out at 5° C., to reach the target final ratio. Afterwards, stirring continued at 5° C. for another ca. 4 h. The experiments (slurries) were vacuum filtered and the cakes each washed with 0.9 mL of the respective organic solvent (pre-cooled at 5° C.). The solids were dried under vacuum at ambient for ca. 48 h. The dried solids were characterised. The mother liquors were subsampled and analysed by HPLC for concentration and solution purity determination. The rest of the mother liquors were left open in an oven, to allow the solvents to evaporate under vacuum, at ambient. After 3 days, the residual solids were analysed by XRPD and HPLC (purity).

Results

All isolated solids were consistent with Pattern 1 of the succinate salt. Table 40 summarises the findings of the study.

TABLE 40 results from polymorph study for AP1189 succinate. Succ. Patt. 1 is succinate Pattern 1. PC is poorly crystalline.

| | | Yield (%) | | | Purity (% area) | | XRPD |
|---|---|---|---|---|---|---|---|
| Solvent | | | ML Conc. | | | | |
| system | Sample | Isolated | (mg/mL) | HPLC | Solid | ML | (Dried) |
| 1-propanol:water 50:50 v/v % | After cooling-only | — | 10.91 | 88.0 | 95.64 | 83.03 | — |
| | After isolation | 77.1 | 8.14 | 88.8 | 95.83 | 83.35 | Succ. Patt. 1 |
| | ML Evaporation | — | — | — | 88.82 | — | Succ Patt. 1, PC |
| Ethanol:water 50:50 v/v % | After cooling-only | — | 6.15 | 90.3 | 95.69 | 82.42 | — |
| | After isolation | 57.5 | 6.14 | 87.0 | 95.67 | 79.73 | Succ. Patt. 1 |
| | ML evaporation | — | — | — | 91.20 | — | Succ. Patt. 1, PC |

Conclusion

AP1189 succinate exhibiting the crystal form of Pattern 1 was obtained using various crystallisation conditions. Isolated yield obtained was between 65 and 80%. Addition of water as anti-solvent improved the theoretical yield by 2 to 6% % w/w.

Example 9: Polymorph Study of AP1189 Succinate

Materials and Methods

Approximately 5 g of AP1189 succinate was added to temperature controlled reactor in an EasyMax 102 (100 mL vessel). 55.6 mL (11.1 vol.) of 1-propanol/water (50:50 v/v %) was added to the reactor, and the experiment was stirred at 70° C. Target concentration was 90 mg/mL. Stirring speed was 200 rpm. When complete dissolution was observed, the experiment was cooled to 55° C., and seeded with AP1189 succinate. 2% seed load was used, and it persisted with evidence of slurry formation. Post-seeding, stirring continued at 55° C. for 2 hours to allow experiment to equilibrate. The experiment was cooled to 5° C. at 0.1° C./min, and allowed to stir at 5° C. for 1 h. Stirring speed was increased to 300 rpm during the cooling step. At 5° C., water (pH 7.22) was added to the experiment as an anti-solvent at 1 vol./hr, to reach a target ratio of 40:60% v/v. 14 mL (2.8 vol.) of water was added. Post-addition, stirring continued at 5° C. for ca. 6 hours. A subsample of the slurry was extracted into a 0.2 μm nylon tube and centrifuged. The concentration and solution purity of the isolated mother liquor were determined by HPLC. The isolated solid was dried under vacuum at ambient for ca. 4 days, and analysed by HPLC for purity analysis. At 5° C., more water was added as anti-solvent at 1 vol./hr, to reach a target ratio of 30:70% v/v. 23.4 mL (4.6 vol.) of water was added. Stirring speed was increased further to 350 rpm during the addition. Post-addition, stirring continued at 5° C. for another 90 min. At 5° C., the slurry was vacuum-filtered using Buchner funnel. The filter cake was washed with 10 mL (2 vol.) of water (precooled to 5° C.) and dried under vacuum at ambient for ca. 4 days. XRPD analysis was carried out on both the damp and dried solid sample. The dried solid was characterised. 10 mL aliquot of the mother liquor was left open in an oven to allow the solvent to evaporate under vacuum at ambient. The residual solid was analysed by XRPD and HPLC (purity). The concentration and solution purity of the rest of the mother liquor and the wash were determined by HPLC.

Results

All samples were consistent with AP1189 succinate salt having XRPD Pattern 1. The results are shown in Table 41.

TABLE 41 results from polymorph study for AP1189 succinate. Succ. Patt. 1 is succinate Pattern 1. PC is poorly crystalline. Starting solvent system: 1-propanol:water (50:50% v/v).

| Sample | Yield (%) Isolated | ML conc. (mg/mL) | HPLC | Purity (% area) Solid | ML | XRPD Wet | Dry |
|---|---|---|---|---|---|---|---|
| After ASA 1 (40:60 v/v) | — | 6.21 | 88.3 | 97.06 | 84.36 | — | Succ. Patt 1. |
| Final sample | 80.9 | 3.37 | 92.4 | 96.56 | 84.86 | Succ. Patt 1. | Succ. Patt 1. |
| Crust | 6.4 | — | — | 95.78 | — | — | Succ. Patt 1. |
| ML-Evap | — | — | — | 84.32 | — | — | Succ. Patt 1. |

Conclusion

AP1189 succinate exhibiting the crystal form of Pattern 1 was obtained.

Example 10: Polymorph Study of AP1189 Succinate

Materials and Methods

Approximately 10 g of the AP1189 succinate was added to temperature-controlled reactor in an EasyMax 402 (400 mL vessel). 100 mL (10 vol.) of 1-propanol:water (50:50 v/v %) was added to the reactor, and the experiment was stirred at 68° C. Concentration was 100 mg/mL. Stirring speed was 200 rpm. When complete dissolution was observed, the experiment was polish-filtered at 70° C. to remove any insoluble impurities, and the filtrate was added back into the reactor. 5 mL (0.5 vol.) of 1-propanol:water (50:50 v/v %) was used to wash the reactor and passed through the filter. 7 mL (0.7 vol.) of 1.propanol:water (50:50 v/v %) was used to filter into the reactor. Concentration was 90 mg/mL. The experiment was allowed to equilibrate at 65° C., and then cooled to 55° C. At 55° C., the experiment was seeded with 1% seed load, using AP1189 succinate. Post-seeding, the experiment was allowed to equilibrate at 55° C. for ca. 1 hour. At 5° C., water was added to the experiment as an anti-solvent at 1 vol./hr, to reach a target ratio of 30:70% v/v. 74.7 mL (7.4 vol.) of water was added. Stirring speed was increased stepwise to 250 rpm during the addition. Post-addition, stirring continued at 5° C. for ca. 2.5 hours. At 5° C., the slurry was vacuum filtered using Buchner funnel. The cake was washed with 10 mL (1 vol.) of water (pre-cooled to 5° C.), and dried under vacuum at ambient for 4 days. XRPD analysis was carried out on both the damp and dried solid sample. The dried solid was characterised. 10 mL aliquot of the mother liquor was left open in an oven to allow the solvent to evaporate under vacuum at ambient. The residual solid was analysed by XRPD and HPLC (purity). The concentration and solution purity of the rest of the mother liquor and the wash were determined by HPLC.

Results

All samples were consistent with AP1189 succinate salt having XRPD Pattern 1. The results are shown in Table 42.

TABLE 42 results from polymorph study for AP1189 succinate. Succ. Patt. 1 is succinate Pattern 1. PC is poorly crystalline. Starting solvent system: 1-propanol:water (50:50% v/v).

| | Yield (%) | | | | | | |
|---|---|---|---|---|---|---|---|
| | | ML conc. | | Purity (% area) | | XRPD | |
| Sample | Isolated | (mg/mL) | HPLC | Solid | ML | Wet | Dry |
| Final sample | 67.4 | 3.19 | 93.3 | 96.51 | 82.39 | Succ. Patt. 1 | Succ. Patt. 1 |
| Crust | 20.1 | — | — | 95.46 | — | — | Succ. Patt. 1 |
| ML-Evap | — | — | — | 81.57 | — | — | Succ. Patt. 1 |

Conclusion

AP1189 succinate exhibiting the crystal form of Pattern 1 was obtained.

Example 11: Further Solubility Study of AP1189 Acetate and AP1189 Succinate

Materials and Methods 3.4 g of AP1189 succinate and 2.9 g of AP1189 acetate were added to separate vials containing 10.0 mL of buffer solution pH 1.2 (one determination per salt). For the AP1189 acetate and AP1189 succinate solutions, the pH was measured to 3.9 and 2.2 respectively. As a result, the pH was adjusted to 1.2 with concentrated hydrochloric acid in both solutions. Both sample preparations were diluted 500 times with the sample diluent (acetonitrile:water 1:1 v/v).

The diluted samples preparations were analysed by HPLC within 5 hours from preparation and the content of AP1189 was determined from the area under the curve by comparing to standard solutions of AP1189 acetate and AP1189 succinate respectively.

Equilibrium solubilities were also assessed at pH 4.5 and pH 6.8 following the procedure as described in WHO Technical Report Series 1019, 2019 annex 4: Protocol to conduct equilibrium solubility experiments for the purpose of Biopharmaceutics Classification System-based classification of active pharmaceutical ingredients for biowaiver.

Results

The sample materials in both vials were fully dissolved prior to dilution.

The solubilities of the test compounds at pH 1.2 are shown in Table 43. The solubilities of the test compounds at pH 4.5 and pH 6.8 are shown in Table 44, where all purities were found to be within 92% and 95%.

TABLE 43

Determined concentration of AP1189 acetate and AP1189 succinate in pH 1.2 samples. The HPLC purities are also included in the table. The first purity results are obtained from the CoAs for the lots and the second purity results were measured in the solubility experiment.

| Sample | pH 1.2 (time) | HPLC purity |
|---|---|---|
| AP1189 acetate | >617 mM (5 h)<br>>223 mg/mL | 99.3% → 92.5% |
| AP1189 succinate | >593 mM (0.5 h)<br>>245 mg/mL | 99.4% → 91.9% |

TABLE 44

Summarized equilibrium solubilities (including standard deviations) for AP1189 acetate and AP1189 succinate at 37° C. in buffer pH solutions 4.5 and 6.8. The HPLC purities are also included in the table. The first purity results are obtained from the CoAs for the lots and the second purity results were measured in the solubility experiment.

| Sample | pH 4.5 (time) | pH 6.8 (time) |
|---|---|---|
| AP1189 acetate | 3.2 mM ± 0.0 mM (22 h)<br>284 mg ± 3 mg/250 mL<br>99.3% → 91.9% | 2.4 mM ± 0.0 mM (22 h)<br>216 mg ± 2 mg/250 mL<br>99.3% → 94.5% |
| AP1189 succinate | 3.6 mM ± 0.0 mM (22 h)<br>370 mg ± 3 mg/250 mL<br>99.4% → 92.2% | 2.5 mM ± 0.1 mM (22 h)<br>261 mg ± 13 mg/250 mL<br>99.4% → 93.7% |

Example 12: Preparation of Further Polymorphs of AP1189 Salts

Tosylate Pattern 1

The tosylate salt of AP1189 having XRPD pattern 1 was prepared by crystallisation from methanol.

Fumarate Pattern 1

The fumarate salt of AP1189 having XRPD pattern 1 was prepared by crystallisation from isopropylalcohol:water 90:10 v/v.

Naphthalene-1,5-Disulfonic Acid Pattern 1

Naphthalene-1,5-Disulfonic Acid having XRPD Pattern 1 was prepared as follows: 50 mg of AP1189 Acetate was weighed into a 1.5 mL HPLC vial and dissolved in 500 μL 2-Propanol:water 90:10% v/v. A further 500 μL 2-Propanol: water 90:10% v/v was added to Naphthalene-1,5-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Naphthalene-1,5-Disulfonic Acid Pattern 2

Naphthalene-1,5-Disulfonic Acid having XRPD Pattern 2 was prepared as follows: 50 mg of AP1189 Acetate was weighed into a 1.5 mL HPLC vial and dissolved in 500 μL THF. A further 500 μL of THF was added to Naphthalene-1,5-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Ethanesulfonic Acid Pattern 1

Ethanesulfonic Acid having XRPD Pattern 1 was prepared as follows: 50 mg of AP1189 Acetate was weighed into a 1.5 mL HPLC vial and dissolved in 1 mL of methylethyl ketone. Ethanesulfonic acid (1.1 molar equivalents) was transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Ethane-1,2-disulfonic Acid Pattern 1

Ethane-1,2-disulfonic Acid having XRPD Pattern 1 was prepared as follows: 50 mg of AP1189 Acetate was weighed into a 1.5 mL HPLC vial and dissolved in 500 μL 2-Propanol:water (80:20% v/v). A further 500 μL of 2-Propanol: water (80:20% v/v) was added to Ethane-1,2-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD giving Pattern 1. Sample was dried at 40° C. under vacuum for 24 hours then reanalysed by XRPD giving Pattern 5. After storage at 40° C./75% RH for 24 hours the diffractogram was consistent with pattern 1 by XRPD.

Ethane-1,2-disulfonic Acid Pattern 2

Ethane-1,2-disulfonic having XRPD Acid Pattern 2 was prepared as follows: 50 mg of AP1189 Acetate was weighed into a 1.5 mL HPLC vial and dissolved in 500 μL methylethyl ketone. A further 500 μL of methylethyl ketone was added to Ethane-1,2-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Ethane-1,2-disulfonic Acid Pattern 4

Ethane-1,2-disulfonic Acid having XRPD Pattern 4 was prepared as follows: 50 mg of AP1189 Acetate was weighed into a 1.5 mL HPLC vial and dissolved in 500 μL THF. A further 500 μL of THF was added to Ethane-1,2-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Ethane-1,2-disulfonic Acid Pattern 5

Ethane-1,2-disulfonic Acid having XRPD Pattern 5 was prepared as follows: 50 mg of AP1189 Acetate was weighed into a 1.5 mL HPLC vial and dissolved in 500 μL 2-Propanol:water (80:20% v/v). A further 500 μL of 2-Propanol: water (80:20% v/v) was added to Ethane-1,2-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Nitric Acid Pattern 1

Nitric Acid having XRPD Pattern 1 was prepared as follows: 50 mg of AP1189 Acetate was weighed into a 1.5 mL HPLC vial and dissolved in 1 mL of THF. Nitric acid (1.1 molar equivalents) was transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Cyclamic Acid Pattern 2

Cyclamic Acid having XRPD Pattern 2 was prepared as follows: 50 mg of AP1189 Acetate was weighed into a 1.5 mL HPLC vial and dissolved in 500 μL THF. A further 500 μL of THF was added to Cyclamic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Cyclamic Acid Pattern 4

Cyclamic Acid having XRPD Pattern 4 was prepared as follows:

50 mg of AP1189 Acetate was weighed into a 1.5 mL HPLC vial and dissolved in 500 μL Acetone. A further 500 μL of Acetone was added to Cyclamic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Cyclamic Acid Pattern 5

Cyclamic Acid having XRPD Pattern 5 was prepared as follows:

50 mg of AP1189 Acetate was weighed into a 1.5 mL HPLC vial and dissolved in 500 μL THF. A further 500 μL of THF was added to Ethane-1,2-disulfonic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD. After storage at 40° C./75% RH for 24 hours the diffractogram was consistent with pattern 5 by XRPD.

Benzenesulfonic Acid Pattern 1

Benzenesulfonic Acid having XRPD Pattern 1 was prepared as follows:

50 mg of AP1189 Acetate was weighed into a 1.5 mL HPLC vial and dissolved in 1 mL of 2-Propanol:water 80:20% v/v. Benzenesulfonic acid (1.1 molar equivalents) was transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Oxalic Acid Pattern 1

Oxalic Acid having XRPD Pattern 1 was prepared as follows:

50 mg of AP1189 Acetate was weighed into a 1.5 mL HPLC vial and dissolved in 500 μL 2-Propanol:water 80:20% v/v. A further 500 μL of 2-Propanol:water 80:20% v/v was added to Oxalic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Oxalic Acid Pattern 2

Oxalic Acid having XRPD Pattern 2 was prepared as follows:

50 mg of AP1189 Acetate was weighed into a 1.5 mL HPLC vial and dissolved in 500 μL Acetone. A further 500 μL of Acetone was added to Oxalic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Oxalic Acid Pattern 4

Oxalic Acid having XRPD Pattern 4 was prepared as follows:

50 mg of AP1189 Acetate was weighed into a 1.5 mL HPLC vial and dissolved in 500 μL THF. A further 500 μL of THF was added to Oxalic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

(+)-Camphor-10-Sulfonic Acid Pattern 1

(+)-Camphor-10-Sulfonic Acid having XRPD Pattern 1 was prepared as follows:

50 mg of AP1189 Acetate was weighed into a 1.5 mL HPLC vial and dissolved in 1 mL of 2-Propanol:water 80:20% v/v. (+)-camphor-10-sulfonic acid (1.1 molar equivalents) was transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Ketoglutaric Acid Pattern 1

Ketoglutaric Acid having XRPD Pattern 1 was prepared as follows:

50 mg of AP1189 Acetate was weighed into a 1.5 mL HPLC vial and dissolved in 1 mL of Acetone. Ketoglutaric acid (1.1 molar equivalents) was transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

DL-Mandelic Acid Pattern 2

DL-Mandelic Acid having XRPD Pattern 2 was prepared as follows:

50 mg of AP1189 Acetate was weighed into a 1.5 mL HPLC vial and dissolved in 500 μL methylethyl ketone. A further 500 μL of methylethyl ketone was added to DL-Mandelic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

DL-Mandelic Acid Pattern 3

DL-Mandelic Acid having XRPD Pattern 3 was prepared as follows:

50 mg of AP1189 Acetate was weighed into a 1.5 mL HPLC vial and dissolved in 500 μL Acetone. A further 500 μL of Acetone was added to DL-Mandelic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Hippuric Acid Pattern 1

Hippuric Acid having XRPD Pattern 1 was prepared as follows:

50 mg of AP1189 Acetate was weighed into a 1.5 mL HPLC vial and dissolved in 500 μL methylethyl ketone. A further 500 μL of methylethyl ketone was added to Hippuric acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Formic Acid Pattern 1

Formic Acid having XRPD Pattern 1 was prepared as follows:

50 mg of AP1189 Acetate was weighed into a 1.5 mL HPLC vial and dissolved in 1 mL of Acetone. Formic acid (1.1 molar equivalents) was transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

L-Lactic Acid Pattern 1

L-Lactic Acid having XRPD Pattern 1 was prepared as follows:

50 mg of AP1189 Acetate was weighed into a 1.5 mL HPLC vial and dissolved in 500 μL Acetone. A further 500 μL of Acetone was added to L-Lactic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

DL-Lactic Acid Pattern 1

DL-Lactic Acid having XRPD Pattern 1 was prepared as follows:

50 mg of AP1189 Acetate was weighed into a 1.5 mL HPLC vial and dissolved in 500 μL 2-propanol:water 80:20% v/v. A further 500 μL of 2-propanol:water 80:20% v/v was added to DL-Lactic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Glutaric Acid Pattern 1

Glutaric Acid having XRPD Pattern 1 was prepared as follows:

50 mg of AP1189 Acetate was weighed into a 1.5 mL HPLC vial and dissolved in 500 μL Acetone. A further 500 μL of Acetone was added to Glutaric acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Glutaric Acid Pattern 2

Glutaric Acid having XRPD Pattern 2 was prepared as follows:

50 mg of AP1189 Acetate was weighed into a 1.5 mL HPLC vial and dissolved in 500 μL methylethyl ketone. A further 500 μL of methylethyl ketone was added to Glutaric acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Glutaric Acid Pattern 4

50 mg of AP1189 Acetate was weighed into a 1.5 mL HPLC vial and dissolved in 500 μL Acetone. A further 500 μL of Acetone was added to Glutaric acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD giving Pattern 1. Storage of Pattern 1 at 40° C./75% RH for 24 hours resulted in a new pattern by XRPD (Pattern 4)

Adipic Acid Pattern 1

Adipic Acid having XRPD Pattern 1 was prepared as follows:

50 mg of AP1189 Acetate was weighed into a 1.5 mL HPLC vial and dissolved in 500 μL 2-Propanol:water 80:20% v/v. A further 500 μL of 2-Propanol:water 80:20% v/v was added to Adipic acid (1.1 molar equivalents), which was then transferred by pipette into the API. The resulting mixture was thermally cycled for 3 days between 40° C. and 5° C. (Ramp rate: 0.1° C./min with isothermal holds of 1 hour at 40° C. and 5° C.). Solids were isolated by centrifuge filtration and analysed wet by XRPD. Sample was dried at 40° C. under vacuum for 24 hours then reanalysed by XRPD.

Example 13: FT-IR Measurements

Materials and Methods

Infrared spectroscopy was carried out on a Bruker ALPHA P spectrometer. Sufficient material was placed onto the centre of the plate of the spectrometer and the spectra were obtained using the following parameters: Resolution: 4 $cm^{-1}$; Background Scan Time: 16 scans; Sample Scan Time: 16 scans; Data Collection: 4000 to 400 $cm^{-1}$, Result Spectrum: Transmittance; Software: OPUS version 6.

Results

Tables 45-68 show the FT-IR peak lists for various AP1189 salt polymorphs.

FIG. 92 shows the IR spectrum of AP1189 acetate Pattern 1.

TABLE 45

FT-IR peak list for AP1189 napadisylate Pattern 1

| Wavenumber | Absolute Intensity | Relative Intensity |
|---|---|---|
| 3466.6868 | 0.886 | 0.028 |
| 3348.6067 | 0.877 | 0.078 |
| 3191.3211 | 0.895 | 0.005 |
| 3151.5669 | 0.898 | 0.001 |
| 3118.6795 | 0.9 | 0.002 |
| 3043.0897 | 0.901 | 0.006 |
| 2968.754 | 0.91 | 0.007 |
| 2872.5429 | 0.92 | 0.003 |
| 1675.6159 | 0.787 | 0.084 |
| 1632.1472 | 0.684 | 0.245 |
| 1531.9778 | 0.681 | 0.269 |
| 1494.9203 | 0.83 | 0.074 |
| 1440.297 | 0.795 | 0.138 |
| 1347.2845 | 0.725 | 0.209 |
| 1295.435 | 0.881 | 0.05 |
| 1237.4246 | 0.815 | 0.084 |

TABLE 45-continued

FT-IR peak list for AP1189 napadisylate Pattern 1

| Wavenumber | Absolute Intensity | Relative Intensity |
|---|---|---|
| 1217.2817 | 0.79 | 0.064 |
| 1193.3462 | 0.747 | 0.08 |
| 1166.4915 | 0.664 | 0.26 |
| 1081.1736 | 0.832 | 0.063 |
| 1025.0437 | 0.574 | 0.373 |
| 1025.0437 | 0.574 | 0.373 |
| 968.7163 | 0.7 | 0.182 |
| 890.1769 | 0.892 | 0.035 |
| 870.6032 | 0.916 | 0.008 |
| 855.9669 | 0.849 | 0.085 |
| 839.5018 | 0.918 | 0.012 |
| 793.4597 | 0.734 | 0.182 |
| 776.4759 | 0.797 | 0.047 |
| 758.5855 | 0.743 | 0.113 |
| 721.6015 | 0.622 | 0.243 |
| 661.4094 | 0.796 | 0.022 |
| 644.2371 | 0.781 | 0.024 |
| 644.2371 | 0.781 | 0.024 |
| 599.9555 | 0.586 | 0.086 |
| 558.3191 | 0.596 | 0.048 |
| 518.543 | 0.562 | 0.118 |
| 518.543 | 0.562 | 0.182 |
| 463.4629 | 0.572 | 0.096 |
| 463.4629 | 0.572 | 0.115 |
| 441.8127 | 0.655 | 0.02 |

TABLE 46

FT-IR peak list for AP1189 napadisylate Pattern 2

| Wavenumber | Absolute Intensity | Relative Intensity |
|---|---|---|
| 3457.0059 | 0.915 | 0.001 |
| 3330.9717 | 0.895 | 0.001 |
| 3121.7024 | 0.877 | 0.003 |
| 1676.3847 | 0.833 | 0.053 |
| 1624.8494 | 0.789 | 0.109 |
| 1606.2505 | 0.811 | 0.009 |
| 1579.1694 | 0.836 | 0.017 |
| 1527.463 | 0.779 | 0.142 |
| 1493.3067 | 0.835 | 0.034 |
| 1444.2738 | 0.846 | 0.036 |
| 1414.9494 | 0.881 | 0.005 |
| 1395.9339 | 0.875 | 0.018 |
| 1348.1145 | 0.836 | 0.062 |
| 1297.3292 | 0.888 | 0.01 |
| 1237.2278 | 0.839 | 0.019 |
| 1189.0537 | 0.713 | 0.019 |
| 1155.8105 | 0.703 | 0.143 |
| 1029.7055 | 0.641 | 0.249 |
| 969.3187 | 0.744 | 0.036 |
| 888.0521 | 0.823 | 0.022 |
| 850.9679 | 0.824 | 0.037 |
| 790.0213 | 0.729 | 0.102 |
| 765.1716 | 0.725 | 0.122 |
| 720.6873 | 0.77 | 0.013 |
| 700.4846 | 0.759 | 0.033 |
| 662.5114 | 0.753 | 0.034 |
| 601.4669 | 0.575 | 0.152 |
| 601.4669 | 0.575 | 0.152 |
| 564.0144 | 0.639 | 0.029 |
| 525.7536 | 0.621 | 0.051 |
| 491.9536 | 0.652 | 0.005 |
| 462.2125 | 0.621 | 0.049 |

TABLE 47

| FT-IR peak list for AP1189 esylate Pattern 1. | | |
|---|---|---|
| Wavenumber | Absolute Intensity | Relative Intensity |
| 3349.7247 | 0.955 | 0.001 |
| 3277.377 | 0.957 | 0.005 |
| 3187.823 | 0.947 | 0.001 |
| 3141.9143 | 0.934 | 0.06 |
| 3017.314 | 0.958 | 0.007 |
| 2935.0847 | 0.962 | 0.009 |
| 2879.2134 | 0.971 | 0.001 |
| 1684.2122 | 0.907 | 0.046 |
| 1656.4218 | 0.942 | 0.006 |
| 1627.0362 | 0.864 | 0.117 |
| 1612.4111 | 0.888 | 0.016 |
| 1526.9552 | 0.886 | 0.091 |
| 1494.7631 | 0.919 | 0.04 |
| 1459.0201 | 0.908 | 0.057 |
| 1446.057 | 0.924 | 0.017 |
| 1416.6283 | 0.964 | 0.007 |
| 1360.4768 | 0.918 | 0.055 |
| 1335.6655 | 0.926 | 0.033 |
| 1297.1634 | 0.948 | 0.021 |
| 1240.7436 | 0.939 | 0.027 |
| 1189.9984 | 0.855 | 0.112 |
| 1150.3317 | 0.869 | 0.044 |
| 1134.1169 | 0.873 | 0.009 |
| 1103.8023 | 0.909 | 0.016 |
| 1036.5662 | 0.826 | 0.155 |
| 1010.6467 | 0.936 | 0.008 |
| 982.056 | 0.898 | 0.059 |
| 982.056 | 0.898 | 0.059 |
| 982.056 | 0.898 | 0.059 |
| 982.056 | 0.898 | 0.059 |
| 887.7475 | 0.939 | 0.039 |
| 849.2158 | 0.95 | 0.028 |
| 783.8148 | 0.924 | 0.032 |
| 745.9402 | 0.869 | 0.104 |
| 745.9402 | 0.869 | 0.104 |
| 699.2813 | 0.877 | 0.066 |
| 651.1217 | 0.883 | 0.017 |
| 629.68 | 0.884 | 0.013 |
| 604.5022 | 0.88 | 0.036 |
| 577.5411 | 0.88 | 0.028 |
| 530.9237 | 0.871 | 0.084 |
| 490.6684 | 0.926 | 0.008 |
| 471.9556 | 0.888 | 0.055 |
| 471.9556 | 0.888 | 0.055 |
| 455.469 | 0.913 | 0.016 |
| 406.1926 | 0.94 | 0.007 |

TABLE 48

| FT-IR peak list for AP1189 edisylate Pattern 2. | | |
|---|---|---|
| Wavenumber | Absolute Intensity | Relative Intensity |
| 3462.9446 | 0.995 | 0.001 |
| 3257.0805 | 0.991 | 0.002 |
| 3150.1577 | 0.99 | 0.012 |
| 2884.3168 | 0.998 | 0 |
| 2866.5313 | 0.997 | 0 |
| 2866.5313 | 0.997 | 0 |
| 2826.2672 | 0.995 | 0.005 |
| 2242.0076 | 0.994 | 0.006 |
| 2159.6369 | 0.994 | 0.007 |
| 2135.3353 | 0.994 | 0.008 |
| 2035.2014 | 0.993 | 0.011 |
| 1985.1016 | 0.995 | 0.009 |
| 1926.5194 | 0.996 | 0.001 |
| 1901.158 | 0.996 | 0.002 |
| 1841.97 | 0.997 | 0.002 |
| 1816.3004 | 0.998 | 0.001 |
| 1808.22 | 0.998 | 0 |
| 1777.6607 | 0.997 | 0.002 |

TABLE 48-continued

| FT-IR peak list for AP1189 edisylate Pattern 2. | | |
|---|---|---|
| Wavenumber | Absolute Intensity | Relative Intensity |
| 1734.3136 | 0.997 | 0.002 |
| 1684.9728 | 0.984 | 0.009 |
| 1655.6732 | 0.989 | 0.003 |
| 1625.4399 | 0.974 | 0.026 |
| 1625.4399 | 0.974 | 0.026 |
| 1615.0231 | 0.98 | 0.001 |
| 1527.2346 | 0.982 | 0.014 |
| 1496.9895 | 0.991 | 0.004 |
| 1442.4714 | 0.989 | 0.008 |
| 1356.9431 | 0.989 | 0.008 |
| 1297.8821 | 0.995 | 0.002 |
| 1229.6559 | 0.981 | 0.008 |
| 1207.4986 | 0.981 | 0.007 |
| 1176.4347 | 0.981 | 0.016 |
| 1139.4076 | 0.988 | 0.003 |
| 1106.709 | 0.992 | 0.001 |
| 1065.3893 | 0.995 | 0.001 |
| 1027.718 | 0.973 | 0.026 |
| 1027.718 | 0.973 | 0.026 |
| 983.2416 | 0.986 | 0.009 |
| 983.2416 | 0.986 | 0.009 |
| 958.9998 | 0.994 | 0.002 |
| 958.9998 | 0.994 | 0.002 |
| 916.0674 | 0.996 | 0.001 |
| 898.6396 | 0.997 | 0 |
| 864.6502 | 0.996 | 0.001 |
| 850.6436 | 0.994 | 0.004 |
| 813.3872 | 0.995 | 0.001 |
| 790.6623 | 0.991 | 0.004 |
| 766.2961 | 0.988 | 0.007 |
| 731.909 | 0.983 | 0.013 |
| 702.5531 | 0.992 | 0.003 |

TABLE 49

| FT-IR peak list for AP1189 edisylate Pattern 4. | | |
|---|---|---|
| Wavenumber | Absolute Intensity | Relative Intensity |
| 2952.4532 | 0.953 | 0.003 |
| 2923.0149 | 0.912 | 0.087 |
| 2923.0149 | 0.912 | 0.087 |
| 2853.1668 | 0.945 | 0.024 |
| 2177.7444 | 0.991 | 0.003 |
| 2177.7444 | 0.991 | 0.003 |
| 2134.4653 | 0.989 | 0.009 |
| 1953.93 | 0.991 | 0.007 |
| 1742.2199 | 0.992 | 0.003 |
| 1684.2966 | 0.988 | 0.008 |
| 1601.1227 | 0.988 | 0 |
| 1523.9903 | 0.988 | 0.004 |
| 1494.8295 | 0.987 | 0.002 |
| 1457.1297 | 0.974 | 0.026 |
| 1376.8764 | 0.983 | 0.007 |
| 1362.1338 | 0.985 | 0.002 |
| 1338.7981 | 0.987 | 0.001 |
| 1315.6263 | 0.989 | 0.001 |
| 1228.4413 | 0.986 | 0.002 |
| 1191.3421 | 0.983 | 0.002 |
| 1163.1826 | 0.982 | 0.008 |
| 1081.7777 | 0.984 | 0.003 |
| 1026.5845 | 0.982 | 0.009 |
| 965.9176 | 0.983 | 0.005 |
| 949.699 | 0.985 | 0.001 |
| 848.3372 | 0.986 | 0.003 |
| 768.2207 | 0.983 | 0.008 |
| 734.2275 | 0.986 | 0.001 |
| 710.1008 | 0.985 | 0.001 |
| 686.0188 | 0.987 | 0.002 |
| 665.3046 | 0.985 | 0.003 |
| 616.5624 | 0.985 | 0.001 |

TABLE 49-continued

| FT-IR peak list for AP1189 edisylate Pattern 4. | | |
|---|---|---|
| Wavenumber | Absolute Intensity | Relative Intensity |
| 546.6271 | 0.98 | 0.009 |
| 526.3169 | 0.982 | 0.004 |
| 487.214 | 0.979 | 0.018 |
| 472.8975 | 0.983 | 0.001 |
| 438.7736 | 0.982 | 0.006 |
| 407.2507 | 0.984 | 0.003 |

TABLE 50

FT-IR peak list for AP1189 edisylate Pattern 5.

| Wavenumber | Absolute Intensity | Relative Intensity |
|---|---|---|
| 3474.8306 | 0.986 | 0.001 |
| 3411.0414 | 0.984 | 0 |
| 3359.3266 | 0.981 | 0.003 |
| 3174.2727 | 0.98 | 0.016 |
| 2472.9486 | 0.99 | 0.003 |
| 2428.6704 | 0.99 | 0.004 |
| 2346.2568 | 0.991 | 0.003 |
| 2304.5187 | 0.99 | 0.003 |
| 2256.8486 | 0.99 | 0.005 |
| 2237.9225 | 0.994 | 0 |
| 2199.0413 | 0.987 | 0.008 |
| 2153.65 | 0.987 | 0.009 |
| 1979.1896 | 0.992 | 0.004 |
| 1674.6247 | 0.964 | 0.02 |
| 1635.7648 | 0.96 | 0.036 |
| 1562.1009 | 0.986 | 0.002 |
| 1524.5681 | 0.964 | 0.025 |
| 1495.236 | 0.976 | 0.01 |
| 1445.9543 | 0.979 | 0.011 |
| 1427.2528 | 0.987 | 0.002 |
| 1412.9172 | 0.987 | 0.004 |
| 1353.4254 | 0.976 | 0.015 |
| 1297.1385 | 0.987 | 0.005 |
| 1241.464 | 0.972 | 0.015 |
| 1191.238 | 0.967 | 0.023 |
| 1134.2407 | 0.975 | 0.005 |
| 1080.2047 | 0.979 | 0.005 |
| 1025.609 | 0.95 | 0.043 |
| 1025.609 | 0.95 | 0.043 |
| 1008.4288 | 0.979 | 0.002 |
| 972.1472 | 0.976 | 0.011 |
| 888.5929 | 0.988 | 0.005 |
| 851.0858 | 0.984 | 0.008 |
| 775.0492 | 0.968 | 0.021 |
| 734.6082 | 0.969 | 0.013 |
| 734.6082 | 0.969 | 0.013 |
| 701.1599 | 0.979 | 0.006 |
| 701.1599 | 0.979 | 0.006 |
| 680.0768 | 0.985 | 0.001 |
| 608.8946 | 0.97 | 0.007 |
| 577.0193 | 0.97 | 0.004 |
| 555.0791 | 0.962 | 0.022 |
| 500.426 | 0.969 | 0.004 |
| 490.8807 | 0.969 | 0.013 |
| 459.2056 | 0.973 | 0.005 |
| 459.2056 | 0.973 | 0.005 |
| 449.358 | 0.973 | 0.004 |
| 408.8247 | 0.976 | 0.008 |

TABLE 51

FT-IR peak list for AP1189 nitrate Pattern 1.

| Wavenumber | Absolute Intensity | Relative Intensity |
|---|---|---|
| 3406.5302 | 0.962 | 0.013 |
| 3366.0481 | 0.967 | 0.003 |
| 3323.5268 | 0.967 | 0.001 |
| 3212.388 | 0.961 | 0.001 |
| 3163.9009 | 0.957 | 0.038 |
| 3127.5574 | 0.962 | 0.003 |
| 3005.5918 | 0.971 | 0 |
| 2913.8193 | 0.974 | 0.005 |
| 2871.3217 | 0.978 | 0.001 |
| 1680.7274 | 0.91 | 0.054 |
| 1680.7274 | 0.91 | 0.054 |
| 1624.0671 | 0.899 | 0.095 |
| 1528.6756 | 0.915 | 0.059 |
| 1528.6756 | 0.915 | 0.059 |
| 1497.3045 | 0.932 | 0.034 |
| 1497.3045 | 0.932 | 0.034 |
| 1466.4331 | 0.957 | 0.005 |
| 1447.1912 | 0.939 | 0.03 |
| 1447.1912 | 0.939 | 0.03 |
| 1384.114 | 0.9 | 0.078 |
| 1384.114 | 0.9 | 0.078 |
| 1359.8347 | 0.909 | 0.015 |
| 1331.1636 | 0.907 | 0.023 |
| 1242.2081 | 0.953 | 0.006 |
| 1186.1164 | 0.922 | 0.045 |
| 1186.1164 | 0.922 | 0.045 |
| 1154.2162 | 0.942 | 0.009 |
| 1132.4738 | 0.937 | 0.02 |
| 1081.0367 | 0.947 | 0.011 |
| 1048.6406 | 0.959 | 0.007 |
| 1038.6568 | 0.956 | 0.014 |
| 1003.3579 | 0.963 | 0.007 |
| 975.7122 | 0.916 | 0.059 |
| 936.6737 | 0.961 | 0.009 |
| 889.5881 | 0.962 | 0.017 |
| 851.0713 | 0.957 | 0.023 |
| 851.0713 | 0.957 | 0.023 |
| 820.317 | 0.952 | 0.025 |
| 820.317 | 0.952 | 0.025 |
| 781.2615 | 0.943 | 0.03 |
| 781.2615 | 0.943 | 0.03 |
| 753.3192 | 0.951 | 0.013 |
| 728.8132 | 0.927 | 0.02 |
| 684.2259 | 0.922 | 0.029 |
| 641.2375 | 0.935 | 0.005 |
| 607.5582 | 0.915 | 0.014 |
| 574.157 | 0.923 | 0.002 |
| 554.4784 | 0.915 | 0.004 |
| 523.0893 | 0.91 | 0.019 |
| 473.9605 | 0.901 | 0.045 |

TABLE 52

FT-IR peak list for AP1189 cyclamate Pattern 2

| Wavenumber | Absolute Intensity | Relative Intensity |
|---|---|---|
| 3327.5952 | 0.894 | 0.015 |
| 3256.7062 | 0.896 | 0.005 |
| 3133.7961 | 0.861 | 0.101 |
| 3051.8543 | 0.9 | 0.003 |
| 2926.2906 | 0.873 | 0.049 |
| 2852.1869 | 0.897 | 0.02 |
| 1681.758 | 0.816 | 0.086 |
| 1623.3821 | 0.737 | 0.216 |
| 1623.3821 | 0.737 | 0.216 |
| 1623.3821 | 0.737 | 0.216 |
| 1623.3821 | 0.737 | 0.216 |
| 1529.9469 | 0.745 | 0.192 |
| 1494.8375 | 0.836 | 0.08 |
| 1445.9552 | 0.819 | 0.104 |

TABLE 52-continued

| FT-IR peak list for AP1189 cyclamate Pattern 2 | | |
|---|---|---|
| Wavenumber | Absolute Intensity | Relative Intensity |
| 1415.3786 | 0.903 | 0.016 |
| 1353.8559 | 0.845 | 0.091 |
| 1336.4044 | 0.856 | 0.021 |
| 1296.3806 | 0.894 | 0.034 |
| 1264.8937 | 0.922 | 0.005 |
| 1242.4293 | 0.895 | 0.017 |
| 1184.9897 | 0.742 | 0.018 |
| 1156.8898 | 0.727 | 0.193 |
| 1134.2283 | 0.744 | 0.018 |
| 1083.0619 | 0.84 | 0.023 |
| 1029.6039 | 0.583 | 0.357 |
| 1029.6039 | 0.583 | 0.357 |
| 974.7489 | 0.79 | 0.1 |
| 903.7209 | 0.922 | 0.007 |
| 889.7243 | 0.878 | 0.046 |
| 864.5368 | 0.866 | 0.069 |
| 850.5855 | 0.867 | 0.033 |
| 836.2203 | 0.908 | 0.013 |
| 784.6589 | 0.827 | 0.065 |
| 751.7587 | 0.818 | 0.029 |
| 700.9984 | 0.722 | 0.055 |
| 630.931 | 0.735 | 0.005 |
| 605.618 | 0.677 | 0.216 |
| 559.4107 | 0.76 | 0.011 |
| 530.7647 | 0.749 | 0.052 |
| 471.4197 | 0.74 | 0.113 |
| 455.4746 | 0.767 | 0.028 |
| 410.2427 | 0.837 | 0.024 |

TABLE 53

| FT-IR peak list for AP1189 cyclamate Pattern 4 | | |
|---|---|---|
| Wavenumber | Absolute Intensity | Relative Intensity |
| 3604.5853 | 0.935 | 0.007 |
| 3343.728 | 0.852 | 0.036 |
| 3257.5858 | 0.868 | 0.007 |
| 3129.6006 | 0.825 | 0.127 |
| 3042.9076 | 0.871 | 0.01 |
| 2921.4146 | 0.831 | 0.067 |
| 2850.5435 | 0.857 | 0.036 |
| 2133.8407 | 0.95 | 0.003 |
| 2005.1942 | 0.955 | 0.012 |
| 1714.6479 | 0.927 | 0.006 |
| 1680.2622 | 0.728 | 0.136 |
| 1623.7709 | 0.65 | 0.268 |
| 1607.6163 | 0.658 | 0.066 |
| 1529.9951 | 0.653 | 0.254 |
| 1496.3013 | 0.77 | 0.113 |
| 1446.2453 | 0.746 | 0.151 |
| 1358.0905 | 0.779 | 0.122 |
| 1336.0631 | 0.812 | 0.053 |
| 1295.8377 | 0.862 | 0.033 |
| 1264.2435 | 0.872 | 0.012 |
| 1243.4692 | 0.829 | 0.032 |
| 1187.9086 | 0.642 | 0.24 |
| 1165.1333 | 0.65 | 0.04 |
| 1132.1103 | 0.701 | 0.023 |
| 1080.3651 | 0.783 | 0.051 |
| 1031.1931 | 0.507 | 0.409 |
| 1031.1931 | 0.507 | 0.409 |
| 1031.1931 | 0.507 | 0.409 |
| 972.5047 | 0.727 | 0.116 |
| 908.6013 | 0.876 | 0.017 |
| 889.2883 | 0.812 | 0.068 |
| 889.2883 | 0.812 | 0.068 |
| 869.394 | 0.809 | 0.088 |
| 851.4427 | 0.817 | 0.045 |
| 851.4427 | 0.817 | 0.045 |
| 837.7939 | 0.865 | 0.021 |

TABLE 53-continued

| FT-IR peak list for AP1189 cyclamate Pattern 4 | | |
|---|---|---|
| Wavenumber | Absolute Intensity | Relative Intensity |
| 800.6091 | 0.822 | 0.041 |
| 783.2208 | 0.754 | 0.103 |
| 752.268 | 0.756 | 0.054 |
| 701.8152 | 0.639 | 0.113 |
| 672.5668 | 0.657 | 0.014 |
| 640.3004 | 0.647 | 0.024 |
| 610.5714 | 0.586 | 0.268 |
| 555.1012 | 0.691 | 0.017 |
| 529.8224 | 0.691 | 0.043 |
| 472.8574 | 0.66 | 0.135 |
| 413.9675 | 0.796 | 0.009 |

TABLE 54

| FT-IR peak list for AP1189 cyclamate Pattern 5 | | |
|---|---|---|
| Wavenumber | Absolute Intensity | Relative Intensity |
| 3330.1338 | 0.845 | 0.025 |
| 3257.8603 | 0.847 | 0.007 |
| 3128.0082 | 0.787 | 0.091 |
| 3050.923 | 0.842 | 0.005 |
| 3015.2804 | 0.845 | 0.006 |
| 2923.7029 | 0.729 | 0.224 |
| 2852.3392 | 0.775 | 0.056 |
| 1683.2005 | 0.746 | 0.119 |
| 1621.6978 | 0.651 | 0.015 |
| 1607.4517 | 0.642 | 0.252 |
| 1528.9946 | 0.631 | 0.287 |
| 1494.4844 | 0.763 | 0.107 |
| 1445.2176 | 0.727 | 0.157 |
| 1415.5026 | 0.85 | 0.028 |
| 1353.5039 | 0.768 | 0.132 |
| 1336.1138 | 0.79 | 0.026 |
| 1296.8249 | 0.839 | 0.052 |
| 1265.711 | 0.882 | 0.008 |
| 1242.2991 | 0.848 | 0.022 |
| 1183.5642 | 0.656 | 0.026 |
| 1155.3181 | 0.64 | 0.02 |
| 1131.4271 | 0.625 | 0.169 |
| 1083.7773 | 0.716 | 0.014 |
| 1029.0064 | 0.472 | 0.439 |
| 1029.0064 | 0.472 | 0.439 |
| 971.4767 | 0.68 | 0.102 |
| 904.6085 | 0.874 | 0.013 |
| 889.124 | 0.8 | 0.074 |
| 865.1575 | 0.789 | 0.105 |
| 865.1575 | 0.789 | 0.105 |
| 865.1575 | 0.789 | 0.105 |
| 837.8596 | 0.851 | 0.014 |
| 784.4749 | 0.75 | 0.119 |
| 784.4749 | 0.75 | 0.119 |
| 752.6207 | 0.748 | 0.055 |
| 700.5195 | 0.634 | 0.033 |
| 659.5072 | 0.623 | 0.027 |
| 606.4863 | 0.549 | 0.302 |
| 555.7751 | 0.651 | 0.027 |
| 530.6326 | 0.663 | 0.043 |
| 469.1368 | 0.639 | 0.154 |
| 453.1841 | 0.681 | 0.033 |
| 408.2296 | 0.747 | 0.04 |

TABLE 55

| FT-IR peak list for AP1189 besylate Pattern 1. | | |
|---|---|---|
| Wavenumber | Absolute Intensity | Relative Intensity |
| 3381.0336 | 0.893 | 0.053 |
| 3335.7129 | 0.912 | 0.006 |
| 3262.156 | 0.906 | 0.017 |
| 3166.2704 | 0.87 | 0.011 |
| 3128.0067 | 0.867 | 0.111 |
| 3053.0452 | 0.911 | 0.007 |
| 3017.5919 | 0.916 | 0.005 |
| 2770.6051 | 0.953 | 0.003 |
| 1727.6199 | 0.956 | 0.014 |
| 1683.2305 | 0.825 | 0.09 |
| 1661.1658 | 0.877 | 0.017 |
| 1625.152 | 0.753 | 0.206 |
| 1614.6217 | 0.758 | 0.024 |
| 1526.8978 | 0.724 | 0.238 |
| 1495.0095 | 0.848 | 0.073 |
| 1456.8814 | 0.854 | 0.043 |
| 1443.6263 | 0.818 | 0.125 |
| 1350.1157 | 0.835 | 0.116 |
| 1334.7203 | 0.876 | 0.022 |
| 1334.7203 | 0.876 | 0.022 |
| 1299.5393 | 0.909 | 0.03 |
| 1266.1667 | 0.933 | 0.009 |
| 1243.167 | 0.924 | 0.011 |
| 1203.5849 | 0.787 | 0.014 |
| 1187.6114 | 0.745 | 0.036 |
| 1162.458 | 0.745 | 0.083 |
| 1123.4106 | 0.658 | 0.309 |
| 1123.4106 | 0.658 | 0.309 |
| 1098.2649 | 0.81 | 0.021 |
| 1033.8037 | 0.727 | 0.183 |
| 1015.9959 | 0.715 | 0.214 |
| 996.3734 | 0.782 | 0.115 |
| 966.4141 | 0.772 | 0.137 |
| 921.5827 | 0.933 | 0.008 |
| 891.0203 | 0.886 | 0.07 |
| 850.9437 | 0.898 | 0.058 |
| 784.81 | 0.828 | 0.11 |
| 751.3821 | 0.765 | 0.113 |
| 730.5034 | 0.703 | 0.172 |
| 688.9137 | 0.717 | 0.031 |
| 670.5872 | 0.697 | 0.034 |
| 648.9273 | 0.689 | 0.056 |
| 628.6312 | 0.702 | 0.024 |
| 608.8258 | 0.647 | 0.259 |
| 608.8258 | 0.647 | 0.259 |
| 568.5532 | 0.663 | 0.127 |
| 552.345 | 0.674 | 0.023 |
| 485.2531 | 0.788 | 0.053 |
| 469.715 | 0.724 | 0.151 |
| 453.4275 | 0.809 | 0.024 |

TABLE 56

| FT-IR peak list for AP1189 oxalate Pattern 1. | | |
|---|---|---|
| Wavenumber | Absolute Intensity | Relative Intensity |
| 3425.6525 | 0.99 | 0.007 |
| 2950.9765 | 0.989 | 0 |
| 2263.6431 | 0.993 | 0.007 |
| 2224.0341 | 0.993 | 0.007 |
| 2189.4208 | 0.992 | 0.002 |
| 2094.4029 | 0.992 | 0.007 |
| 2051.0775 | 0.992 | 0.011 |
| 2033.9801 | 0.997 | 0.003 |
| 1999.5002 | 0.994 | 0.003 |
| 1999.5002 | 0.994 | 0.003 |
| 1985.8891 | 0.996 | 0 |
| 1678.8294 | 0.974 | 0.013 |
| 1629.9945 | 0.954 | 0.041 |
| 1531.0679 | 0.96 | 0.025 |

TABLE 56-continued

| FT-IR peak list for AP1189 oxalate Pattern 1. | | |
|---|---|---|
| Wavenumber | Absolute Intensity | Relative Intensity |
| 1495.3869 | 0.967 | 0.014 |
| 1448.2014 | 0.976 | 0.008 |
| 1365.3126 | 0.973 | 0.014 |
| 1334.8102 | 0.978 | 0.006 |
| 1299.4122 | 0.967 | 0.022 |
| 1271.9425 | 0.982 | 0.001 |
| 1245.3147 | 0.982 | 0.004 |
| 1193.0299 | 0.964 | 0.025 |
| 1142.4289 | 0.98 | 0.006 |
| 1107.9208 | 0.969 | 0.018 |
| 1082.1335 | 0.972 | 0.006 |
| 1041.1368 | 0.978 | 0.009 |
| 1002.3102 | 0.985 | 0.003 |
| 972.8647 | 0.96 | 0.029 |
| 972.8647 | 0.96 | 0.029 |
| 972.8647 | 0.96 | 0.029 |
| 936.0322 | 0.985 | 0.003 |
| 913.8475 | 0.988 | 0.001 |
| 891.0902 | 0.976 | 0.011 |
| 853.3722 | 0.974 | 0.006 |
| 797.5541 | 0.953 | 0.002 |
| 775.2629 | 0.941 | 0.033 |
| 775.2629 | 0.941 | 0.033 |
| 775.2629 | 0.941 | 0.033 |
| 717.0275 | 0.919 | 0.041 |
| 698.1751 | 0.937 | 0.011 |
| 662.3845 | 0.949 | 0.004 |
| 639.5379 | 0.936 | 0.015 |
| 610.0509 | 0.916 | 0.045 |
| 560.327 | 0.922 | 0.022 |
| 478.1393 | 0.878 | 0.084 |
| 478.1393 | 0.878 | 0.084 |
| 448.8653 | 0.935 | 0.015 |
| 412.7337 | 0.95 | 0.011 |

TABLE 57

| FT-IR peak list for AP1189 oxalate Pattern 2. | | |
|---|---|---|
| Wavenumber | Absolute Intensity | Relative Intensity |
| 3469.2855 | 0.966 | 0.015 |
| 3388.4016 | 0.972 | 0.007 |
| 3208.2501 | 0.969 | 0 |
| 3178.2688 | 0.964 | 0.005 |
| 3081.3694 | 0.964 | 0.025 |
| 1717.1041 | 0.972 | 0.002 |
| 1676.3502 | 0.94 | 0.013 |
| 1638.0497 | 0.892 | 0.096 |
| 1638.0497 | 0.892 | 0.096 |
| 1606.9259 | 0.92 | 0.006 |
| 1584.1888 | 0.929 | 0.006 |
| 1526.4462 | 0.9 | 0.05 |
| 1526.4462 | 0.9 | 0.05 |
| 1496.0078 | 0.93 | 0.024 |
| 1496.0078 | 0.93 | 0.024 |
| 1446.6016 | 0.945 | 0.019 |
| 1411.6974 | 0.962 | 0.005 |
| 1350.7637 | 0.935 | 0.037 |
| 1297.892 | 0.961 | 0.01 |
| 1268.8868 | 0.972 | 0.002 |
| 1219.9916 | 0.933 | 0.006 |
| 1195.0947 | 0.922 | 0.055 |
| 1133.3026 | 0.946 | 0.01 |
| 1109.5923 | 0.949 | 0.002 |
| 1078.7344 | 0.948 | 0.01 |
| 1040.2025 | 0.959 | 0.005 |
| 1009.5453 | 0.967 | 0.002 |
| 970.6392 | 0.937 | 0.036 |
| 889.7046 | 0.97 | 0.012 |
| 849.9818 | 0.963 | 0.019 |

TABLE 57-continued

FT-IR peak list for AP1189 oxalate Pattern 2.

| Wavenumber | Absolute Intensity | Relative Intensity |
|---|---|---|
| 838.3275 | 0.976 | 0.002 |
| 783.9531 | 0.944 | 0.025 |
| 750.869 | 0.946 | 0.019 |
| 711.2381 | 0.894 | 0.084 |
| 711.2381 | 0.894 | 0.085 |
| 632.4438 | 0.95 | 0.01 |
| 607.1294 | 0.947 | 0.006 |
| 532.9389 | 0.93 | 0.011 |
| 476.4709 | 0.913 | 0.053 |

TABLE 58

FT-IR peak list for AP1189 oxalate Pattern 4.

| Wavenumber | Absolute Intensity | Relative Intensity |
|---|---|---|
| 3461.2741 | 0.94 | 0.007 |
| 3433.1516 | 0.94 | 0.005 |
| 3401.1149 | 0.939 | 0.003 |
| 3401.1149 | 0.939 | 0.003 |
| 3118.5203 | 0.916 | 0.057 |
| 1714.3801 | 0.927 | 0.005 |
| 1675.5708 | 0.87 | 0.023 |
| 1621.3503 | 0.822 | 0.071 |
| 1605.3663 | 0.825 | 0.008 |
| 1525.658 | 0.811 | 0.105 |
| 1525.658 | 0.811 | 0.105 |
| 1494.204 | 0.842 | 0.039 |
| 1444.5779 | 0.848 | 0.049 |
| 1414.708 | 0.885 | 0.01 |
| 1351.0291 | 0.854 | 0.055 |
| 1335.9272 | 0.863 | 0.007 |
| 1297.156 | 0.872 | 0.025 |
| 1188.4546 | 0.829 | 0.081 |
| 1162.4208 | 0.854 | 0.004 |
| 1127.9079 | 0.843 | 0.022 |
| 1080.6836 | 0.856 | 0.014 |
| 1039.6416 | 0.865 | 0.015 |
| 1001.676 | 0.883 | 0.002 |
| 970.2682 | 0.837 | 0.053 |
| 888.3688 | 0.874 | 0.028 |
| 849.9282 | 0.864 | 0.039 |
| 783.2574 | 0.841 | 0.052 |
| 749.7977 | 0.853 | 0.024 |
| 699.2885 | 0.788 | 0.052 |
| 631.9542 | 0.823 | 0.01 |
| 608.1246 | 0.812 | 0.017 |
| 570.4806 | 0.815 | 0.002 |
| 543.3487 | 0.794 | 0.01 |
| 513.8479 | 0.793 | 0.009 |
| 466.0991 | 0.747 | 0.05 |
| 444.8321 | 0.76 | 0.007 |

TABLE 59

FT-IR peak list for AP1189 (+)-camphor-10-sulfonic acid Pattern 1

| Wavenumber | Absolute Intensity | Relative Intensity |
|---|---|---|
| 3340.5146 | 0.896 | 0.022 |
| 3269.6418 | 0.901 | 0.011 |
| 3133.0809 | 0.857 | 0.119 |
| 3047.6991 | 0.92 | 0.003 |
| 3013.6744 | 0.916 | 0.006 |
| 2958.3394 | 0.905 | 0.025 |
| 2919.5524 | 0.919 | 0.002 |

TABLE 59-continued

FT-IR peak list for AP1189 (+)-camphor-10-sulfonic acid Pattern 1

| Wavenumber | Absolute Intensity | Relative Intensity |
|---|---|---|
| 2889.1522 | 0.93 | 0.002 |
| 2828.226 | 0.951 | 0.001 |
| 2774.1878 | 0.954 | 0.001 |
| 1746.602 | 0.779 | 0.179 |
| 1683.0383 | 0.754 | 0.139 |
| 1625.0654 | 0.666 | 0.278 |
| 1529.6827 | 0.652 | 0.299 |
| 1495.1053 | 0.813 | 0.095 |
| 1455.3026 | 0.802 | 0.122 |
| 1455.3026 | 0.802 | 0.122 |
| 1445.0707 | 0.81 | 0.023 |
| 1416.4506 | 0.891 | 0.041 |
| 1391.8206 | 0.914 | 0.017 |
| 1352.9555 | 0.781 | 0.152 |
| 1336.8328 | 0.849 | 0.025 |
| 1296.9587 | 0.879 | 0.043 |
| 1282.3231 | 0.886 | 0.011 |
| 1226.9819 | 0.862 | 0.021 |
| 1190.9074 | 0.666 | 0.256 |
| 1167.1669 | 0.683 | 0.06 |
| 1152.9806 | 0.69 | 0.018 |
| 1134.1984 | 0.724 | 0.016 |
| 1134.1984 | 0.724 | 0.016 |
| 1134.1984 | 0.724 | 0.016 |
| 1134.1984 | 0.724 | 0.016 |
| 1134.1984 | 0.724 | 0.016 |
| 1134.1984 | 0.724 | 0.016 |
| 1134.1984 | 0.724 | 0.016 |
| 1040.839 | 0.529 | 0.434 |
| 1040.839 | 0.529 | 0.434 |
| 1040.839 | 0.529 | 0.434 |
| 1006.9516 | 0.883 | 0.021 |
| 975.42 | 0.79 | 0.135 |
| 936.6847 | 0.937 | 0.008 |
| 889.5805 | 0.89 | 0.068 |
| 850.4344 | 0.873 | 0.081 |
| 786.0655 | 0.752 | 0.15 |
| 753.8361 | 0.794 | 0.058 |
| 729.8806 | 0.758 | 0.083 |
| 701.7408 | 0.676 | 0.208 |
| 651.2693 | 0.72 | 0.012 |
| 634.9463 | 0.709 | 0.022 |
| 608.3725 | 0.684 | 0.097 |

TABLE 60

FT-IR peak list for AP1189 oxoglutarate Pattern 1

| Wavenumber | Absolute Intensity | Relative Intensity |
|---|---|---|
| 3434.1072 | 0.973 | 0.008 |
| 3316.28 | 0.973 | 0.005 |
| 3079.0769 | 0.965 | 0.024 |
| 2748.1019 | 0.974 | 0.001 |
| 1974.6528 | 0.979 | 0.015 |
| 1744.1048 | 0.973 | 0.004 |
| 1725.7973 | 0.965 | 0.004 |
| 1711.8043 | 0.955 | 0.012 |
| 1682.1477 | 0.936 | 0.043 |
| 1622.6454 | 0.937 | 0.012 |
| 1599.5051 | 0.936 | 0.033 |
| 1529.649 | 0.935 | 0.056 |
| 1529.649 | 0.935 | 0.053 |
| 1498.9929 | 0.954 | 0.018 |
| 1447.8637 | 0.963 | 0.012 |
| 1393.3645 | 0.956 | 0.017 |
| 1393.3645 | 0.956 | 0.017 |
| 1360.1431 | 0.95 | 0.026 |
| 1336.6705 | 0.957 | 0.005 |

TABLE 60-continued

| FT-IR peak list for AP1189 oxoglutarate Pattern 1 | | |
|---|---|---|
| Wavenumber | Absolute Intensity | Relative Intensity |
| 1336.6705 | 0.957 | 0.005 |
| 1298.4765 | 0.973 | 0.001 |
| 1229.0516 | 0.968 | 0.008 |
| 1190.0286 | 0.944 | 0.034 |
| 1159.4946 | 0.953 | 0.018 |
| 1132.3278 | 0.964 | 0.007 |
| 1080.9647 | 0.955 | 0.021 |
| 1027.079 | 0.973 | 0.007 |
| 1000.7884 | 0.978 | 0.002 |
| 969.5172 | 0.958 | 0.023 |
| 969.5172 | 0.958 | 0.023 |
| 930.5613 | 0.977 | 0.004 |
| 890.4947 | 0.972 | 0.009 |
| 828.1089 | 0.96 | 0.017 |
| 828.1089 | 0.96 | 0.017 |
| 813.6562 | 0.973 | 0.001 |
| 779.5765 | 0.95 | 0.031 |
| 779.5765 | 0.95 | 0.032 |
| 754.0045 | 0.961 | 0.009 |
| 711.9895 | 0.951 | 0.022 |
| 642.9228 | 0.964 | 0.004 |
| 624.4739 | 0.967 | 0.002 |
| 606.95 | 0.964 | 0.006 |
| 589.2528 | 0.969 | 0.001 |
| 560.2316 | 0.97 | 0.006 |
| 532.2474 | 0.967 | 0.01 |
| 467.9573 | 0.967 | 0.012 |
| 412.8724 | 0.971 | 0.012 |

TABLE 61

| FT-IR peak list for AP1189 DL mandelic acid Pattern 2 | | |
|---|---|---|
| Wavenumber | Absolute Intensity | Relative Intensity |
| 3324.9282 | 0.82 | 0.119 |
| 3152.8917 | 0.841 | 0.014 |
| 3069.0933 | 0.823 | 0.057 |
| 3040.9086 | 0.824 | 0.002 |
| 3015.6015 | 0.825 | 0.001 |
| 2979.4458 | 0.827 | 0.003 |
| 2933.1051 | 0.84 | 0.015 |
| 2874.4871 | 0.865 | 0.009 |
| 2786.4381 | 0.871 | 0.001 |
| 2748.2612 | 0.871 | 0.001 |
| 2646.4095 | 0.878 | 0.001 |
| 2609.8399 | 0.878 | 0.003 |
| 2588.4994 | 0.879 | 0.003 |
| 1699.5562 | 0.748 | 0.037 |
| 1674.6619 | 0.463 | 0.397 |
| 1674.6619 | 0.463 | 0.397 |
| 1643.6605 | 0.579 | 0.06 |
| 1606.2055 | 0.687 | 0.059 |
| 1579.8052 | 0.734 | 0.056 |
| 1524.8976 | 0.448 | 0.485 |
| 1524.8976 | 0.448 | 0.485 |
| 1494.5467 | 0.631 | 0.18 |
| 1494.5467 | 0.631 | 0.18 |
| 1454.4981 | 0.687 | 0.141 |
| 1404.3973 | 0.733 | 0.093 |
| 1360.7749 | 0.542 | 0.069 |
| 1346.1451 | 0.493 | 0.354 |
| 1346.1451 | 0.493 | 0.354 |
| 1294.554 | 0.771 | 0.044 |
| 1270.4268 | 0.83 | 0.014 |
| 1270.4268 | 0.83 | 0.014 |
| 1246.9404 | 0.824 | 0.043 |
| 1193.6969 | 0.575 | 0.305 |
| 1135.9058 | 0.771 | 0.055 |

TABLE 61-continued

| FT-IR peak list for AP1189 DL mandelic acid Pattern 2 | | |
|---|---|---|
| Wavenumber | Absolute Intensity | Relative Intensity |
| 1114.6922 | 0.741 | 0.091 |
| 1080.9246 | 0.714 | 0.146 |
| 1042.4307 | 0.661 | 0.211 |
| 1002.6618 | 0.825 | 0.045 |
| 974.7184 | 0.599 | 0.284 |
| 974.7184 | 0.599 | 0.284 |
| 929.9534 | 0.733 | 0.157 |
| 889.4518 | 0.74 | 0.135 |
| 850.1391 | 0.662 | 0.219 |
| 783.2 | 0.518 | 0.346 |
| 755.5291 | 0.618 | 0.208 |
| 734.8637 | 0.524 | 0.292 |
| 704.2896 | 0.44 | 0.398 |
| 646.4857 | 0.51 | 0.047 |
| 635.2889 | 0.51 | 0.206 |
| 561.6984 | 0.661 | 0.041 |

TABLE 62

| FT-IR peak list for AP1189 DL-mandelic acid Pattern 3 | | |
|---|---|---|
| Wavenumber | Absolute Intensity | Relative Intensity |
| 3438.9914 | 0.945 | 0.004 |
| 3414.2546 | 0.945 | 0.002 |
| 3305.8784 | 0.934 | 0.001 |
| 3029.7727 | 0.921 | 0.05 |
| 2736.8009 | 0.936 | 0.001 |
| 1676.8694 | 0.871 | 0.044 |
| 1676.8694 | 0.871 | 0.044 |
| 1624.7713 | 0.862 | 0.068 |
| 1605.7456 | 0.87 | 0.006 |
| 1579.8096 | 0.885 | 0.007 |
| 1525.2321 | 0.839 | 0.122 |
| 1525.2321 | 0.839 | 0.122 |
| 1493.2721 | 0.87 | 0.036 |
| 1453.0437 | 0.887 | 0.028 |
| 1406.6532 | 0.895 | 0.016 |
| 1348.6562 | 0.854 | 0.065 |
| 1335.9744 | 0.858 | 0.002 |
| 1294.6387 | 0.896 | 0.01 |
| 1237.9816 | 0.91 | 0.005 |
| 1191.3174 | 0.868 | 0.053 |
| 1191.3174 | 0.868 | 0.053 |
| 1191.3174 | 0.868 | 0.053 |
| 1132.5099 | 0.895 | 0.009 |
| 1132.5099 | 0.895 | 0.009 |
| 1114.6238 | 0.896 | 0.004 |
| 1080.2331 | 0.888 | 0.02 |
| 1056.0946 | 0.896 | 0.006 |
| 1028.7992 | 0.897 | 0.003 |
| 1001.0851 | 0.913 | 0.005 |
| 971.5213 | 0.879 | 0.04 |
| 930.8348 | 0.902 | 0.022 |
| 888.9418 | 0.905 | 0.02 |
| 888.9418 | 0.905 | 0.02 |
| 849.8642 | 0.89 | 0.036 |
| 781.182 | 0.866 | 0.047 |
| 750.3994 | 0.877 | 0.016 |
| 733.4775 | 0.864 | 0.013 |
| 699.6274 | 0.834 | 0.063 |
| 699.6274 | 0.834 | 0.063 |
| 634.7914 | 0.853 | 0.009 |
| 606.2778 | 0.849 | 0.018 |
| 568.7299 | 0.858 | 0.002 |
| 532.1813 | 0.858 | 0.003 |
| 510.4669 | 0.856 | 0.008 |
| 469.0286 | 0.836 | 0.038 |
| 469.0286 | 0.836 | 0.038 |

TABLE 62-continued

| FT-IR peak list for AP1189 DL-mandelic acid Pattern 3 | | |
|---|---|---|
| Wavenumber | Absolute Intensity | Relative Intensity |
| 451.8363 | 0.844 | 0.009 |
| 407.8772 | 0.862 | 0.01 |

TABLE 63

| FT-IR peak list for AP1189 hippuric acid Pattern 1 | | |
|---|---|---|
| Wavenumber | Absolute Intensity | Relative Intensity |
| 3478.5092 | 0.986 | 0.004 |
| 3462.8585 | 0.987 | 0.002 |
| 3391.5891 | 0.98 | 0.014 |
| 3351.9339 | 0.983 | 0.003 |
| 2019.2428 | 0.988 | 0.01 |
| 1692.0022 | 0.965 | 0.016 |
| 1625.0168 | 0.953 | 0.026 |
| 1625.0168 | 0.953 | 0.026 |
| 1573.5216 | 0.97 | 0.005 |
| 1560.279 | 0.972 | 0.001 |
| 1523.7117 | 0.952 | 0.042 |
| 1483.5359 | 0.963 | 0.015 |
| 1453.7204 | 0.974 | 0.004 |
| 1445.2105 | 0.973 | 0.011 |
| 1395.626 | 0.953 | 0.034 |
| 1395.626 | 0.953 | 0.034 |
| 1348.9271 | 0.971 | 0.012 |
| 1320.0629 | 0.98 | 0.003 |
| 1296.3458 | 0.98 | 0.002 |
| 1272.1234 | 0.985 | 0.002 |
| 1243.1359 | 0.983 | 0.003 |
| 1199.7151 | 0.973 | 0.015 |
| 1165.661 | 0.983 | 0.003 |
| 1136.9015 | 0.98 | 0.008 |
| 1114.0689 | 0.984 | 0.002 |
| 1082.649 | 0.982 | 0.006 |
| 1042.5752 | 0.987 | 0.004 |
| 982.3329 | 0.98 | 0.011 |
| 938.7359 | 0.985 | 0.005 |
| 888.4103 | 0.982 | 0.007 |
| 850.5125 | 0.981 | 0.009 |
| 783.0247 | 0.979 | 0.011 |
| 751.2867 | 0.975 | 0.007 |
| 729.0162 | 0.977 | 0.005 |
| 708.0583 | 0.967 | 0.003 |
| 696.2757 | 0.966 | 0.024 |
| 656.1822 | 0.973 | 0.009 |
| 637.5248 | 0.975 | 0.004 |
| 599.4983 | 0.976 | 0.005 |
| 576.4886 | 0.975 | 0.003 |
| 552.808 | 0.973 | 0.009 |
| 552.808 | 0.973 | 0.009 |
| 517.638 | 0.978 | 0.003 |
| 489.6767 | 0.973 | 0.005 |
| 467.5258 | 0.967 | 0.021 |
| 434.7231 | 0.975 | 0.007 |

TABLE 64

| FT-IR peak list for AP1189 formic acid Pattern 1 | | |
|---|---|---|
| Wavenumber | Absolute Intensity | Relative Intensity |
| 3432.3814 | 0.874 | 0.059 |
| 2981.6644 | 0.826 | 0.129 |
| 2812.6797 | 0.836 | 0.033 |

TABLE 64-continued

| FT-IR peak list for AP1189 formic acid Pattern 1 | | |
|---|---|---|
| Wavenumber | Absolute Intensity | Relative Intensity |
| 2723.0736 | 0.852 | 0.015 |
| 2631.8709 | 0.857 | 0.013 |
| 1676.7328 | 0.763 | 0.047 |
| 1627.8235 | 0.584 | 0.226 |
| 1605.8813 | 0.663 | 0.018 |
| 1581.7727 | 0.741 | 0.007 |
| 1531.3788 | 0.582 | 0.318 |
| 1531.3788 | 0.582 | 0.318 |
| 1493.4246 | 0.626 | 0.148 |
| 1493.4246 | 0.626 | 0.148 |
| 1447.5484 | 0.711 | 0.078 |
| 1351.0058 | 0.58 | 0.348 |
| 1351.0058 | 0.58 | 0.348 |
| 1296.5694 | 0.798 | 0.03 |
| 1271.9368 | 0.835 | 0.018 |
| 1242.541 | 0.824 | 0.042 |
| 1199.1381 | 0.669 | 0.205 |
| 1138.5633 | 0.799 | 0.019 |
| 1120.1193 | 0.727 | 0.114 |
| 1081.2687 | 0.762 | 0.077 |
| 1043.2571 | 0.789 | 0.064 |
| 999.926 | 0.847 | 0.024 |
| 973.6776 | 0.682 | 0.209 |
| 935.6882 | 0.864 | 0.019 |
| 890.7174 | 0.801 | 0.094 |
| 851.1643 | 0.801 | 0.021 |
| 807.8253 | 0.725 | 0.059 |
| 767.7829 | 0.633 | 0.201 |
| 712.4497 | 0.582 | 0.284 |
| 712.4497 | 0.582 | 0.238 |
| 698.69 | 0.6 | 0.029 |
| 640.9999 | 0.697 | 0.057 |
| 610.1032 | 0.674 | 0.105 |
| 610.1032 | 0.674 | 0.105 |
| 594.6837 | 0.736 | 0.009 |
| 545.17 | 0.683 | 0.078 |
| 486.8537 | 0.731 | 0.033 |
| 472.0881 | 0.681 | 0.103 |
| 448.1613 | 0.733 | 0.05 |
| 403.3132 | 0.771 | 0.003 |

TABLE 65

| FT-IR peak list for AP1189 L-lactic acid Pattern 1 | | |
|---|---|---|
| Wavenumber | Absolute Intensity | Relative Intensity |
| 3443.026 | 0.899 | 0.022 |
| 3301.6603 | 0.841 | 0.122 |
| 3104.1943 | 0.855 | 0.006 |
| 3077.6911 | 0.848 | 0.037 |
| 2980.2002 | 0.87 | 0.015 |
| 2964.0623 | 0.876 | 0.005 |
| 2930.9886 | 0.889 | 0.006 |
| 2865.3491 | 0.891 | 0.001 |
| 2846.9568 | 0.888 | 0.013 |
| 2790.497 | 0.892 | 0.002 |
| 2748.4106 | 0.891 | 0.001 |
| 2685.0933 | 0.894 | 0.004 |
| 1703.147 | 0.711 | 0.162 |
| 1678.0314 | 0.715 | 0.101 |
| 1625.7241 | 0.631 | 0.188 |
| 1607.9149 | 0.703 | 0.037 |
| 1527.4719 | 0.564 | 0.388 |
| 1527.4719 | 0.564 | 0.388 |
| 1495.0557 | 0.684 | 0.108 |
| 1458.6145 | 0.693 | 0.143 |
| 1445.9522 | 0.703 | 0.069 |
| 1403.0228 | 0.741 | 0.091 |

TABLE 65-continued

FT-IR peak list for AP1189 L-lactic acid Pattern 1

| Wavenumber | Absolute Intensity | Relative Intensity |
|---|---|---|
| 1359.487 | 0.668 | 0.184 |
| 1359.487 | 0.668 | 0.184 |
| 1336.7196 | 0.752 | 0.051 |
| 1291.4634 | 0.749 | 0.115 |
| 1270.3898 | 0.832 | 0.01 |
| 1237.741 | 0.848 | 0.025 |
| 1200.7797 | 0.734 | 0.143 |
| 1165.9727 | 0.845 | 0.022 |
| 1119.7668 | 0.659 | 0.225 |
| 1089.3157 | 0.769 | 0.042 |
| 1043.8629 | 0.783 | 0.106 |
| 1031.9237 | 0.838 | 0.013 |
| 975.0628 | 0.711 | 0.189 |
| 956.7339 | 0.794 | 0.066 |
| 956.7339 | 0.794 | 0.066 |
| 888.356 | 0.826 | 0.077 |
| 876.9653 | 0.874 | 0.008 |
| 848.4237 | 0.721 | 0.15 |
| 796.0445 | 0.819 | 0.013 |
| 775.3283 | 0.708 | 0.161 |
| 750.9077 | 0.712 | 0.14 |
| 717.6257 | 0.618 | 0.193 |
| 700.7775 | 0.675 | 0.041 |
| 656.2251 | 0.745 | 0.024 |
| 633.1683 | 0.701 | 0.045 |
| 611.8089 | 0.658 | 0.118 |
| 586.2594 | 0.669 | 0.05 |
| 532.3279 | 0.701 | 0.019 |

TABLE 66

FT-IR peak list for AP1189 DL-lactic acid Pattern 1

| Wavenumber | Absolute Intensity | Relative Intensity |
|---|---|---|
| 3282.8423 | 0.848 | 0.114 |
| 3137.2294 | 0.891 | 0.002 |
| 3106.7371 | 0.878 | 0.007 |
| 3078.3359 | 0.874 | 0.026 |
| 3054.1371 | 0.876 | 0.003 |
| 2980.1703 | 0.887 | 0.016 |
| 2959.8998 | 0.886 | 0.019 |
| 2928.186 | 0.906 | 0.006 |
| 2863.9284 | 0.907 | 0.01 |
| 2830.9054 | 0.914 | 0.001 |
| 2767.7562 | 0.911 | 0.002 |
| 1706.6962 | 0.769 | 0.13 |
| 1677.4684 | 0.777 | 0.089 |
| 1628.5031 | 0.704 | 0.167 |
| 1606.954 | 0.769 | 0.032 |
| 1527.8575 | 0.642 | 0.325 |
| 1527.8575 | 0.642 | 0.325 |
| 1494.7078 | 0.744 | 0.096 |
| 1494.7078 | 0.744 | 0.096 |
| 1456.7346 | 0.751 | 0.124 |
| 1446.5759 | 0.758 | 0.027 |
| 1409.4495 | 0.755 | 0.114 |
| 1409.4495 | 0.755 | 0.114 |
| 1359.0736 | 0.728 | 0.16 |
| 1336.0661 | 0.8 | 0.04 |
| 1299.0075 | 0.825 | 0.075 |
| 1284.0812 | 0.848 | 0.01 |
| 1269.9398 | 0.876 | 0.009 |
| 1237.0916 | 0.883 | 0.024 |
| 1202.4033 | 0.78 | 0.132 |
| 1168.1212 | 0.879 | 0.02 |
| 1118.8217 | 0.697 | 0.219 |
| 1088.5536 | 0.819 | 0.048 |
| 1046.0438 | 0.799 | 0.12 |

TABLE 66-continued

FT-IR peak list for AP1189 DL-lactic acid Pattern 1

| Wavenumber | Absolute Intensity | Relative Intensity |
|---|---|---|
| 1046.0438 | 0.799 | 0.12 |
| 1046.0438 | 0.799 | 0.12 |
| 1032.0492 | 0.873 | 0.012 |
| 1000.5308 | 0.911 | 0.007 |
| 975.3702 | 0.747 | 0.182 |
| 975.3702 | 0.747 | 0.182 |
| 957.32 | 0.837 | 0.064 |
| 887.9494 | 0.86 | 0.071 |
| 877.4801 | 0.897 | 0.011 |
| 848.442 | 0.755 | 0.17 |
| 827.5387 | 0.842 | 0.018 |
| 797.1482 | 0.851 | 0.026 |
| 775.3905 | 0.776 | 0.109 |
| 750.5948 | 0.757 | 0.132 |
| 718.7205 | 0.669 | 0.174 |
| 718.7205 | 0.669 | 0.174 |

TABLE 67

FT-IR peak list for AP1189 glutaric acid Pattern 1

| Wavenumber | Absolute Intensity | Relative Intensity |
|---|---|---|
| 3451.4823 | 0.909 | 0.051 |
| 3273.8599 | 0.904 | 0.035 |
| 3247.2814 | 0.908 | 0.001 |
| 3213.4294 | 0.908 | 0.005 |
| 2950.2826 | 0.884 | 0.09 |
| 2772.9078 | 0.908 | 0.002 |
| 1983.7185 | 0.959 | 0.001 |
| 1945.1815 | 0.956 | 0.01 |
| 1912.7557 | 0.958 | 0.004 |
| 1681.2131 | 0.733 | 0.119 |
| 1632.9309 | 0.694 | 0.203 |
| 1608.0157 | 0.79 | 0.018 |
| 1555.0838 | 0.833 | 0.029 |
| 1525.973 | 0.679 | 0.273 |
| 1525.973 | 0.679 | 0.273 |
| 1493.208 | 0.753 | 0.082 |
| 1493.208 | 0.753 | 0.082 |
| 1453.6917 | 0.765 | 0.12 |
| 1453.6917 | 0.765 | 0.12 |
| 1411.5581 | 0.797 | 0.084 |
| 1411.5581 | 0.797 | 0.084 |
| 1347.2594 | 0.773 | 0.016 |
| 1340.1909 | 0.771 | 0.137 |
| 1306.3792 | 0.834 | 0.038 |
| 1265.4491 | 0.856 | 0.047 |
| 1223.6023 | 0.766 | 0.045 |
| 1192.895 | 0.728 | 0.137 |
| 1148.2185 | 0.704 | 0.212 |
| 1148.2185 | 0.704 | 0.212 |
| 1081.9008 | 0.812 | 0.043 |
| 1041.9241 | 0.824 | 0.044 |
| 1024.5139 | 0.83 | 0.019 |
| 997.3686 | 0.859 | 0.017 |
| 969.7962 | 0.784 | 0.105 |
| 926.2335 | 0.868 | 0.048 |
| 889.0404 | 0.889 | 0.037 |
| 889.0404 | 0.889 | 0.037 |
| 852.9313 | 0.827 | 0.092 |
| 804.882 | 0.811 | 0.037 |
| 785.2951 | 0.749 | 0.136 |
| 785.2951 | 0.749 | 0.136 |
| 785.2951 | 0.749 | 0.136 |
| 751.9143 | 0.744 | 0.132 |
| 751.9143 | 0.744 | 0.132 |
| 727.2603 | 0.746 | 0.125 |
| 682.267 | 0.746 | 0.07 |

TABLE 67-continued

| FT-IR peak list for AP1189 glutaric acid Pattern 1 | | |
|---|---|---|
| Wavenumber | Absolute Intensity | Relative Intensity |
| 640.5213 | 0.77 | 0.055 |
| 640.5213 | 0.77 | 0.055 |
| 610.3421 | 0.801 | 0.039 |
| 520.4538 | 0.75 | 0.051 |

TABLE 68

| FT-IR peak list for AP1189 glutaric acid Pattern 2 | | |
|---|---|---|
| Wavenumber | Absolute Intensity | Relative Intensity |
| 3430.3134 | 0.879 | 0.076 |
| 3288.1782 | 0.887 | 0.052 |
| 3209.4296 | 0.905 | 0.008 |
| 3132.4855 | 0.911 | 0.008 |
| 3113.8608 | 0.911 | 0.004 |
| 3016.0295 | 0.878 | 0.093 |
| 2941.5484 | 0.884 | 0.025 |
| 2922.1175 | 0.889 | 0.012 |
| 2872.472 | 0.906 | 0.005 |
| 2769.5575 | 0.902 | 0.014 |
| 1678.217 | 0.671 | 0.146 |
| 1630.5087 | 0.636 | 0.248 |
| 1552.6043 | 0.798 | 0.045 |
| 1527.0178 | 0.612 | 0.325 |
| 1493.0553 | 0.67 | 0.138 |
| 1452.4984 | 0.712 | 0.136 |
| 1409.1509 | 0.762 | 0.093 |
| 1352.9723 | 0.691 | 0.205 |
| 1352.9723 | 0.691 | 0.205 |
| 1318.4605 | 0.804 | 0.028 |
| 1318.4605 | 0.804 | 0.028 |
| 1298.4179 | 0.83 | 0.029 |
| 1267.3811 | 0.835 | 0.049 |
| 1229.3818 | 0.752 | 0.043 |
| 1194.241 | 0.642 | 0.213 |
| 1131.5232 | 0.615 | 0.284 |
| 1131.5232 | 0.615 | 0.284 |
| 1131.5232 | 0.615 | 0.284 |
| 1081.7286 | 0.706 | 0.058 |
| 1047.651 | 0.772 | 0.024 |
| 1047.651 | 0.772 | 0.024 |
| 1047.651 | 0.772 | 0.024 |
| 1026.3725 | 0.78 | 0.04 |
| 1011.9658 | 0.808 | 0.013 |
| 967.7876 | 0.745 | 0.114 |
| 926.12 | 0.802 | 0.096 |
| 889.4235 | 0.836 | 0.066 |
| 852.4417 | 0.747 | 0.149 |
| 802.3239 | 0.762 | 0.059 |
| 802.3239 | 0.762 | 0.059 |
| 782.8912 | 0.642 | 0.227 |
| 782.8912 | 0.642 | 0.227 |
| 752.8624 | 0.706 | 0.134 |
| 724.9698 | 0.638 | 0.213 |
| 702.3892 | 0.718 | 0.076 |
| 665.9727 | 0.695 | 0.02 |
| 641.3229 | 0.66 | 0.148 |
| 609.8383 | 0.756 | 0.033 |
| 550.6147 | 0.558 | 0.342 |
| 550.6147 | 0.558 | 0.342 |

What is claimed is:

1. A method of treating a disease or disorder that is an arthritic disease, a kidney disease, a cardiovascular disease, atherosclerosis, a viral disease or disorder, or a systemic inflammatory disorder in a subject in need thereof, said method comprising administering a crystalline Form of the N-{3-[1-(2-nitrophenyl)-1H-pyrrol-2-yl]-allylidene}-aminoguanidinium salt to the subject, wherein the crystalline Form of the N-{3-[1-(2-nitrophenyl)-1H-pyrrol-2-yl]-allylidene}-aminoguanidinium salt is:

i. a crystalline Form A of N-{3-[1-(2-nitrophenyl)-1H-pyrrol-2-yl]-allylidene}-aminoguanidinium acetate exhibiting at least X-ray lines (2-theta values) in a powder diffraction pattern when measured using Cu $K_\alpha$ radiation at 11.5±0.2, 23.5±0.2, and 27.0±0.2, ii. a crystalline Form B of N-{3-[1-(2-nitrophenyl)-1H-pyrrol-2-yl]-allylidene}-aminoguanidinium succinate exhibiting at least X-ray lines (2-theta values) in a powder diffraction pattern when measured using Cu Kα radiation at 9.7±0.2, 22.8±0.2, and 26.7±0.2, iii. a crystalline Form C of N-{3-[1-(2-nitrophenyl)-1H-pyrrol-2-yl]-allylidene}-aminoguanidinium tosylate exhibiting at least X-ray lines (2-theta values) in a powder diffraction pattern when measured using Cu Kα radiation at 14.5±0.2, 21.0±0.2, and 25.2±0.2, iv. a crystalline Form D of N-{3-[1-(2-nitrophenyl)-1H-pyrrol-2-yl]-allylidene}-aminoguanidinium fumarate exhibiting at least X-ray lines (2-theta values) in a powder diffraction pattern when measured using Cu Kα radiation at 17.6±0.2, 21.2±0.2, and 26.3±0.2, v. a crystalline Form I of N-{3-[1-(2-nitrophenyl)-1H-pyrrol-2-yl]-allylidene}-aminoguanidinium acetate exhibiting X-ray lines (2-theta values) in a powder diffraction pattern when measured using Cu Kα radiation at 23.5±0.2, 24.2±0.2, and 26.9±0.2, vi. a crystalline Form II of N-{3-[1-(2-nitrophenyl)-1H-pyrrol-2-yl]-allylidene}-aminoguanidinium exhibiting X-ray lines (2-theta values) in a powder diffraction pattern when measured using Cu Kα radiation at 13.3±0.2, 21.1±0.2, and 23.1±0.2, vii. a crystalline Form III of N-{3-[1-(2-nitrophenyl)-1H-pyrrol-2-yl]-allylidene}-aminoguanidinium napadisylate exhibiting at least X-ray lines (2-theta values) in a powder diffraction pattern when measured using Cu Kα radiation at 13.4±0.2, 22.2±0.2, and 26.8±0.2, viii. a crystalline Form IV of N-{3-[1-(2-nitrophenyl)-1H-pyrrol-2-yl]-allylidene}-aminoguanidinium napadisylate exhibiting at least X-ray lines (2-theta values) in a powder diffraction pattern when measured using Cu Kα radiation at 5.4±0.2, 15.6±0.2, and 23.4±0.2, ix. a crystalline Form V of N-{3-[1-(2-nitrophenyl)-1H-pyrrol-2-yl]-allylidene}-aminoguanidinium esylate exhibiting at least X-ray lines (2-theta values) in a powder diffraction pattern when measured using Cu Kα radiation at 14.5±0.2, 16.5±0.2, and 18.6±0.2, x. a crystalline Form VI of N-{3-[1-(2-nitrophenyl)-1H-pyrrol-2-yl]-allylidene}-aminoguanidinium edisylate exhibiting at least X-ray lines (2-theta values) in a powder diffraction pattern when measured using Cu Kα radiation at 4.8±0.2, 12.8±0.2, and 16.5±0.2, xi. a crystalline Form VII of N-{3-[1-(2-nitrophenyl)-1H-pyrrol-2-yl]-allylidene}-aminoguanidinium edisylate exhibiting at least X-ray lines (2-theta values) in a powder diffraction pattern when measured using Cu Kα radiation at 6.1±0.2, 15.7±0.2, and 23.6±0.2, xii. a crystalline Form VIII of N-{3-[1-(2-nitrophenyl)-1H-pyrrol-2-yl]-allylidene}-aminoguanidinium edisylate exhibiting at least X-ray lines (2-theta values) in a powder diffraction pattern when measured using Cu Kα radiation at 15.5±0.2, 20.7±0.2, and 21.7±0.2, xiii. a crystalline Form IX of N-{3-[1-(2-nitrophenyl)-1H-pyrrol-2-yl]-allylidene}-aminoguanidinium edisylate exhibiting at least X-ray lines (2-theta values) in a powder diffraction pattern when measured using Cu Kα radiation at 4.5±0.2, 16.7±0.2, and 24.7±0.2, xiv. a crystalline Form X of N-{3-[1-(2-nitrophenyl)-1H-pyrrol-2-yl 1-allylidene}-aminoguanidinium nitrate exhibiting at least X-ray lines (2-theta values) in a powder diffraction pattern when measured using Cu Kα radiation at 15.3±0.2, 21.4±0.2, and 25.1±0.2, xv. a crystalline Form XI of N-{3-[1-(2-nitrophenyl)-1H-pyrrol-2-yl]-allylidene}-aminoguanidinium cyclamate exhibiting at least X-ray lines (2-theta values) in a powder diffraction pattern when measured using Cu Kα radiation at 7.0±0.2, 13.8±0.2, and 15.7±0.2, xvi. a crystalline Form XII of N-{3-[1-(2-nitrophenyl)-1H-pyrrol-2-yl]-allylidene}-aminoguanidinium cyclamate exhibiting at least X-ray lines (2-theta values) in a powder diffraction pattern when measured using Cu Kα radiation at 7.3±0.2, 15.3±0.2, and 17.9±0.2, xvii. a crystalline Form XIII of N-{3-[1-(2-nitrophenyl)-1H-pyrrol-2-yl]-allylidene}-aminoguanidinium cyclamate exhibiting at least X-ray lines (2-theta values) in a powder diffraction pattern when measured using Cu Kα radiation at 15.3±0.2, 18.5±0.2, and 18.7±0.2, xviii. a crystalline Form XIV of N-{3-[1-(2-nitrophenyl)-1H-pyrrol-2-yl]-allylidene}-aminoguanidinium besylate exhibiting at least X-ray lines (2-theta values) in a powder diffraction pattern when measured using Cu Kα radiation at 13.0±0.2, 15.1±0.2, and 19.9±0.2, xix. a crystalline Form XV of N-{3-[1-(2-nitrophenyl)-1H-pyrrol-2-yl]-allylidene}-aminoguanidinium oxalate exhibiting at least X-ray lines (2-theta values) in a powder diffraction pattern when measured using Cu Kα radiation at 19.5±0.2, 23.3±0.2, and 25.8±0.2, xx. a crystalline Form XVI of N-{3-[1-(2-nitrophenyl)-1H-pyrrol-2-yl]-allylidene}-aminoguanidinium oxalate exhibiting at least X-ray lines (2-theta values) in a powder diffraction pattern when measured using Cu Kα radiation at 17.1±0.2, 17.9±0.2, and 19.6±0.2, xxi. a crystalline Form XVII of N-{3-[1-(2-nitrophenyl)-1H-pyrrol-2-yl]-allylidene}-aminoguanidinium oxalate exhibiting at least X-ray lines (2-theta values) in a powder diffraction pattern when measured using Cu Kα radiation at 6.3±0.2, 10.6±0.2, and 19.8±0.2, xxii. a crystalline Form XVIII of N-{3-[1-(2-nitrophenyl)-1H-pyrrol-2-yl]-allylidene}-aminoguanidine (+)-camphor-10-sulfonic acid exhibiting at least X-ray lines (2-theta values) in a powder diffraction pattern when measured using Cu Kα radiation at 6.5±0.2, 11.5±0.2, and 14.8±0.2, xxiii. a crystalline Form XIX of N-{3-[1-(2-nitrophenyl)-1H-pyrrol-2-yl]-allylidene}-aminoguanidinium oxoglutarate exhibiting at least X-ray lines (2-theta values) in a powder diffraction pattern when measured using Cu Kα radiation at 16.8±0.2, 23.4±0.2, and 23.6±0.2, xxiv. a crystalline Form XX of N-{3-[1-(2-nitrophenyl)-1H-pyrrol-2-yl]-allylidene}-aminoguanidine DL-mandelic acid exhibiting at least X-ray lines (2-theta values) in a powder diffraction pattern when measured using Cu Kα radiation at 14.8±0.2, 24.2±0.2, and 25.5±0.2, xxv. a crystalline Form XXI of N-{3-[1-(2-nitrophenyl)-1H-pyrrol-2-yl]-allylidene}-aminoguanidine DL-mandelic acid exhibiting at least X-ray lines (2-theta values) in a powder diffraction pattern when measured using Cu Kα radiation at 5.4±0.2, 10.0±0.2, and 24.6±0.2, xxvi. a crystalline Form XXII of N-{3-[1-(2-nitrophenyl)-1H-pyrrol-2-yl]-allylidene}-aminoguanidine hippuric acid exhibiting at least X-ray lines (2-theta values) in a powder diffraction pattern when measured using Cu Kα radiation at 20.1±0.2, 24.1±0.2, and 24.5±0.2, xxvii. a crystalline Form XXIII of N-{3-[1-(2-nitrophenyl)-1H-pyrrol-2-yl]-allylidene}-aminoguanidinium formate exhibiting at least X-ray lines (2-theta values) in a powder diffraction pattern when measured using Cu Kα radiation at 13.3±0.2, 15.1±0.2, and 25.6±0.2, xxviii. a crystalline Form XXIV of N-{3-[1-(2-nitrophenyl)-1H-pyrrol-2-yl]-allylidene}-aminoguanidine L-lactic acid exhibiting at least X-ray lines (2-theta values) in a powder diffraction pattern when measured using Cu Kα radiation at 3.8±0.2, 9.9±0.2, and 11.9±0.2, xxix. a crystalline Form XXV of N-{3-[1-(2-nitrophenyl)-1H-pyrrol-2-yl]-allylidene}-aminoguanidine DL-lactic acid exhibiting at least X-ray lines (2-theta values) in a powder diffraction pattern when measured using Cu Kα radiation at 9.8±0.2, 11.9±0.2, and 27.6±0.2, xxx. a crystalline Form XXVI of N-{3-[1-(2-nitrophenyl)-1H-pyrrol-2-yl]-allylidene}-aminoguanidine glutaric acid exhibiting at least X-ray lines (2-theta values) in a powder diffraction pattern when measured using Cu Kα radiation at 8.3±0.2, 15.9±0.2, and 21.9±0.2, xxxi. a crystalline Form XXVII of N-{3-[1-(2-nitrophenyl)-1H-pyrrol-2-yl]-allylidene}-aminoguanidine glutaric acid further exhibiting one or more X-ray lines (2-theta values) in a powder diffraction pattern when measured using Cu Kα radiation selected from the group consisting of 16.9±0.2, 25.6±0.2, 27.1±0.2, 28.2±0.2, and 28.7±0.2, xxxii. a crystalline Form XXVIII of N-{3-[1-(2-nitrophenyl)-1H-pyrrol-2-yl]-allylidene}-aminoguanidine glutaric acid exhibiting at least X-ray lines (2-theta values) in a powder diffraction pattern when measured using Cu Kα radiation at 14.2±0.2, 16.9±0.2, and 24.5±0.2, or xxxiii. a crystalline Form XXIX of N-{3-[1-(2-nitrophenyl)-1H-pyrrol-2-yl]-allylidene}-aminoguanidine adipic acid exhibiting at least X-ray lines (2-theta values) in a powder diffraction pattern when measured using Cu Kα radiation at 13.4±0.2, 14.5±0.2, and 25.5±0.2.

2. The method according to claim 1, wherein the crystalline Form is:

i. the crystalline Form A of N-{3-[1-(2-nitrophenyl)-1H-pyrrol-2-yl]-allylidene}-aminoguanidinium acetate, ii. the crystalline Form B of N-{3-[1-(2-nitrophenyl)-1H-pyrrol-2-yl]-allylidene}-aminoguanidinium succinate, iii. the crystalline Form XIV of N-{3-[1-(2-nitrophenyl)-1H-pyrrol-2-yl]-allylidene}-aminoguanidinium besylate, iv. the crystalline Form XIX of N-{3-[1-(2-nitrophenyl)-1H-pyrrol-2-yl]-allylidene}-aminoguanidinium oxoglutarate, v. the crystalline Form XX of N-{3-[1-(2-nitrophenyl)-1H-pyrrol-2-yl]-allylidene}-aminoguanidine DL-mandelic acid, vi. the crystalline Form XXII of N-{3-[1-(2-nitrophenyl)-1H-pyrrol-2-yl]-allylidene}-aminoguanidine hippuric acid, vii. the crystalline Form XXIII of N-{3-[1-(2-nitrophenyl)-1H-pyrrol-2-yl]-allylidene}-aminoguanidinium formate, viii. the crystalline Form XXIV of N-{3-[1-(2-nitrophenyl)-1H-pyrrol-2-yl]-allylidene}-aminoguanidine L-lactic acid, ix. the crystalline Form XXV of N-{3-[1-(2-nitrophenyl)-1H-pyrrol-2-yl]-allylidene}-aminoguanidine DL-lactic acid, x. the crystalline Form XXVI of N-{3-[1-(2-nitrophenyl)-1H-pyrrol-2-yl]-allylidene}-aminoguanidine glutaric acid, or xi the crystalline Form XXIX of N-{3-[1-(2-nitrophenyl)-1H-pyrrol-2-yl]-allylidene}-aminoguanidine adipic acid.

3. The method according to claim 1, wherein the arthritic disease is:

i. an auto-immune disease and/or an inflammatory disease that presents with joint inflammation, ii. inflammatory arthritis, iii. degenerative arthritis, iv. metabolic arthritis, v. reactive arthritis, vi. infectious arthritis, or vii. arthritis as part of a systemic inflammatory disease.

4. The method according to claim 3, wherein the inflammatory arthritis is Rheumatoid Arthritis.

5. The method according to claim 4, wherein said subject is a subject with an inappropriate response to methotrexate (MTX).

6. The method according to claim 1, wherein the kidney disease is:

i. kidney disease presenting with proteinuria, ii. proteinuric kidney disease, iii glomerular disease, iv. nephrotic syndrome (glomerulonephrosis), v. primary nephrotic syndrome (primary glomerulonephrosis), vi. secondary nephrotic syndrome (secondary glomerulonephrosis), vii. an inflammatory kidney disease, viii. glomerulonephritis (GN), or ix. idiopathic membranous nephropathy (iMN).

7. The method according to claim 1, wherein the viral disease or disorder is:

i. a symptomatic viral disease or disorder, ii. a symptomatic viral disease or disorder with inflammation, iii. an inflammatory viral disease or disorder, iv. a viral respiratory infection, V. a viral respiratory disease or disorder, vi. a viral disease or disorder of the lung, vii. a viral disease or disorder with inflammation in the respiratory system, viii. a viral disease or disorder with one or more respiratory symptoms, ix. severe disease, x. critical disease, xi. viral pneumonia, xii. viral bronchiolitis, xiii. viral diseases or disorders with respiratory failure, xiv. acute respiratory distress syndrome (ARDS), xv. viral acute respiratory distress syndrome (ARDS), xvi. symptomatic COVID-19 with acute respiratory distress syndrome (ARDS), xvii. a viral disease or disorder with systemic inflammatory distress syndrome (SIDS) and/or sepsis, xviii. a viral disease or disorder with pulmonary insufficiency, xix. a viral disease or disorder with cytokine release syndrome (CRS) and/or a cytokine storm (hypercytokinemia), or xx. a viral disease or disorder caused by a viral infection selected from Severe Acute Respiratory Syndrome Corona Virus 2 (SARS-CoV-2); SARS-CoV, MERS-CoV, the dengue virus and influenza virus.

8. The method according to claim 7, wherein the influenza virus is Type A, Type B or Type C).

* * * * *